(12) United States Patent
Borzilleri et al.

(10) Patent No.: US 7,173,031 B2
(45) Date of Patent: Feb. 6, 2007

(54) PYRROLOTRIAZINE KINASE INHIBITORS

(75) Inventors: Robert M. Borzilleri, New Hope, PA (US); Zhong Chen, Princeton, NJ (US); John T. Hunt, Princeton, NJ (US); Tram Huynh, Pennington, NJ (US); Michael A. Poss, Lawrenceville, NJ (US); Gretchen M. Schroeder, Ewing, NJ (US); Wayne Vaccaro, Yardley, PA (US); Tai W. Wong, Belle Mead, NJ (US); Xiao-Tao Chen, Furlong, PA (US); Kyoung S. Kim, North Brunswick, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 11/167,049

(22) Filed: Jun. 24, 2005

(65) Prior Publication Data

US 2006/0004006 A1 Jan. 5, 2006

Related U.S. Application Data

(60) Provisional application No. 60/612,563, filed on Sep. 23, 2004, provisional application No. 60/583,459, filed on Jun. 28, 2004.

(51) Int. Cl.
C07D 487/04 (2006.01)
C07D 401/02 (2006.01)
A61K 31/53 (2006.01)
A61P 35/00 (2006.01)

(52) U.S. Cl. ...................... 514/243; 544/183
(58) Field of Classification Search ............... 544/183; 514/243
See application file for complete search history.

(56) References Cited

U.S. PATENT DOCUMENTS

| | | |
|---|---|---|
| 3,646,202 A | 2/1972 | Mrozik |
| 4,602,912 A | 7/1986 | de Sousa et al. |
| 4,663,341 A | 5/1987 | Jacobson |
| 4,753,940 A | 6/1988 | Sturm et al. |
| 4,845,093 A | 7/1989 | Haga et al. |
| 4,908,056 A | 3/1990 | Tseng |
| 5,132,314 A | 7/1992 | Maienfisch et al. |
| 5,135,949 A | 8/1992 | von der Saal et al. |
| 5,646,176 A | 7/1997 | Golik et al. |
| 6,022,884 A | 2/2000 | Mantlo et al. |
| 6,143,743 A | 11/2000 | Wilde et al. |
| 6,143,764 A | 11/2000 | Kubo et al. |
| 6,214,344 B1 | 4/2001 | Schwall et al. |
| 6,232,320 B1 | 5/2001 | Stewart et al. |
| 6,262,094 B1 | 7/2001 | Hoefle et al. |
| 6,355,660 B1 | 3/2002 | Ricks et al. |
| 6,380,386 B2 | 4/2002 | Seitz et al. |
| 6,521,622 B1 | 2/2003 | Ricks et al. |
| 6,559,341 B2 | 5/2003 | Tohnishi et al. |
| 6,603,044 B1 | 8/2003 | Tohnishi et al. |
| 6,620,827 B2 | 9/2003 | De la Brouse-Elwood et al. |
| 6,670,357 B2 | 12/2003 | Leftheris et al. |
| 6,696,487 B2 | 2/2004 | Gerusz et al. |
| 6,706,740 B2 | 3/2004 | Ricks et al. |
| 6,750,246 B1 | 6/2004 | Kadow et al. |
| 6,867,300 B2 | 3/2005 | Godfrey, Jr. et al. |
| 6,900,208 B2 | 5/2005 | Salvati et al. |
| 6,951,859 B2 | 10/2005 | Bhide et al. |
| 6,982,265 B1 | 1/2006 | Hunt et al. |
| 2001/0041673 A1 | 11/2001 | Fossa |
| 2003/0082631 A1 | 5/2003 | Gustavsson et al. |

(Continued)

FOREIGN PATENT DOCUMENTS

| | | |
|---|---|---|
| AU | 200195986 | 4/2002 |
| DE | 31 39 457 | 4/1983 |
| DE | 197 10 609 | 9/1998 |
| EP | 0 151 962 | 8/1985 |
| EP | 0 119 774 | 6/1987 |

(Continued)

OTHER PUBLICATIONS

Cecil Textbook of Medicine, edited by Bennet, J.C., and Plum F., 20th edition,vol. 1, 1004-1010, 1996.*
Mass, R. D., Int. J. Radiation Oncology Bio. Phys.vol 58(3): 932-940, 2004.*
Fabbro et al. Pharmacology & therapeutics 93, 79-98, 2002.*
U.S. Appl. No. 09/573,829, filed May 18, 2000, Hunt et al.
U.S. Appl. No. 11/152,650, filed Jun. 14, 2005, Cai et al.
U.S. Appl. No. 11/168,682, filed Jun. 28, 2005, Shi et al.

(Continued)

Primary Examiner—Venkataraman Balasubramanian
(74) Attorney, Agent, or Firm—Maureen S. Gibbons

(57) ABSTRACT

In general, the instant invention comprises compounds of Formulas I and II

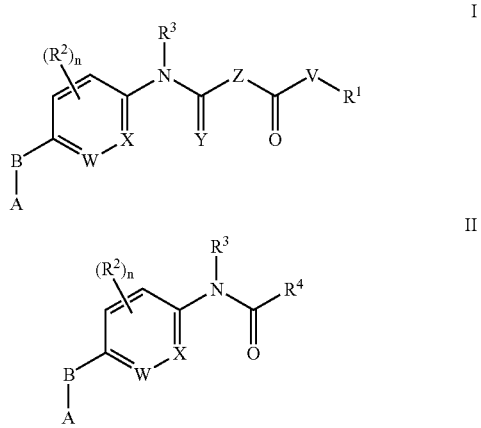

including pharmaceutically acceptable salts thereof. The compounds of the invention are useful as protein kinase inhibitors and therefore are useful for treating cancer and other protein kinase mediated diseases.

18 Claims, No Drawings

U.S. PATENT DOCUMENTS

| | | | |
|---|---|---|---|
| 2003/0232765 A1 | 12/2003 | Carter et al. |
| 2003/0232831 A1 | 12/2003 | Dyckman et al. |
| 2004/0044203 A1 | 3/2004 | Wittman et al. |
| 2004/0048891 A1 | 3/2004 | Kato et al. |
| 2004/0053908 A1 | 3/2004 | Funahashi et al. |
| 2004/0082582 A1 | 4/2004 | Dyckman et al. |
| 2004/0157846 A1 | 8/2004 | Chen et al. |
| 2004/0209886 A1 | 10/2004 | Salvati et al. |
| 2004/0229877 A1 | 11/2004 | Leftheris et al. |
| 2004/0242603 A1 | 12/2004 | Fujiwara et al. |
| 2005/0038035 A1 | 2/2005 | Takasugi et al. |
| 2005/0043306 A1 | 2/2005 | Leftheris et al. |
| 2005/0107462 A1 | 5/2005 | Godfrey, Jr. et al. |
| 2005/0143398 A1 | 6/2005 | Das et al. |
| 2005/0182058 A1 | 8/2005 | Fink et al. |
| 2005/0239820 A1 | 10/2005 | Borzilleri et al. |
| 2005/0245530 A1 | 11/2005 | Borzilleri et al. |
| 2005/0288289 A1 | 12/2005 | Crispino et al. |
| 2005/0288290 A1 | 12/2005 | Borzilleri et al. |
| 2006/0003967 A1 | 1/2006 | Shi et al. |
| 2006/0009454 A1 | 1/2006 | Cai et al. |
| 2006/0030708 A1 | 2/2006 | Lobben |

FOREIGN PATENT DOCUMENTS

| | | |
|---|---|---|
| EP | 0 152 910 | 7/1989 |
| EP | 0 919 542 | 6/1999 |
| EP | 1 243 582 | 9/2002 |
| EP | 1 411 046 | 4/2004 |
| GB | 2 106 500 | 4/1983 |
| JP | 54-115384 | 9/1979 |
| JP | 57-51835 | 3/1982 |
| JP | 62-62 | 1/1987 |
| JP | 62-5959 | 1/1987 |
| JP | 62-5960 | 1/1987 |
| JP | 62-135463 | 6/1987 |
| JP | 2003-321472 | 11/2003 |
| SU | 1761753 | 9/1992 |
| WO | WO 97/17329 | 5/1997 |
| WO | WO 98/41513 | 9/1998 |
| WO | WO 99/01454 | 1/1999 |
| WO | WO 99/02514 | 1/1999 |
| WO | WO 99/24404 | 5/1999 |
| WO | WO 00/43366 | 7/2000 |
| WO | WO 00/50405 | 8/2000 |
| WO | WO 00/56738 | 9/2000 |
| WO | WO 00/71129 | 11/2000 |
| WO | WO 00/75145 | 12/2000 |
| WO | WO 01/21576 | 3/2001 |
| WO | WO 01/21596 | 3/2001 |
| WO | WO 01/42243 | 6/2001 |
| WO | WO 01/47890 | 7/2001 |
| WO | WO 01/94353 | 12/2001 |
| WO | WO 02/32872 | 4/2002 |
| WO | WO 02/40486 | 5/2002 |
| WO | WO 02/44156 | 6/2002 |
| WO | WO 02/051397 | 7/2002 |
| WO | WO 02/085859 | 10/2002 |
| WO | WO 03/000194 | 1/2003 |
| WO | WO 03/000660 | 1/2003 |
| WO | WO 03/011028 | 2/2003 |
| WO | WO 03/033472 | 4/2003 |
| WO | WO 03/042172 | 5/2003 |
| WO | WO 03/082208 | 10/2003 |
| WO | WO 03/091229 | 11/2003 |
| WO | WO 03/099286 | 12/2003 |
| WO | WO 2004/001059 | 12/2003 |
| WO | WO 2004/002410 | 1/2004 |
| WO | WO 2004/009542 | 1/2004 |
| WO | WO 2004/032846 | 4/2004 |
| WO | WO 2004/048386 | 6/2004 |
| WO | WO 2004/054514 | 7/2004 |
| WO | WO 2004/058144 | 7/2004 |
| WO | WO 2004/060305 | 7/2004 |
| WO | WO 2004/072030 | 8/2004 |
| WO | WO 2005/005389 | 1/2005 |
| WO | WO 2005/026124 | 3/2005 |
| WO | WO 2005021554 | 3/2005 |
| WO | WO 2005/030140 | 4/2005 |
| WO | WO 2005/042537 | 5/2005 |
| WO | WO 2005/058891 | 6/2005 |
| WO | WO 2005/082854 | 9/2005 |
| WO | WO 2005/082855 | 9/2005 |
| WO | WO 2005/097790 | 10/2005 |

OTHER PUBLICATIONS

U.S. Appl. No. 11/197,970, filed Aug. 5, 2005, Lobben.

U.S. Appl. No. 60/696,394, filed Jul. 1, 2005, Gavai et al.

U.S. Appl. No. 60/703,086, filed Jul. 28, 2005, Norris et al.

Bardelli, A. et al., "Concomitant activation of pathways downstream of Grb2 and PI 3-kinase is required for *MET*-mediated metastasis", Oncogene, vol. 18, pp. 1139-1146 (1999).

Barker, J.M. et al., "Thienopyridines. Part 7. Some Electrophilic Substitution Reactions of Thieno[2,3-*b*]- and -[3,2-*b*]pyridine Isosteres of 4-Oxygenated and 2,4-Dioxygenated Quinolines", J. Chem. Research (S), pp. 122-123 (1986).

Bottaro, D.P. et al., "Identification of the Hepatocyte Growth Factor Receptor as the *c-met* Proto-Oncogene Product", Science, vol. 251, pp. 802-804 (1991).

Bussolino, F. et al., "Hepatocyte Growth Factor Is a Potent Angiogenic Factor Which Stimulates Endothelial Cell Motility and Growth", The Journal of Cell Biology, vol. 119, No. 3, pp. 629-641 (1992).

Camp, R.L. et al., "*Met* Expression Is Associated with Poor Outcome in Patients with Axillary Lymph Node Negative Breast Carcinoma", Cancer, vol. 86, No. 11, pp. 2259-2265 (1999).

Cheng, C.C. et al., "Potential Purine Antagonist. XII. Synthesis of 1-Alkyl(aryl)-4,6-disubstituted Pyrazolo[3-4-*d*]pyrimidines", J. Org. Chem., vol. 23, pp. 852-861 (1958).

Chi, S.-M. et al., "Palladium-catalyzed functionalization of 5- and 7-azaindoles", Tetrahedron Letters, vol. 41, pp. 919-922 (2000).

Christensen, J.G. et al., "A Selective Small Molecule Inhibitor of c-Met Kinase Inhibits c-Met-Dependent Phenotypes *in Vitro* and Exhibits Cytoreductive Antitumor Activity *in Vivo*", Cancer Research, vol. 63, pp. 7345-7355 (2003).

Cooper, C.S. et al., "Amplification and overexpression of the met gene in spontaneously transformed NIH3T3 mouse fibroblasts", The EMBO Journal, vol. 5, No. 10, pp. 2623-2628 (1986).

Di Renzo, M.F. et al., "Overexpression and Amplification of the Met/HGF Receptor Gene during the Progression of Colorectal Cancer", Clinical Cancer Research, vol. 1, pp. 147-154 (1995).

Dorn, H. et al., "Unambiguous Synthesis of 4,7-Dihydro-4-oxo-1H-pyrazolo[3,4-b]pyridine—Further Comments on the '(N-C)-Rearrangement' of (2-Alkoxycarbonyl-vinyl-amino) pyrazols", J. Prakt. Chem., vol. 324, No. 4, pp. 557-562 (1982).

Fry, D.W., Chapter 16: "Recent Advances in Tyrosine Kinase Inhibitors", Annual Reports in Medicinal Chemistry, vol. 31, Academic Press, publ., Bristol, J.A., ed., pp. 151-160 (1996).

Furge, K.A. et al., "Met receptor tyrosine kinase: enhanced signaling through adapter proteins", Oncogene, vol. 19, pp. 5582-5589 (2000).

Gero, T.W. et al., "Halogenation of 2-Hydroxynicotinic Acid", Synthetic Communications, vol. 19, Nos. 3&4, pp. 553-559 (1989).

Greene, T.W. et al., Protective Groups in Organic Synthesis, 2nd Ed., John Wiley & Sons, Inc., publ., pp. ix-x (table of contents) (1991).

Gual, P. et al., "Sustained recruitment of phospholipase C-γ to Gab1 is required for HGF-induced branching tubulogenesis", Oncogene, vol. 19, pp. 1509-1518 (2000).

Hamdouchi, C. et al., "Imidazo[1,2-*b*]pyridazines, Novel Nucleus with Potent and Broad Spectrum Activity against Human Picornaviruses: Design, Synthesis, and Biological Evaluation", J. Med. Chem., vol. 46, No. 20, pp. 4333-4341 (2003).

Itoh, T. et al., "Studies on the Chemical Synthesis of Potential Antimetabolites. 30. Regioselective Introduction of a Chlorine Atom into the Imidazo[4,5-*b*]pyridine Nucleus", J. Heterocyclic Chem., vol. 19, pp. 513-517 (1982).

Jiang, W.G. et al., "Reduction of Stromal Fibroblast-induced Mammary Tumor Growth, by Retroviral Ribozyme Transgenes to Hepatocyte Growth Factor/Scatter Factor and its Receptor, c-MET", Clinical Cancer Research, vol. 9, pp. 4274-4281 (2003).

Kenworthy, P. et al., "The presence of scatter factor in patients with metastatic spread to the pleura", Br. J. Cancer, vol. 66, pp. 243-247 (1992).

Kitamura, C. et al., "Synthesis and reactions of 3,3'-dibromodihydrodipyrrins", J. Chem. Soc. Perkin Trans. 1, pp. 1443-1447 (1997).

Koch, V. et al., "Chemistry of 3-Hydroxypyridine Part 2: Synthesis of 5,6-Dihalo-3-hydroxypyridines", Synthesis, pp. 499-501 (1990).

Lai, J.-F. et al., "Involvement of Focal Adhesion Kinase in Hepatocyte Growth Factor-induced Scatter of Madin-Darby Canine Kidney Cells", The Journal of Biological Chemistry, vol. 275, No. 11, pp. 7474-7480 (2000).

Lee, J.-H. et al., "A novel germ line juxtamembrane *Met* mutation in human gastric cancer", Oncogene, vol. 19, pp. 4947-4953 (2000).

Lubensky, I.A. et al., "Hereditary and Sporadic Papillary Renal Carcinomas with *c-met* Mutations Share a Distinct Morphological Phenotype", American Journal of Pathology, vol. 155, No. 2, pp. 517-526 (1999).

Masuya, D. et al., "The tumour-stromal interaction between intratumoral c-Met and stromal hepatocyte growth factor associated with tumour growth and prognosis in non-small-cell lung cancer patients", British Journal of Cancer, vol. 90, pp. 1555-1562 (2004).

Matsumoto, K. et al., "Hepatocyte Growth Factor: Molecular Structure, Roles in Liver Regeneration, and Other Biological Functions", Critical Reviews in Oncogenesis, vol. 3, Nos. 1,2, pp. 27-54 (1992).

Montesano, R. et al., "Identification of a Fibroblast-Derived Epithelial Morphogen as Hepatocyte Growth Factor", Cell, vol. 67, pp. 901-908 (1991).

Morrill, C. et al., "Synthesis of Functionalized Vinyl Boronates via Ruthenium-Catalyzed Olefin Cross-Metathesis and Subsequent Conversion to Vinyl Halides", J. Org. Chem., vol. 68, No. 15, pp. 6031-6034 (2003).

Park, M. et al., "Sequence of *MET* protooncogene cDNA has features characteristic of the tyrosine kinase family of growth-factor receptors", Proc. Natl. Acad. Sci. USA, vol. 84, pp. 6379-6383 (1987).

Patil, S.A. et al., "Synthesis of Pyrrolo[2,1-*f*][1,2,4]triazine Congeners of Nucleic Acid Purines *via* the *N*-Amination of 2-Substituted Pyrroles", J. Heterocyclic Chem., vol. 31, pp. 781-786 (1994).

Quintela, J.M. et al., "A Ready One-pot Preparation for Pyrrolo[2,1-*f*][1,2,4]triazine and Pyrazolo[5,1-*c*]pyrimido[4,5-*e*][1,2,4]triazine Derviatives", Tetrahedron, vol. 52, No. 8, pp. 3037-3048 (1996).

Rong, S. et al., "Met Expression and Sarcoma Tumorigenicity", Cancer Research, vol. 53, pp. 5355-5360 (1993).

Rong, S. et al., "Met Proto-oncogene Product Is Overexpressed in Tumors of p53-deficient Mice and Tumors of Li-Fraumeni Patients", Cancer Research, vol. 55, pp. 1963-1970 (1995).

Sachs, M. et al., "Essential role of Gab1 for Signaling by the c-Met Receptor In Vivo", The Journal of Cell Biology, vol. 150, No. 6, pp. 1375-1384 (2000).

Sanghvi, Y.S. et al., "Synthesis and Biological Evaluation of Certain C-4 Substituted Pyrazolo[3,4-*b*]pyridine Nucleosides", J. Med. Chem., vol. 32, No. 5, pp. 945-951 (1989).

Scarpino, S. et al., "Hepatocyte Growth Factor (HGF) Stimulates Tumour Invasiveness in Papillary Carcinoma of the Thyroid", Journal of Pathology, vol. 189, pp. 570-575 (1999).

Schaeper, U. et al., "Coupling of Gab1 to c-Met, Grb2, and Shp2 Mediates Biological Responses", The Journal of Cell Biology, vol. 149, No. 7, pp. 1419-1432 (2000).

Soman, N.R. et al., "The *TPR-MET* oncogenic rearrangement is present and expressed in human gastric carcinoma and precursor lesions", Proc. Natl. Acad. Sci. USA, vol. 88, pp. 4892-4896 (1991).

Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", The Journal of Cell Biology, vol. 123, No. 1, pp. 223-235 (1993).

Stabile, L.P. et al., "Inhibition of human non-small cell lung tumors by a c-Met antisense/U6 expression plasmid strategy", Gene Therapy, vol. 11, pp. 325-335 (2004).

Stella, M.C. et al., "HGF: a multifunctional growth factor controlling cell scattering", The International Journal of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K.A. et al., "Hepatocyte growth factor/scatter factor-induced intracellular signalling", International Journal of Experimental Pathology, vol. 81, pp. 17-30 (2000).

Takayama, H. et al., "Diverse tumorigenesis associated with aberrant development in mice overexpressing hepatocyte growth factor/scatter factor", Proc. Natl. Acad. Sci. USA, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Tedder, M.E. et al., "Structure-based design, synthesis, and antimicrobial activity of purine derived SAH/MTA nucleosidase inhibitors", Bioorganic & Medicinal Chemistry Letters, vol. 14, pp. 3165-3168 (2004).

Temple, Jr., C. et al., "Preparation and Properties of Some Isomeric *v*-Triazolopyridines. 1- and 3-Deaza-8-azapurines", J. Org. Chem., vol. 37, No. 23, pp. 3601-3604 (1972).

Thibault, C. et al., "Concise and Efficient Synthesis of 4-Fluoro-1*H*-pyrrolo[2,3-*b*]pyridine", Organic Letters, vol. 5, No. 26, pp. 5023-5025 (2003).

Zhang, Z. et al., "A General Method for the Preparation of 4- and 6-Azaindoles", J. Org. Chem., vol. 67, pp. 2345-2347 (2002).

Bryant, R.D. et al., "A Large Scale Synthesis of 3-Chloro-5-methoxypyridazine", J. Heterocyclic Chem., vol. 32, pp. 1473-1476 (1995).

Burckhalter, J.H. et al., "Aminoalkylphenols as Antimalarials. II. (Heterocyclic-amino)-α-amino-*o*-cresols. The Synthesis of Camoquin", J. Am. Chem. Soc., vol. 70, pp. 1363-1373 (1948).

Cañibano, V. et al., "Mild Regioselective Halogenation of Activated Pyridines with *N*-Bromosuccinimide", Synthesis, vol. 14, pp. 2175-2179 (2001).

Cheng, C.-C. et al., "Comprehensive Studies on Dual Excitation Behavior of Double Proton versus Charge Transfer in 4-(*N*-Substituted amino)-1H-pyrrolo[2,3-*b*]pyridines", J. Phys. Chem. A, vol. 107, No. 10, pp. 1459-1471 (2003).

Chung, H.-A. et al., "Direct Functionalization of 4,5-Dichloropyridazin-6-one", J. Heterocyclic Chem., vol. 36, pp. 905-910 (1999).

Frey, L.F. et al., "Practical routes toward the synthesis of 2-halo- and 2-alkylamino-4-pyridinecarboxaldehydes", Tetrahedron Letters, vol. 42, pp. 6815-6818 (2001).

Gemma, S. et al., "Polycondensed heterocycles. Part 12: An approach to the synthesis of 2-acetyl-1'-methyl-1,2,3,4-tetrahydrospiro-[isoquinoline-1,4'-pyrrolidine]-2'-one", Tetrahedron, vol. 58, pp. 3689-3692 (2002).

Girgis, N.S. et al., "The Synthesis of 5-Azaindoles by Substitution-Rearrangement of 7-Azaindoles upon Treatment with Certain Primary Amines", J. Heterocyclic Chem., vol. 26, pp. 317-325 (1989).

Kirk, K.L., "Synthesis of Ring-Fluorinated Serotonins and Melatonins", J. Heterocyclic Chem., vol. 13, pp. 1253-1256 (1976).

Nicolaou, I. et al., "[1-(3,5-Difluoro-4-hydroxyphenyl)-1*H*-pyrrol-3-yl]phenylmethanone as a Bioisostere of a Carboxylic Acid Aldose Reductase Inhibitor", J. Med. Chem., vol. 47, No. 10, pp. 2706-2709 (2004).

Schaus, J.M. et al., "Synthesis and Structure-Activity Relationships of Potent and Orally Active 5-HT$_4$ Receptor Antagonists: Indazole and Benzimidazolone Derivatives", J. Med. Chem., vol. 41, No. 11, pp. 1943-1955 (1998).

Tabanella, S. et al., "Preparation of enantiomerically pure pyridyl amino acids from serine", Org. Biomol. Chem., vol. 1, pp. 4254-4261 (2003).

U.S. Appl. No. 11/111,144, filed Apr. 21, 2005, Borzilleri et al.
U.S. Appl. No. 11/113,838, filed Apr. 25, 2005, Borzilleri et al.
U.S. Appl. No. 11/165,875, filed Jun. 24, 2005, Crispino et al.
U.S. Appl. No. 11/167,043, filed Jun. 24, 2005, Borzilleri et al.
Search Report "A", dated Dec. 16, 2004.
Kempter, G. et al., "Synthesis of potential plant protective agents and pesticides from substituted anilines", Wissenschaftliche Zeitschrift, vol. 27, No. 1, pp. 101-120 (1983) (with English abstract).
Search Report "A", dated Jul. 2, 2003.
Dumas, J. et al., "Synthesis and Structure Activity Relationships of Novel Small Molecule Cathepsin D Inhibitors", Bioorganic & Medicinal Chemistry Letters, vol. 9, pp. 2531-2536 (1999).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Kurogi, Y. et al., "Discovery of Novel Mesangial Cell Proliferation Inhibitors Using a Three-Dimensional Database Searching Method", J. Med. Chem., vol. 44, No. 14, pp. 2304-2307 (2001).
Okada, H. et al., "Synthesis and Antitumor Activities of Novel Benzoylphenylurea Derivatives", Chem. Pharm. Bull., vol. 39, No. 9, pp. 2308-2315 (1991).

Xue, C.-B. et al., "Rational Design, Synthesis and Structure-Activity Relationships of a Cyclic Succinate Series of TNF-α Converting Enzyme Inhibitors. Part 2: Lead Optimization", Bioorganic & Medicinal Chemistry Letters, vol. 13, pp. 4299-4304 (2003).
Database Crossfire Beilstein Beilstein Institut Zur Foerderung Der Chemischen Wissenschaft, Frankfurt AM Main, DE; XP002362294 Database accession No. BRN 667921.
Database Crossfire Beilstein Beilstein Institut Zur Foerderung Der Chemischen Wissenschaft, Frankfurt AM Main, DE; XP002362295 Database accession No. BRN 413351.
Database Crossfire Beilstein Beilstein Institut Zur Foerderung Der Chemischen Wissenschaft, Frankfurt AM Main, DE; XP002362296 Database accession No. BRN 450834.
Database Crossfire Beilstein Beilstein Institut Zur Foerderung Der Chemischen Wissenschaft, Frankfurt AM Main, DE; XP002362297 Database accession No. BRN 448780.
"Hepatocyte growth factor/scatter factor, Met and cancer references", Van Andel Institute, http://www.vai.org/vari/metandcancer/ (as revised Oct. 4, 2005).

* cited by examiner

PYRROLOTRIAZINE KINASE INHIBITORS

RELATED APPLICATIONS

This application claims priority benefit under Title 35 § 119(e) of U.S. Provisional Application Nos. 60/583,459, filed Jun. 28, 2004, and 60/612,563, filed Sep. 23, 2004, the contents of which are herein incorporated by reference.

FIELD OF INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223–235, 1993; Matsumato et al., *Crit. Rev. Oncog.* 3:27–54,1992; and Stoker et al., *Nature* 327:239–242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901–908, 1991), and promotion of invasion (Stella et al., *Int. J. Biochem. Cell Biol.* 12:1357–62, 1999 and Stuart et al., *Int. J. Exp. Path.* 81:17–30, 2000), all critical processes underlying metastasis. HGF has also been reported to promote angiogenesis (Bussolino et al., *J. Cell Biol.* 119:629–641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379–83, 1987 and Bottaro et al., *Science* 251:802–4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582–9, 2000). These include the p85 subunit of the PI3-kinase, phospholipase Cγ (Gaul et al., *Oncogene* 19:1509–18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149: 1419–32, 2000; Bardelli, et al., *Oncogene* 18:1139–46, 1999 and Sachs et al., *J. Cell Biol.* 150:1375–84, 2000). Activation of other signaling molecules has been reported in HGF stimulated cells, most notably Ras, MAP kinases, STATs, ERK-1, -2 and FAK (Tanimura et al., *Oncogene* 17:57–65, 1998; Lai et al., *J. Biol. Chem.* 275:7474–80 2000 and Furge et al., *Oncogene* 19:5582–9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517–26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.,* 63:7345–55, 2003; Lee et al., *Oncogene,* 19:4947–53, 2000 and Direnzo et al., *Clin. Cancer Res.,* 1: 147–54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963–1970, 1995; Rong et al., *Cancer Res.* 53:5355–5360, 1993; Kenworthy et al., *Br. J. Cancer* 66:243–247, 1992 and Scarpino et al. *J. Pathology* 189: 570–575, 1999). TPR-Met (an activated form similar to BCR/Abl in CML) has been described and identified in human gastric carcinoma (PNAS 88:4892–6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259–65 1999 and Masuya et al., *Br. J. Cancer,* 90:1555–62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS,* 94:701–6, 1997) and an amplified/ overexpressed Met spontaneously transforms NIH-3T3 cells (Cooper et al., *EMBO J.,* 5:2623–8, 1986).

Biological agents, such as ribozymes, antibodies and antisense RNA targeting either HGF or Met have been shown to inhibit tumorogenesis (Stabile et al., *Gene Therapy,* 11:325–35, 2004, Jiang et al., *Clin. Cancer Res,* 9:4274–81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY

The present invention is also directed to pharmaceutical compositions comprising therapeutically effective amounts of a compound of Formula I or II, or a salt or solvate thereof, together with a pharmaceutically acceptable carrier.

1. A compound having Formula I or II:

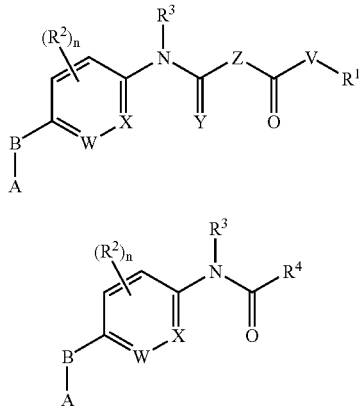

including pharmaceutically acceptable salts thereof, wherein:

$R^1$ is H, alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclo, substituted heterocyclo, heteroarylalkyl, substituted heteroarylalkyl, heterocycloalkyl, or substituted heterocycloalkyl;

each $R^2$ is independently, H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, arylalkyl, substituted arylalkyl, heterocycloalkyl, or substituted heterocycloalkyl;

B is O, $NR^8$, S, SO, $SO_2$, $CR^9R^{10}$;

V is $NR^{11}$ or $-(CR^{47}R^{48})_p-$;

W or X are independently C or N;

Y is O, S, or $NR^{12}$;

Z is $-CR^{13}R^{14}-$, $-(CR^{13}R^{14})_mNR^{15}-$;

l is 0 to 4;

m is 0 to 2;

n is 0 to 4;

p is 0 to 4;

$R^3$, $R^5$, $R^6$, $R^7$, $R^8$, $R^{11}$ and $R^{15}$ are each independently H, alkyl, substituted alkyl, cycloalkyl, substituted cycloalkyl, aryl, substituted aryl, heteroaryl, substituted heteroaryl, heterocycloalkyl, or substituted heterocycloalkyl;

$R^4$ is aryl, substituted aryl, heteroaryl, substituted heteroaryl, heterocycloalkyl, or substituted heterocycloalkyl;

$R^9$ and $R^{10}$ are independently H, halogen, hydroxyl, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{12}$ is H, alkyl, substituted alkyl, CN, $NO_2$ or $SO_2NH_2$ $R^{13}$, $R^{14}$, $R^{15}$, $R^{47}$ and $R^{48}$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form a carbocyclic or heterocyclic ring of 3 to 8 atoms;

A is:

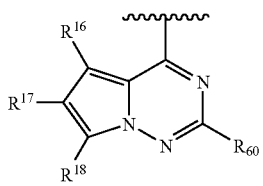

wherein $R^{16}$ and $R^{17}$, are independently H, halogen, $NO_2$, cyano, $OR^{26}$, $NR^{27}R^{28}$, $CO_2R^{29}$, $C(O)NR^{30}OR^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, $-CO(CH_2)_lR^{41}$, $-CONH(CH_2)_lR^{42}$, $-OCONH(CH_2)_lR^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{18}$ and $R^{60}$ are H;

$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

The present invention also provides methods for the treatment of cancer comprising administering to a patient in need thereof a pharmaceutically effective amount of a compound of Formula I or II or a salt or solvate thereof, optionally including administering to the patient at least one additional anticancer agent.

DESCRIPTION

The present invention provides for compounds of Formulas I and II defined above, pharmaceutical compositions employing such compounds, methods of making and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine, The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups such as amino, alkylamino, etc.

The numbers in the subscript after the symbol "C" define the number of carbon atoms a particular group can contain. For example "$C_1$ to $C_6$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_1$ to $C_6$ alkyl" can also refer to $C_1$ to $C_6$ alkylene which bridges two groups; examples include propane-1,3-diyl, butane-1,4-diyl, 2-methyl-butane-1,4-diyl, etc. "$C_2$ to $C_6$ alkyenyl means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_2$ to $C_6$ alkenyl" can also refer to $C_2$ to $C_6$ alkenediyl which bridges two groups; examples include ethylene-1,2-diyl (vinylene), 2-methyl-2-butene-1,4-diyl, 2-hexene-1,6-diyl, etc. "$C_2$ to $C_6$ alkynyl" means a straight or branched carbon chain having at least one carbon-carbon triple bond, and from two to six carbon atoms; examples include ethynyl, propynyl, butynyl, and hexynyl.

The terms "alkoxy" or "alkylthio" herein alone or as part of another group denote an alkyl group as described above bonded through an oxygen linkage (—O—) or a sulfur linkage (—S—), respectively.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group or —C(O)R.

The term "alkylcarbonyloxy" herein alone or as part of another group denotes an alkylcarbonyl group bonded through an oxygen linkage.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, such as Br, F, or Cl, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=O, 1, 2), or thiol.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$O_2H$, —C(=O)H, —$CO_2$-alkyl, —C(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The term "heterocycloalkyl" herein alone or as part of another group refers to a stable, saturated, or partially unsaturated monocyclic ring system containing 5 to 7 ring members of carbon atoms and other atoms selected from nitrogen, sulfur and/or oxygen. A heterocyclic ring may be a 5, 6 or 7-membered monocyclic ring and contain one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower] alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocycloalkyl groups include piperazine, piperidine, morpholine, homomorpholine, thiomorpholine, pyrrolidine, and azetidine.

A heteroaryl or heterocycloalkyl group may also be an 8–11 membered bicyclic ring which consists of carbon atoms and contains one, two, or three heteroatoms selected from nitrogen, oxygen and/or sulfur. Some preferred bicyclic rings include benzodioxole, quinoxaline, indolyl, and quinolinyl. The term "optionally substituted" as it refers to "heteraryl" or heterocycloalkyl herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

The term "anticancer" agent includes any known agent that is useful for the treatment of cancer including 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, matrix metalloproteinase inhibitors, VEGF inhibitors, including as anti-VEGF antibodies such as Avastin, and small molecules such as ZD6474 and SU6668, vatalanib, BAY-43-9006, SU11248, CP-547632, and CEP-7055 are also included. Anti-Her2 antibodies from Genentech (such as Herceptin) may also be utilized. Suitable EGFR inhibitors include gefitinib, erlotinib, and cetuximab. Pan Her inhibitors include canertinib, EKB-569, and GW-572016. Also included are Src inhibitors, dasatinib (BMS-354825) as well as Casodex® (bicalutamide, Astra Zeneca), Tamoxifen, MEK-1 kinase inhibitors, MAPK kinase inhibitors, PI3 inhibitors, and PDGF inhibitors, such as imatinib. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kinases, and inhibitors of integrin signaling. Additional anticancer agents include microtubule-stabilizing agents such as paclitaxel (also known as Taxol®), docetaxel (also known as Taxotere®), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*,11R*, 12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (disclosed in WO 99/02514), [1S-[1R*,3R*(E),7R*, 10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins.

Pyridine-N-oxy refers to a pyridine ring having an oxygen substituted on the N atom of the pyridine ring.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

The phrase "pharmaceutically acceptable salt(s)", as used herein, unless otherwise indicated, includes salts of acidic or basic groups which may be present in the compounds of formulas I and II. The compounds of formulas I and II that are basic in nature are capable of forming a wide variety of salts with various inorganic and organic acids. The acids that may be used to prepare pharmaceutically acceptable acid addition salts of such basic compounds of formulas I and II are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

The compounds of the present invention have the following Formula I or II:

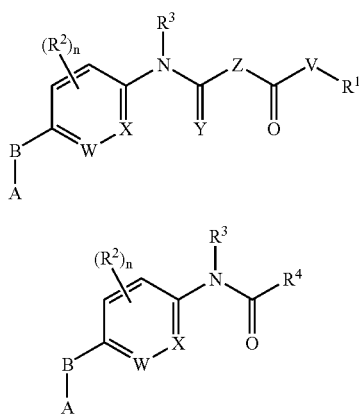

including pharmaceutically acceptable salts thereof, wherein:

$R^1$ is H, alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclo, substituted heterocyclo, heteroarylalkyl, substituted heteroarylalkyl, heterocycloalkyl, or substituted heterocycloalkyl;

each $R^2$ is independently, H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, aryalkyl, substituted arylalkyl, heterocycloalkyl, or substituted heterocycloalkyl;

B is O, $NR^8$, S, SO, $SO_2$, $CR^9R^{10}$;

V is $NR_{11}$ or $-(CR^{47}R^{48})_p-$;

W or X are independently C or N;

Y is O, S, or $NR^{12}$;

Z is $-CR^{13}R^{14}-$, $-(CR^{13}R^{14})_mNR^{15}-$;

l is 0 to 4;

m is 0 to 2;

n is 0 to 4;

p is 0 to 4;

$R^3$, $R^5$, $R^6$, $R^7$, $R^8$, $R^{11}$ and $R^{15}$ are each independently H, alkyl, substituted alkyl, cycloalkyl, substituted cycloalkyl, aryl, substituted aryl, heteroaryl, substituted heteroaryl, heterocycloalkyl, or substituted heterocycloalkyl;

$R^4$ is aryl, substituted aryl, heteroaryl, substituted heteroaryl, heterocycloalkyl, or substituted heterocycloalkyl;

$R^9$ and $R^{10}$ are independently H, halogen, hydroxyl, alkyl, substituted alkyl, cycloalkyl, substituted cycloalkyl, aryl, substituted aryl, heteroaryl, substituted heteroaryl, heterocycloalkyl, or substituted heterocycloalkyl;

$R^{12}$ is H, alkyl, substituted alkyl, CN, $NO_2$ or $SO_2NH_2$ $R^{13}$, $R^{14}$, $R^{15}$, $R^{47}$ and $R^{48}$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form a carbocyclic or heterocyclic ring of 3 to 8 atoms;

A is:

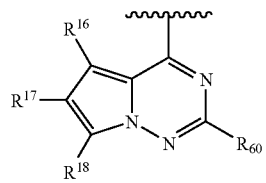

wherein $R^{16}$ and $R^{17}$, are independently H, halogen, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, $-CO(CH_2)_lR^{41}$, $-CONH(CH_2)_lR^{42}$, $-OCONH(CH_2)_l R^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{18}$ and $R^{60}$ are H;

$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

In some embodiments of the present invention, $R^1$ is an optionally substituted $C_1$ to $C_6$ alkyl, $C_2$ to $C_6$ alkenyl, $C_2$ to $C_6$ alkynyl, optionally substituted $C_3$ to $C_7$ cycloalkyl, $C_3$ to $C_7$ heterocycloalkyl, optionally substituted phenyl, optionally substituted biphenyl, or a $C_5$ to $C_{11}$ optionally substituted monocyclic or bicyclic heteroaryl.

In a preferred embodiment, $R^1$ is phenyl, fluorophenyl, or cyclopropyl.

According to one embodiment of the present invention, $R^2$ is $C_1$ to $C_4$ alkyl, prefereably methyl, alkoxy, such as methoxy, halo, such as F or Cl, haloalkyl, such as $CF_3$ or CN.

In one preferred embodiment of the present invention, $R^4$ is an optionally substituted phenyl, an optionally substituted pyridyl, an optionally substituted furanyl, an optionally substituted thiophene, an optionally substituted pyridinyl, an optionally substituted pyrimidyl, an optionally substituted isoxazole, an optionally substituted thiazole, an optionally substituted benzothiazole, or an optionally substituted quinoxaline. Preferred substituents include halo, methyl, acetyl, methoxy, amino, cyano, —SCH$_3$, nitro, pyridyl, SO$_2$CH$_3$, haloalkyl, and phenoxy.

In some embodiments of the present invention, A is

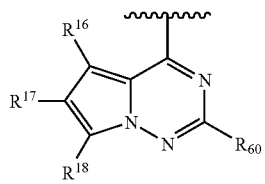

wherein preferably, R$^{16}$ and R$^{17}$ are independently H, C$_1$ to C$_4$ alkyl, —C=CR$^a$R$^b$ wherein R$^a$ and R$^b$ together with the C to which they are connected form a cyclohexyl, wherein the cyclohexyl may be further substituted with, for example, amino, hydroxyl, oxo, or aminoalkyl; halo; hydroxyalkyl; —COR$^{41}$ wherein R$^{41}$ is H or C$_1$ to C alkyl; —OR$^{26}$ wherein R$^{26}$ is C$_1$ to C$_6$ alkyl, such as an alkyl substituted with amino or substituted with a 4 to 6 membered heterocycloalkyl containing at least one nitrogen atom, such as morpholine, piperazine, or piperidine; —C(O)$_2$R$^{29}$ wherein R$^{29}$ is C$_1$ to C$_4$ alkyl; —OCH$_2$NHR$^{42}$ or —CONHR$^{42}$ wherein R$^{42}$ is C$_1$ to C$_6$ alkyl; phenyl or substituted phenyl; thiophene; pyridine; pyrimidine, isoxazol; pyrazol; or oxadiazole.

According to some embodiments of the present invention, R$^{16}$ and R$^{17}$ may be alkyl or alkenyl, alternatively substituted with cycloalkyl or heterocycloalkyl, such as morpholine, piperidine, pyrrolidine, or azetidine, which may further be substituted with, for example, amino, hydroxyl, aminoalkyl, or amido. The invention also provides a method for treating a proliferative disease, such as cancer, by administering to a patient in need of such treatment an effective amount of a compound of formula I or II, as defined above.

In another embodiment of the invention, a method is provided for treating a proliferative disease via modulation of Met kinase by administering to a patient in need of such treatment an effective amount of a compound of formula I or II, as defined above, in combination (simultaneously or sequentially) with at least one other anti-cancer agent. In a preferred embodiment, the proliferative disease is cancer.

The invention further provides pharmaceutical compositions comprising compounds having formula I or II together with a pharmaceutically acceptable carrier.

More specifically, the compounds of Formulas I and II are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formulas I and II as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulas I and II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formulas I and II may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulas I and II may also be useful in inhibiting tumor angiogenesis and metastasis.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen;

thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying-agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formulas I and II may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formulas I and II may also be administered sequentially with known anticancer or cytotoxic agents when a combination formulation is inappropriate. The invention is not limited in the sequence of administration; compounds of Formulas I and II may be administered either prior to or after administration of the known anticancer or cytotoxic agent(s).

Certain compounds of Formulas I and II may generally be prepared according to the following Schemes 1–16. The compounds are synthesized readily using synthetic methods known to one skilled in the art. Tautomers and solvates (e.g., hydrates) of the compounds of Formulas I and II are also within the scope of the present invention. Methods of solvation are generally known in the art. Accordingly, the compounds of the instant invention may be in the free or hydrate form, and may be obtained by methods exemplified by the following schemes below.

In general, the desired fused heterocycles can be prepared using the synthetic routes outlined in Schemes 1–3. The leaving group (Lg), such as a halogen (or triflate) of a heterocycle (A, whereby open positions may be optionally substituted) 1 can be displaced with a substituted phenol 2 to provide ether 3 (Scheme 1). Groups A-Lg can be prepared according to the general procedures outlined in, for example, Hunt, J. T. et al. WO 00/071129; Hunt, J. T. et al. *J. Med. Chem.* 2004, 47, 4054–4059; Leftheris, K. et al. WO 02/040486; Mastalerz, H. et al. WO 03/042172; Dyckman, A. et al. WO 03/091229; Vite, G. D. et al. WO 04/054514; Salvati, M. E. et al. WO 03/082208; Thibault, C. et al. *Org. Lett.* 2003, 5, 5023–5025; Zhang, Z. et al. *J. Org. Chem.* 2002, 67, 2345–2347; Itoh, T. et al. *J. Heterocyclic Chem.* 1982, 19, 513–517; Tedder, M. E. et al. *Bioorg. Med. Chem. Lett.* 2004, 14, 3165–3168; Dorn, H. et al. *J Prakt. Chem.* 1982, 324, 557; Sanghvi, Y. S. et al. *J. Med. Chem.* 1989, 32, 945–951; Temple, C. Jr. et al *J. Org. Chem.* 1972, 37, 3601–3604; Hurst, J. et al. EP119774; Hurst, J. et al. EP151962; Ward, R. W. et al. EP152910; Luzzio, M. J. et al. WO 01/094353; Marx, M. A. et al. WO 03/000194; Boschelli, D. H. et al. WO 04/048386; He, M. et al. WO 05/021554; Barker, J. M. et al. *J. Chem. Res., Synopses* 1986, 4, 122–123, the disclosures of which are herein incorporated by reference. Reduction of the nitro group of intermediate 3 with, for example either zinc dust and ammonium chloride or Adam's catalyst (platinum(IV) oxide) under catalytic hydrogenation conditions can furnish the aniline 4. Treatment of the aniline 4 with an isocyanate 5 (X=O) or isothiocyanate 5 (X=S) affords the desired acylurea or acylthiourea 6, respectively.

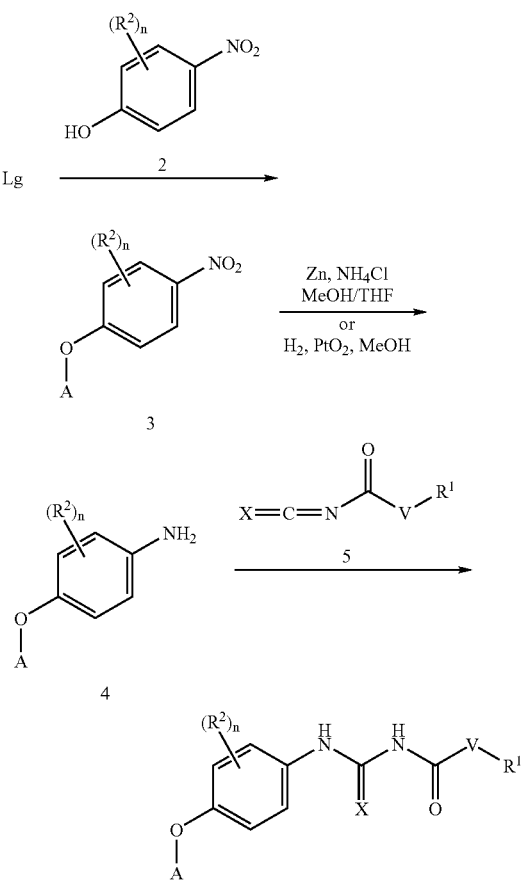

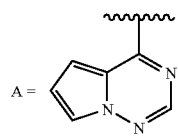

Lg = leaving group, such as a halogen
X = O or S
V = as defined above

Alternatively, the appropriately substituted aniline 7 can be treated with an isocyanate 5 (X=O) or isothiocyanate 5 (X=S) to give the phenol 8 (Scheme 2). Reaction of intermediate 8 with a heterocycle (A-Lg) 1 can provide the desired compound 6.

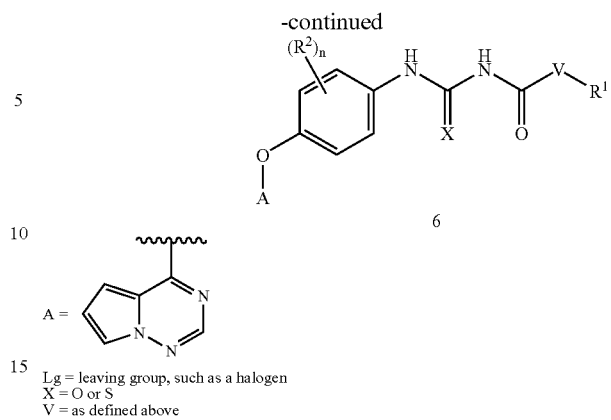

Lg = leaving group, such as a halogen
X = O or S
V = as defined above

In general, amide derivatives described in the invention can be prepared using the chemistry outlined in Scheme 3. For example, aniline 9 (derived from Scheme 1) can be acylated with compound 10 to provide amide 11. Hydrolysis of the ester 11 with, for example sodium hydroxide can afford carboxylic acid 12. Desired compound 13 can then be obtained from intermediate 12 using known amide-bond forming conditions. Alternatively, aniline 9 can be converted directly to compound 13 using carboxylic acid 14 and a coupling agent, such as benzotriazol-1-yloxytris(trimethylamino)phosphonium hexafluorophosphate, 1-(dimethylaminopropyl)-3-ethylcarbodiimide hydrochloride, or bromotripyrrolidinophosphonium hexafluorophosphate. Treatment of aniline 9 with an acid chloride 15 (X=Cl) or a carboxylic acid 15 (X=OH) and a coupling reagent can provide amides of the type 16.

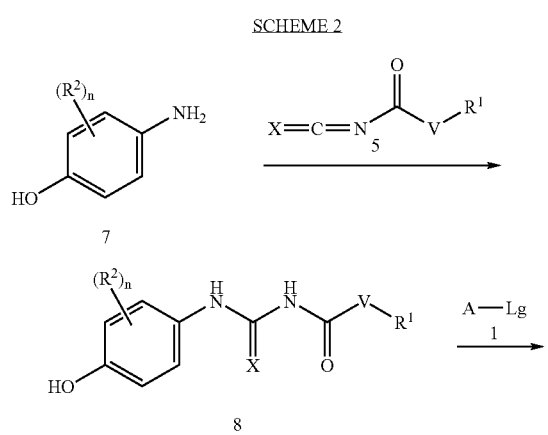

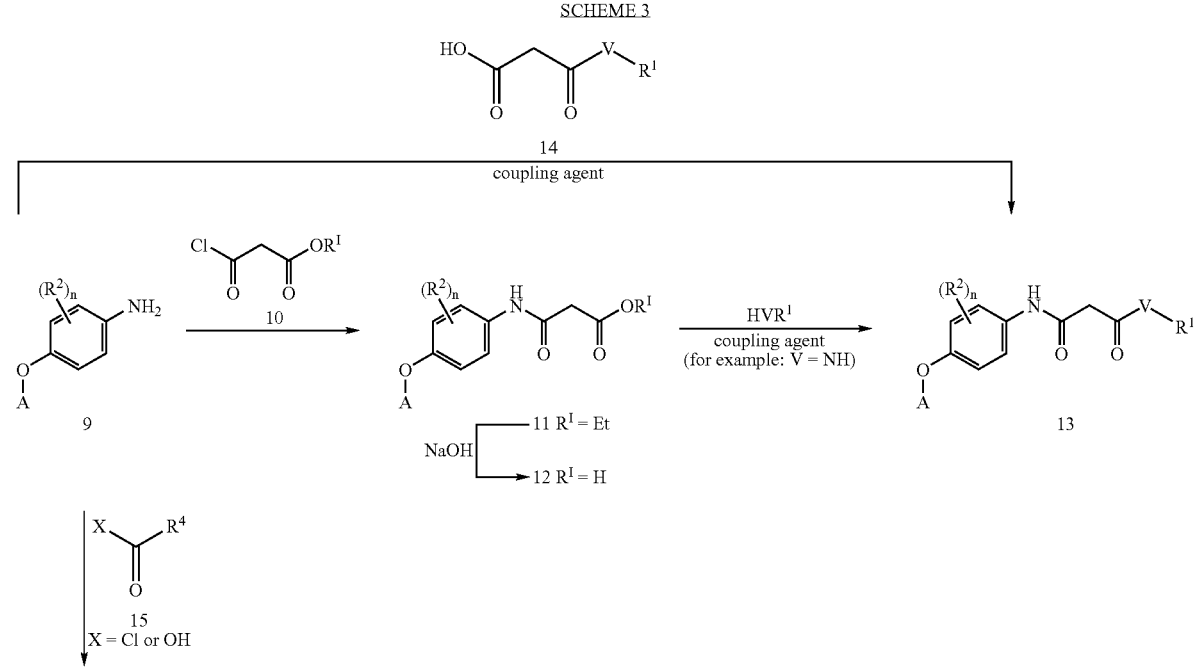

-continued

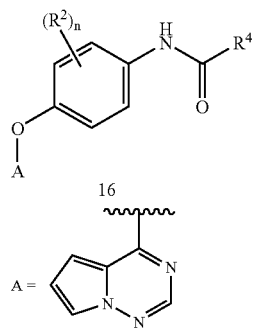

16

A =

V = as defined above

A substituted heterocyclic derivative, for example pyrrolotriazine compound 26a/b (Scheme 5), can be prepared using the synthetic routes outlined in Schemes 4 and 5. Carboxylic esters, wherein R can be an alkyl or an aryl (such as phenyl) 17 can be contacted with no less than 2 equivalents of an alkyl or aryl organometallic agent such as a Grignard reagent, organolithium, organozinc, etc. to produce the tertiary alcohol 18 (Scheme 4). The reaction is generally performed in an ether solvent, such as tetrahydrofuran, dibutylether, or diethyl ether, or any other non-reactive solvent such as benzene, toluene, or hexane, for example. Tertiary alcohol 18 can be treated with a mixture of acid in the presence of hydrogen peroxide or organic peroxides such as t-butylhydroperoxide, cumenehydroperoxide to affect the rearrangement to hydroxypyrrolotriazine 19. Almost any acid could be used as the catalyst for the oxidative rearrangement, the reaction has been demonstrated with organic acids, mineral acids, and Lewis acids. Some acids which have been used for this type of reaction include: p-toluenesulfonic acid, methansulfonic acid, formic acid, sulfuric acid, nitric acid, $BF_3$—$OEt_2$, trifluoroacetic acid, acidic zeolites, and acidic ion exchange resins. The concentration of the acid can be varied, the concentration and strength of the acid is used to control the kinetics of the reaction. The concentration of the peroxide can be varied from 30–50%. Any reducing agent which reacts to decompose hydrogen peroxide could be used in the quenching of this reaction, including, but not limited to sodium metabisulfite, sodium hydrogen sulfite, sodium thiosulfate, sodium hydrosulfite. A variety of bases can be used while quenching the reaction to control the pH. Hydroxypyrrolotriazine 19 can be reacted with a variety of acylating reagents, to furnish 20 (where, for example, P can be pivalate ester). Compound 20 can be contacted with an appropriate halogenating agent (for example, phosphorous oxychloride, $POCl_3$) to afford 21 (L=Cl). Other reagents can be used to accomplish this transformation besides $POCl_3$, including $PCl_5$, mixtures of $PCl_5$/$POCl_3$, $PhP(O)Cl_2$, $SOCl_2$. Usually an amine is used to catalyze the reaction, including $Et_3N$, $PhNMe_2$, DABCO, etc. Additionally, formamides such as, for example N,N-dimethylformamide and alkylamides such as N-methylpyrrolidinone can also be used to catalyze the reaction. The reaction can be run in any solvent inert to the halogenating agent, including benzene, toluene, THF, etc.

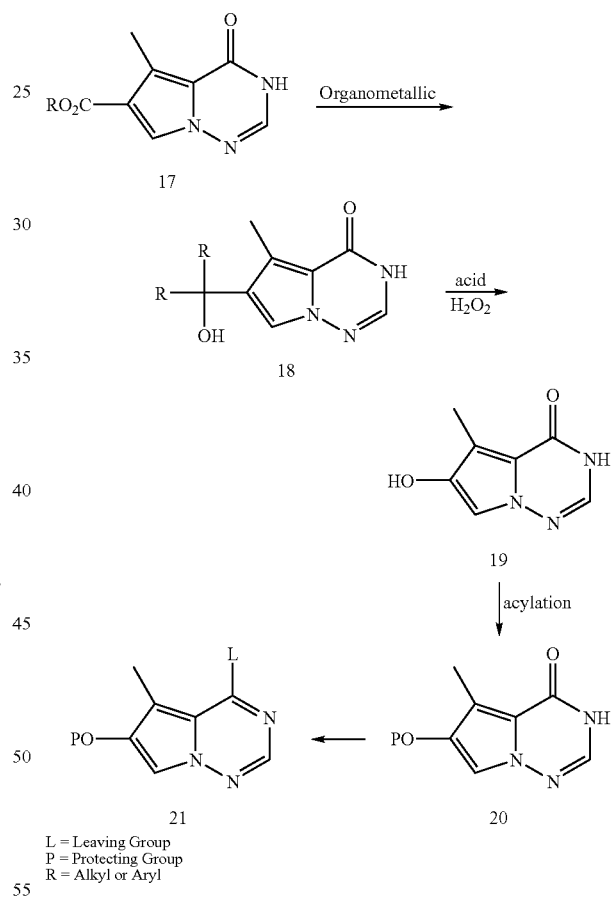

SCHEME 4

L = Leaving Group
P = Protecting Group
R = Alkyl or Aryl

The appropriately protected imidate 21 (Scheme 5) can be treated with an optionally substituted phenol 2 to provide intermediate 22. Phenol 23, derived from deprotection of compound 22 (using sodium hydroxide in the case where P=pivalate) can be converted to ether 24 via a Mitsunobu reaction with an alcohol. Reduction of the nitro substituent of 24 using the same conditions described above in Scheme 1 can furnish the aniline 25. Conversion of aniline 25 to the desired acylurea, acylthiourea or amide 26a/b can be accomplished using chemistry previously described in Schemes 1 and 3.

SCHEME 5

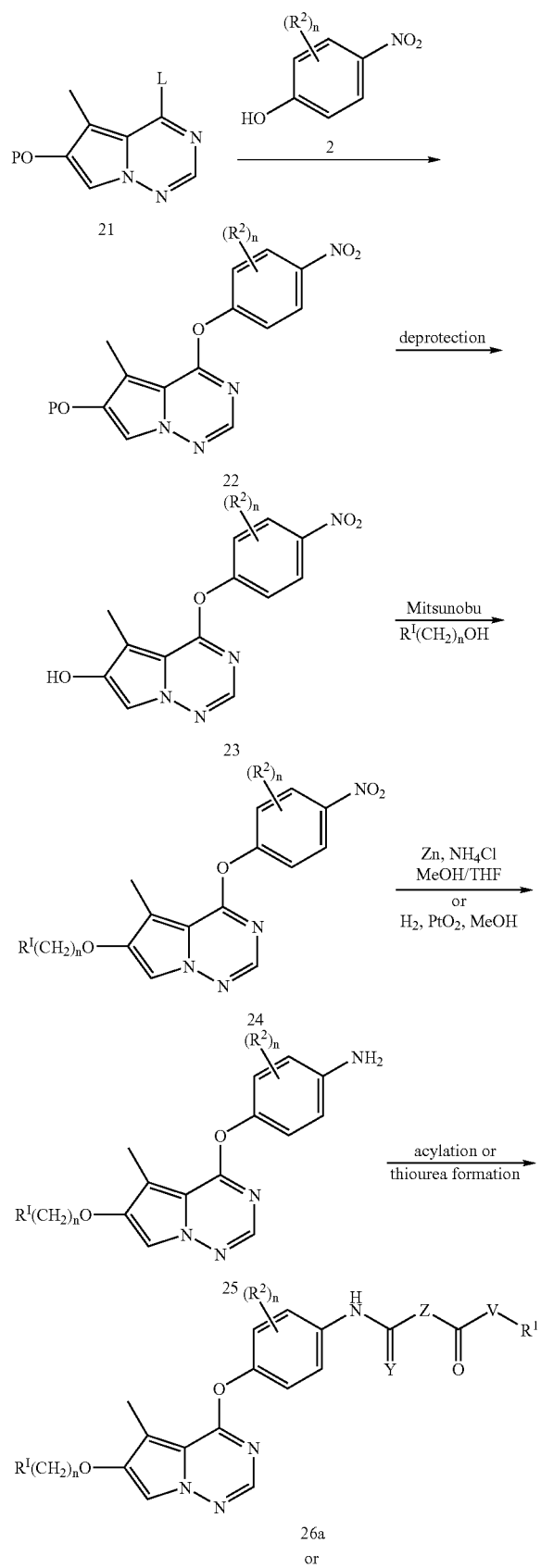

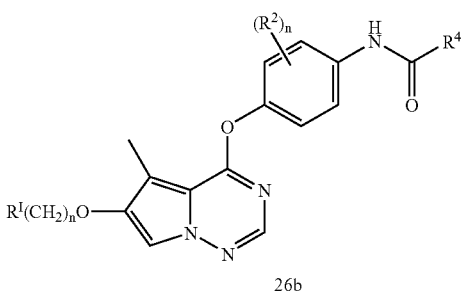

$R^I(CH_2)_nOH$ = any alcohol, but for example: n = 2–4
$R^I$ = N(CH$_3$)$_2$, morpholine, N—Me piperazine, etc Amine compounds 30 can be prepared using the chemistry described in Scheme 6. Reduction of ester 27 with for example, diisobutylaluminum hydride (DIBAL-H) can provide alcohol 28. Oxidation of compound 28 with for example Dess-Martin periodinane (1,1,1-tris(acetyloxy)-1,1-dihydro-1,2-benziodoxol-3-(1H)-one) can afford aldehyde 29. Reductive amination of aldehyde 29 with an appropriately substituted amine in the presence of a reducing agent, such as sodium triacetoxyborohydride can furnish the desired amine 30.

SCHEME 6

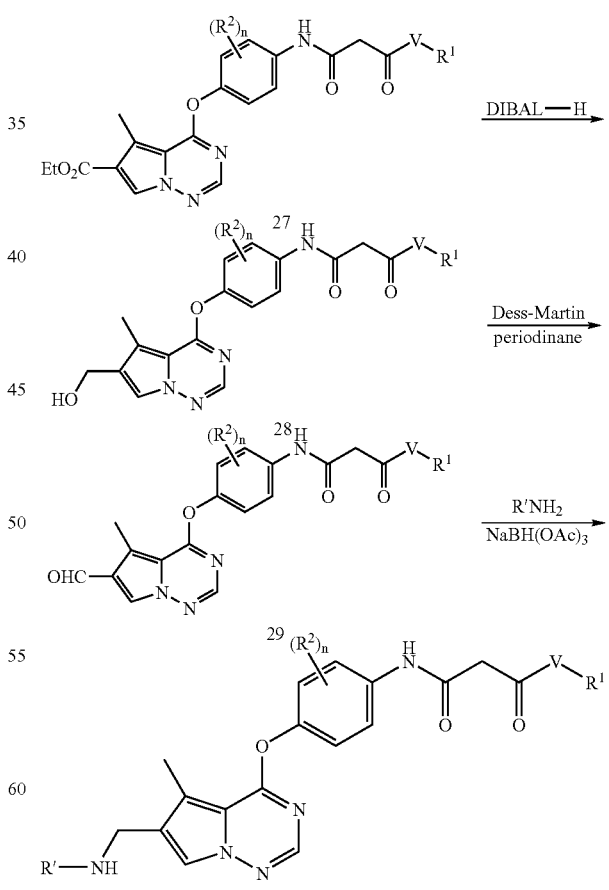

Various substituents, such as optionally substituted aryl, heteroaryl or vinyl groups can be introduced onto the 5-position of the pyrrolo[2,1-f][1,2,4]triazine ring using the chemistry outlined in Scheme 7. The aminopyrrole derivative 31 can be cyclized in the presence of formamide to produce 5-chloropyrrolo[2,1-f][1,2,4]triazin-4(3H)-one (32). Treatment of intermediate 32 with POCl₃ in the presence of a base, such as Hunig's base at elevated temperatures can afford 4,5-dichloropyrrolo[2,1-f][1,2,4]triazine (33). The coupling of an appropriately substituted phenol 2 with compound 33 in the presence of a base, such as potassium carbonate can provide intermediate 34. The nitro group of 34 can be reduced using zinc dust and ammonium chloride to generate the aniline 35. Palladium-mediated coupling reactions with various boronic acids can provide intermediate 36, which can be converted to the desired compounds 37 or 38 using chemistry described above.

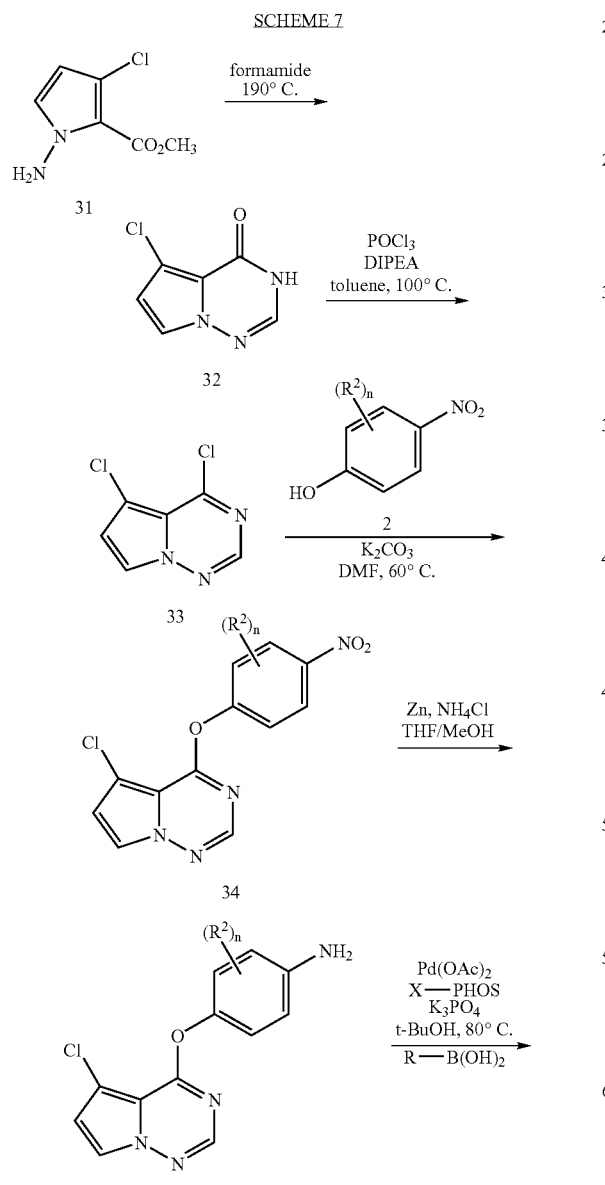

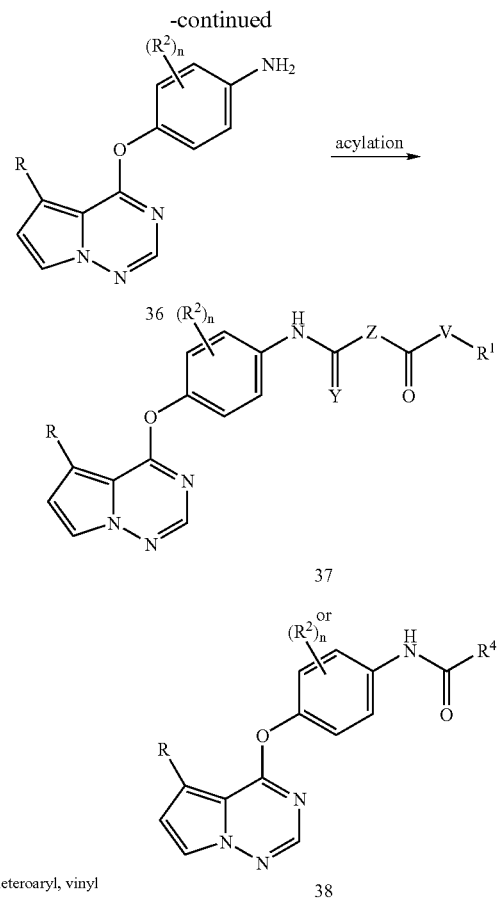

Substitution at the 5-position of the pyrrolo[2,1-f][1,2,4] triazine ring can also be accomplished by coupling the triethylammonium salt 39 with an appropriately substituted phenol 7 followed by treatment with an amine (HNR'R") in the presence of a base, such as Hunig's base to afford the aniline 40 (Scheme 8). Aniline 40 can be further processed as described previously to produce the desired compounds 41 or 42.

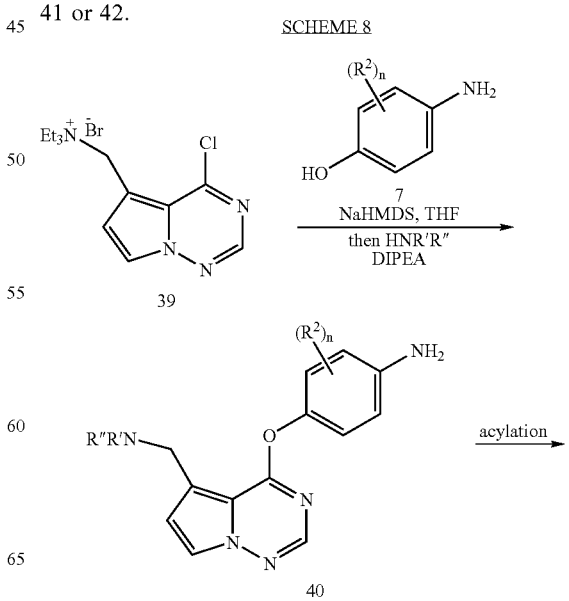

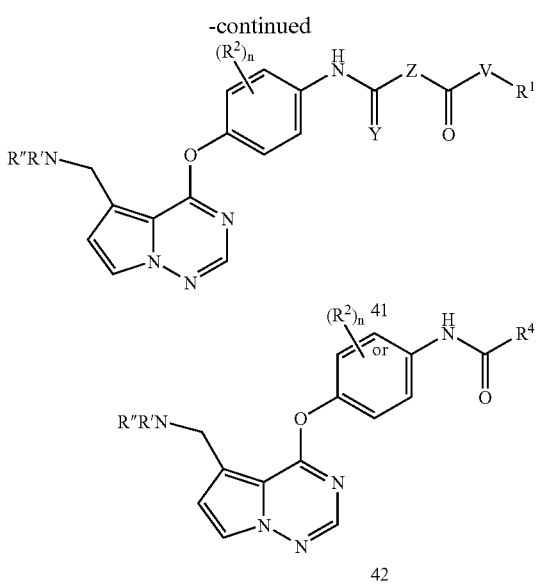

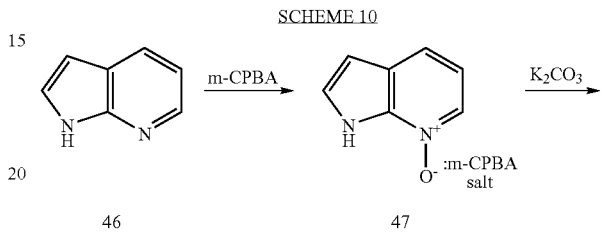

The pyrrolo[2,3-b]pyridine intermediate 50 can be prepared using chemistry outlined in Scheme 10. 4-Chloro-1H-pyrrolo[2,3-b]pyridine (49) can be obtained from commercially available 1H-pyrrolo[2,3-b]pyridine (46) using the synthetic sequence described by Thibault C. and coworkers (*Org. Lett.* 2003, 5, 5023–5025) which is illustrated in Scheme 10. Treatment of intermediate 49 with the phenol 2 at elevated temperatures can afford the key intermediate 50, which can be converted to the desired compounds using chemistry described in Schemes 1 and 3.

Alternatively, 5-methyl-4-(methylthio)pyrrolo[2,1-f][1,2,4]triazine (43) can be brominated with, for example N-bromosuccinimide (NBS) and 2, 2'-azobisisobutyronitrile (AIBN) in carbontetrachloride at elevated temperatures (Scheme 9). Treatment of the bromide intermediate with an amine (HNR'R") in the presence of a base, such as Hunig's base can provide intermediate 44. Oxidation of the thiomethyl group of 44 can be accomplished with, for example 3-chloroperbenzoic acid (m-CPBA). Treatment of the sulfone intermediate with the phenoxide generated from compound 7 and sodium bis(trimethylsilyl)amide (NaHMDS) can provide the aniline intermediate 45.

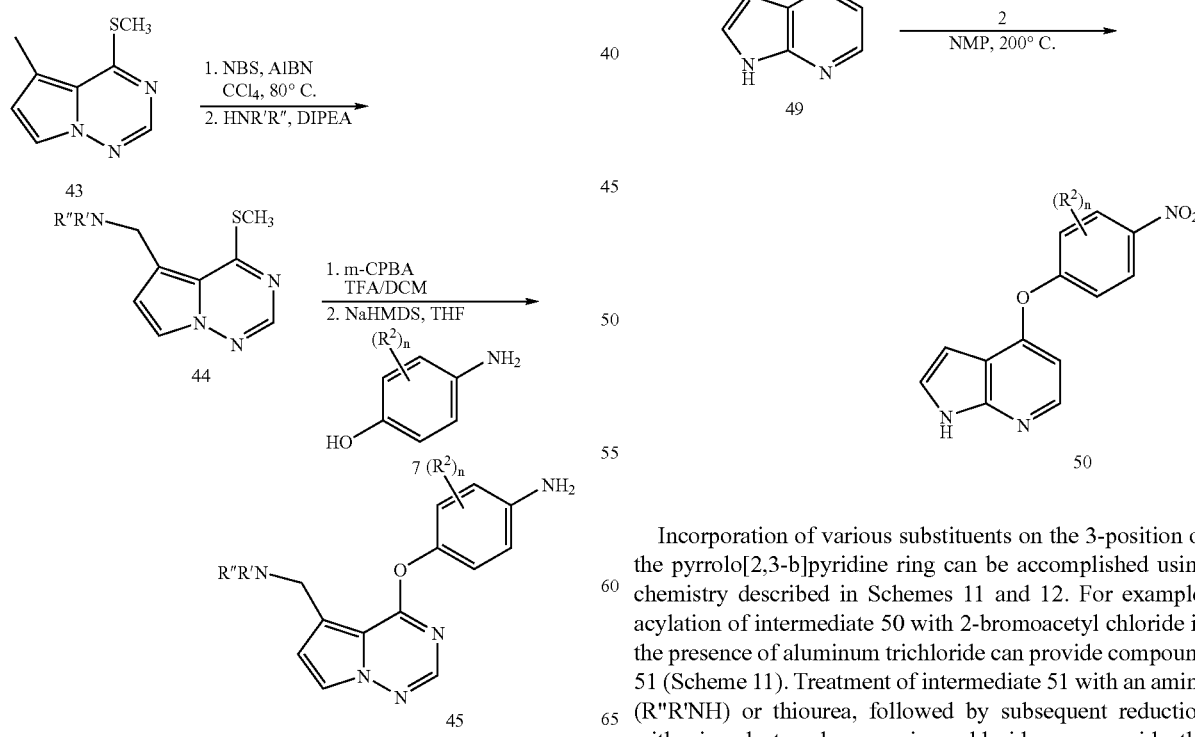

Incorporation of various substituents on the 3-position of the pyrrolo[2,3-b]pyridine ring can be accomplished using chemistry described in Schemes 11 and 12. For example, acylation of intermediate 50 with 2-bromoacetyl chloride in the presence of aluminum trichloride can provide compound 51 (Scheme 11). Treatment of intermediate 51 with an amine (R"R'NH) or thiourea, followed by subsequent reduction with zinc dust and ammonium chloride can provide the anilines 52 and 54, respectively.

SCHEME 11

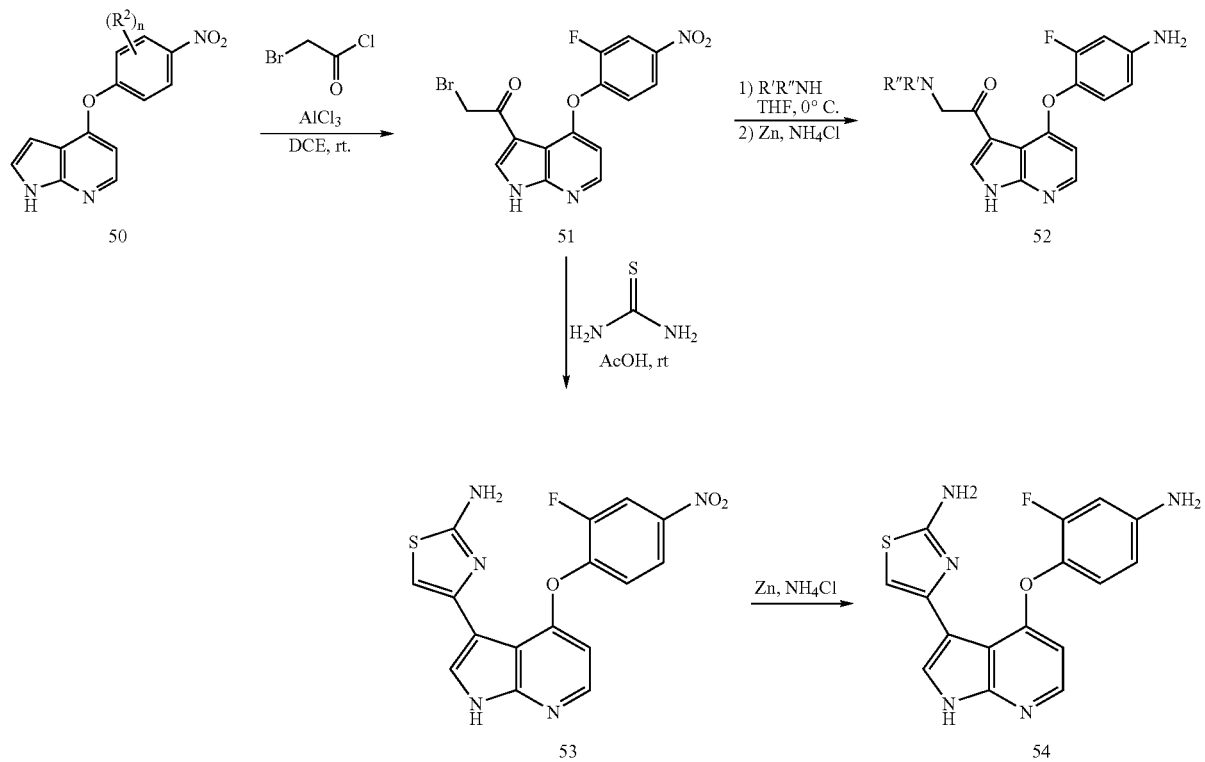

Alternatively, protection of compound 50 with, for example (2-(chloromethoxy)ethyl)trimethylsilane in the presence of a base, such as sodium hydride, followed by bromination with NBS can provide intermediate 55 (Scheme 12). The bromide 55 can then be treated with substituted alkynes 56, arylboronates/arylboronic acids 57, or vinylstannanes 58 in the presence of a palladium and/or copper catalyst to afford the intermediates 59–61, respectively. Removal of the protecting group of 59–61 with tetrabutylammonium fluoride (TBAF) followed by reduction of the nitro groups can provide the corresponding aniline intermediates, which can be acylated using chemistry previously described in Schemes 1 and 3.

SCHEME 12

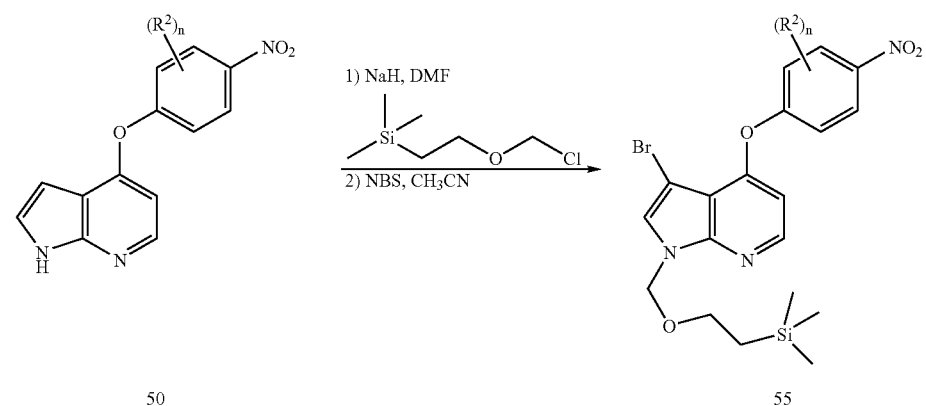

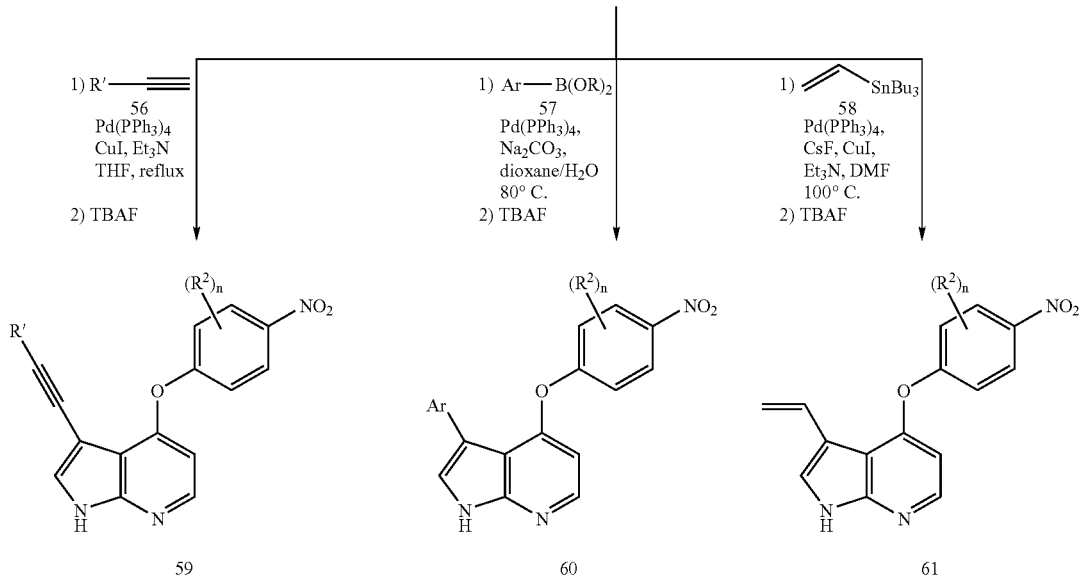

Incorporation of various substituents at the 2-position of the pyrrolo[2,3-b]pyridine nucleus can be accomplished using the chemistry outlined in Schemes 13 and 14. The protected azaindole derivative 62, derived from compound 49 (Scheme 10) can be treated with n-butyllithium at low temperature followed by triisopropylborate (Scheme 13). The requisite intermediate can then be hydrolyzed to generate the boronic acid 63. Coupling of the boronic acid 63 with various aryl or heteroaryl halides 64 can be accomplished using a palladium catalyst to furnish intermediate 65. Removal of the protecting group of 65 with TBAF can afford compound 66, which can be treated with phenol 2 at elevated temperature to provide the intermediate 67. Compound 67 can be further modified to furnish the desired compounds using similar chemistry described above.

SCHEME 13

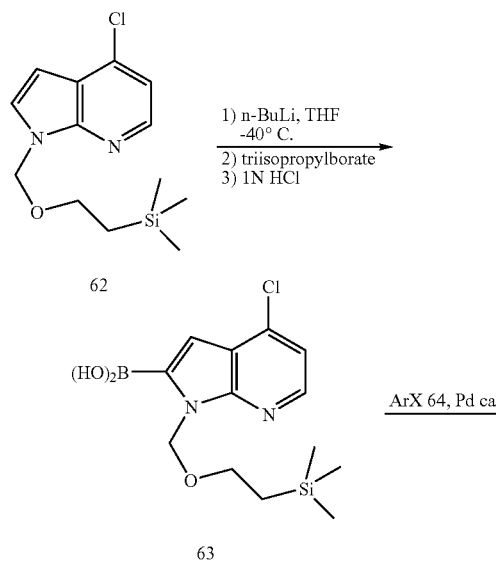

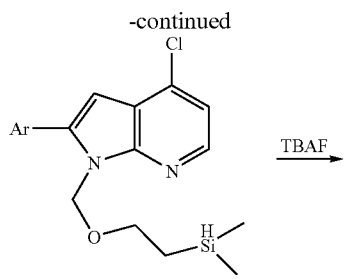

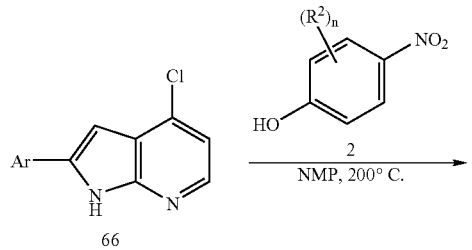

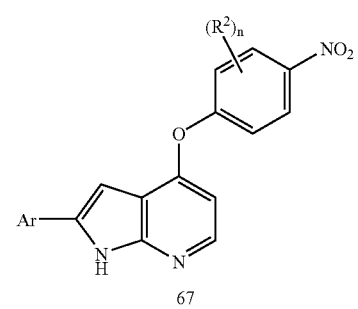

Alternatively, compound 62 can be converted to iodide 68 using chemistry described in Scheme 14. Intermediate 68 can be coupled with a variety of reagents, such boronic acids, organostannes or substituted olefins in the presence of a transition metal catalyst [i.e., Pd(OAc)$_2$—cf. Chi, S. M. et al. *Tetrahedron Lett.* 2000, 919–922] to give 69. Intermediate 69 can be converted to the desired analogues using chemistry previously described.

SCHEME 14

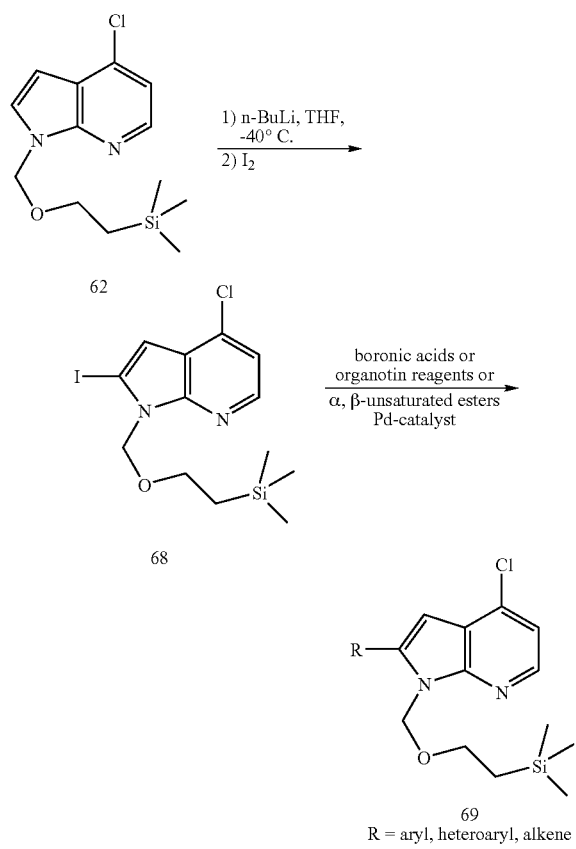

The pyridinone intermediate 74 can be obtained by a two step process beginning with commercially available (E)-dimethyl 2-(3-methoxyallylidene)malonate (70) (Scheme 15). Thus, treatment of compound 70 with an amine or aniline 71 at room temperature can provide intermediate 72, which can then be cyclized in the presence of a base, such as sodium hydride in dimethylsulfoxide to generate 73. Hydrolysis of intermediate 73 under basic conditions can provide the desired pyridinone intermediate 74, which can be coupled to various anilines as described in the aforementioned Schemes.

SCHEME 15

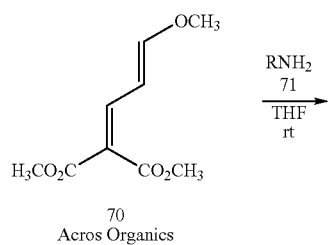

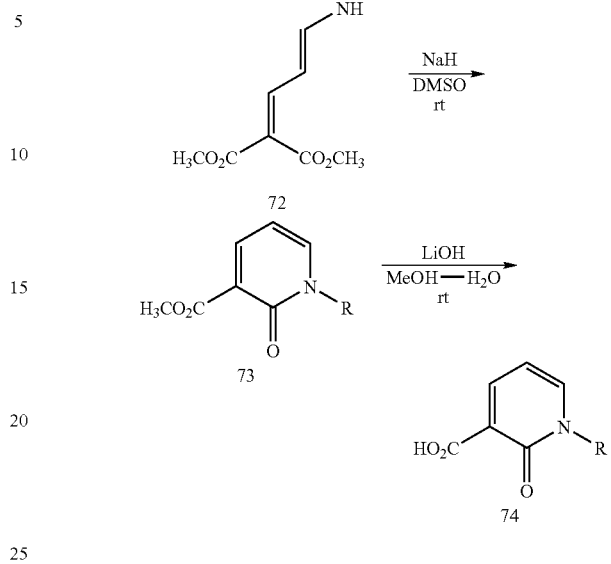

The pyridyl N-oxide intermediate 78 (Scheme 16) can be obtained by a two-step process in which the commercially available 6-bromopicolinic acid (75) is coupled with boronic acid or borinate 76 in the presence of a palladium(0) catalyst and sodium carbonate, followed by oxidation of the requisite intermediate 77 at elevated temperature. Intermediate 78 can then be coupled to various anilines as described in the aforementioned Schemes.

SCHEME 16

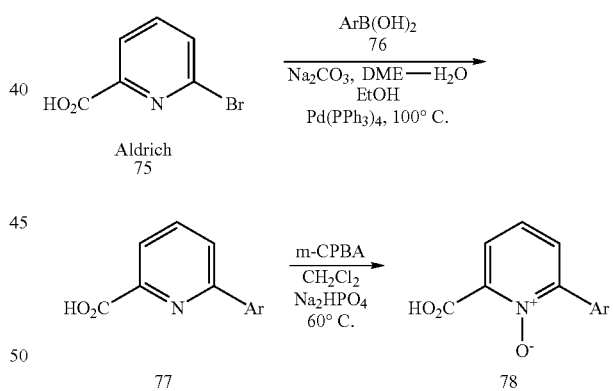

The following examples and preparations describe the manner and process of making and using the invention and are illustrative rather than limiting. It should be understood that there may be other embodiments which fall within the spirit and scope of the invention as defined by the claims appended hereto.

ASSAYS

The pharmacological properties of the compounds of this invention may be confirmed by a number of pharmacological assays. The exemplified pharmacological assays which follow have been carried out with the compounds according to the invention and/or their pharmaceutically acceptable salts.

| Met Kinase assay | |
|---|---|
| Reagents | Substrate Mix Final Concentration |
| Stock Solution | |
| Tris-HCl, (1 M, pH 7.4) | 20 mM |
| MnCl$_2$ (1 M) | 1 mM |
| DTT(1 M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |
| Buffer | Enzyme mix |
| 20 ul 1 M DTT | 4 ul GST/Met enzyme(3.2 mg/ml) = 10 ng/rxn |
| 200 ul 1 M Tris-HCL, pH 7.4 | qs 12 ml Buffer |
| 20 ul 100 mg/ml BSA | |
| qs 20 ml H$_2$0 | |

Incubation mixtures employed for the Met kinase assay contain the synthetic substrate polyGlu:Tyr, (4:1), ATP, ATP-γ-$^{33}$P and buffer containing Mn$^{++}$ and/or Mg$^{++}$, DTT, BSA, and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves are generated to determine the concentration required to inhibit 50% of kinase activity (IC$_{50}$). Compounds are dissolved at 10 mM in dimethyl sulfoxide (DMSO) and evaluated at six concentrations, each in quadruplicate. The final concentration of DMSO in the assay is 1%. IC$_{50}$ values are derived by non-linear regression analysis and have a coefficient of variance (SD/mean, n=6)=16%.

The compounds of the invention inhibit the Met kinase enzyme with IC$_{50}$ values between 0.01 to 100 μM. Preferred compounds have IC$_{50}$ values less than 1.0 μM, and more preferably, less than about 0.5 μM.

The following examples and preparations describe the manner and process of making and using the invention and are illustrative rather than limiting. It should be understood that there may be other embodiments which fall within the spirit and scope of the invention as defined by the claims appended hereto.

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040–0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: % 0 B to 0% A: 100% B) was used with the following mobile phase system: A=90% H$_2$O/MeOH+0.2% H$_3$PO$_4$; B=90% MeOH/H$_2$O+0.2% H$_3$PO$_4$ at flow rate=4 mL/min and detection at 220 nm.

Preparative Reverse Phase (RP) HPLC was performed with a linear gradient elution using H$_2$O/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT: room temperature; t$_R$: retention time; h: hour(s); min: minute(s); PyBrOP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt: hydroxybenzotriazole; HATU: O-(7-azabenzotriazol-1-yl)-N,N,N',N'-tetramethyluronium hexafluorophosphate; DIBAL-H: diisobutylaluminum hydride; Na(OAc)$_3$BH: sodium triacetoxyborohydride; HOAc: acetic acid; TFA: trifluoroacetic acid; LiHMDS: lithium bis(trimethylsilyl)amide; m-CPBA: m-chloro: 3-chloroperbenzoic acid; AIBN: 2,2-azobisisobutyronitrile; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether.

Example 1

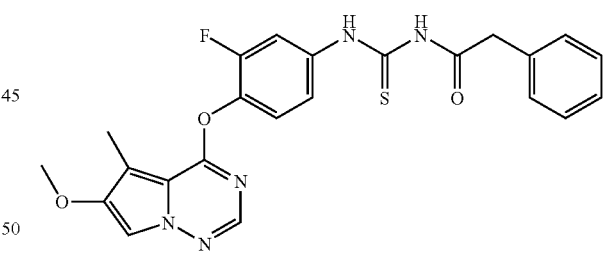

1-(3-Fluoro-4-(6-methoxy-5-methylpyrrolo[2,1-f][1,2,4] triazin-4-yloxy)phenyl)-3-(2-phenylacetyl)thiourea

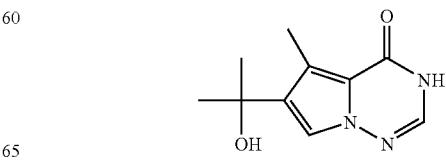

A) 6-(1-Hydroxy-1-methyl-ethyl)-5-methyl-3H-pyrrolo[2,1-f]1,2,4]triazin-4-one A mixture of 1.9 kg of 5-methyl-4-oxo-3,4-dihydro-pyrrolo[2,1-f][1,2,4]triazine-6-carboxylic acid ethyl ester, prepared generally according to the procedures described in, U.S. patent application Ser. No. 09/573,829, and 17.9 kg of THF was prepared under an inert atmosphere and cooled to −10° C. To this mixture was added 14.2 kg methylmagnesium chloride as a 3 M solution in THF at a rate to maintain the reaction temperature<35° C. The reaction mixture was held at 25–45° C. until complete, then cooled to 0° C. A solution of 9.9 kg ammonium chloride in 36.7 kg water was prepared and cooled to 5° C. The organic reaction mixture was added to the ammonium chloride solution at a rate to maintain the internal temperature<15° C. The phases were allowed to settle and the lower aqueous phase drained off and re-extracted with 9.5 kg additional THF. To the combined organic phases was added 8.6 kg EtOAc and the mixture washed with 7.6 kg of saturated aqueous sodium chloride solution. The reaction mixture was filtered, then solvent was removed in vacuo (temperature<40° C.) to about ⅓ the original volume. Additional EtOAc was added with continuing distillation until the THF level was <7%. The resulting slurry was cooled to 0–5° C., then the solid collected by filtration. The wet cake was washed with cold (−10° C.) EtOAc, then dried in vacuo at 40° C. to produce 1.5 kg 6-(1-hydroxy-1-methyl-ethyl)-5-methyl-3H-pyrrolo[2,1-f]1,2,4]triazin-4-one with a purity of 96–99%.

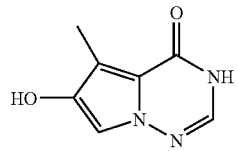

B) 6-Hydroxy-5-methyl-3H-pyrrolo[2,1-f][1,2,4]triazin-4-one

A one liter, 3-neck, round bottom flask as equipped with mechanical stirrer and a cooling bath of ice/acetone. To this was charged 20 g of 6-(1-hydroxy-1-methyl-ethyl)-5-methyl-3H-pyrrolo[2,1-f][1,2,4]triazin-4-one, 235 mL of THF and 47 mL 50% aqueous hydrogen peroxide. An exotherm from −7° C. to 7.3° C. was observed and the mixture became a solution. To this was added a pre-cooled solution of 28.5 mL water and 63 mL methanesulfonic acid over 40 min, keeping the temperature between −5° C. and −0.7° C. The solution was stirred at −2° C. for 95 min until HPLC indicated reaction was complete; reaction mixture was quenched, while keeping it at −2° C., by adding it portion wise to a cooled solution of 28.5 mL water, 89 g NaHSO₃ and 128 mL 28% aqueous ammonium hydroxide over 40 min, at 15° C. to 25° C. The mixture was stirred at room temperature for 20 min; pH was 6.80 and a peroxide test was negative. The layers were separated and the aqueous layer was extracted with 100 mL THF. The two organic layers were combined and concentrated, removing 280 mL solvent. To the thick slurry was added 250 mL water and the concentration continued until 88 mL of solvent was removed. The slurry was filtered and the cake was washed with 25 mL water twice and then 25 mL acetonitrile. It was dried by suction on the filter to constant weight to yield 12.51 g of 6-hydroxy-5-methyl-3H-pyrrolo[2,1-f][1,2,4]triazin-4-one, 75.9% yield, 96.5% purity.

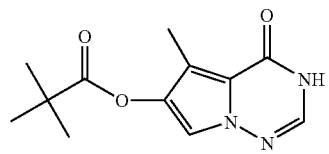

C) 2,2-Dimethyl-propionic acid 5-methyl-4-oxo-3,4-dihydro-pyrrolo[2,1-f][1,2,4]triazin-6-yl ester A mixture of 2.9 kg 6-hydroxy-5-methyl-3H-pyrrolo[2,1-f][1,2,4]triazin-4-one, 4.6 kg of diisopropylethylamine and 17.0 kg of THF was cooled to 0–10° C., then treated with 2.6 kg pivaloyl chloride at a rate to maintain the temperature<20° C. The mixture was stirred until the reaction was complete by HPLC, then 17.8 kg of toluene was added, followed by 20.6 kg of 15% aqueous potassium dihydrogen phosphate solution. The phases were separated and the organic was washed with 10.2 kg water. The organic phase was filtered, then distilled under vacuum with a maximum temperature of 65° C. Additional toluene can be added and distillation continued until the concentration of THF was <8%, and the total reactor volume was reduced to 31 L. The resulting slurry was cooled to 20–25° C. and treated with 20.3 kg heptane over 1.5 h. The slurry was cooled to 0–5° C. and held for 1 h, then the solid was collected by filtration and dried to yield 4.0 kg of 2,2-dimethyl-propionic acid 5-methyl-4-oxo-3,4-dihydro-pyrrolo[2,1-f][1,2,4]triazin-6-yl ester with a purity of 95-99%.

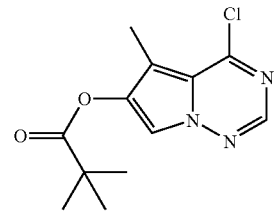

D) 4-Chloro-5-methylpyrrolo[2,1-f][1,2,4]triazin-6-yl pivalate

To a mixture of 5-methyl-4-oxo-3,4-dihydropyrrolo[2,1-f][1,2,4]triazin-6-yl pivalate (300 mg, 1.20 mmol), phosphorus oxychloride (2.0 mL, 21.4 mmol) and DIEA (0.5 mL, 2.80 mmol) was added toluene (10 mL). The reaction was heated at 110° C. for 4 hours and then cooled to room temperature. The mixture was diluted with ethyl acetate (10 mL) and water (5 mL). The organic layer was separated and dried with sodium sulfate, concentrated in vacuo and purified by silica gel flash chromatography (eluted with 1–25% EtOAc/CH₂Cl₂) to give the title compound (250 mg, 78%) as a white solid.

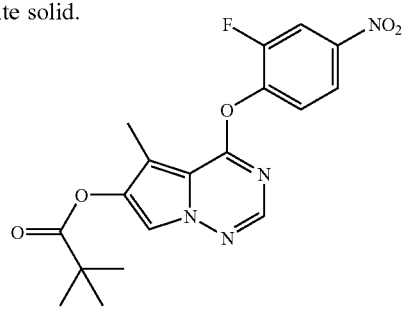

E) 4-(2-Fluoro-4-nitrophenoxy)-5-methylpyrrolo[2,1-f][1,2,4]triazin-6-yl pivalate To a mixture 4-chloro-5-methylpyrrolo[2,1-f][1,2,4]triazin-6-yl pivalate (250 mg, 0.94 mmol), 2-fluoro-4-nitrophenol (176 mg, 1.12 mmol, Aldrich) and $K_2CO_3$ (154 mg, 1.12 mmol) was added DMF (5 mL). The reaction was stirred at room temperature for 24 h. The reaction was quenched with water (5 mL) and $CH_2Cl_2$ (10 mL). The organic layer was separated, dried with sodium sulfate, concentrated in vacuo, and purified by silica gel flash chromatography (eluted with 1–25% EtOAc/$CH_2Cl_2$) to give the title compound (160 mg, 44%) as a white solid.

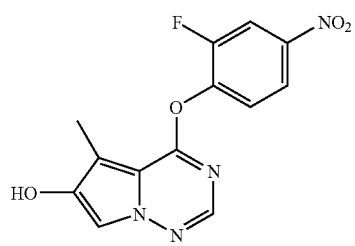

F) 4-(2-Fluoro-4-nitrophenoxy)-5-methylpyrrolo[2,1-f][1,2,4]triazin-6-ol

To a solution of 4-(2-fluoro-4-nitrophenoxy)-5-methylpyrrolo[2,1-f][1,2,4]triazin-6-yl pivalate (80 mg, 0.2 mmol) in THF (1 mL) was added a solution of NaOH in MeOH/$H_2O$ (0.2 mL, 1 M). The solution turned red instantly. After 5 minutes, the reaction was quenched with EtOAc (5 mL) and $H_2O$ (5 mL). The organic layer was separated, dried with sodium sulfate and concentrated in vacuo to give the title compound (52 mg, 85%) as a yellow solid.

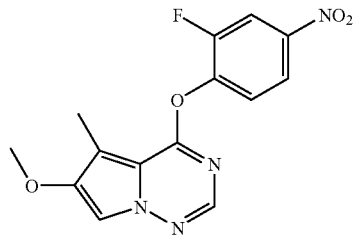

G) 4-(2-Fluoro-4-nitrophenoxy)-6-methoxy-5-methylpyrrolo[2,1-f][1,2,4]triazine To a solution of 4-(2-fluoro-4-nitrophenoxy)-5-methylpyrrolo[2,1-f][1,2,4]triazin-6-ol (52 mg, 0.17 mmol) in DMF (2 mL) was added $Cs_2CO_3$ (65 mg, 0.2 mmol) and the mixture was stirred at RT for 10 minutes. A solution of methyl iodide in DMF (0.2 mL, 0.2 mmol, 1 M) was added and the reaction solution was stirred at RT for 2 h. The reaction was quenched with EtOAc (5 mL) and $H_2O$ (5 mL). The organic layer was separated, dried with sodium sulfate and concentrated in vacuo to give the title compound (35 mg, 65%) as a yellow solid.

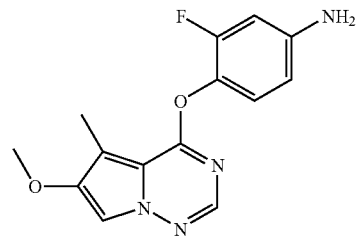

H) 3-Fluoro-4-(6-methoxy-5-methylpyrrolo[2,1-f][1,2,4]triazin-4-yloxy)benzenamine To a solution of 4-(2-fluoro-4-nitrophenoxy)-6-methoxy-5-methylpyrrolo[2,1-f][1,2,4]triazine (35 mg, 0.11 mmol) in THF (1.0 mL) was added MeOH (1.0 mL) followed by Zn (100 mg, 1.5 mmol) and $NH_4Cl$ (43 mg, 0.80 mmol). The reaction was heated at 60° C. for 3 h. The solution was filtered through Celite® and concentrated in vacuo. The product mixture was purified by a SCX cartridge (eluted with ammonia in methanol (2 M) to give the title compound (15 mg, 50%) as a white solid.

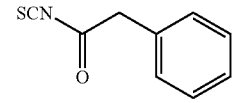

I) 2-Phenyl-1-thiocyanatoethanone

To a solution of NaSCN (49 mg, 0.60 mmol) in EtOAc (2 mL) was added phenylacetyl chloride (0.066 mL, 0.50 mmol, Aldrich) to provide a 0.25 M solution of 2-phenyl-1-thiocyanatoethanone. After 10 min, completion of the reaction was determined by reacting an aliquot of the reaction mixture with 4-(phenyloxy)aniline to form the corresponding thiocyanate which was detected by LCMS (ESI$^+$) m/z 363 (M+H)$^+$. The 2-phenyl-1-thiocyanatoethanone was used directly without isolation or further purification.

J) 1-(3-Fluoro-4-(6-methoxy-5-methylpyrrolo[2,1-f][1,2,4] triazin-4-yloxy)phenyl)-3-(2-phenylacetyl)thiourea To a solution of 3-fluoro-4-(6-methoxy-5-methylpyrrolo[2,1-f][1,2,4]triazin-4-yloxy)benzenamine (7.5 mg, 0.026 mmol) in $CH_2Cl_2$ (1 mL) was added a solution of 2-phenyl-1-thiocyanatoethanone (0.133 mL, 0.033 mmol, 0.25 M in ethyl acetate). The reaction was stirred at room temperature for 20 minutes, concentrated in vacuo and purified by silica gel flash chromatography (eluted with 1–25% EtOAc/$CH_2Cl_2$) to give the title compound (6.1 mg, 50%) as a pale yellow solid. $^1$H NMR (CDCl$_3$) δ 8.51 (s, 1H), 7.87 (m, 1H), 7.83 (s, 1H), 7.47 (m, 5H), 7.31 (m, 4H), 3.89 (s, 3H)3.74 (d, 2H, J=10.5 Hz), 2.44 (s, 3H); MS(ESI$^+$) m/z 466 (M+H)$^+$.

Example 2

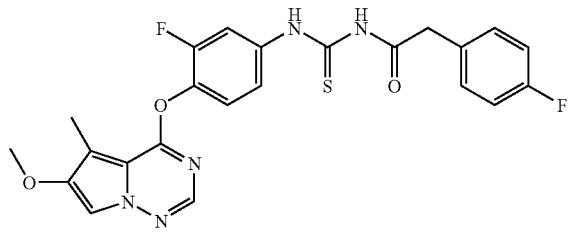

1-(3-Fluoro-4-(6-methoxy-5-methylpyrrolo[2,1-f][1,2,4]triazin-4-yloxy)phenyl)-3-(2-(4-fluorophenyl)acetyl)thiourea

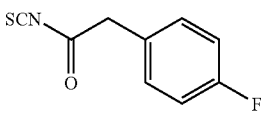

A) 2-(4-Fluorophenyl)-1-thiocyanatoethanone

To a solution of NaSCN (49 mg, 0.60 mmol) in EtOAc (2 mL) was added 4-fluorophenylacetyl chloride (0.066 mL, 0.50 mmol, Aldrich). The reaction was stirred at room temperature for 1 h to give a 0.25 M solution of 2-(4-fluorophenyl)-1-thiocyanatoethanone in EtOAc, which was used directly without further purification.

B) 1-(3-Fluoro-4-(6-methoxy-5-methylpyrrolo[2,1-f][1,2,4]triazin-4-yloxy)phenyl)-3-(2-(4-fluorophenyl)acetyl)thiourea The title compound was prepared from 3-fluoro-4-(6-methoxy-5-methylpyrrolo[2,1-f][1,2,4]triazin-4-yloxy)benzenamine and 2-(4-fluorophenyl)-1-thiocyanatoethanone in a similar manner as described for Compounds H and J of Example 1. $^1$H NMR (CDCl$_3$) δ 8.49 (s, 1H), 7.88 (m, 1H), 7.83 (s, 1H), 7.45 (s, 1H), 7.28 (m, 5H), 7.12 (m, 2H), 3.89 (s, 3H), 3.71 (s, 2H) 2.44 (s, 3H); MS (ESI$^+$) m/z 484 (M+H)$^+$.

Example 3

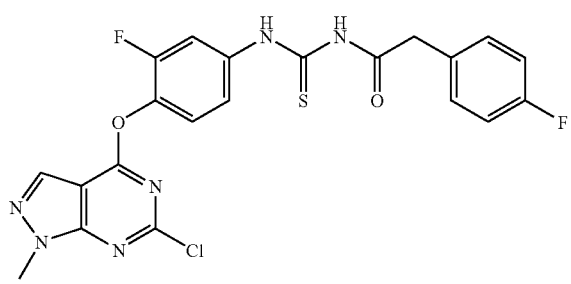

1-(4-(6-Chloro-1-methyl-1H-pyrazolo[3,4-d]pyrimidin-4-yloxy)-3-fluorophenyl)-3-(2-(4-fluorophenyl)acetyl)thiourea

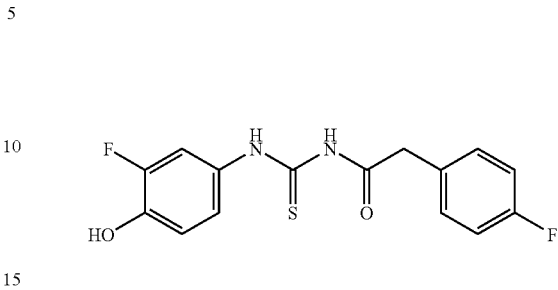

A) 1-(3-Fluoro-4-hydroxyphenyl)-3-(2-(4-fluorophenyl)acetyl)thiourea

To a solution of 4-amino-2-fluorophenol (50 mg, 0.3 mmol, Indofine Chemical Co.) in CH$_2$Cl$_2$ (5 mL) was added a 0.25 M solution of 2-(4-fluorophenyl)-1-thiocyanatoethanone (prepared using a similar procedure for the synthesis of Compound A of Example 2) in EtOAc (1.6 mL, 0.4 mmol). The reaction was stirred at room temperature for 20 minutes, concentrated in vacuo and purified by silica gel flash chromatography (eluted with 1–25% EtOAc/CH$_2$Cl$_2$) to give the title compound (100 mg, 95%) as a white solid.

B) 1-(4-(6-Chloro-1-methyl-1H-pyrazolo[3,4-d]pyrimidin-4-yloxy)-3-fluorophenyl)-3-(2-(4-fluorophenyl)acetyl)thiourea To a mixture of 1-(3-fluoro-4-hydroxyphenyl)-3-(2-(4-fluorophenyl)acetyl)thiourea (24 mg, 0.075 mmol), 4,6-dichloro-1-methyl-1H-pyrazolo[3,4-d]pyrimidine (15.3 mg, 0.075 mmol, preparation: *J. Org. Chem.* 1958, 23, 852, the disclosure of which is herein incorporated by reference) and K$_2$CO$_3$ (10 mg, 0.075 mmol) was added DMF (2 mL). The reaction was stirred at RT for 24 h. The reaction was quenched with water (2 mL) and CH$_2$Cl$_2$ (5 mL). The organic layer was separated, dried with sodium sulfate, concentrated in vacuo and purified by reverse phase preparative HPLC to give the title compound (22.9 mg, 60%) as a white solid. MS(ESI$^+$) m/z 457 (M+H)$^+$.

Example 4

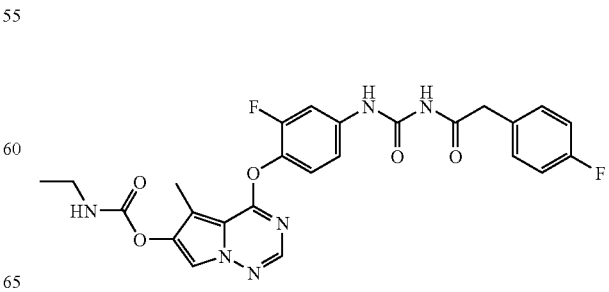

4-(2-Fluoro-4-(3-(2-(4-fluorophenyl)acetyl)ureido)phenoxy)-5-methylpyrrolo[2,1-f][1,2,4]triazin-6-yl ethylcarbamate

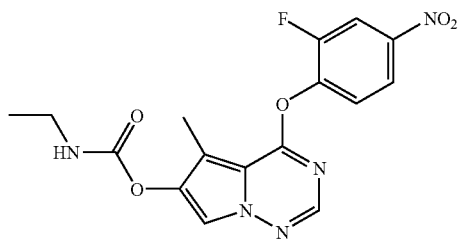

A) 4-(2-Fluoro-4-nitrophenoxy)-5-methylpyrrolo[2,1-f][1,2,4]triazin-6-yl ethylcarbamate To a mixture of 4-(2-fluoro-4-nitrophenoxy)-5-methylpyrrolo[2,1-f][1,2,4]triazin-6-ol (25 mg, 0.082 mmol, Compound F of Example 1), DIEA (0.017 mL, 0.1 mmol) in CH$_2$Cl$_2$ (5 mL) was added ethyl isocyanate (0.078 mL, 0.1 mL) and stirred at room temperature for 2 h. The reaction was quenched with water (5 mL). The organic layer was separated, dried and concentrated in vacuo. The mixture was purified by flash chromatography (1–5% Methanol/CH$_2$Cl$_2$) to give the title compound (12.5 mg, 32%) as a white solid.

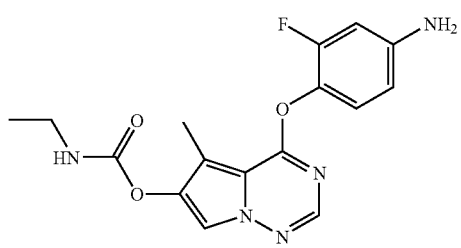

B) 4-(4-Amino-2-fluorophenoxy)-5-methylpyrrolo[2,1-f][1,2,4]triazin-6-yl ethylcarbamate To a solution of 4-(2-fluoro-4-nitrophenoxy)-5-methylpyrrolo[2,1-f]A[1,2,4]triazin-6-yl ethylcarbamate (12.5 mg, 0.033 mmol) in ethanol (2 mL) was added Zn (20 mg, 0.3 mmol) and NH$_4$Cl (20 mg, 0.37 mmol). The reaction was stirred at room temperature for 1 h, filtered through Celite® and concentrated in vacuo to give the title compound (8 mg, 70%) as a white solid.

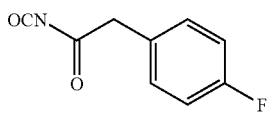

C) 2-(4-Fluorophenyl)acetyl isocyanate

To a solution/suspension of 4-fluorophenylacetamide (77 mg, 0.50 mmol, see generally, *J. Med. Chem.* 2003, 46, 4333–4341, the disclosure of which is herein incorporated by referene) in dichloroethane (2 mL) was added oxalyl chloride (0.175 mL, 2.00 mmol). The reaction was heated at 80° C. for 24 h and then 70° C. for two days. By this time, most of the solids had dissolved and the reaction was yellow. LC/MS analysis found a peak with a molecular weight of 211 corresponding to methyl 2-(4-fluorophenyl)acetylcarbamate, resulting from quenching of the isocyanate with methanol. The reaction was concentrated in vacuo to give a yellow slurry. The slurry was redissolved in dichloroethane (2 mL) and again concentrated in vacuo. The resulting residue was redissolved again in dichloroethane (2 mL) to give a 0.25 M solution of 2-(4-fluorophenyl)acetyl isocyanate in dichloroethane, which was used directly in subsequent reactions.

D) 4-(2-Fluoro-4-(3-(2-(4-fluorophenyl)acetyl)ureido)phenoxy)-5-methylpyrrolo[2,1-f][1,2,4]triazin-6-yl ethylcarbamate To a solution of 4-(4-amino-2-fluorophenoxy)-5-methylpyrrolo[2,1-f][1,2,4]triazin-6-yl ethylcarbamate (10 mg, 0.029 mmol) in CH$_2$Cl$_2$ (1 mL) was added a solution of 2-(4-fluorophenyl)acetyl isocyanate (2 mL, 0.25 M in dichloroethane). The reaction was stirred at room temperature for 1 h, LC/MS analysis indicated consumption of starting carbamate. The mixture was concentrated in vacuo and the residue was suspended in methanol and filtered to give the title compound. The filtrate was purified by flash chromatography to provide more of the title compound as a pale yellow solid (combined yield 5.9 mg, 40%). $^1$H NMR (CDCl$_3$) δ 10.63 (s, 1H), 8.42 (s, 1H), 7.88 (s, 1H), 7.82 (s, 1H), 7.67 (dd, 1H, J=12.1, 2.2 Hz), 7.28 (m, 4H), 7.10 (m, 2H), 3.73 (s, 3H), 3.36 (m, 2H), 2.48 (s, 3H), 1.26 (m, 3H); MS (ESI$^+$) m/z 525 (M+H)$^+$.

Example 5

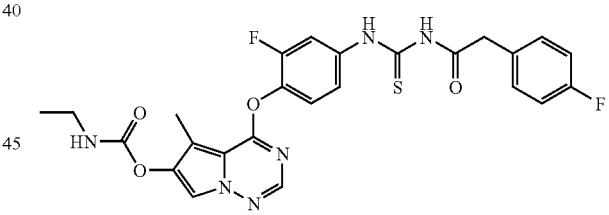

4-(2-Fluoro-4-(3-(2-(4-fluorophenyl)acetyl)thioureido)phenoxy)-5-methylpyrrolo[2,1-f][1,2,4]triazin-6-yl ethylcarbamate To a solution of 4-(4-amino-2-fluorophenoxy)-5-methylpyrrolo[2,1-f][1,2,4]triazin-6-yl ethylcarbamate (8 mg, 0.023 mmol, preparation Compound B of Example 4) in CH$_2$Cl$_2$ (1 mL) was added a solution of 2-(4-fluorophenyl)-1-thiocyanatoethanone (0.120 mL, 0.025 mmol, 0.25 M in ethyl acetate, Compound A of Example 2). The reaction was stirred at room temperature for 1 h, concentrated in vacuo and purified by silica gel flash chromatography (eluted with 1–25% EtOAc/CH$_2$Cl$_2$) to give the title compound (5.4 mg, 43%) as a pale yellow solid. $^1$H NMR (CDCl$_3$) δ 12.41 (s, 1H), 8.58 (s, 1H), 7.88 (m, 3H), 7.28 (m, 5H), 7.12 (m, 2H), 3.72 (s, 2H), 3.37 (m, 2H), 2.46 (m, 3H), 1.26 (m, 3H); MS(ESI$^+$) m/z 541 (M+H)$^+$.

Example 6

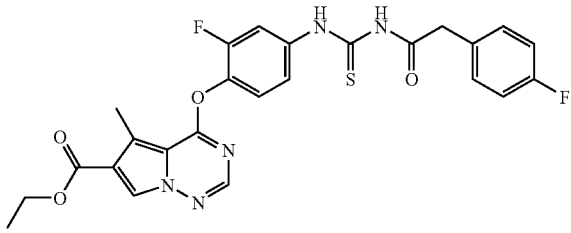

Ethyl 4-(2-fluoro-4-(3-(2-(4-fluorophenyl)acetyl)
thioureido)phenoxy)-5-methylpyrrolo[2,1-f][1,2,4]
triazine-6-carboxylate

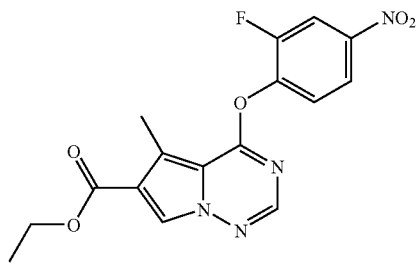

A) Ethyl 4-(2-fluoro-4-nitrophenoxy)-5-methylpyrrolo[2,1-f][1,2,4]triazine-6-carboxylate To a mixture of ethyl 4-chloro-5-methylpyrrolo[2,1-f][1,2,4]triazine-6-carboxylate (24 mg, 0.10 mmol, preparation: See, U.S. Pat. No. 6,670,357, especially example 61, the disclosure of which is hererin incorporated by reference), 2-fluoro-4-nitrophenol (20 mg, 0.125 mmol) and $K_2CO_3$ (28 mg, 0.20 mmol) was added DMF (0.5 mL). The reaction was heated at 70° C. for 20 minutes, cooled to room temperature and 2 mL of water was added. The mixture was filtered, the solid was washed with water, and dried to give the title compound (36 mg, 100%) as a light yellow solid.

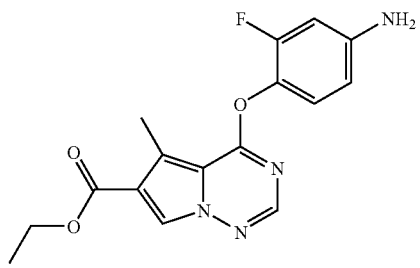

B) Ethyl 4-(4-amino-2-fluorophenoxy)-5-methylpyrrolo[2,1-f][1,2,4]triazine-6-carboxylate To a solution of ethyl 4-(2-fluoro-4-nitrophenoxy)-5-methylpyrrolo[2,1-f][1,2,4]triazine-6-carboxylate (36 mg, 0.1 mmol) in THF (1.0 mL) was added MeOH (0.7 mL) followed by Zn (130 mg, 2.0 mmol) and $NH_4Cl$ (53 mg, 1.0 mmol). The reaction was heated at 70° C. overnight. LC/MS analysis indicated mostly starting material. The solution was shaken vigorously and then heated to 75° C. LC/MS analysis after 4 h showed the desired product and many other peaks. The reaction was filtered through a coarse filter, and the filtrate was concentrated to a give 55 mg of a brown residue. The residue was suspended in THF and passed through an HPLC filter resulting in a clear filtrate. The filtrate was concentrated in vacuo to give 54 mg of the title compound as a crude mixture which was used in the next step without further purification.

C) Ethyl 4-(2-fluoro-4-(3-(2-(4-fluorophenyl)acetyl)
thioureido)phenoxy)-5-methylpyrrolo[2,1-f][1,2,4]
triazine-6-carboxylate To a suspension of ethyl 4-(4-amino-2-fluorophenoxy)-5-methylpyrrolo[2,1-f][1,2,4]triazine-6-carboxylate (54 mg) in $CH_2Cl_2$ (0.6 mL) was added a solution of 2-(4-fluorophenyl)-1-thiocyanatoethanone (0.5 mL, 0.12 mmol, 0.25 M in ethyl acetate Compound A of Example 2). The reaction was stirred at room temperature for 15 minutes, LC/MS analysis indicated mostly starting material. The reaction was warmed to 45° C., after 30 min most of the suspension had dissolved to give a cloudy solution. LC/MS analysis indicated mostly desired product. The reaction was shaken at room temperature for an additional 2 h, evaporated to dryness, and purified by column chromatography eluting with 1–7% ethyl acetate/dichloromethane to the title compound (9 mg, 17% overall yield for 3 steps) as a white solid. $^1H$ NMR ($CDCl_3$) δ 12.45 (s, 1H), 8.66 (s, 1H), 8.18 (s, 1H), 7.92 (dd, 1H, J=11.4, 2.4 Hz), 7.90 (s, 1H), 7.41 (m, 1H), 7.29 (m, 3H), 7.12 (m, 2H), 4.38 (q, 2H, J=7.1 Hz), 3.73 (s, 2H), 2.82 (s, 3H), 1.40 (t, 3H, J=7.1 Hz); MS($ESI^+$) m/z 526 (M+H)$^+$.

Example 7

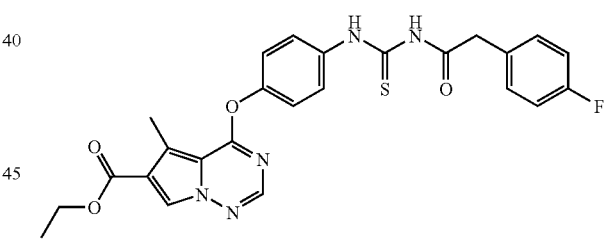

Ethyl 4-(4-(3-(2-(4-fluorophenyl)acetyl)thioureido)
phenoxy)-5-methylpyrrolo[2,1-f][1,2,4]triazine-6-
carboxylate

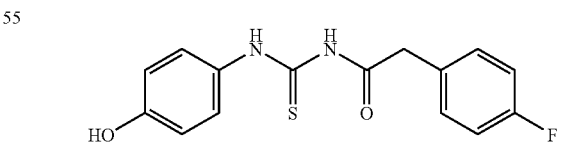

A) 1-(2-(4-Fluorophenyl)acetyl)-3-(4-hydroxyphenyl)thiourea

To a solution of 4-amino-phenol (11 mg, 0.1 mmol, Aldrich) in $CH_2Cl_2$ (0.55 mL) was added a solution of 2-(4-fluorophenyl)-1-thiocyanatoethanone (0.5 mL, 0.125 mmol, 0.25 M in ethyl acetate, Compound A of Example 2). The reaction was stirred at room temperature for 10 minutes, LC/MS analysis indicated formation of the title compound. The crude reaction mixture was used directly in the next reaction.

B) Ethyl 4-(4-(3-(2-(4-fluorophenyl)acetyl)thioureido)phenoxy)-5-methylpyrrolo[2,1-f][1,2,4]triazine-6-carboxylate To a room temperature solution of ethyl 4-chloro-5-methylpyrrolo[2,1-f][1,2,4]triazine-6-carboxylate (7.2 mg, 0.03 mmol) (for preparation see U.S. Pat. No. 6,670,357, the disclosure of which is herein incorporated by reference) and DABCO (7 mg, 0.06 mmol) in acetonitrile (0.5 mL) was added 1-(2-(4-fluorophenyl)acetyl)-3-(4-hydroxyphenyl)thiourea (0.5 mL, 0.05 mmol). The reaction was shaken at room temperature. After 30 min, LC/MS analysis indicated mostly product. The reaction was stirred at room temperature overnight. The mixture was evaporated to dryness. Purification by silica gel chromatography (eluting with 1% methanol/dichloromethane) provided the desired product contaminated with impurities. A second purification by silica gel chromatography (1–6% Ethyl acetate/dichloromethane) again did not remove all of the impurities. The resulting solid mixture was washed with methanol and dried to provide the title compound (6 mg, 39%) as a yellow solid. $^1$H NMR (CDCl$_3$) δ 12.32 (s, 1H), 8.62 (s, 1H), 8.16 (s, 1H), 7.91 (s, 1H), 7.76 (m, 2H), 7.29 (m, 4H), 7.12 (m, 2H), 4.38 (q, 2H, J=7.1 Hz), 3.72 (s, 2H), 2.82 (s, 3H), 1.40 (t, 3H, J=7.1 Hz); MS(ESI$^+$) m/z 508 (M+H)$^+$.

Example 8

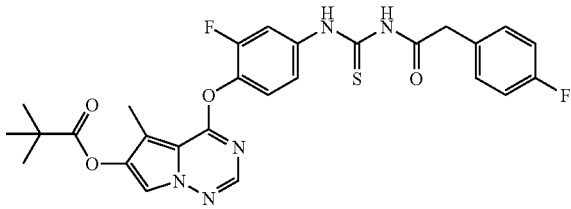

4-(2-Fluoro-4-(3-(2-(4-fluorophenyl)acetyl)thioureido)phenoxy)-5-methylpyrrolo[2,1-f][1,2,4]triazin-6-yl pivalate To a mixture of 1-(3-fluoro-4-hydroxyphenyl)-3-(2-(4-fluorophenyl)acetyl)thiourea (60 mg, 0.19 mmol, Compound A of Example 3), 4-chloro-5-methylpyrrolo[2,1-f][1,2,4]triazin-6-yl pivalate (50 mg, 0.19 mmol, Compound D of Example 1) and 1,4-diazabicyclo[2.2.2]octane (DABCO, 21.3 mg, 0.19 mmol) was added MeCN (5 mL). The reaction was stirred at RT for 1 h and concentrated in vacuo. The residue was purified by flash chromatography (eluted with 1–15% MeOH/CH$_2$Cl$_2$) to give the title compound (91 mg, 86%) as a white solid. $^1$H NMR (CDCl$_3$) δ 12.40 (s, 1H), 8.54 (s, 1H), 7.87 (m, 3H), 7.29 (m, 4H), 7.12 (m, 2H), 3.71 (s, 2H), 2.43 (s, 3H), 1.39 (s, 9H); MS(ESI$^+$) m/z 554 (M+H)$^+$.

Example 9

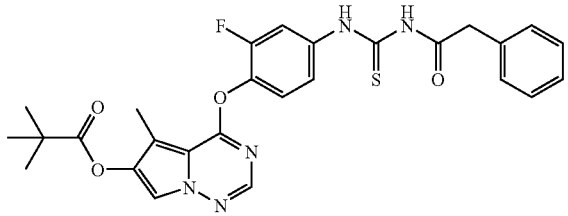

4-(2-Fluoro-4-(3-(2-phenylacetyl)thioureido)phenoxy)-5-methylpyrrolo[2,1-f][1,2,4]triazin-6-yl pivalate

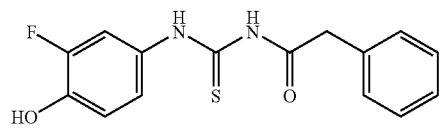

A) 1-(3-Fluoro-4-hydroxyphenyl)-3-(2-phenylacetyl)thiourea

To a solution of 4-amino-3-fluorophenol (50 mg, 0.3 mmol) in CH$_2$Cl$_2$ (2 mL) was added a solution of 2-phenyl-1-thiocyanatoethanone (2 mL, 0.4 mmol, 0.2 M in ethyl acetate, Compound I of Example 1). The reaction was stirred at room temperature for 20 minutes, LC/MS analysis indicated formation of the title compound. The mixture was concentrated to give a residue that was used without further purification.

B) 4-(2-Fluoro-4-(3-(2-phenylacetyl)thioureido)phenoxy)-5-methylpyrrolo[2,1-f][1,2,4]triazin-6-yl pivalate A vial was charged with 4-chloro-5-methylpyrrolo[2,1-f][1,2,4]triazin-6-yl pivalate (13.3 mg, 0.19 mmol, Compound D of Example 1), 1-(3-fluoro-4-hydroxyphenyl)-3-(2-phenylacetyl)thiourea (16 mg, 0.05 mmol), cesium carbonate (spatula tip) and DMF (2 mL) and warmed to 100° C. for 26 h. The mixture was concentrated in vacuo. The residue was purified by flash chromatography to give the title compound (6.2 mg, 25%) as a white solid. $^1$H NMR (CDCl$_3$) δ 12.46 (s, 1H), 8.50 (s, 1H), 7.88 (m, 3H), 7.40 (m, 4H), 7.31 (m, 2H), 3.75 (s, 3H), 2.44 (s, 3H), 1.40 (s, 9H); MS(ESI$^+$) m/z 536 (M+H)$^+$.

Example 10

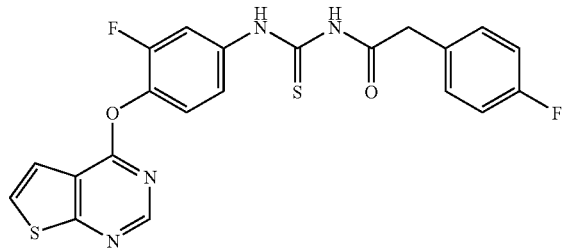

1-(4-(4a,7a-Dihydrothieno[2,3-d]pyrimidin-4-yloxy)-3-fluorophenyl)-3-(2-(4-fluorophenyl)acetyl)thiourea To a mixture of 1-(3-fluoro-4-hydroxyphenyl)-3-(2-(4-fluorophenyl)acetyl)thiourea (24 mg, 0.075 mmol, Compound A of Example 3), 4-chloro-5-thieno[2,3-d]pyrimidine (12.8 mg, 0.075 mmol, commercially available) and 1,4-diazabicyclo[2.2.2]octane (DABCO, 8.4 mg, 0.075 mmol) was added MeCN (2 mL). The reaction was stirred at RT for 4 h and concentrated in vacuo. The residue was purified by reverse phase preparative HPLC to give the title compound (13.8 mg, 40%) as a white solid. $^1$H NMR (CDCl$_3$) δ 12.41 (s, 1H), 8.62 (s, 1H), 8.53 (s, 1H), 7.93 (dd, 1H, J=13.8, 2.2 Hz), 7.56 (m, 2H) 7.46 (m, 1H), 7.29 (m, 3H), 7.12 (m, 2H), 3.73 (s, 2H); MS(ESI$^+$) m/z 457 (M+H)$^+$.

Example 11

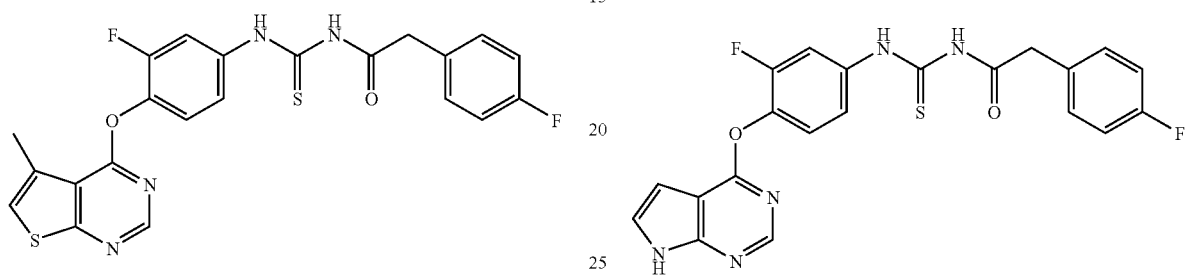

1-(3-Fluoro-4-(5-methyl-4a,7a-dihydrothieno[2,3-d]pyrimidin-4-yloxy)phenyl)-3-(2-(4-fluorophenyl)acetyl)thiourea In a similar manner as described for the preparation of Example 10, the title compound was prepared from commercially available 4-chloro-5-methylthieno[2,3-d]pyrimidine and 1-(3-fluoro-4-hydroxyphenyl)-3-(2-(4-fluorophenyl)acetyl)thiourea (24 mg, 0.075 mmol, Compound A of Example 3). $^1$H NMR (CDCl$_3$) δ 12.42 (s, 1H), 8.67 (s, 1H), 8.53 (s, 1H), 7.88 (dd, 1H, J=13.8, 2.2 Hz), 7.43 (s, 1H), 7.32 (m, 3 H), 7.09 (m, 3H), 3.72 (S, 2H), 2.67 (s, 3H); MS(ESI$^+$) m/z 471 (M+H)$^+$.

Example 12

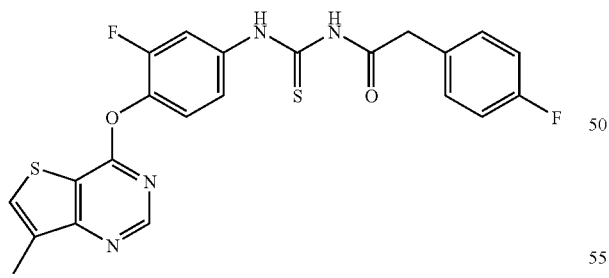

1-(3-Fluoro-4-(7-methyl-4a,7a-dihydrothieno[3,2-d]pyrimidin-4-yloxy)phenyl)-3-(2-(4-fluorophenyl)acetyl)thiourea To a mixture of 1-(3-fluoro-4-hydroxyphenyl)-3-(2-(4-fluorophenyl)acetyl)thiourea (24 mg, 0.075 mmol, Compound A of Example 3), 4-chloro-7-methylthieno[3,2-d]pyrimidine (13.8 mg, 0.075 mmol, commercially available) and 1,4-diazabicyclo[2.2.2]octane (DABCO, 8.4 mg, 0.075 mmol) was added MeCN (2 mL). The reaction was stirred at RT for 4 h and concentrated in vacuo. The residue was purified by reverse phase preparative HPLC to give the title compound (11.2 mg, 31%) as a white solid. $^1$H NMR (CDCl$_3$) δ 12.45 (s, 1H), 8.79 (s, 1H), 8.61 (s, 1H), 7.93 (dd, 1H, J=13.8, 2.2 Hz), 7.46 (s, 1H), 7.43 (m, 1H), 7,28 (m, 3H), 7.12 (m, 2H), 3.72 (s, 2H), 2.51 (s, 3H); MS(ESI$^+$) m/z 471 (M+H)$^+$.

Example 13

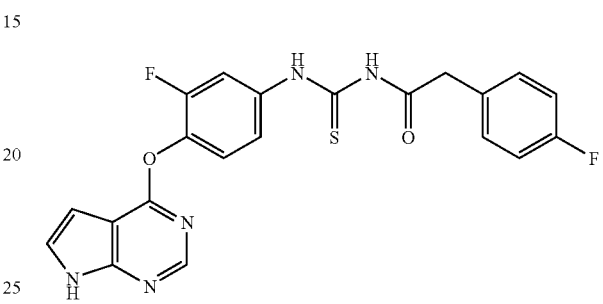

1-(4-(7,7a-Dihydro-4aH-pyrrolo[2,3-d]pyrimidin-4-yloxy)-3-fluorophenyl)-3-(2-(4-fluorophenyl)acetyl)thiourea To a mixture 1-(3-fluoro-4-hydroxyphenyl)-3-(2-(4-fluorophenyl)acetyl)thiourea (24 mg, 0.075 mmol, Compound A of Example 3), 4-chloro-7H-pyrrolo[2,3-d]pyrimidine (11 mg, 0.075 mmol, commercially available) and 1,4-diazabicyclo[2.2.2]octane (DABCO, 8.4 mg, 0.075 mmol) was added MeCN (2 mL). The reaction was stirred at RT for 4 h and concentrated in vacuo. The residue was purified reverse phase preparative HPLC to give the title compound (5.3 mg, 16%) as a white solid. $^1$H NMR (CDCl$_3$) δ 12.46 (s, 1H), 8.48 (s, 1H), 8.44 (s, 1H), 7.95 (dd, 1H, J=11.6, 2.8 Hz), 7.43 (m, 1H), 7.34 (m, 1H), 7.29 (m, 4H), 7.13 (app. T, 2H, J=8.6 Hz), 6.80 (s, 1H), 3.72 (s, 2H); MS(ESI$^+$) m/z 440 (M+H)$^+$.

Example 14

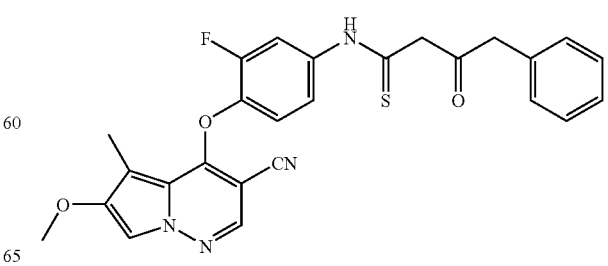

N-(4-(3-Cyano-6-methoxy-5-methylH-pyrrolo[1,2-b]pyridazin-4-yloxy)-3-fluorophenyl)-3-oxo-4-phenylbutanethioamide

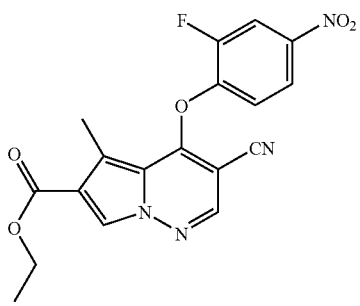

A) Ethyl 3-cyano-4-(2-fluoro-4-nitrophenoxy)-5-methylH-pyrrolo[1,2-b]pyridazine-6-carboxylate To a mixture of ethyl 4-chloro-3-cyano-5-methylH-pyrrolo[1,2-b]pyridazine-6-carboxylate (500 mg, 1.90 mmol, see U.S. Pat. Application No. 2004/063712, especially example 1, the disclosure of which is herein incorporated by reference in its entirety), 2-fluoro-4-nitrophenol (361 mg, 2.3 mmol) and K$_2$CO$_3$ (315 mg, 2.3 mmol) was added DMF (5 mL). The reaction stirred at RT for 2 h. The reaction was quenched with water (5 mL). The mixture was filtered and the solid was washed with water, dried to give the title compound (630 mg, 86%) as a light yellow solid.

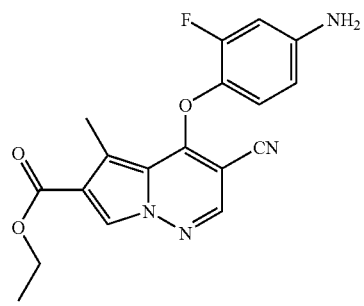

B) Ethyl 4-(4-amino-2-fluorophenoxy)-3-cyano-5-methylH-pyrrolo[1,2-b]pyridazine-6-carboxylate To a solution of ethyl 3-cyano-4-(2-fluoro-4-nitrophenoxy)-5-methylH-pyrrolo[1,2-b]pyridazine-6-carboxylate (630 mg, 1.64 mmol) in THF (5 mL) was added MeOH (5 mL) followed by Zn (200 mg, 3.0 mmol) and NH$_4$Cl (200 mg, 3.7 mmol). The reaction was heated at 60° C. for 2 h, filtered and concentrated in vacuo. The filtrate was purified by a SCX cartridge (eluted with 2M ammonia in MeOH) to give the title compound (420 mg, 72%) as a white solid.

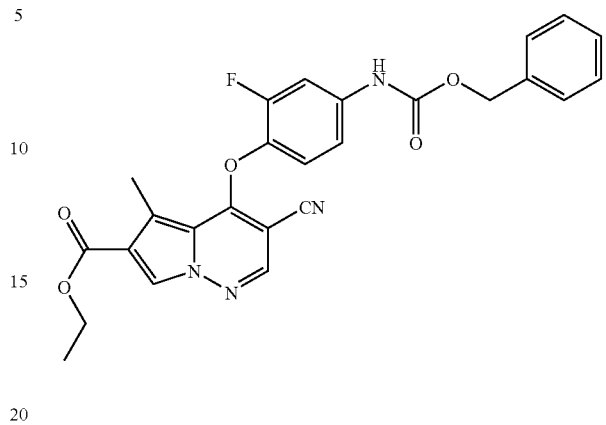

C) Ethyl 4-(4-(benzyloxycarbonyl)-2-fluorophenoxy)-3-cyano-5-methylH-pyrrolo[1,2-b]pyridazine-6-carboxylate To a solution of ethyl 4-(4-amino-2-fluorophenoxy)-3-cyano-5-methylH-pyrrolo[1,2-b]pyridazine-6-carboxylate (420 mg, 1.19 mmol) in CH$_2$Cl$_2$ (10 mL) was added potassium carbonate (200 mg. 1.43 mmol) and benzyl chloroformate (0.261 mL, 1.43 mmol). The solution was stirred at RT for 24 h. The solution was filtered, concentrated in vacuo and recrystallized from EtOAc/CH$_2$Cl$_2$ to give the title compound (490 mg, 84%) as a white solid.

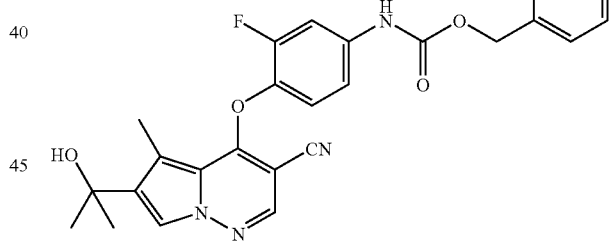

D) Benzyl 4-(3-cyano-6-(2-hydroxypropan-2-yl)-5-methylH-pyrrolo[1,2-b]pyridazin-4-yloxy)-3-fluorophenylcarbamate A solution of ethyl 4-(4-(benzyloxycarbonyl)-2-fluorophenoxy)-3-cyano-5-methylH-pyrrolo[1,2-b]pyridazine-6-carboxylate (123 mg, 0.25 mmol) in THF (5 mL) was cooled to 0° C. A solution of methylmagnesium bromide (0.336 mL, 1.00 mmol, 3 M in THF) was added and the solution stirred at RT for 30 minutes. More methylmagnesium bromide (0.336 mL, 1.00 mmol, 3 M in THF) was added, and the solution was heated to 60° C. for 30 minutes. Ethyl acetate (10 mL) and water (5 mL) was added and the organic layer was washed, separated, dried and concentrated in vacuo. The mixture was purified by flash chromatography (20–50% EtOAc in CH$_2$Cl$_2$) to give the title compound (97 mg, 81%) as a white solid.

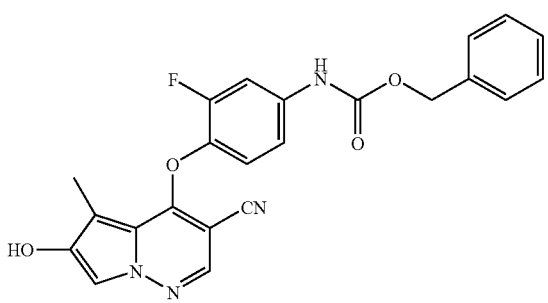

E) Benzyl 4-(3-cyano-6-hydroxy-5-methylH-pyrrolo[1,2-b]pyridazin-4-yloxy)-3-fluorophenylcarbamate To a solution of benzyl 4-(3-cyano-6-(2-hydroxypropan-2-yl)-5-methylH-pyrrolo[1,2-b]pyridazin-4-yloxy)-3-fluorophenylcarbamate (97 mg, 0.2 mmol) in CH$_2$Cl$_2$ (2 mL) was added to a premixed solution of hydrogen peroxide (0.033 mL) in water and boron trifluoride dietherate (0.570 mL) at −5° C. After 10 minutes, the reaction was quenched with sodium sulfite solution, dried, concentrated in vacuo and the residue recrystallized with EtOAc and hexane to give the title compound (70 mg, 80%) as a white solid.

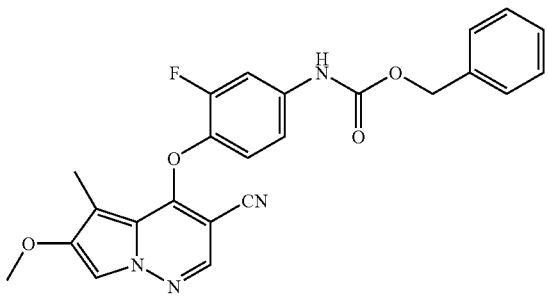

F) Benzyl 4-(3-cyano-6-methoxy-5-methylH-pyrrolo[1,2-b]pyridazin-4-yloxy)-3-fluorophenylcarbamate To a solution of benzyl 4-(3-cyano-6-hydroxy-5-methylH-pyrrolo[1,2-b]pyridazin-4-yloxy)-3-fluorophenylcarbamate (25 mg, 0.06 mmol) in DMF (1 mL) was added cesium carbonate (39 mg. 0.12 mmol) and methyl iodide (0.05 mL, 0.072 mmol). The solution was stirred at RT for 2 h. Water (1 mL) was added and the product was extracted with ethyl acetate (2×5 mL), dried and concentrated to give the title compound (20 mg, 74%) as a white solid.

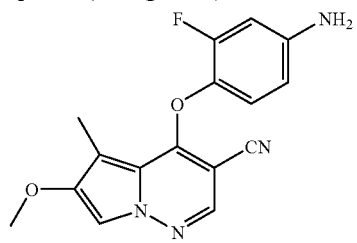

G) 4-(4-Amino-2-fluorophenoxy)-6-methoxy-5-methylH-pyrrolo[1,2-b]pyridazine-3-carbonitrile To a solution of benzyl 4-(3-cyano-6-methoxy-5-methylH-pyrrolo[1,2-b]pyridazin-4-yloxy)-3-fluorophenylcarbamate (20 mg, 0.045 mmol) in ethanol (3 mL) was added 10% palladium on carbon (20 mg) and the mixture was stirred under balloon of hydrogen for 2 h. The solution was filtered through a pad of Celite® and concentrated in vacuo to give the title compound (12 mg, 85%).

H) N-(4-(3-Cyano-6-methoxy-5-methylH-pyrrolo[1,2-b]pyridazin-4-yloxy)-3-fluorophenyl)-3-oxo-4-phenylbutanethioamide To a solution of 4-(4-amino-2-fluorophenoxy)-6-methoxy-5-methylH-pyrrolo[1,2-b]pyridazine-3-carbonitrile (6 mg, 0.02 mmol) in CH$_2$Cl$_2$ (1 mL) was added a solution of 2-phenyl-1-thiocyanatoethanone (0.1 mL, 0.025 mmol, 0.25 M in ethyl acetate, Compound F of Example 1). The reaction was stirred at room temperature for 20 minutes, concentrated in vacuo and purified by silica gel flash chromatography (eluted with 1–25% EtOAc/CH$_2$Cl$_2$) to afford the title compound (3.90 mg, 40%) as a pale yellow solid. $^1$H NMR (CD$_3$OD) δ 8.01 (d, 1H, J=12.7 Hz), 7.86 (s, 1H), 7.72 (s, 1H), 7.19 (m, 5H), 6.75 (m, 2H), 3.79 (s, 3H), 3.20 (m, 2H), 2.18 (s, 3H); MS(ESI$^+$) m/z 490 (M+H)$^+$.

Example 15

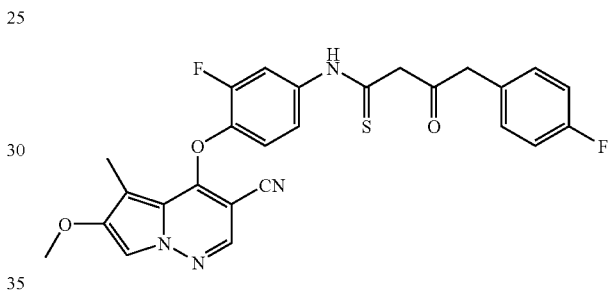

N-(4-(3-Cyano-6-methoxy-5-methylH-pyrrolo[1,2-b]pyridazin-4-yloxy)-3-fluorophenyl)-4-(4-fluorophenyl)-3-oxobutanethioamide The title compound was prepared from 4-(4-amino-2-fluorophenoxy)-6-methoxy-5-methylH-pyrrolo[1,2-b]pyridazine-3-carbonitrile (Compound G of Example 14) and 2-(4-fluorophenyl)-1-thiocyanatoethanone (Compound A of Example 2) by the procedure described for Compound H of Example 14. $^1$H NMR (CD$_3$OD) δ 8.08 (dd, 1H, J=12.7, 1.7 Hz), 7.95 (s, 1H), 7.80 (s, 1H), 7.34 (m, 3H), 7.19 (m, 1H), 7.04 (s, 2H), 6.87 (m, 2H), 3.89 (s, 3H), 3.30 (m, 2H), 2.27 (s, 3H); MS(ESI$^+$) m/z 508 (M+H)$^+$.

Example 16

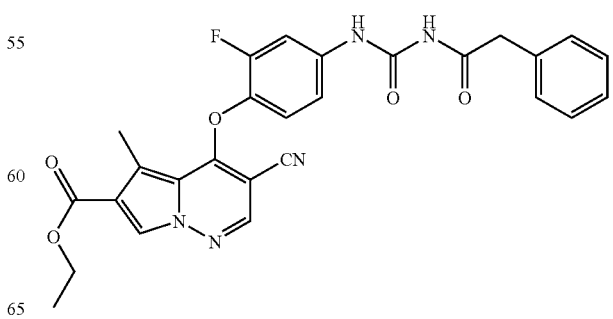

Ethyl 3-cyano-4-(2-fluoro-4-(3-(2-phenylacetyl)
ureido)phenoxy)-5-methylH-pyrrolo[1,2-b]py-
ridazine-6-carboxylate

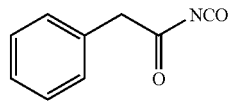

A) 2-Phenylacetyl isocyanate

To a suspension of 2-phenylacetamide (68 mg, 0.5 mmol) in dichloroethane (2 mL) was added oxalyl chloride (0.175 mL, 2.0 mmol). The suspension dissolved quickly and a new suspension formed. LC/MS analysis of the reaction mixture after 5 min indicated none of the desired product had formed. The mixture was warmed to 80° C., LC/MS after 30 min indicated a small amount of product. The reaction was heated at 70° C. for 2 days and became mostly clear. LC/MS analysis indicated mostly product. The mixture was shaken and heated at 80° C. for another 4 h. Almost all of the yellow solid on the walls of the reaction vessel had dissolved. The mixture was concentrated in vacuo. The residue dissolved in dichloroethane (1.5 mL), concentrated, and redissolved in dichloroethane (2 mL). The resulting 0.25 M solution was used without further purification.

B) Ethyl 3-cyano-4-(2-fluoro-4-(3-(2-phenylacetyl)
ureido)phenoxy)-5-methylH-pyrrolo[1,2-b]py-
ridazine-6-carboxylate To a solution of ethyl 4-(4-amino-2-fluorophenoxy)-3-cyano-5-methylH-pyrrolo[1,2-b]pyridazine-6-carboxylate (7 mg, 0.02 mmol, Compound B of Example 14) in dichloromethane (0.3 mL) was added a solution of 2-phenylacetyl isocyanate (0.04 mmol, 0.25 M in dichloroethane,). The reaction was shaken at room temperature and monitored by LC/MS. After 2 h, all of the starting material had been consumed. The mixture was concentrated and the residue was purified by silica gel chromatography (1–10% ethyl acetate/dichloromethane) to give the title compound (8 mg, 78%) as a yellow solid. $^1$H NMR (CDCl$_3$) δ 10.77 (s, 1H), 8.51 (s, 1H), 8.21 (s, 1H), 7.86 (s, 1H), 7.73 (dd, 1H, J=12.2, 2.2 Hz), 7.43–7.21 (m, 7H), 4.37 (q, 2H, J=7.1 Hz), 3.76 (s, 2H), 2.80 (s, 3H), 1.40 (t, 3H, J=7.1 Hz); MS(ESI$^+$) m/z 516 (M+H)$^+$.

Example 17

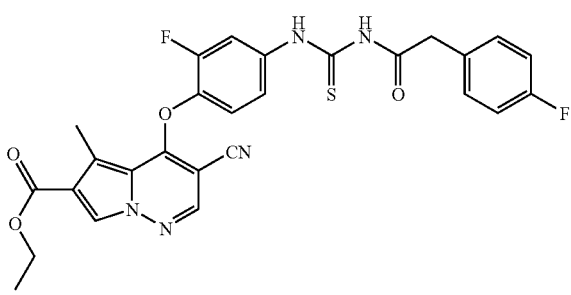

Ethyl 3-cyano-4-(2-fluoro-4-(3-(2-(4-fluorophenyl)
acetyl)thioureido)phenoxy)-5-methylH-pyrrolo[1,2-
b]pyridazine-6-carboxylate To a solution of ethyl 4-(4-amino-2-fluorophenoxy)-3-cyano-5-methylH-pyrrolo[1,2-b]pyridazine-6-carboxylate (10.6 mg, 0.03 mmol, Compound B of Example 14) in dichloromethane (0.5 mL) was added a solution of 2-(4-fluorophenyl)-1-thiocyanatoethanone (0.04 mmol, 0.25 M in ethyl acetate, Compound A of Example 2). The reaction instantly became cloudy. The reaction was shaken at room temperature for 2 h and then at 40° C. for 1 h. LC/MS analysis indicated that the reaction was complete. The reaction was concentrated and the residue was purified by silica gel chromatography (1–6% ethyl acetate/dichloromethane) to give the title compound (16 mg, 97%) as a yellow film/solid. $^1$H NMR (CDCl$_3$) δ 12.52 (s, 1H), 8.63 (s, 1H), 8.24 (s, 1H), 8.01 (dd, 1H, J=11.9, 2.4 Hz), 7.88 (s, 1H), 7.41 (m, 1H), 7.29 (m, 3H), 7.11 (m, 2H), 4.37 (q, 2H, J=7.1 Hz), 3.71 (s, 2H), 2.78 (s, 3H), 1.40 (t, 3H, J=7.1 Hz); MS(ESI$^+$) m/z 550 (M+H)$^+$.

Example 18

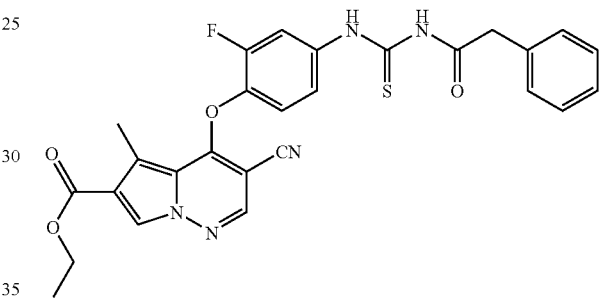

Ethyl 3-cyano-4-(2-fluoro-4-(3-(2-phenylacetyl)
thioureido)phenoxy)-5-methylH-pyrrolo[1,2-b]py-
ridazine-6-carboxylate The title compound was prepared from ethyl 4-(4-amino-2-fluorophenoxy)-3-cyano-5-methylH-pyrrolo[1,2-b]pyridazine-6-carboxylate (Compound B of Example 14) and 2-phenyl-1-thiocyanatoethanone (0.1 mL, 0.025 mmol, 0.25 M in ethyl acetate, Compound I of Example 1) by the method described in Example 17. $^1$H NMR (CDCl$_3$) δ 12.55 (s, 1H), 8.58 (s, 1H), 8.23 (s, 1H), 8.01 (dd, 1H, J=11.9, 2.4 Hz), 7.88 (s, 1H), 7.42 (m, 4H), 7.30 (m, 3H), 4.37 (q, 2H, J=7.1 Hz), 3.74 (s, 2H), 2.78 (s, 3H), 1.40 (t, 3H, J=7.1 Hz); MS(ESI$^+$) t/z 532 (M+H)$^+$.

Example 19

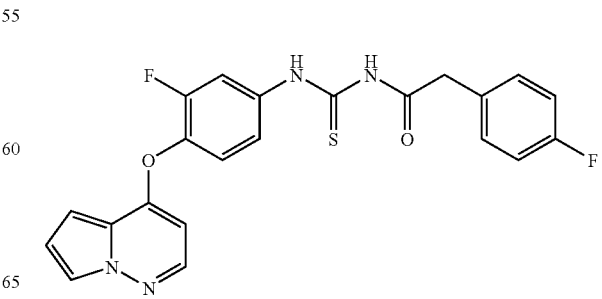

1-(4-(H-Pyrrolo[1,2-b]pyridazin-4-yloxy)-3-fluorophenyl)-3-(2-(4-fluorophenyl)acetyl)thiourea

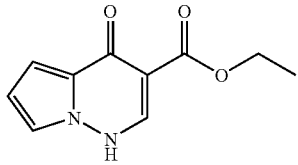

A) Ethyl 4-oxo-1,4-dihydropyrrolo[1,2-b]pyridazine-3-carboxylate

A mixture of N-aminopyrrole (575 mg, 7.0 mmol, commercially available) and diethyl ethoxymethylenemalonate (1.82 g, 8.4 mmol) was heated at 125° C. for 2 hours to give crude diethyl 2-((1H-pyrrol-1-ylamino)methylene)malonate. To this intermediate was added diphenyl ether (2 mL). The reaction was put under nitrogen and heated at 220° C. for 2 hours, while allowing the ethanol formed in the reaction to be distilled off. The reaction was cooled to room temperature and purified by silica gel flash chromatography (eluted with 100% $CH_2Cl_2$) to give the title compound (1.03 g, 71%) as a yellow solid.

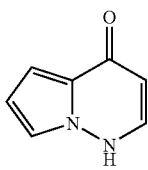

B) Pyrrolo[1,2-b]pyridazin-4 (1H)-one

A mixture of ethyl 4-oxo-1,4-dihydropyrrolo[1,2-b]pyridazine-3-carboxylate (206 mg, 1.0 mmol), NaCl (64 mg, 1.1 mmol), water (0.054 mL, 3.0 mmol) and DMSO (2 mL) was heated at 150° C. for 3 hours. At the end of the reaction DMSO was distilled off and the residue was purified by silica gel flash chromatography (eluted with 1–10% EtOAc/$CH_2Cl_2$) to give the title compound (90 mg, 67%) as a light yellow solid.

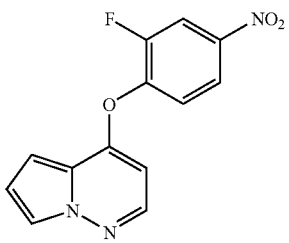

C) 4-(2-Fluoro-4-nitrophenoxy)H-pyrrolo[1,2-b]pyridazine

To a mixture of pyrrolo[1,2-b]pyridazin-4 (1H)-one (13.4 mg, 0.10 mmol), 3,4-difluoronitrobenzene (24 mg, 0.15 mmol) and 1,4-diazabicyclo[2.2.2]octane (DABCO, 22 mg, 0.20 mmol) was added MeCN (0.7 mL). The reaction was heated at 70° C. for 72 h and concentrated in vacuo. The residue was purified by silica gel flash chromatography (eluted with 100% $CH_2Cl_2$) to give the title compound (20 mg, 73%) as a yellow solid.

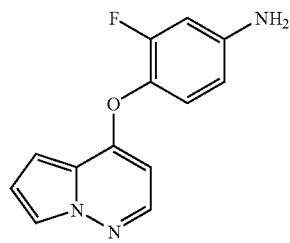

D) 4-(H-Pyrrolo[1,2-b]pyridazin-4-yloxy)-3-fluorobenzenamine

To a solution of 4-(2-fluoro-4-nitrophenoxy)H-pyrrolo[1,2-b]pyridazine (17 mg, 0.062 mmol) in THF (1.2 mL) was added MeOH (0.8 mL) followed by Zn (100 mg, 1.5 mmol) and $NH_4Cl$ (43 mg, 0.80 mmol). The reaction was heated at 70° C. for 90 minutes and concentrated in vacuo. To the residue was added $CH_2Cl_2$ (2 mL) and a few drops of $Et_3N$. The solid was partially dissolved and the mixture was filtered. The filtrate was concentrated in vacuo and purified by silica gel flash chromatography (eluted with 1–6% EtOAc/$CH_2Cl_2$) to give the title compound (15 mg, 99%) as a white solid.

E) 1-(4-(H-Pyrrolo[1,2-b]pyridazin-4-yloxy)-3-fluorophenyl)-3-(2-(4-fluorophenyl)acetyl)thiourea To a solution of 4-(H-pyrrolo[1,2-b]pyridazin-4-yloxy)-3-fluorobenzenamine (7 mg, 0.03 mmol) in $CH_2Cl_2$ (0.3 mL) was added a 0.25 M solution of isocyante (0.16 mL, 0.04 mmol, 0.25 M in ethyl acetate, Compound A of Example 2) in EtOAc. The reaction was stirred at room temperature for 20 minutes, concentrated in vacuo and purified by silica gel flash chromatography (eluted with 1–5% EtOAc/$CH_2Cl_2$) to give the title compound (12 mg, 95%) as a pale yellow solid. $^1$H NMR ($CDCl_3$) δ 12.46 (s, 1H), 8.67 (s, 1H), 7.92 (dd, 1H, J=11.5, 2.4 Hz), 7.85 (d, 1H, J=5.3 Hz), 7.77 (dd, 1H, J=2.6, 1.5 Hz), 7.39 (m, 1H), 7.28 (m, 3H), 7.13 (m, 2H), 6.83 (dd, 1H, J=4.3, 2.6 Hz), 6.74 (dd, 1H, J=4.3, 1.5 Hz), 5.70 (d, 1H, J=5.3 Hz), 3.73 (s, 2H); MS(ESI$^+$) m/z 439 (M+H)$^+$.

Example 20

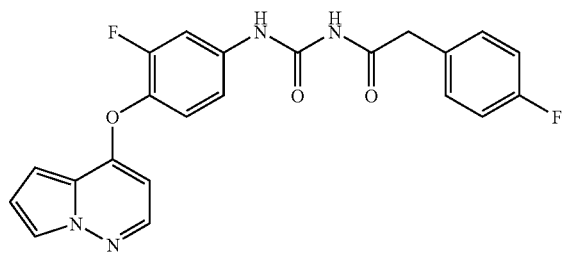

1-(4-(H-Pyrrolo[1,2-b]pyridazin-4-yloxy)-3-fluorophenyl)-3-(2-(4-fluorophenyl)acetyl)urea To a solution of the 4-(H-pyrrolo[1,2-b]pyridazin-4-yloxy)-3-fluorobenzenamine (5 mg, 0.02 mmol, Compound D of Example 19) in CH$_2$Cl$_2$ (0.3 mL) was added a solution of 2-(4-fluorophenyl)acetyl isocyanate (0.16 mL, 0.04 mmol, 0.25 M in dichloromethane, Compound C of Example 4). The reaction was stirred at room temperature for 2 h, concentrated in vacuo and purified by silica gel flash chromatography (eluted with 1–15% EtOAc/CH$_2$Cl$_2$) to give the title compound (5.5 mg, 63%) as a pale yellow solid. $^1$H NMR (CDCl$_3$) δ 10.68 (s, 1H), 8.69 (s, 1H), 7.83 (d, 1H, J=5.3 Hz), 7.77 (dd, 1H, J=2.6, 1.5 Hz), 7.68 (dd, 1H, J=11.5, 2.4 Hz), 7.33–7.17 (m, 4H), 7.09 (m, 2H), 6.82 (dd, 1H, J=4.3, 2.6 Hz), 6.74 (dd, 1H, J=4.3, 1.5 Hz), 5.69 (d, 1H, J=5.3 Hz), 3.76 (s, 2H); MS(ESI$^+$) m/z 423 (M+H)$^+$.

Example 21

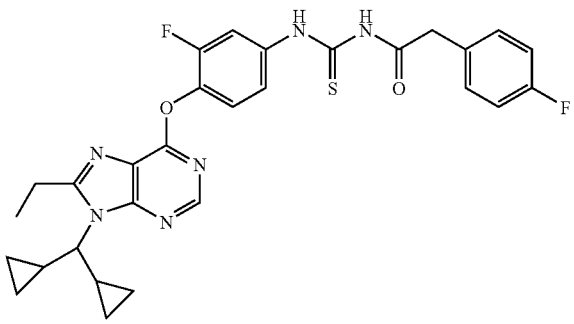

1-(4-(9-(Dicyclopropylmethyl)-8-ethyl-9H-purin-6-yloxy)-3-fluorophenyl)-3-(2-(4-fluorophenyl)acetyl)thiourea To a mixture 1-(3-fluoro-4-hydroxyphenyl)-3-(2-(4-fluorophenyl)acetyl)thiourea (24 mg, 0.075 mmol, Compound A of Example 3), 6-chloro-9-(dicyclopropylmethyl)-8-ethyl-9H-purine (20.7 mg, 0.075 mmol, PCT Appl. WO 99/01454, U.S. Pat. No. 6,143,743, example 831, the disclosure of which is herein incorporated by reference) and 1,4-diazabicyclo[2.2.2]octane (DABCO, 8.4 mg, 0.075 mmol) was added MeCN (2 mL). The reaction was stirred at RT for 4 h and concentrated in vacuo. The residue was purified by reverse phased preparative HPLC to give the title compound (15.3 mg, 36%) as a white solid. $^1$H NMR (CDCl$_3$) δ 12.43 (m, 1H), 8.48 (m, 1H), 8.40 (m, 1H), 7.92 (m, 1H), 7.28 (m, 4H), 7.13 (m, 2H), 3.72 (s, 2H), 3.34 (m, 3H), 1.53 (m, 3H), 0.81 (m, 2H), 0.46 (m, 4H), 0.23 (m, 2H); MS(ESI$^+$) m/z 489 (M+H)$^+$.

Example 22

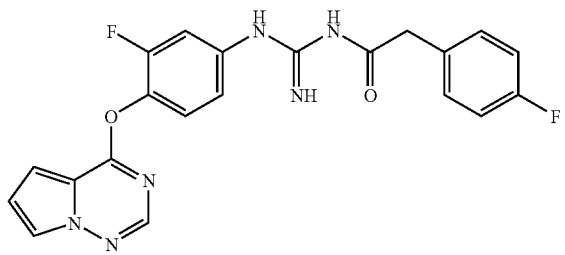

1-(3-Fluoro-4-(pyrrolo[2,1-f][1,2,4]triazin-4-yloxy)phenyl)-3-(2-(4-fluorophenyl)acetyl)guanidine

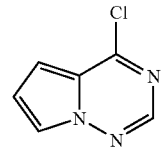

A) 4-Chloropyrrolo[2,1-f][1,2,4]triazine

To a solution of pyrrolo[2,1-f][1,2,4]triazin-4-ol (3.70 g, 27.4 mmol, see generally, PCT Appl. WO 2000/071129 the disclosure of which is herein incorporated by reference in its entirety) in 40 mL of toluene at room temperature was added 4.77 mL (27.4 mmol) of diisopropylethylamine followed by 7.70 mL (82.6 mmol) of phosphorus oxychloride. The reaction mixture was heated at 100° C. for 18 h. After cooling to room temperature, the reaction was slowly added to a solution of 5% aq NaHCO$_3$ solution (100 mL) at 0° C. Upon completion of the addition, the biphasic mixture was allowed to stir at room temperature for 30 min. The aqueous layer was extracted with EtOAc (3×100 mL) and the pooled organic extracts were washed with brine (100 mL), dried over anhydrous MgSO$_4$, and concentrated in vacuo to give the crude product (4.10 g, 97%) as a yellow solid. $^1$H NMR (CDCl$_3$) δ 8.14 (s, 1H), 7.80 (dd, 1H, J=2.4, 1.5 Hz), 6.91 (m, 2H).

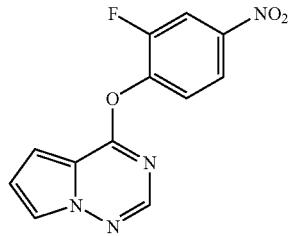

B) 4-(2-Fluoro-4-nitrophenoxy)pyrrolo[2,1-f][1,2,4]triazine

4-Chloropyrrolo[2,1-f][1,2,4]triazine (4.1 g, 27 mmol), 2-fluoro-4-nitrophenol (5.0 g, 32 mmol), and potassium carbonate (7.4 g, 53 mmol) in 100 mL of dimethylformamide was stirred at 60° C. for 15 h. After cooling to room temperature, the reaction mixture was filtered through a plug of silica gel with EtOAc. The filtrate was concentrated in vacuo and the resulting crude product was purified by flash chromatography on silica gel (SiO$_2$, EtOAc/Hexane 1:4) to give the title compound (4.25 g, 58%) as a white solid. $^1$H NMR (CDCl$_3$) δ 8.09 (m, 2H), 7.88 (s, 1H), 7.77 (dd, 1H, J=2.6, 1.2 Hz), 7.46 (t, 1H, J=7.6 Hz), 6.98 (dd, 1H, J=4.6, 1.4 Hz), 6.84 (dd, 1H, J=4.5, 2.6 Hz); $^{13}$C NMR (CDCl$_3$) δ 160.6, 154.3 (J=254 Hz), 146.5, 145.8, 144.8 (J=12.9 Hz), 125.0, 121.7, 120.7, 114.5, 113.9, 113.6 (J=23.2 Hz), 103.6.

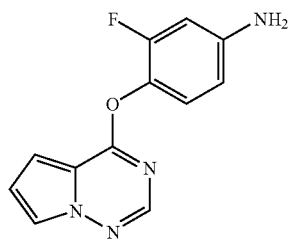

C) 3-Fluoro-4-(pyrrolo[2,1-f][1,2,4]triazin-4-yloxy) benzenamine (4)

To a solution of 4-(2-fluoro-4-nitrophenoxy)pyrrolo[2,1-f][1,2,4]triazine (4.25 g, 15.5 mmol) in 40 mL of tetrahydrofuran and 60 mL of methanol at 0° C. was added zinc dust (3.04 g, 46.5 mmol, <10 micron) followed by ammonium chloride (2.49 g, 46.5 mmol). The mixture was stirred at room temperature overnight. Additional zinc dust (6.08 g, 93 mmol) and ammonium chloride (5.0 g, 93 mmol) were added and the reaction was allowed to stir at room temperature for 4 h. The heterogeneous mixture was filtered through a thin pad of Celite ® with methanol and the filtrate was concentrated in vacuo. Purification by flash chromatography on silica gel (SiO$_2$, EtOAc/Hexane 1:1) gave the title compound (3.5 g, 92%) as a yellow foam. $^1$H NMR (CDCl$_3$) δ 7.92 (s, 1H), 7.70 (dd, 1H, J=2.5, 1.6 Hz), 6.98 (t, 1H, J=8.5 Hz), 6.92 (dd, 1H, J=4.4, 1.4 Hz), 6.77 (m, 1H), 6.42 (m, 2H), 3.71 (br s, 2H); MS(ESI$^+$) m/z 245.2 (M+H)$^+$.

D) 1-(3-Fluoro-4-(pyrrolo[2,1-f][1,2,4]triazin-4-yloxy)phenyl)-3-(2-(4-fluorophenyl)acetyl)guanidine To a test tube containing 3-fluoro-4-(pyrrolo[2,1-f][1,2,4]triazin-4-yloxy)benzenamine (20 mg, 0.082 mmol) and 1-(2-(4-fluorophenyl)acetyl)-2-methylisothiourea (20 mg, 0.086 mmol) was added 0.3 mL of toluene followed by diisopropylethylamine (15 µL, 0.086 mmol). The reaction was stirred at 110° C. for 6 h. Additional portions of 1-(2-(4-fluorophenyl)-acetyl)-2-methylisothiourea (20 mg, 0.086 mmol) and diisopropylethylamine (15 µL, 0.086 mmol) were added. After stirring at 110° C. overnight, the reaction was cooled to room temperature and purified directly by flash chromatography on silica gel (SiO$_2$, EtOAc/Hexane 1:1) to give the title compound as a white solid. The solid was treated with 4 N HCl in dioxane at 0° C. for 30 min. The solution was concentrated in vacuo to give the HCl salt of the title compound (15 mg, 40%) as a white powder. $^1$H NMR (CDCl$_3$) δ 13.8 (br s, 1H), 11.5 (br s, 1H), 9.48 (br s, 1H), 7.85 (s, 1H), 7.78 (dd, 1H, J=2.5, 1.4 Hz), 7.30 (m, 5H), 7.01 (m, 3H), 6.85 (m, 1H); MS(ESI$^+$) m/z 423.1 (M+H)$^+$.

Example 23

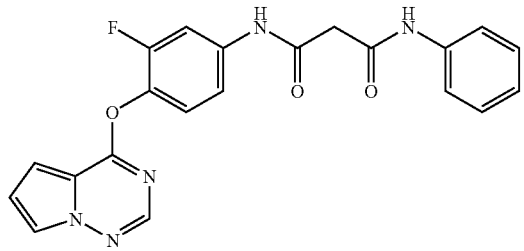

N$^1$-(3-Fluoro-4-(pyrrolo[2,1-f][1,2,4]triazin-4-yloxy) phenyl)-N$^3$-phenylmalonamide

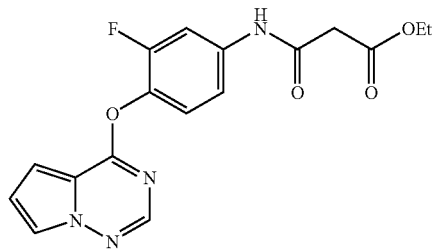

A) Ethyl 3-(3-fluoro-4-(pyrrolo[2,1-f][1,2,4]triazin-4-yloxy)phenylamino)-3-oxopropanoate To a solution of 3-fluoro-4-(pyrrolo[2,1-f][1,2,4]triazin-4-yloxy)benzenamine (112 mg, 0.459 mmol, Compound C of Example 22) in methylene chloride (4 mL) at 0° C. was added 96 µL (0.55 mmol) of diisopropylethylamine followed by 61 µL (0.48 mmol) of ethyl 3-chloro-3-oxopropanoate. The reaction was stirred at 0° C. for 1 h and was then quenched with 10 mL of saturate NaHCO$_3$ solution. The aqueous layer was extracted with chloroform (3×15 mL). The combined organic extracts were dried over anhydrous Na$_2$SO$_4$ and concentrated in vacuo to give the crude product as a yellow oil that solidified on standing (180 mg). $^1$H NMR (CDCl$_3$) δ 9.45 (br s, 1H), 7.89 (s, 1H), 7.71 (dd, 1H, J=2.5, 1.5 Hz), 7.68 (dd, 1H, J=11.8, 2.2 Hz), 7.18 (m, 2H), 6.93 (dd, 1H, J=4.4, 1.4 Hz), 6.78 (dd, 1H, J=4.4, 2.6 Hz), 4.19 (q, 2H, J=7.2 Hz), 3.41 (s, 2H), 1.25 (t, 3H, J=7.2 Hz); MS(ESI$^+$) m/z 359.1 (M+H)$^+$.

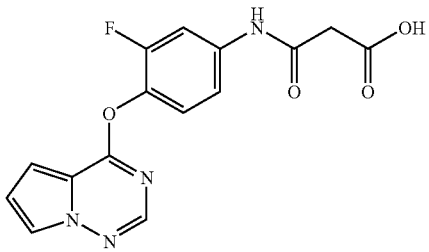

B) 3-(3-Fluoro-4-(pyrrolo[2,1-f][1,2,4]triazin-4-yloxy)phenylamino)-3-oxopropanoic acid To a solution of the above crude ethyl 3-(3-fluoro-4-(pyrrolo[2,1-f][1,2,4]triazin-4-yloxy)phenylamino)-3-oxopropanoate (180 mg) in ethanol (10 mL) at 0° C. was added 1 N aq NaOH solution (10 mL). After stirring at 0° C. for 3 h, the reaction was washed with 20 mL of EtOAc. The EtOAc layer was back-extracted with 20 mL of 1 N aq NaOH solution. The combined aqueous solution was acidified to pH with 1 N aq HCl solution. The aqueous layer was extracted with EtOAc (3×30 mL). The combined organic extracts were dried over anhydrous Na$_2$SO$_4$ and concentrated in vacuo to give the crude acid which was used without further purification (150 mg). MS(ESI$^+$) m/z 331.1 (M$^+$+H)$^+$.

C) N$^1$-(3-Fluoro-4-(pyrrolo[2,1-f][1,2,4]triazin-4-yloxy)phenyl)-N$^3$-phenylmalonamide A solution of 3-(3-fluoro-4-(pyrrolo[2,1-f][1,2,4]triazin-4-yloxy)phenylamino)-3-oxopropanoic acid (17 mg, 0.052 mmol), BOP reagent (34 mg, 0.077 mmol), 4-methylmorpholine (28 µL, 0.26 mmol), and aniline (4.7 µL, 0.052 mmol) in dimethylformamide (0.5 mL) was stirred at room temperature for 16 h. The reaction was diluted with EtOAc (4 mL) and washed with water, 10% aq LiCl solution, and brine (1×3 mL each). The organic solution was dried over anhydrous Na$_2$SO$_4$ and then concentrated in vacuo. Purification by flash chromatography on silica gel (SiO$_2$, EtOAc/Hexane 7:3) gave the desired compound as a white solid. The product was lyophilized with acetonitrile/water to give the title compound (12 mg, 57%) as a white powder. $^1$H NMR (CDCl$_3$) δ 9.23 (br s, 1H), 8.22 (br s, 1H), 7.90 (s, 1H), 7.72 (m, 1H), 7.46 (d, 1H, J=8.2 Hz), 7.20 (m, 7H), 6.95 (m, 1H), 6.78 (m, 1H), 3.47 (s, 2H); MS(ESI$^+$) m/z 406.1 (M+H)$^+$.

Example 24

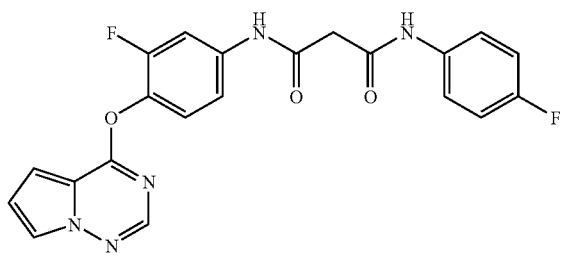

N$^1$-(3-Fluoro-4-(pyrrolo[2,1-f][1,2,4]triazin-4-yloxy)
phenyl)-N$^3$-(4-fluorophenyl)malonamide A solution of 3-(3-fluoro-4-(pyrrolo[2,1-f][1,2,4]triazin-4-yloxy)phenylamino)-3-oxopropanoic acid (18 mg, 0.55 mmol, Compound B of Example 23), BOP reagent (36 mg, 0.082 mmol), 4-methylmorpholine (30 µL, 0.27 mmol), and 4-fluoroaniline (5.2 µL, 0.055 mmol) in dimethylformamide (0.5 mL) was stirred at room temperature for 16 h. The reaction was diluted with EtOAc (4 mL) and washed with water, 10% aq LiCl solution, and brine (1×3 mL each). The organic solution was dried over anhydrous Na$_2$SO$_4$ and then concentrated in vacuo. Purification by flash chromatography on silica gel (SiO$_2$, EtOAc/Hexane 7:3) gave the desired compound as a white solid. The product was lyophilized with acetonitrile/water to give the title compound (14 mg, 61%) as a white powder. $^1$H NMR (CDCl$_3$) δ 9.28 (br s, 1H), 8.64 (br s, 1H), 7.89 (s, 1H), 7.73 (dd, 1H, J=2.5, 1.5 Hz), 7.69 (dd, 1H, J=11.6, 1.9 Hz), 7.42 (m, 3H), 7.21 (m, 1H), 6.97 (m, 3H), 6.80 (dd, 1H, J=4.5, 2.6 Hz), 3.49 (s, 2H); MS(ESI$^+$) m/z 424.1 (M+H)$^+$.

Example 25

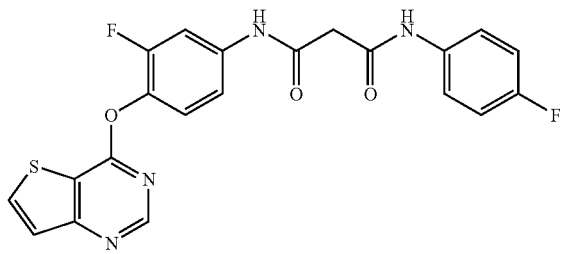

N$^1$-(3-Fluoro-4-(thieno[3,2-d]pyrimidin-4-yloxy)
phenyl)-N$^{33}$-(4-fluorophenyl)malonamide

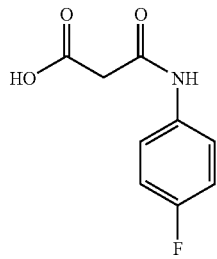

A) 3-(4-Fluorophenylamino)-3-oxopropanoic acid

To a solution of ethyl 3-chloro-3-oxopropanoate (5.0 mL, 40 mmol, Aldrich) in methylene chloride (100 mL) at 0° C. was added diisopropylethylamine (8.4 mL, 48 mmol) followed by 4-fluoroaniline (3.6 mL, 38 mmol, Aldrich). The reaction was stirred at room temperature overnight and was then quenched with 100 mL of saturated NaHCO$_3$ solution. The aqueous layer was extracted with chloroform (3×100 mL). The combined organic extracts were dried over anhydrous Na$_2$SO$_4$ and concentrated in vacuo to give the crude product as a yellow oil that solidified on standing (10 g). $^1$H NMR (CDCl$_3$) δ 9.30 (br s, 1H), 7.55 (m, 2H), 7.05 (t, 2H, J=8.8 Hz), 4.28 (q, 2H, J=7.2 Hz), 3.49 (s, 2H), 1.35 (t, 3H, J=7.1 Hz); MS(ESI$^+$) m/z 226.1 (M+H)$^+$.

The above ester was dissolved in 100 mL of ethanol and cooled to 0° C. 1 N aq NaOH solution (100 mL) was added and the reaction was stirred at 0° C. for 1 h. The reaction was concentrated to remove ethanol. The aqueous solution was extracted with EtOAc (50 mL) and was then made acidic with 1 N aq HCl solution. The aqueous solution was extracted with EtOAc (5×100 mL). The combined organic extracts were dried over anhydrous Na$_2$SO$_4$ and concentrated in vacuo to give the crude product (6.31 g, 84%) as a yellow solid which was used without further purification. $^1$H NMR (DMSO-d$_6$) δ 12.9 (br s, 1H), 10.3 (br s, 1H), 7.59 (m, 2H), 7.16 (t, 2H, J=8.9 Hz), 3.34 (s, 2H); MS(ESI$^+$) m/z 198.4 (M+H)$^+$.

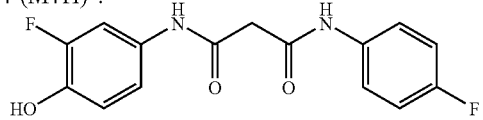

B) N$^1$-(3-Fluoro-4-hydroxyphenyl)-N$^3$-(4-fluorophenyl)malonamide

To a solution of 2-fluoro-4-nitrophenol (1.00 g, 6.37 mmol) in 4 mL of tetrahydrofuran and 6 mL of methanol at 0° C. was added zinc dust (2.08 g, 31.8 mmol, <10 micron) followed by ammonium chloride (1.70 g, 31.8 mmol). The mixture was stirred at room temperature overnight. The heterogeneous mixture was filtered through a thin pad of Celite® with methanol and the filtrate was concentrated in vacuo to give a brown solid which was used without further purification (656 mg, 81%).

3-(4-Fluorophenylamino)-3-oxopropanoic acid (197 mg, 1.00 mmol) was dissolved in 4 mL of dimethylformamide. Triethylamine (140 µL, 1.00 mmol) was added and the solution was cooled to 0° C. 4-Amino-2-fluorophenol (127 mg, 1.00 mmol, Aldrich) was added followed BOP reagent (442 mg, 1.00 mmol). The reaction was allowed to warm to room temperature and was then stirred at room temperature for 3 h. The reaction mixture was concentrated to remove methylene chloride and water was added to precipitate the product. Filtration and trituration with water gave the title compound (211 mg, 69%) as a white solid. $^1$H NMR (CD$_3$OD) δ 7.61 (m, 2H), 7.51 (dd, 1H, J=13, 2.5 Hz), 7.08 (m, 3H), 6.88 (t, 1H, J=9.4 Hz), 3.51 (s, 2H); MS(ESI$^+$) m/z 307.4 (M+H)$^+$.

C) N$^1$-(3-Fluoro-4-(thieno[3,2-d]pyrimidin-4-yloxy)
phenyl)-N$^3$-(4-fluorophenyl)malonamide N$^1$-(3-Fluoro-4-hydroxyphenyl)-N$^3$-(4-fluorophenyl)malonamide (46 mg, 0.15 mmol), 4-chlorothieno[3,2-d]pyrimidine (17 mg, 0.10 mmol), cesium carbonate (49 mg, 0.15 mmol), and copper(I) chloride (10 mg, 0.10 mmol) were placed in a test tube. The tube was sealed, flushed with nitrogen, charged with 1-methyl-2-pyrrolidinone (0.3 mL) followed by 2,2,6,6-tetramethyl-3,5-heptanedione (4.0 µL, 0.02 mmol). The reaction was stirred at 120° C. for 2 h. The reaction mixture was purified by preparative HPLC. The appropriate fraction was concentrated to remove methanol and the resulting aqueous solution was made basic with saturated NaHCO₃ solution (5 mL). The aqueous solution was extracted with EtOAc (3×10 mL) and the combined organic extracts were dried over anhydrous Na₂SO₄ and concentrated in vacuo to give the desired product as a colorless oil. Lyophilization with methanol/water gave the title compound (23 mg, 52%) as a white solid. $^1$H NMR (CD₃OD) δ 8.54 (s, 1H), 8.21 (d, 1H, J=5.5 Hz), 7.69 (dd, 1H, J=12.4, 2.0 Hz), 7.49 (m, 3H), 7.27 (m, 2H), 6.96 (t, 2H, J=8.9 Hz), 3.47 (s, 2H); MS(ESI⁺) m/z 441.1 (M+H)⁺.

Example 26

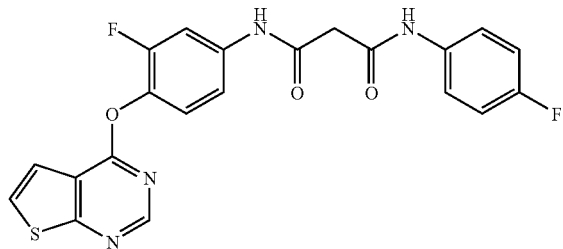

$N^1$-(3-Fluoro-4-(thieno [2,3-d]pyrimidin-4-yloxy)phenyl)-$N^3$-(4-fluorophenyl)malonamide $N^1$-(3-Fluoro-4-hydroxyphenyl)-$N^3$-(4-fluorophenyl)malonamide (46 mg, 0.15 mmol, Compound B of Example 25), 4-chlorothieno[2,3-d]pyrimidine (17 mg, 0.10 mmol), cesium carbonate (49 mg, 0.15 mmol), and copper(I) chloride (10 mg, 0.10 mmol) were placed in a test tube. The tube was sealed, flushed with nitrogen, charged with 1-methyl-2-pyrrolidinone (0.3 mL) followed by 2,2,6,6-tetramethyl-3,5-heptanedione (4.0 µL, 0.02 mmol). The reaction was stirred at 120° C. for 1 h. The reaction mixture was purified by preparative HPLC. The appropriate fraction was concentrated to remove methanol and the resulting aqueous solution was made basic with saturated NaHCO₃ solution (5 mL). The aqueous solution was extracted with EtOAc (3×10 mL) and the combined organic extracts were dried over anhydrous Na₂SO₄ and concentrated in vacuo to give the desired product as a colorless oil. Lyophilization with methanol/water gave the title compound (27 mg, 61%) as a white solid. $^1$H NMR (DMSO-d₆) δ 10.7 (s, 1H), 10.4 (s, 1H), 8.77 (s, 1H), 8.15 (d, 1H, J=5.9 Hz), 7.95 (dd, 1H, J=12.8, 2.0 Hz), 7.85 (d, 1H, J=5.9 Hz), 7.77 (m, 2H), 7.54 (m, 2H), 7.30 (t, 2H, J=8.8 Hz), 3.48 (s, 2H); MS(ESI⁺) m/z 441.1 (M+H)⁺.

Example 27

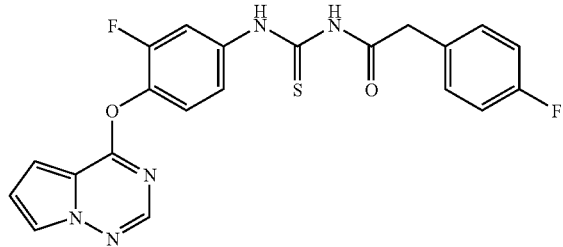

1-(3-Fluoro-4-(pyrrolo[2,1-f][1,2,4]triazin-4-yloxy)phenyl)-3-(2-(4-fluorophenyl)-acetyl)thiourea To a homogeneous solution of sodium thiocyanate (21 mg, 0.26 mmol) in ethyl acetate (1 mL), at room temperature under a nitrogen atmosphere, was added 4-fluorophenyl-acetyl chloride (28 µL, 0.20 mmol). The mixture was stirred for 30 minutes before being added directly to a homogeneous solution of 3-fluoro-4-(pyrrolo[2,1-f][1,2,4]-triazin-4-yloxy)benzenamine (37 mg, 0.15 mmol, Compound C of Example 22) in anhydrous dichloromethane (3 mL), under a nitrogen atmosphere. The mixture was stirred at ambient temperature for 4 h before being concentrated in vacuo. Purification by silica gel (Merck KGaA, 230–400 mesh particle size) flash chromatography, eluting with chloroform, afforded the title compound (55 mg, 83%). $^1$H NMR (CDCl₃) δ 12.41 (s, 1H), 8.50 (s, 1H), 7.97 (s, 1H), 7.92 (m, 1H), 7.81 (m, 1H), 7.42 (m, 1H), 7.35–725 (m, 3H), 7.17–7.10 (m, 2H), 705–7.02 (m, 1H), 6.85–6.90 (m, 1H), 3.72 (s, 2H); HRMS(ESI), 440.0993 (M+H)⁺ calc, 440.0988 (M+H)⁺ found.

Example 28

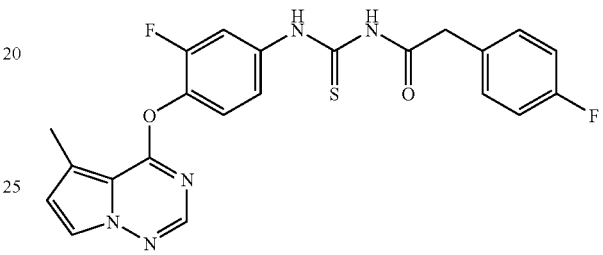

1-(3-Fluoro-4-(5-methylpyrrolo[2,1-f][1,2,4]triazin-4-yloxy)phenyl)-3-(2-(4-fluorophenyl)acetyl)thiourea

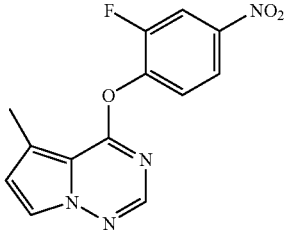

A) 4-(2-Fluoro-4-nitrophenoxy)-5-methylpyrrolo[2,1-f][1,2,4]triazine

To a mixture of 4-chloro-5-methylpyrrolo[2,1-f][1,2,4]triazine (3.37 g, 20.11 mmol, PCT Appl. WO 2000/071129, U.S. pat. application 2003/0186982, the disclosure of which is herein incorporated by reference) and 2-fluoro-4-nitrophenol (3.48 g, 22.12 mmol) in anhydrous DMF (100 mL), stirred for 5 minutes under a nitrogen atmosphere, was added anhydrous potassium carbonate (6.11 g, 44.24 mmol). The mixture was heated at 60° C. for 15 h before 2-fluoro-4-nitrophenol (1.00 g, 6.37 mmol) was added and stirring continued at 60° C. for 4.5 h. The mixture was cooled to room temperature, diluted with dichloromethane, washed sequentially with water and 10% aqueous lithium chloride, dried over anhydrous magnesium sulfate and concentrated in vacuo to yield a tan solid. Purification by silica gel (Merck KGaA, 230–400 mesh particle size) flash chromatography, eluting with chloroform, afforded the title compound (4.19 g, 72%) as a pale yellow solid. $^1$H NMR (CDCl₃) δ 8.20–8.13 (m, 2H), 7.83 (s, 1H), 7.73 (d, 1H, J=2.6 Hz); 7.58–7.53 (m, 1H), 6.69 (d, 1H, J=2.4 Hz), 2.62 (s, 3H); HRMS(ESI), 289.0737 (M+H)⁺ calc, 289.0733 (M+H)⁺ found.

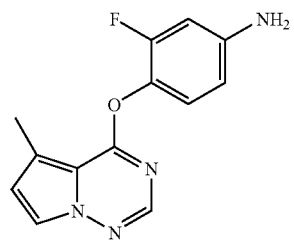

B) 3-Fluoro-4-(5-methylpyrrolo[2,1-f][1,2,4]triazin-4-yloxy)benzenamine

To a heterogeneous mixture of 4-(2-fluoro-4-nitrophenoxy)-5-methylpyrrolo[2,1-f][1,2,4]triazine (3.04 g, 10.55 mmol) in anhydrous methanol (60 mL) and anhydrous tetrahydrofuran (40 mL), at ambient temperature under nitrogen atmosphere, was added zinc dust (6.90 g, 105 mmol) and ammonium chloride (5.64 g, 105 mmol). The mixture was stirred for 7 h before the catalyst was filtered off and the filtrate was concentrated in vacuo to a pale yellow solid which was partitioned between chloroform and water. The aqueous layer was then extracted twice with chloroform. The combined chloroform layers were washed with water, dried over anhydrous magnesium sulfate and concentrated in vacuo to yield the title compound (2.51 g, 92%) as a solid. $^1$H NMR (CDCl$_3$) δ 7.86 (s, 1H), 7.64 (d, 1H, J=2.6 Hz); 7.08–7.03 (m, 1H), 6.61 (d, 1H, J=2.4 Hz), 6.55–6.45 (m, 2H), 3.78 (s, 2H), 2.60 (s, 3H); HRMS(ESI), 259.0995 (M+H)$^+$ calc, 259.0997 (M+H)$^+$ found.

C) 1-(3-Fluoro-4-(5-methylpyrrolo[2,1-f][1,2,4]triazin-4-yloxy)phenyl)-3-(2-(4-fluorophenyl)acetyl)thiourea 3-Fluoro-4-(5-methylpyrrolo[2,1-f][1,2,4]triazin-4-yloxy)benzenamine (39 mg, 0.15 mmol) was converted to the title compound (42 mg, 62%) in a manner similar to the preparation of Example 27. $^1$H NMR (CDCl$_3$) δ 12.41 (s, 1H), 8.48 (s, 1H), 7.92–7.82 (m, 2H), 7.68 (d, 1H, J=2.5 Hz), 7.39–7.27 (m, 4H), 7.15–7.10 (m, 2H), 6.64 (d, 1H, J=2.3 Hz), 3.72 (s, 2H), 2.60 (s, 3H); HRMS(ESI), 454.1149 (M+H)$^+$ calc, 454.1154 (M+H)$^+$ found.

Example 29

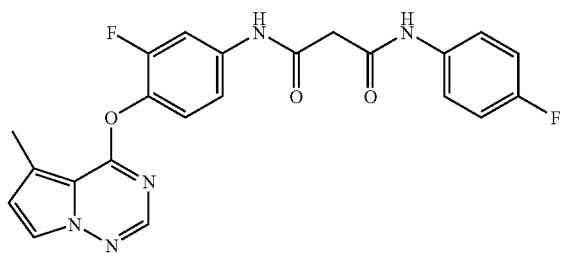

N$^1$-(3-Fluoro-4-(5-methylpyrrolo[2,1-f][1,2,4]triazin-4-yloxy)phenyl)-N$^3$-(4-fluoro-phenyl)malonamide To a homogeneous solution of 3-fluoro-4-(5-methylpyrrolo[2,1-f][1,2,4]triazin-4-yloxy)benzenamine (52 mg, 0.20 mmol, Compound B of Example 28) and 3-(4-fluorophenylamino)-3-oxopropanoic acid (39 mg, 0.20 mmol, Compound A of Example 25) in anhydrous DMF (2 mL), at room temperature under nitrogen atmosphere, was added diisopropylethylamine (52 μL, 0.30 mmol). The mixture was stirred for 5 minutes before o-benzotriazol-1-yl-N,N,N',N'-tetramethyluronium tetrafluoroborate (96 mg, 0.30 mmol) was added in one portion. The mixture was stirred for 17.5 h before the reaction was concentrated in vacuo to remove volatiles. The resultant residue was diluted with ethyl acetate and washed twice with 10% aqueous lithium chloride before being concentrated in vacuo. Purification by silica gel (Merck KGaA, 230–400 mesh particle size) flash chromatography, eluting with 1% methanol in chloroform, afforded an off-white solid that was triturated and sonicated in the presence of anhydrous ethyl ether (3 mL). The title compound (66 mg, 75%) was isolated by filtration as a white solid. $^1$H NMR (CDCl$_3$) δ 9.28 (s, 1H), 8.67 (s, 1H), 7.83 (s, 1H), 7.80–7.73 (m, 1H), 7.67 (d, 1H, J=2.5 Hz), 7.54–7.49 (m, 2H), 7.28–7.26 (m, 2H), 7.10–7.02 (m, 2H), 6.64 (d, 1H, J=2.3 Hz), 3.56 (s, 2H), 2.60 (s, 3H); HRMS(ESI), 436.1221 (M+H)$^+$ calc, 436.1230 (M+H)$^+$ found.

Example 30

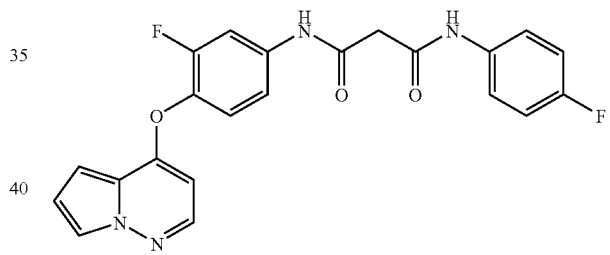

N$^1$-(4-(H-Pyrrolo[1,2-b]pyridazin-4-yloxy)-3-fluorophenyl)-N$^3$-(4-fluorophenyl)malonamide A solution of 4-(H-pyrrolo[1,2-b]pyridazin-4-yloxy)-3-fluorobenzenamine (51 mg, 0.21 mmol, Compound D of Example 19) in DMF (1 mL) was treated with 3-(4-fluorophenylamino)-3-oxopropanoic acid (41 mg, 0.21 mmol, Compound A of Example 25), DIPEA (42 μL, 0.25 mmol) and TBTU (81 mg, 0.25 mmol) and the mixture stirred at RT for 16 h. The mixture was concentrated in vacuo to remove the DMF and the residue was partitioned between EtOAc (2 mL) and saturated sodium bicarbonate solution (2 mL). The EtOAc phase was washed with 10% aqueous LiCl (2 mL), brine (2 mL), dried (MgSO$_4$) and concentrated in vacuo. The crude product was triturated twice with EtOAc and two times with MeOH to give the title compound (17 mg, 19%) as an off-white solid. $^1$H NMR (DMSO-d$_6$) δ 10.56 (s, 1H), 10.28 (s, 1H), 8.01, (d, 1H, J=5.4 Hz), 7.92–7.91 (m, 1H), 7.65–7.62 (m, 2H), 7.48–7.44 (m, 2H), 7.22–7.15 (m, 3H), 6.86 (dd, 1H, J=4.2, 2.7 Hz), 6.72 (dd, 1H, J=4.4, 1.4 Hz), 5.81 (d, 1H, J=5.4 Hz), 3.51 (s, 2H); MS(ESI$^+$) m/z 423.3 (M+H)$^+$.

Example 31

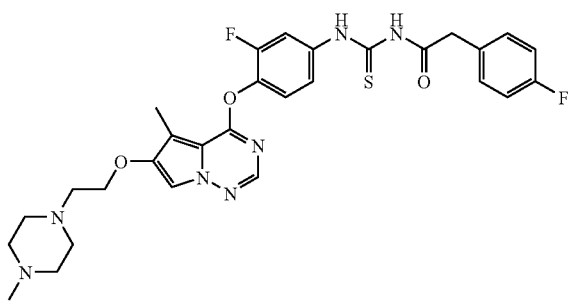

1-(3-Fluoro-4-(5-methyl-6-(2-(4-methylpiperazin-1-yl)ethoxy)pyrrolo[2,1-f]-[1,2,4]triazin-4-yloxy)phenyl)-3-(2-(4-fluorophenyl)acetyl)thiourea, bis-hydrochloride salt

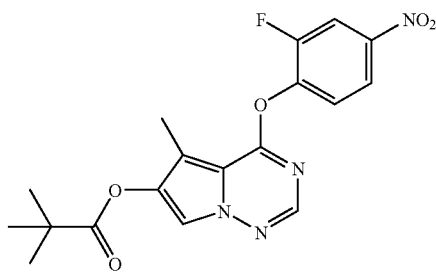

A) 4-(2-Fluoro-4-nitrophenoxy)-5-methylpyrrolo[2,1-f][1,2,4]-triazin-6-yl pivalate To a homogeneous solution of 4-chloro-5-methylpyrrolo[2,1-f][1,2,4]triazin-6-yl pivalate (1.00 g, 3.74 mmol, Compound D of Example 1) and 2-fluoro-4-nitrophenol (588 mg, 3.74 mmol) in anhydrous acetonitrile (25 mL), at room temperature under a nitrogen atmosphere, was added DABCO (462 mg, 4.12 mmol). The mixture was then heated at 50° C. for 3 h. The mixture was cooled to room temperature then partitioned between chloroform and saturated aqueous ammonium chloride. The aqueous layer was extracted twice with chloroform. The combined organic layers were washed once each with saturated aqueous ammonium chloride and saturated aqueous sodium chloride, dried over anhydrous magnesium sulfate and concentrated in vacuo to yield a pale yellow solid that was used in the next step without further purification. MS(ESI$^+$) m/z 389.1 (M+H)$^+$.

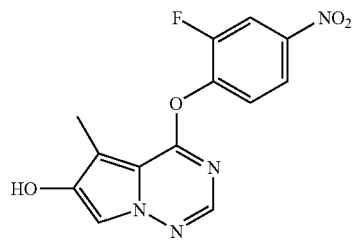

B) 4-(2-Fluoro-4-nitrophenoxy)-5-methylpyrrolo[2,1-f][1,2,4]-triazin-6-ol

To a heterogeneous mixture of 4-(2-fluoro-4-nitrophenoxy)-5-methylpyrrolo[2,1-f][1,2,4]-triazin-6-yl pivalate (1.45 g, 3.74 mmol) in absolute ethanol (19 mL), at room temperature under a nitrogen atmosphere, was added 1 N aqueous sodium hydroxide. The reaction mixture was stirred at ambient temperature for 1.5 h before being neutralized to pH 7 with 1 N aqueous hydrochloride. The reaction mixture was concentrated to remove ethanol, before being partitioned between ethyl acetate and water. The aqueous layer was extracted twice with ethyl acetate. The combined organic extracts were washed twice with water, once with saturated aqueous sodium chloride, dried over anhydrous magnesium sulfate and concentrated in vacuo. Purification by silica gel (Merck KGaA, 230–400 mesh particle size) flash chromatography, eluting with 2:1 hexane/ethyl acetate, afforded the title compound (602 mg, 53% for Steps A-B) as a yellow solid. $^1$H NMR (CDCl$_3$) δ 8.20–8.12 (m, 2H), 7.84 (s, 1H), 7.58–7.53 (m, 1H), 7.53 (s, 1H), 4.76 (s, 1H), 2.48 (s, 3H); MS(ESI$^+$) m/z 305.2 (M+H)$^+$.

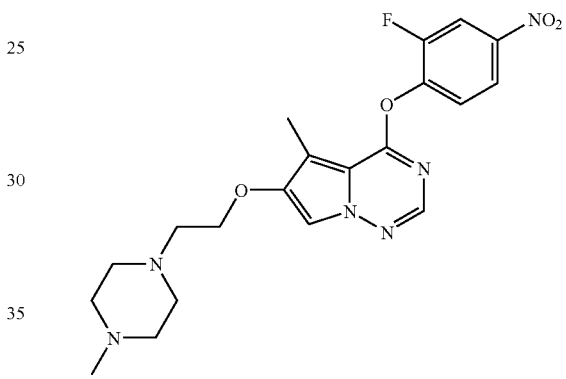

C) 4-(2-Fluoro-4-nitrophenoxy)-5-methyl-6-(2-(4-methylpiperazin-1-yl)-ethoxy)pyrrolo[2,1-f][1,2,4]triazine To a homogeneous mixture of 4-(2-fluoro-4-nitrophenoxy)-5-methylpyrrolo[2,1-f][1,2,4]-triazin-6-ol (100 mg, 0.33 mmol) and triphenylphosphine (129 mg, 0.49 mmol) in 4 mL of 1:1 anhydrous dichlormethane/anhydrous tetrahydrofuran, cooled to 0° C. under a nitrogen atmosphere, was added dropwise a mixture of 2-(4-methylpiperazin-1-yl) ethanol (71 mg, 0.49 mmol) and diisopropylazodicarboxylate (0.10 μL, 0.49 mmol) in 2 mL of 1:1 anhydrous dichlormethane/anhydrous tetrahydrofuran. The mixture was stirred and allowed to warm to room temperature. The reaction was stirred for twelve hours before being concentrated in vacuo. The residue was purified by preparative HPLC (YMC S10 ODS, 30×500 mm, 30 minute gradient from 50% to 90% aqueous methanol with 0.1% TFA). The appropriate fractions were combined, neutralized with saturated aqueous sodium bicarbonate, and then concentrated in vacuo to remove methanol. The mixture was extracted with chloroform (3×10 mL). The combined organic layers were washed once each with water and brine, dried over anhydrous magnesium sulfate, and concentrated in vacuo to yield the title compound (34 mg, 24%) as a yellow solid. $^1$H NMR (CDCl$_3$) δ 8.20–8.10 (m, 2H), 7.82 (s, 1H), 7.58–7.52 (m, 1H), 7.49 (s, 1H), 4.16 (t, 2H, J=5.7 Hz), 2.87 (t, 2H, J=5.7 Hz), 2.80–2.40 (m, 8H), 2.45 (s, 3H), 2.31 (s, 3H); MS(ESI$^+$) m/z 431.3 (M+H)$^+$.

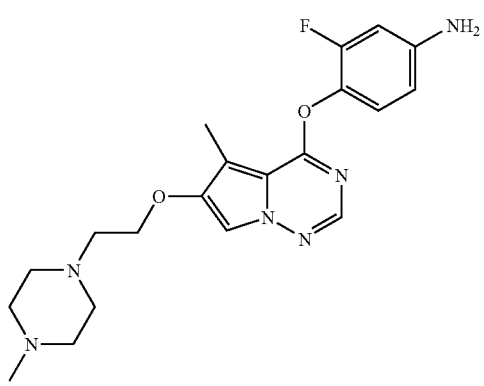

D) 3-Fluoro-4-(5-methyl-6-(2-(4-methylpiperazin-1-yl)ethoxy)pyrrolo[2,1-f][-1,2,4]triazin-4-yloxy)benzenamine 4-(2-Fluoro-4-nitrophenoxy)-5-methyl-6-(2-(4-methylpiperazin-1-yl)ethoxy)pyrrolo[2,1-f][1,2,4]triazine (20 mg, 0.05 mmol) was converted to the title compound (16 mg, 87%) in a manner similar to the preparation of Compound B of Example 28. $^1$H NMR (CDCl$_3$) δ 7.86–7.83 (m, 1H), 7.50–7.38 (m, 2H), 7.09–7.00 (m, 1H), 6.56–6.45 (m, 1H), 4.14 (t, 2H, J=5.5 Hz), 2.99–2.38 (m, 18H); MS(ESI$^+$) m/z 401.4 (M+H)$^+$.

E) 1-(3-Fluoro-4-(5-methyl-6-(2-(4-methylpiperazin-1-yl)ethoxy)pyrrolo[2,1-f][1,2,4] triazin-4-yloxy)phenyl)-3-(2-(4-fluorophenyl)acetyl)thiourea, bis-hydrochloride salt 3-Fluoro-4-(5-methyl-6-(2-(4-methylpiperazin-1-yl)ethoxy)pyrrolo[2,1-f][1,2,4]-triazin-4-yloxy)benzenamine (18 mg, 0.05 mmol) was converted to the title compound (7 mg, 26%) in a manner similar to the preparation of Example 27. Treatment with 1 N aqueous hydrochloric acid (0.05 mL, 0.05 mmol), followed by lyophilization, resulted in the title compound as a pale yellow solid (5 mg, 64%). $^1$H NMR (CD$_3$OD) δ 8.06–7.99 (m, 2H), 7.83 (s, 1H), 7.79 (s, 1H), 7.48–7.30 (m, 4H), 7.13–7.02 (m, 2H), 4.56–4.45 (m, 2H), 3.87–3.59 (m, 4H), 3.09–2.44 (m, 15H); HRMS(ESI), 596.2255 (M+H)$^+$ calc, 596.2261 (M+H)$^+$ found.

Example 32

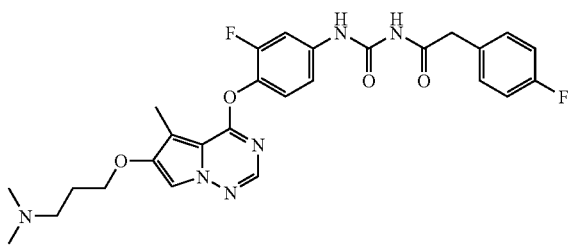

1-(4-(6-(3-(Dimethylamino)propoxy)-5-methylpyrrolo[2,1-f][1,2,4]triazin-4-yloxy)-3-fluorophenyl)-3-(2-(4-fluorophenyl)acetyl)urea, hydrochloride salt

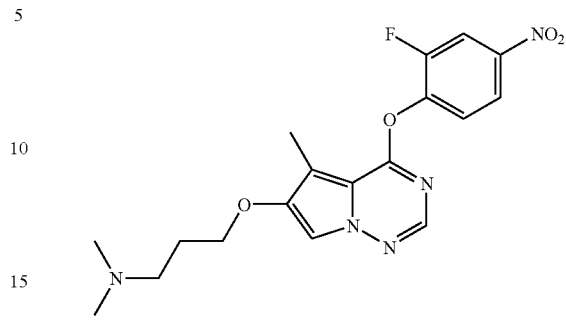

A) 3-(4-(2-Fluoro-4-nitrophenoxy)-5-methylpyrrolo[2,1-f][1,2,4]triazin-6-yloxy)-N,N-dimethylpropan-1-amine To a mixture of polymer bound triphenylphosphine (3 mmol triphenylphosphine per 1 g of resin, 583 mg, 1.75 mmol) in anhydrous tetrahydrofuran (5 mL), at 0° C. under a nitrogen atmosphere, was added diethylazodicarboxylate (138 μL, 0.87 mmol) dropwise via syringe. The mixture was stirred for 15 minutes before 3-dimethyl-aminopropanol (103 μL, 0.87 mmol) was added. After 30 minutes at 0° C., 4-(2-fluoro-4-nitrophenoxy)-5-methylpyrrolo[2, 1-f][1,2,4]-triazin-6-ol (133 mg, 0.44 mmol, Compound B of Example 31) was added, and the mixture was allowed to slowly warm to room temperature. After 14.5 h, the resin was removed by filtration and rinsed with 1:1 methanol/tetrahydrofuran. The combined filtrate was concentrated in vacuo to a yellow residue that was used in the next step without further purification. MS(ESI$^+$) m/z 390.2 (M+H)$^+$.

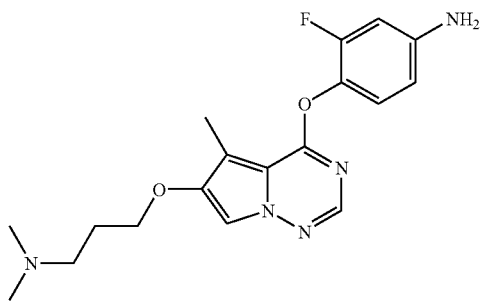

B) 4-(6-(3-(Dimethylamino)propoxy)-5-methylpyrrolo[2,1-f][1,2,4]triazin-4-yloxy)-3-fluorobenzenamine 3-(4-(2-fluoro-4-nitrophenoxy)-5-methylpyrrolo[2,1-f][1,2,4]triazin-6-yloxy)-N,N-dimethylpropan-1-amine (170 mg, 0.44 mmol) was converted to the title compound in a manner similar to the preparation of Compound B of Example 28. The resultant yellow solid was used in the next step without further purification. MS(ESI$^+$) m/z 360.3 (M+H)$^+$.

C) 1-(4-(6-(3-(Dimethylamino)propoxy)-5-methylpyrrolo[2,1-f][1,2,4]triazin-4-yloxy)-3-fluorophenyl)-3-(2-(4-fluorophenyl)acetyl)urea, hydrochloride salt 4-(6-(3-(Dimethylamino)propoxy)-5-methylpyrrolo[2,1-f][1,2,4]triazin-4-yloxy)-3-fluorobenzenamine (12 mg, 0.03 mmol) was converted to the title compound (2.5 mg, 13%)

in a manner similar to the preparation of Compound E of Example 31, except that 2-(4-fluorophenyl)-acetyl isocyanate (0.10 mL, 0.04 mmol, Compound C of Example 4) was used instead of benzenesulfonyl isocyanate. ¹H NMR (CD₃OD) δ 10.77 (s, 1H), 7.80 (s, 1H), 7.69 (s, 1H), 7.40–7.23 (m, 5H), 7.11–7.02 (m, 3 H), 4.15–4.12 (m, 2H), 3.71 (s, 2H), 3.41–3.36 (m, 2H), 2.97 (s, 6H), 2.44 (s, 3H), 2.31–2.22 (m, 2H); HRMS(ESI), 539.2218 (M+H)⁺ calc, 539.2218 (M+H)⁺ found.

Example 33

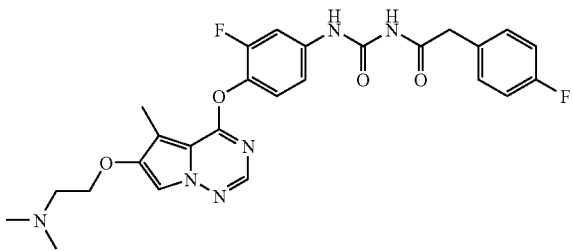

1-(4-(6-(2-(Dimethylamino)ethoxy)-5-methylpyrrolo[2,1-f][1,2,4]triazin-4-yloxy)-3-fluorophenyl)-3-(2-(4-fluorophenyl)acetyl)urea, hydrochloride salt

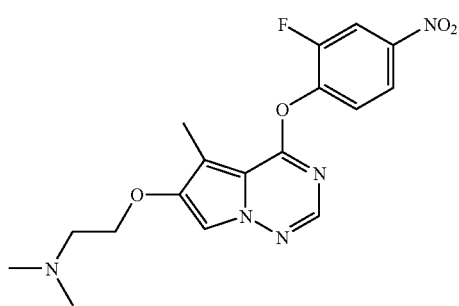

A) 2-(4-(2-Fluoro-4-nitrophenoxy)-5-methylpyrrolo[2,1-f][1,2,4]triazin-6-yloxy)-N,N-dimethylethanamine 4-(2-Fluoro-4-nitrophenoxy)-5-methylpyrrolo[2,1-f][1,2,4]-triazin-6-ol (91 mg, 0.30 mmol, Compound B of Example 31) was converted to the title compound in a manner similar to the preparation of Compound A of Example 32, except that N,N-dimethylethanolamine (75 μL, 0.75 mmol) was used instead of 3-dimethylaminopropanol and diisopropylazodicarboxylate (148 μL, 0.75 mmol) was used instead of diethylazodicarboxylate. The residue was purified by preparative HPLC (YMC S10 ODS, 30×500 mm, 30 minute gradient from 70% to 90% aqueous methanol with 0.1% TFA). The appropriate fractions were combined, neutralized with saturated aqueous sodium bicarbonate, and then concentrated in vacuo to remove methanol. The mixture was extracted with chloroform (3×10 mL). The combined organic layers were washed once each with water and brine, dried over anhydrous magnesium sulfate, and concentrated in vacuo to yield the title compound (22 mg, 19%) as a solid. MS(ESI⁺) m/z 376.2 (M+H)⁺.

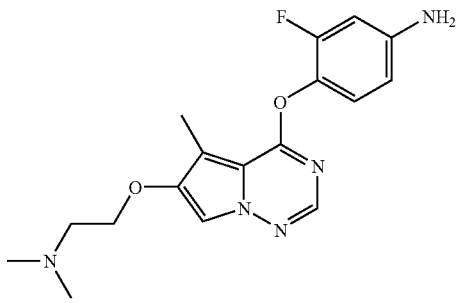

B) 4-(6-(2-(Dimethylamino)ethoxy)-5-methylpyrrolo[2,1-f][1,2,4]triazin-4-yloxy)-3-fluorobenzenamine 2-(4-(2-Fluoro-4-nitrophenoxy)-5-methylpyrrolo[2,1-f][1,2,4]triazin-6-yloxy)-N,N-dimethylethanamine (22 mg, 0.06 mmol) was converted to the title compound (20 mg, 100%) in a manner similar to the preparation of Compound B of Example 28. The resultant yellow glass was used in the next step without further purification. MS(ESI⁺) m/z 346.3 (M+H)⁺.

C) 1-(4-(6-(2-(Dimethylamino)ethoxy)-5-methylpyrrolo[2,1-f][1,2,4]triazin-4-yloxy)-3-fluorophenyl)-3-(2-(4-fluorophenyl)acetyl)urea, hydrochloride salt 4-(6-(2-(Dimethylamino)ethoxy)-5-methylpyrrolo[2,1-f][1,2,4]triazin-4-yloxy)-3-fluorobenzenamine (20 mg, 0.06 mmol) was converted to the title compound (6.5 mg, 19%) in a manner similar to the preparation of Compound C of Example 32. ¹H NMR (CD₃OD) δ 10.79 (s, 1H), 7.84 (s, 1H), 7.77 (s, 1H), 7.40–7.21 (m, 5H), 7.10–6.97 (m, 3H), 4.43–4.39 (m, 2H), 3.71 (s, 2H), 3.68–3.62 (m, 2H), 3.03 (s, 6H), 2.48 (s, 3H); HRMS(ESI), 525.2062 (M+H)⁺ calc, 525.2079 (M+H)⁺ found.

Example 34

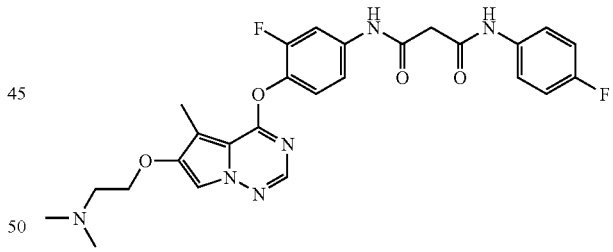

N¹-(4-(6-(2-(Dimethylamino)ethoxy)-5-methylpyrrolo[2,1-f][1,2,4]triazin-4-yloxy)-3-fluorophenyl)-N³-(4-fluorophenyl)malonamide, hydrochloride salt 4-(6-(2-(Dimethylamino)ethoxy)-5-methylpyrrolo[2,1-f][1,2,4]triazin-4-yloxy)-3-fluorobenzenamine (35 mg, 0.10 mmol, Compound B of Example 33) was converted to the title compound (4.2 mg, 8%) in a manner similar to the preparation of Example 29, except that PyBroP (52 mg, 0.11 mmol) was used instead of o-benzotriazol-1-yl-N,N,N',N'-tetramethyl-uronium tetrafluoroborate. Treatment with 1 N aqueous hydrochloric acid (1 mL, 1 mmol), followed by lyophilization, resulted in the title compound (1.7 mg, 38%) as a pale yellow solid. ¹H NMR (CD₃OD) δ 7.83 (s, 1H), 7.77 (s, 1H), 7.62–7.58 (m, 2H), 7.40–7.27 (m, 5H), 7.09–7.04 (m, 2H), 4.43–4.41 (m, 2H), 3.70–3.54 (m, 4H), 3.04 (s, 6H), 2.50 (s, 3H); HRMS(ESI), 525.2062 (M+H)+ calc, 525.2059 (M+H)+ found.

Example 35

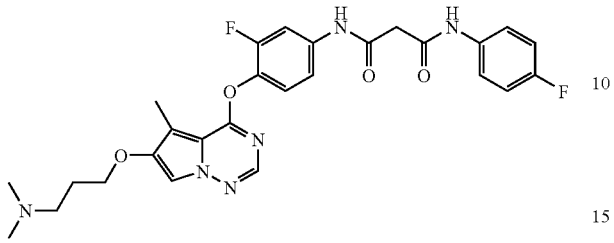

N¹-(4-(6-(3-(Dimethylamino)propoxy)-5-methylpyrrolo[2,1-f][1,2,4]triazin-4-yloxy)-3-fluorophenyl)-N³-(4-fluorophenyl)malonamide, hydrochloride salt 4-(6-(3-(Dimethylamino)propoxy)-5-methylpyrrolo[2,1-f][1,2,4]triazin-4-yloxy)-3-fluorobenzenamine (54 mg, 0.15 mmol, Compound B of Example 32) was converted to the title compound (13 mg, 15%) in a manner similar to the preparation of Example 34. ¹H NMR (CD₃OD) δ 7.83–7.75 (m, 2H), 7.67 (s, 1H), 7.63–7.57 (m, 2H), 7.39–7.27 (m, 2H), 7.09–7.02 (m, 2H), 4.18–4.13 (m, 2H), 3.58 (s, 2H) 3.42–3.36 (m, 2H), 2.96 (s, 6H), 2.48–2.42 (m, 4H), 2.32–2.25 (m, 2H); HRMS(ESI), 537.2062 (M–H)⁻ calc, 537.2073 (M–H)⁻ found.

Example 36

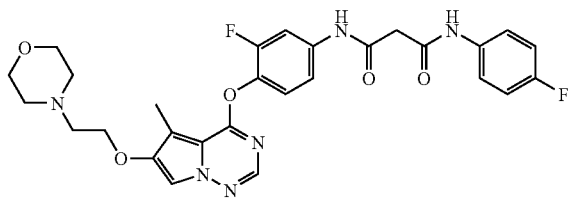

N¹-(3-Fluoro-4-(5-methyl-6-(2-morpholinoethoxy)pyrrolo[2,1-f][1,2,4]triazin-4-yloxy)phenyl)-N³-(4-fluorophenyl)malonamide, hydrochloride salt

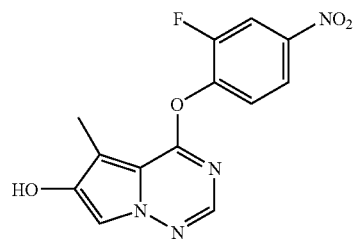

A) 4-(2-Fluoro-4-nitrophenoxy)-5-methylpyrrolo[2,1-f][1,2,4]triazin-6-ol

To a solution of 4-(2-fluoro-4-nitrophenoxy)-5-methylpyrrolo[2,1-f][1,2,4]triazin-6-yl pivalate (2.40 g, 6.19 mmol, Compound E of Example 1) in a mixture of 20 mL of THF and 30 mL of EtOH was added 1 N NaOH (12 mL, 12 mmol) dropwise at room temperature. The resulting solution was allowed to stir for 45 min, by that time HPLC analysis indicated the completion of the reaction. The reaction was thus quenched with 13 mL of 1 N HCl. After the organic solvent was removed under reduced pressure, the product precipitated out and was collected through filtration. The product obtained is 4-(2-fluoro-4-nitrophenoxy)-5-methylpyrrolo[2,1-f][1,2,4]triazin-6-ol (1.65 g, 88%). MS(ESI⁺) m/z 305.1 (M+H)⁺.

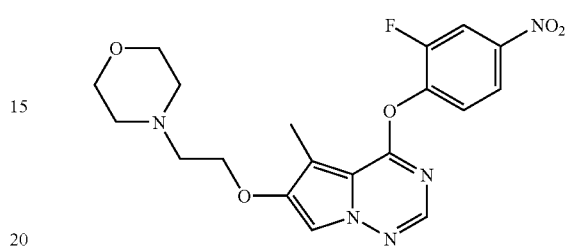

B) 4-(2-Fluoro-4-nitrophenoxy)-5-methyl-6-(2-morpholinoethoxy)pyrrolo[2,1-f][1,2,4]triazine To a solution of 4-(2-fluoro-4-nitrophenoxy)-5-methylpyrrolo[2,1-f][1,2,4]triazin-6-ol (55 mg, 0.18 mmol), 2-morpholinoethanol (47 mg, 0.36 mmol), and polymer-bound PPh₃ (3.0 mmol/g, 167 mg, 0.50 mmol) in 1 mL of THF at room temperature was added DIAD (72 mg, 0.36 mmol). The mixture was stirred for 1 h and HPLC analysis indicated most of the starting material disappeared. The polymer was filtered off through Celite® and the filtrate was concentrated and purified by preparative HPLC to afford the title compound (50 mg, 67%). MS(ESI⁺) m/z 418.2 (M+H)⁺.

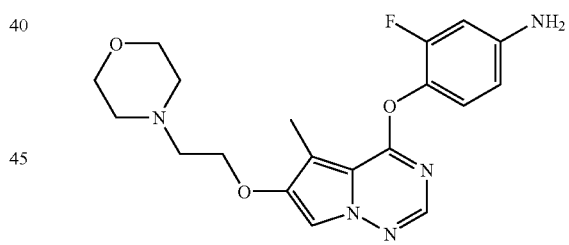

C) 3-Fluoro-4-(5-methyl-6-(2-morpholinoethoxy)pyrrolo[2,1-f][1,2,4]triazin-4-yloxy)benzenamine To a solution of 4-(2-fluoro-4-nitrophenoxy)-5-methyl-6-(2-morpholinoethoxy)pyrrolo[2,1-f][1,2,4]triazine (54 mg, 0.13 mmol) in a mixture of 0.8 mL of THF and 1.2 mL of MeOH were added NH₄Cl (70 mg, 1.3 mmol) and Zn powder (85 mg, 1.3 mmol). The suspension was allowed to stir at room temperature for 2 h. Both HPLC analysis and LC-MS analysis indicated the completion of the reaction and the solid was thus filtered off. After concentration of the filtrate, the residue was taken into 10% MeOH in CH₂Cl₂. The solution was then filtered again and the filtrate was concentrated in vaco to provide the title compound (50 mg, 92%). MS(ESI⁺) m/z 388.4 (M+H)⁺.

D) N⁴-(3-Fluoro-4-(5-methyl-6-(2-morpholinoethoxy)pyrrolo[2,1-f][1,2,4]triazin-4-yloxy)phenyl)-N³-(4-fluorophenyl)malonamide, hydrochloride salt To a solution of 3-fluoro-4-(5-methyl-6-(2-morpholinoethoxy)pyrrolo[2,1-f][1,2,4]triazin-4-yloxy)benzenamine (16 mg, 0.041 mmol), 3-(4-fluorophenylamino)-3-oxopropanoic acid (12 mg, 0.06 mmol, Compound A of Example 25) in 1 mL of THF were added DIEA (0.04 mL) and PyBrOP (32 mg, 0.06 mmol) at room temperature. The reaction was allowed to stir over the weekend and LC-MS analysis indicated the formation of the product, although there was still some staring material left. The solution was directly subject to preparative HPLC purification and the HPLC fraction containing the desired product was passed through a Waters Oasis® MCX 20 cc 500 mg LP Extraction cartridge and washed with MeOH to remove TFA. After that, the cartridge was eluted with 7 N NH₃ in MeOH and the ammonia solution was concentrated under reduced pressure to dryness. The residue was then suspended in a mixture of MeOH and H₂O and a few drops of 1 N HCl was added. The suspension became a clear solution and it was frozen in dry ice-acetone bath. The frozen solution was then lyophilized to afford the title compound (20 mg, 80%). ¹H NMR (CD₃OD) δ 7.71 (m, 2H), 7.60 (s, 1H), 7.53 (m, 2H), 7.28 (m, 2H), 7.00 (m, 2H), 4.13 (s, 2H), 3.67 (s, 4H), 2.80 (s, 2H), 2.58 (s, 4H), 2.37 (s, 3H); MS(ESI⁺) m/z 567.2 (M+H)⁺.

Example 37

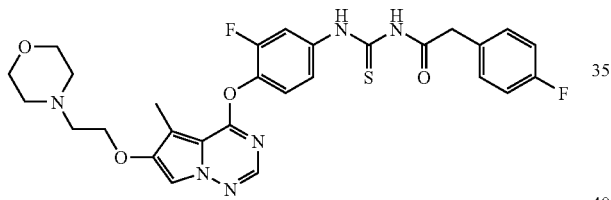

1-(3-Fluoro-4-(5-methyl-6-(2-morpholinoethoxy)pyrrolo[2,1-f][1,2,4]triazin-4-yloxy)phenyl)-3-(2-(4-fluorophenyl)acetyl)thiourea, hydrochloride salt To a solution of 3-fluoro-4-(5-methyl-6-(2-morpholinoethoxy)pyrrolo[2, 1-f][1,2,4]triazin-4-yloxy)benzenamine (30 mg, 0.072 mmol, Compound C of Example 36) in 1 mL of THF was added 2-(4-fluorophenyl)ethanoyl isothiocyanate (19 mg, 0.1 mmol, Compound A of Example 2). The solution was allowed to stir at room temperature for 2 h and HPLC analysis indicated the completion of the reaction. The reaction was then quenched with NH₃ in propanol and the resulting solution was loaded on a preparative HPLC to be purified. Following a work-up procedure similar to that for Compound D of Example 36, the title compound (13 mg, 30%) was obtained as a HCl salt. ¹H NMR (DMSO-d₆) δ 12.45 (s, 1H), 11.85 (s, 1H), 11.50 (br s, 1H), 8.15 (s, 1H), 8.10 (s, 1H), 7.90 (d, 1H), 7.50 (m, 2H), 7.40 (m, 2H), 7.20 (m, 2H), 4.50 (br s, 2H), 4.00 (m, 2H), 3.85 (s, 2H), 3.25-3.70 (m, 8H), 2.40 (s, 3H); MS(ESI⁺) m/z 583.2 (M+H)⁺.

Example 38

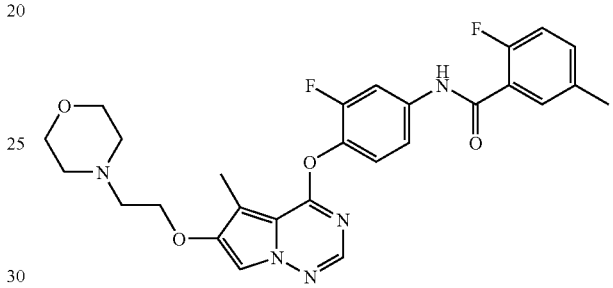

2-Fluoro-N-(3-fluoro-4-(5-methyl-6-(2-morpholinoethoxy)pyrrolo[2,1-f][1,2,4]triazin-4-yloxy)phenyl)-5-methylbenzamide, hydrochloride salt Following a procedure similar to that for the synthesis of Compound D of Example 36, 3-fluoro-4-(5-methyl-6-(2-morpholinoethoxy)pyrrolo[2,1-f][1,2,4]triazin-4-yloxy) benzenamine (16 mg, 0.042 mmol, Compound C of Example 36) was converted to the title compound (5.6 mg, 23%) as a HCl salt. ¹H NMR (CD₃OD) δ 7.85 (d, 1H), 7.80 (s, 1H), 7.69 (s, 1H), 7.55 (m, 1H), 7.50 (m, 1H), 7.35 (m, 2H), 7.13 (m, 1H), 4.22 (m, 2H), 3.73 (m, 4H), 2.88 (m, 2H), 2.66 (m, 4H), 2.44 (s, 3H), 2.38 (s, 3H); MS(ESI⁺) m/z 262.3 (M+H)⁺.

Example 39

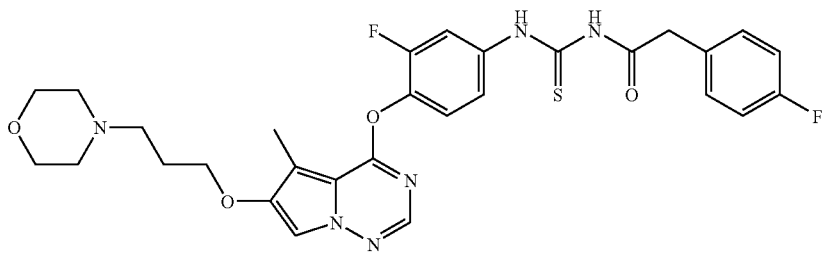

1-(3-Fluoro-4-(5-methyl-6-(3-morpholinopropoxy) pyrrolo[2,1-f][1,2,4]triazin -4 yloxy)phenyl)-3-(2-(4-fluorophenyl)acetyl)thiourea, hydrochloride salt

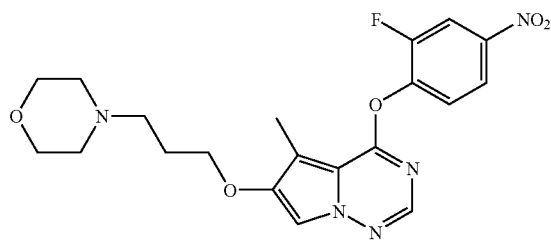

A) 4-(2-Fluoro-4-nitrophenoxy)-5-methyl-6-(3-morpholinopropoxy)pyrrolo[2,1-f][1,2,4]triazine Following a procedure similar to that for the synthesis of Compound B of Example 36, 4-(2-fluoro-4-nitrophenoxy)-5-methylpyrrolo[2,1-f][1,2,4]triazin-6-ol (50 mg, 0.16 mmol, Compound A of Example 36) was converted to the title compound (32 mg, 46%). MS(ESI⁺) m/z 432.2 (M+H)⁺.

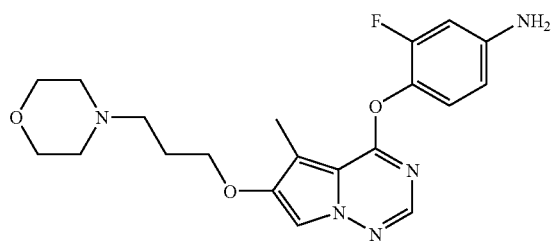

B) 3-Fluoro-4-(5-methyl-6-(3-morpholinopropoxy) pyrrolo[2,1-f][1,2,4]triazin-4-yloxy)benzenamine Following a procedure similar to that for the synthesis of Compound C of Example 36, 4-(2-fluoro-4-nitrophenoxy)-5-methyl-6-(3-morpholinopropoxy)pyrrolo[2,1-f][1,2,4]triazine (31 mg, 0.072 mmol) was converted to the title compound (28 mg, 95%). MS(ESI⁺) m/z 402.3 (M+H)⁺.

C) 1-(3-Fluoro-4-(5-methyl-6-(3-morpholinopropoxy)pyrrolo[2,1-f][1,2,4]triazin-4-yloxy)phenyl)-3-(2-(4-fluorophenyl)acetyl)thiourea, hydrochloride salt Following a procedure similar to Compound D of Example 36, 3-fluoro-4-(5-methyl-6-(3-morpholinopropoxy)pyrrolo[2,1-f][1,2,4]triazin-4-yloxy)benzenamine (28 mg, 0.07 mmol) was converted to the title compound (30 mg, 68%) as a HCl salt. $^1$H NMR (DMSO-d$_6$) 12.45 (s, 1H), 11.80 (s, 1H), 11.65 (br s, 1H), 8.00 (s, 2H), 790 (d, 1H), 7.50 (m, 2H), 7.40 (m, 2H), 7.25 (m, 2H), 3.10-4.10 (m, 16H), 2.40 (s, 3H); MS(ESI⁺) m/z 597.2 (M+H)⁺.

Example 40

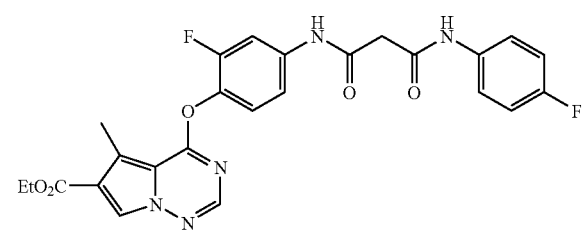

Ethyl 4-(2-fluoro-4-(3-(4-fluorophenylamino)-3-oxopropanamido)phenoxy)-5-methylpyrrolo[2,1-f] [1,2,4]triazine-6-carboxylate Following a procedure similar to that for the synthesis of Compound D of Example 36, ethyl 4-(4-amino-2-fluorophenoxy)-5-methylpyrrolo[2,1-f][1,2,4]triazine-6-carboxylate (70 mg, 0.21 mmol, Compound B of Example 6) was converted to the title compound (50 mg, 47%). $^1$H NMR (DMSO-d$_6$) δ 10.50 (s, 1H), 10.30 (s, 1H), 8.45 (s, 1H), 8.16 (s, 1H), 7.90 (d, 1H), 7.67 (m, 2H), 7.51 (t, 1H), 7.40 (t, 1H), 7.20 (m, 2H), 4.33 (q, 2H), 3.52 (s, 2H), 2.77 (s, 3H), 1.35 (t, 3H); MS(ESI⁺) m/z 510.1 (M+H)⁺.

Example 41

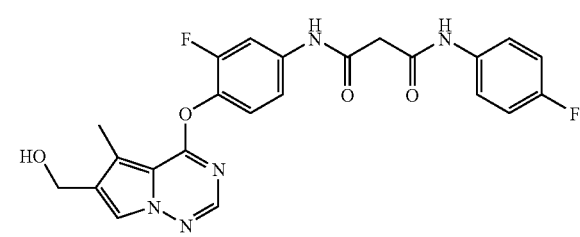

N¹-(3-Fluoro-4-(6-(hydroxymethyl)-5-methylpyrrolo [2,1-f][1,2,4]triazin-4-yloxy)phenyl)-N³-(4-fluorophenyl)malonamide To a solution of ethyl 4-(2-fluoro-4-(3-(4-fluorophenylamino)-3-oxopropanamido)phenoxy)-5-methylpyrrolo[2,1-f][1,2,4]triazine-6-carboxylate (66 mg, 0.13 mmol, Example 40) in 20 mL of THF at −78° C. was added DIBAL-H (1 M, 1.65 mL). The reaction mixture was allowed to stir at −78° C. for 1 h and then at room temperature for 2 h. At that time, HPLC analysis indicated the completion of the reaction. The reaction was quenched with 4 mL of MeOH, followed by addition of 4 mL of H$_2$O. The mixture was allowed to stir for 0.5 h and then Na$_2$SO$_4$ was added. The stirring was continued for 1 h. Filtration and concentration gave rise to the title compound (50 mg, 82%). $^1$H NMR (CD$_3$OD) δ 7.70 (m, 3H), 7.50 (m, 2H), 7.25 (m, 2H), 7.00 (m, 2H), 4.60 (s, 2H), 3.45 (s, 2H), 2.50 (s, 3H); MS(ESI⁺) m/z 468.2 (M+H)⁺.

Example 42

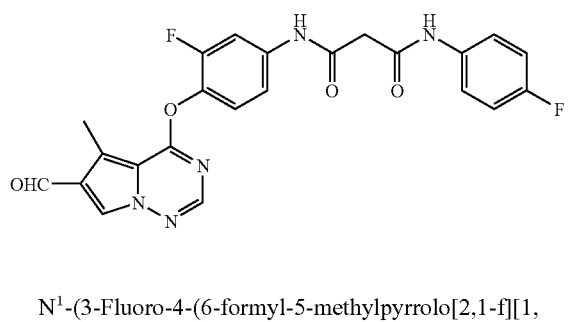

N¹-(3-Fluoro-4-(6-formyl-5-methylpyrrolo[2,1-f][1,2,4]triazin-4-yloxy)phenyl) N³-(4-fluorophenyl)malonamide To a solution of N¹-(3-fluoro-4-(6-(hydroxymethyl)-5-methylpyrrolo[2,1-f][1,2,4]triazin-4-yloxy)phenyl)-N³-(4-fluorophenyl)malonamide (12 mg, 0.026 mmol, Example 41) in 1 mL of THF was added Dess-Martin periodinane (48 mg, 0.11 mmol, Aldrich) at room temperature. The mixture was allowed to stir for 2 h and HPLC analysis indicated total consumption of the starting material. The mixture was filtered through a plug of SiO$_2$, washed with EtOAc. The organic solvent was then removed under reduced pressure and the residue was purified on preparative HPLC to afford the title compound (10 mg, 83%). MS(ESI⁺) m/z 466.2 (M+H)⁺.

Example 43

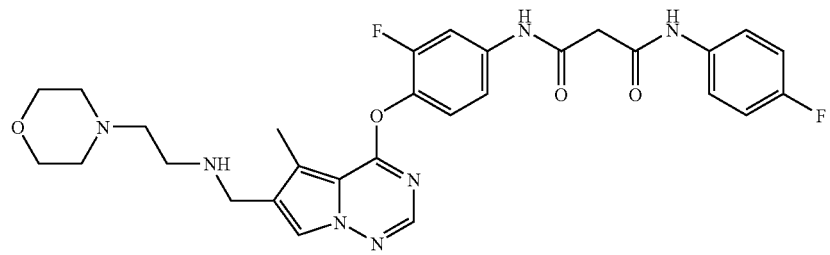

N¹-(3-Fluoro-4-(5-methyl-6-((2-morpholinoethylamino)methyl)pyrrolo[2,1-f][1,2,4]triazin-4-yloxy)phenyl)-N³-(4-fluorophenyl)malonamide, bis-trifluoroacetic acid salt To a solution of N¹-(3-fluoro-4-(6-formyl-5-methylpyrrolo[2,1-f][1,2,4]triazin-4-yloxy)phenyl)-N³-(4-fluorophenyl)malonamide. (15 mg, 0.032 mmol, Example 42) in 1 mL of DMF were added 2-morpholinoethanamine (21 mg, 0.16 mmol), DIEA (0.04 mL) and NaBH(OAc)$_3$ (52 mg, 0.2 mmol). The mixture was allowed to stir at room temperature for 4 days. HPLC analysis and LC-MS analysis indicated formation of the product. The solution was then dissolved in MeOH and purified by preparative HPLC to give the title compound (4 mg, 21%) as a 2.TFA salt. ¹H NMR (CD$_3$OD) δ 7.92 (s, 1H), 7.82 (s, 1H), 7.70 (d, 1H), 7.50 (m, 2H), 7.28 (m, 2H), 6.98 (m, 2H), 4.31 (s, 2H), 3.68 (s, 4H), 3.20 (m, 4H), 2.82 (m, 2H), 2.65 (s, 4H), 2.56 (s, 3H); MS(ESI⁺) m/z 580.2 (M+H)⁺.

Example 44

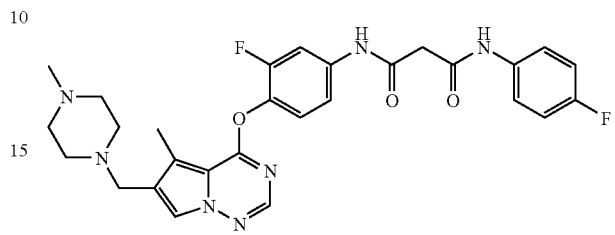

N¹-(3-Fluoro-4-(5-methyl-6-((4-methylpiperazin-1-yl)methyl)pyrrolo[2,1-f][1,2,4]triazin-4-yloxy)phenyl)-N³-(4-fluorophenyl)malonamide, bis-trifluoroacetic acid salt Following a procedure similar to that for the synthesis of Example 43, N¹-(3-fluoro-4-(6-formyl-5-methylpyrrolo[2,1-f][1,2,4]triazin-4-yloxy)phenyl)-N³-(4-fluorophenyl)malonamide (15 mg, 0.032 mmol, Example 42) was converted to the title compound (4 mg, 23%) as a 2.TFA salt. MS(ESI⁺) m/z 550.2 (M+H)⁺.

Example 45

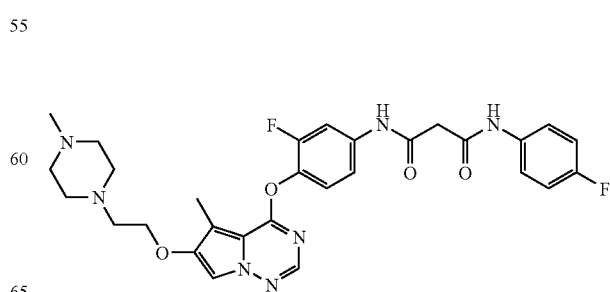

N¹-(3-Fluoro-4-(5-methyl-6-(2-(4-methylpiperazin-1-yl)ethoxy)pyrrolo[2,1-f][1,2,4]triazin-4-yloxy)phenyl)-N³-(4-fluorophenyl)malonamide, bis hydrochloride salt

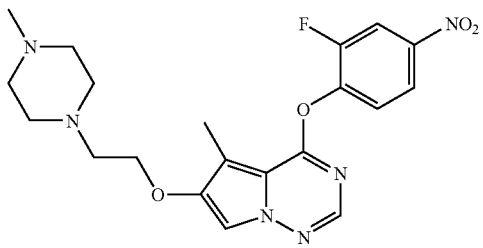

A) 4-(2-Fluoro-4-nitrophenoxy)-5-methyl-6-(2-(4-methylpiperazin-1-yl)ethoxy)pyrrolo[2,1-f][1,2,4]triazine Following a procedure similar to that for the synthesis of Compound B of Example 36, 4-(2-fluoro-4-nitrophenoxy)-5-methylpyrrolo[2,1-f][1,2,4]triazin-6-ol (55 mg, 0.18 mmol, Compound A of Example 36), 2-morpholinoethanol (304 mg, 1.0 mmol) was converted to the title compound (352 mg, 82%). MS(ESI⁺) m/z 431.2 (M+H)⁺.

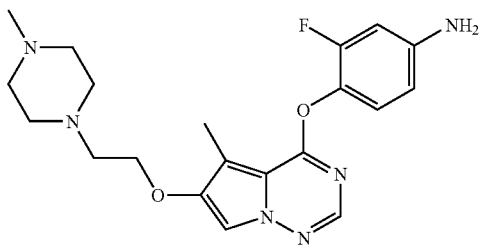

B) 3-Fluoro-4-(5-methyl-6-(2-(4-methylpiperazin-1-yl)ethoxy)pyrrolo[2,1-f][1,2,4]triazin-4-yloxy)benzenamine Following a procedure similar to that for the synthesis of Compound C of Example 36, 4-(2-fluoro-4-nitrophenoxy)-5-methyl-6-(2-(4-methylpiperazin-1-yl)ethoxy)pyrrolo[2,1-f][1,2,4]triazine (2.90 g, 6.74 mmol) was converted to the title compound (1.38 g, 51%). MS(ESI⁺) m/z 401.3 (M+H)⁺.

C) N¹-(3-Fluoro-4-(5-methyl-6-(2-(4-methylpiperazin-1-yl)ethoxy)pyrrolo[2,1-f][1,2,4]triazin-4-yloxy)phenyl)-N³-(4-fluorophenyl)malonamide, bis-hydrochloride salt Following a procedure similar to that for the synthesis of Compound D of Example 36, 3-fluoro-4-(5-methyl-6-(2-(4-methylpiperazin-1-yl)ethoxy)pyrrolo[2,1-f][1,2,4]triazin-4-yloxy)benzenamine (60 mg, 0.15 mmol) was converted the title compound (30 mg, 46%) as a 2.HCl salt. ¹H NMR (DMSO-d₆) δ 10.63 (s, 1H), 10.37 (s, 1H), 8.04 (s, 1H), 7.99 (s, 1H), 7.80 (d, 1H), 7.61 (m, 2H), 7.40 (m, 2H), 7.16 (m, 2H), 4.42 (br s, 2H), 3.38-3.60 (m, 10H), 2.81 (s, 3H), 2.40 (s, 3H);). MS(ESI⁺) m/z 580.3 (M+H)⁺.

Example 46

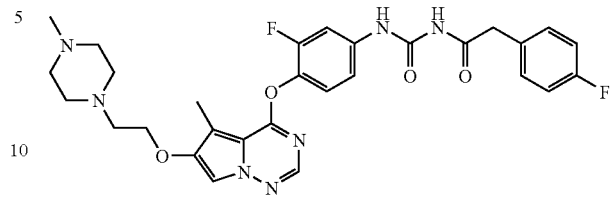

1-(3-Fluoro-4-(5-methyl-6-(2-(4-methylpiperazin-1-yl)ethoxy)pyrrolo[2,1-f][1,2,4]triazin-4-yloxy)phenyl)-3-(2-(4-fluorophenyl)acetyl)urea, bis-hydrochloride salt To a solution of 3-fluoro-4-(5-methyl-6-(2-(4-methylpiperazin-1-yl)ethoxy)pyrrolo[2,1-f][1,2,4]triazin-4-yloxy)benzenamine (20 mg, 0.05 mmol, Compound B of Example 45) in 1 mL of THF at room temperature was added a solution of 2-(4-fluorophenyl)acetyl isocyanate in toluene (0.36 M, 0.18 mL, Compound C of Example 4) and the solution was allowed to stir overnight. HPLC analysis and LC-MS analysis indicated the completion of the reaction and the organic solvent was thus removed under reduced pressure. The residue was purified on preparative HPLC. The title compound (15 mg, 46%) was finally obtained as a 2.HCl salt after a work-up similar to that described for Compound D of Example 36. ¹H NMR (DMSO-d₆) δ 11.02 (s, 1H), 10.58 (s, 1 if), 8.04 (s, 1H), 7.99 (s, 1H), 7.70(d, 1H), 7.35 (m, 4H), 7.16 (m, 2H), 4.44 (br.s, 2H), 3.40–3.70 (m, 12H), 2.81 (s, 3H), 2.39 (s, 3H); MS(ESI⁺) m/z 580.1 (M+H)⁺.

Example 47

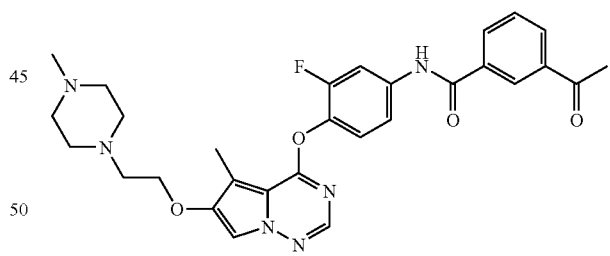

3-Acetyl-N-(3-fluoro-4-(5-methyl-6-(2-(4-methylpiperazin-1-yl)ethoxy)pyrrolo[2,1-f][1,2,4]triazin-4-yloxy)phenyl)benzamide, bis-hydrochloride salt Following a procedure similar to that for the synthesis of Compound D of example 36, 3-fluoro-4-(5-methyl-6-(2-(4-methylpiperazin-1-yl)ethoxy)pyrrolo[2,1-f][1,2,4]triazin-4-yloxy)benzenamine (20 mg, 0.05 mmol, Compound B of Example 45) was converted to the title compound (11 mg, 35%) as a 2.HCl salt. ¹H NMR (CD₃OD) δ 8.20 (m, 1H), 7.90 (m, 2H), 7.84 (s, 1H), 7.80 (s, 1H), 7.70 (m, 1H), 7.50 (m, 2H), 7.32 (m, 1H), 4.54 (m, 2H), 3.60-4.10 (m, 10H), 3.08 (s, 3H), 2.50 (s, 3H); MS(ESI⁺) m/z 547.2 (M+H)⁺.

Example 48

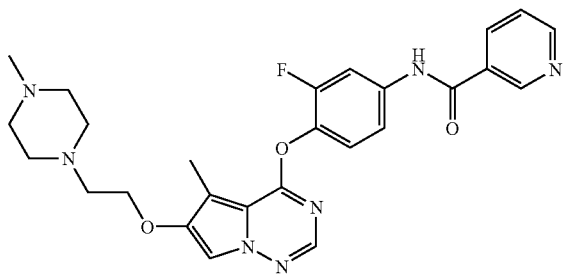

N-(3-Fluoro-4-(5-methyl-6-(2-(4-methylpiperazin-1-yl)ethoxy)pyrrolo[2,1-f][1,2,4]triazin-4-yloxy)phenyl)nicotinamide, tris hydrochloride salt Following a procedure similar to that for the synthesis of Compound D of Example 36,3-fluoro-4-(5-methyl-6-(2-(4-methylpiperazin-1-yl)ethoxy)pyrrolo[2,1-f][1,2,4]triazin-4-yloxy)benzenamine (20 mg, 0.05 mmol, Compound B of Example 45) was converted the tile compound (10 mg, 32%) as a 3.HCl salt. $^1$H NMR (CD$_3$OD) δ 9.46 (s, 1H), 9.20 (d, 1H), 9.08 (d, 1H), 8.29 (m, 1H), 7.92 (d, 1H), 7.81 (s, 1H), 7.82 (s, 1H), 7.61 (m, 1H), 7.42 (m, 1H), 4.54 (m, 2H), 3.82–4.05 (m, 10H), 3.05 (s, 3H), 2.51 (s, 3H); MS(ESI$^+$) m/z 506.2 (M+H)$^+$.

Example 49

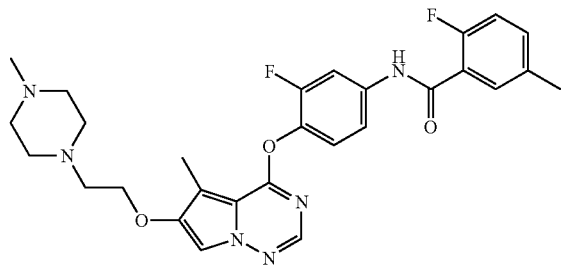

2-Fluoro-N-(3-fluoro-4-(5-methyl-6-(2-(4-methylpiperazin-1-yl)ethoxy)pyrrolo[2,1-f][1,2,4]triazin-4-yloxy)phenyl)-5-methylbenzamide, bis-hydrochloride salt Following a procedure similar to that for the synthesis of Compound D of Example 36, 3-fluoro-4-(5-methyl-6-(2-(4-methylpiperazin-1-yl)ethoxy)pyrrolo[2,1-f][1,2,4]triazin-4-yloxy)benzenamine (20 mg, 0.05 mmol, Compound B of Example 45) was converted to the title compound (8 mg, 26% yield) as a 2.HCl salt. $^1$H NMR (CD$_3$OD) δ 7.85 (d, 1H), 7.85 (s, 1H), 7.80 (s, 1H), 7.55 (m, 1H), 7.50 (m, 1H), 7.33 (m, 2H), 7.13 (t, 1H), 4.54 (m, 2H), 3.70–4.10 (m, 10H), 3.04 (s, 3H), 2.50 (s, 3H), 2.37 (s, 3H); MS(ESI$^+$) m/z 537.2 (M+H)$^+$.

Example 50

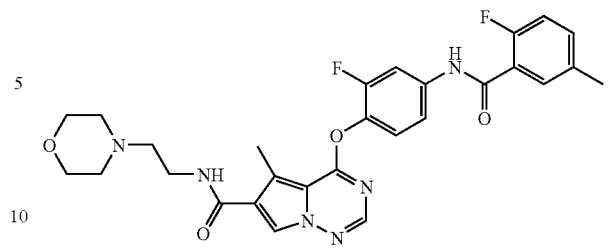

4-(2-Fluoro-4-(2-fluoro-5-methylbenzamido)phenoxy)-5-methyl-N-(2-morpholinoethyl)pyrrolo[2,1-f][1,2,4]triazine-6-carboxamide, hydrochloride salt

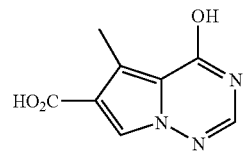

A) 4-Hydroxy-5-methylpyrrolo[2,1-1][1,2,4]triazine-6-carboxylic acid

To a solution of ethyl 4-hydroxy-5-methylpyrrolo[2,1-f][1,2,4]triazine-6-carboxylate (442 mg, 2.0 mmol) (see example 6 of U.S. Pat. App. 2003/0186982, the disclosure of which is herein incorporated by reference) in 10 mL of THF was added a solution of NaOH (1 N, 6.0 mL). The mixture was heated at 60° C. overnight and HPLC analysis indicated the completion of the reaction. After cooling down, the solution was neutralized with 6.0 mL of 1 N HCl. The organic solvent was then removed and the solid was collected after filtration to the title compound (350 mg, 91%). MS(ESI$^+$) m/z 194.2 (M+H)$^+$.

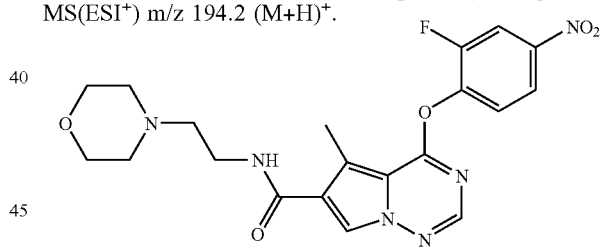

B) 4-(2-Fluoro-4-nitrophenoxy)-5-methyl-N-(2-morpholinoethyl)pyrrolo[2,1-f][1,2,4]triazine-6-carboxamide A suspension of 4-hydroxy-5-methylpyrrolo[2,1-f][1,2,4]triazine-6-carboxylic acid (100 mg, 0.52 mmol) in 2 mL of POCl$_3$ was heated at 110° C. for 4 h. The suspension became a clear solution and the excess of POCl$_3$ was removed with toluene. The residue was then dissolved in 5 mL of acetonitrile at 0° C. To this solution were added Et$_3$N (0.72 mL, 5.2 mmol) and 2-morpholinoethanamine (0.13 mL, 1.04 mmol). The mixture was stirred for 0.5 h and HPLC analysis indicated the formation of the product. The solution was then diluted with EtOAc and washed with H$_2$O and brine. The organic layer was dried over MgSO$_4$. After filtration and concentration, the crude material was carried to the next reaction.

The crude material was dissolved in 2 mL of acetonitrile and to it were added 2-fluoro-4-nitrophenol (94 mg, 0.60 mmol) and DABCO (78 mg, 0.70 mmol). The reaction was allowed to stir for 1 h and HPLC analysis indicated the completion of the reaction. After concentration, the residue was purified on preparative HPLC to give the title compound (75 mg, 33%). MS(ESI+) m/z 445.2 (M+H)+.

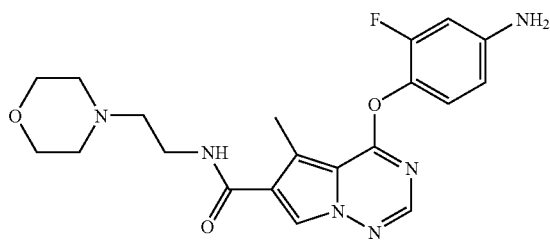

C) 4-(4-Amino-2-fluorophenoxy)-5-methyl-N-(2-morpholinoethyl)pyrrolo[2,1-f][1,2,4]triazine-6-carboxamide Following a procedure similar to that for the synthesis of Compound C of Example 36, 4-(2-fluoro-4-nitrophenoxy)-5-methyl-N-(2-morpholinoethyl)pyrrolo[2,1-f][1,2,4]triazine-6-carboxamide (75 mg, 0.17 mmol) was converted to the title compound (65 mg, 92%). LCMS(ESI+) m/z 415.3 (M+H)+.

D) 4-(2-Fluoro-4-(2-fluoro-5-methylbenzamido)phenoxy)-5-methyl-N-(2-morpholinoethyl)pyrrolo[2,1-f][1,2,4]triazine-6-carboxamide, hydrochloride salt To a solution of 4-(4-amino-2-fluorophenoxy)-5-methyl-N-(2-morpholinoethyl)pyrrolo[2,1-f][1,2,4]triazine-6-carboxamide (25 mg, 0.06 mmol) in 1 mL of THF were added Et$_3$N (0.2 mL) and a solution of 2-fluoro-5-methylbenzoyl chloride (20 mg, 0.11 mmol) in 1 mL of THF at room temperature. The mixture was allowed to stir for 1 h and HPLC analysis indicated the consumption of the starting material. The reaction was quenched with MeOH. The solution was then concentrated in vacuo and the residue was purified by preparative HPLC to give the title compound (8.0 mg, 23%) as a HCl salt. $^1$H NMR (CD$_3$OD) δ 8.48 (d, 1H), 7.83 (m, 3H), 7.28 (m, 3H), 7.00 (m, 1H), 2.90–4.00 (m, 12H), 2.76 (s, 3H), 2.33 (s, 3H); MS(ESI+) m/z 551.2 (M+H)+.

Example 51

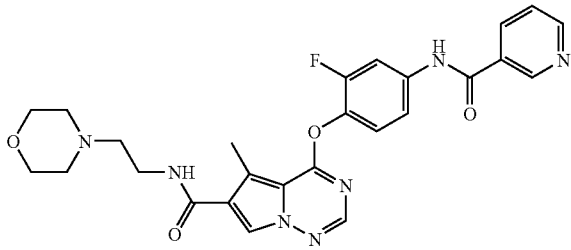

4-(2-Fluoro-4-(nicotinamido)phenoxy)-5-methyl-N-(2-morpholinoethyl)pyrrolo[2,1-f][1,2,4]triazine-6-carboxamide, bis-hydrochloride salt Following a procedure similar to that for the synthesis of Compound D of Example 50, 4-(4-amino-2-fluorophenoxy)-5-methyl-N-(2-morpholinoethyl)pyrrolo[2,1-f][1,2,4]triazine-6-carboxamide (30 mg, 0.07 mmol, Compound C of Example 50) was converted the title compound (16 mg, 39%) as a 2.HCl salt. $^1$H NMR (CD$_3$OD) δ 9.08 (s, 1H), 8.70 (s, 1H), 8.44 (s, 1H), 8.17 (s, 1H), 7.87 (m, 2H), 7.38 (m, 2H), 7.22 (m, 2H), 3.82 (s, 4H), 3.61 (m, 2H), 2.75 (m, 9H); MS(ESI+) m/z 520.2 (M+H)+.

Example 52

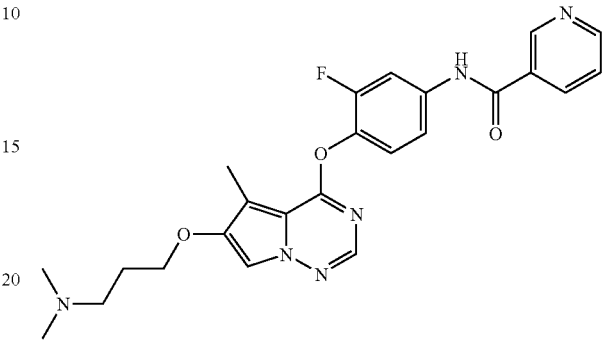

N-(4-(6-(3-(Dimethylamino)propoxy)-5-methylpyrrolo[2,1-f][1,2,4]triazin-4-yloxy)-3-fluorophenyl)nicotinamide, dihydrochloride salt 4-(6-(3-(Dimethylamino)propoxy)-5-methylpyrrolo[2,1-f][1,2,4]triazin-4-yloxy)-3-fluorobenzenamine (54 mg, 0.15 mmol, Compound B of Example 32) as converted to the title compound (8.7 mg, 11%) in a manner similar to the preparation of Compound D of Example 36. $^1$H NMR (CD$_3$OD) δ 9.47 (s, 1H), 9.20–9.19 (m, 1H), 9.08–9.07 (m, 1H), 8.30–8.27 (m, 1H), 7.97–7.93 (m, 1H), 7.82 (s,1H), 7.72 (s, 1H), 7.64–7.61 (m, 1H), 7.43–7.39 (m, 1H), 4.26–4.11 (m, 2H), 3.43–3.39 (m, 2H), 2.98 (s, 6H), 2.46 (s, 3H), 2.34–2.30 (m, 2H); HRMS(ESI), 463.1894 (M–H)− calc, 463.1905 (M–H)− found.

Example 53

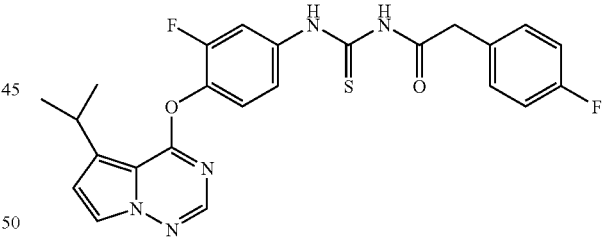

1-(3-Fluoro-4-(5-isopropyl-3,4-dihydropyrrolo[2,1-f][1,2,4]triazin-4-yloxy)phenyl)-3-(2-(4-fluorophenyl)acetyl)thiourea

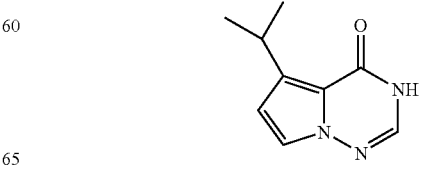

A) 5-Isopropylpyrrolo[2,1-f][1,2,4]triazin-4 (3H)-one

5-Isopropyl-4-oxo-3,4-dihydropyrrolo[2,1-f][1,2,4]triazine-6-carboxylic acid (0.025 g, 1.13 mmol, 1.0 equiv, prepared in a manner similar to that described in patent application: US 2004/063708, herein incorporated by reference in its entiretyz) was added to polyphosphoric acid (5.0 g) and the reaction mixture was heated to 160° C. for 1 h. The reaction was cooled to room temperature and quenched with water (50 ml). The solution was extracted with ethyl acetate (3×50 ml), the combined organic fractions washed with sat NaHCO$_3$ (1×100 ml), dried (Na$_2$SO$_4$), filtered and concentrated in vacuo. Purification by silica gel (Merck KGaA, 230–400 mesh particle size) flash chromatography, eluting with 3/1 ethyl acetate/hexane, afforded the title compound (0.060 g, 30%). MS(ESI$^-$) m/z 176 (M−H)$^-$; HRMS(ESI), 176.0824 (M−H)$^-$ calc, 176.0818(M−H)$^-$ found.

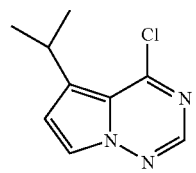

B) 4-Chloro-5-isopropylpyrrolo[2,1-f][1,2,4]triazine

5-Isopropylpyrrolo[2,1-f][1,2,4]triazin-4 (3H)-one (0.035 g, 0.198 mmol, 1.0 equiv) was added to phosphorous oxychloride (2.0 ml, 21.5 mmol, 109 equiv) under a nitrogen atmosphere. The reaction mixture was heated to reflux for 1.5 h. The mixture was cooled to room temperature then concentrated in vacuo. The residue was partitioned between ethyl acetate and saturated aqueous sodium bicarbonate. The aqueous layer was extracted twice with ethyl acetate. The combined organic washes were dried over anhydrous magnesium sulfate and concentrated in vacuo to yield a tan solid that was used in the next step without further purification. MS(ESI$^+$) m/z 196 (M+H)$^+$.

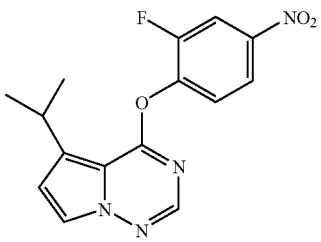

C) 4-(2-Fluoro-4-nitrophenoxy)-5-isopropyl-3,4-dihydropyrrolo[2,1-f][1,2,4]triazine To a mixture of 4-chloro-5-isopropylpyrrolo[2,1-f][1,2,4]triazine (0.038 g, 0.194 mmol, 1.0 equiv) and 2-fluoro-4-nitrophenol (0.062 g, 0.388 mmol, 2.0 equiv) in anhydrous CH$_3$CN (2 mL), stirred for five minutes under a nitrogen atmosphere then was added DABCO (0.044 g, 0.388 mmol, 2.0 equiv) and the reaction mixture was heated at 50° C. for 2 h. The mixture was cooled to room temperature and quenched with 1 N HCl. The solution was extracted with CH$_2$Cl$_2$ (3×30 ml), the combined organic extracts dried over anhydrous magnesium sulfate, filtered and concentrated in vacuo. The residue was purified by silica gel (Merck KGaA, 230–400 mesh particle size) flash chromatography, eluting with 2/1 hexane/ethyl acetate, afforded the title compound (0.048 g, 79%). $^1$H NMR (CDCl$_3$) δ 8.07–8.13 (m, 2H), 7.77 (s, 1H), 7.68–7.69 (m, 1H), 7.46–7.50 (m, 1H), 6.71–6.72 (m, 1H), 3.53–3.56 (m, 1H), 1.29–1.31 (m, 6H); HRMS (ESI), calc, 317.1050 (M+H)$^+$ found, 317.1039.

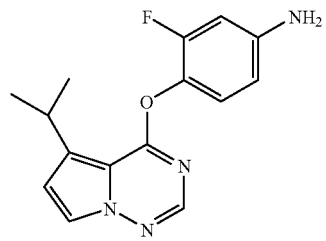

D) 3-Fluoro-4-(5-isopropyl-3,4-dihydropyrrolo[2,1-f][1,2,4]triazin-4-yloxy)benzenamine To a heterogeneous mixture of 4-(2-fluoro-4-nitrophenoxy)-5-isopropyl-3,4-dihydropyrrolo[2,1-f][1,2,4]triazine (0.044 g, 1.39 mmol, 10 equiv) in 1/1 anhydrous methanol/tetrahydrofuran (2 mL), at ambient temperature under nitrogen atmosphere, was added zinc dust (0.090 g, 0.139 mmol, 1.0 equiv) and ammonium chloride (0.075 g, 1.39 mmol, 10 equiv). The mixture was stirred for 4 h before the catalyst was filtered off and the filtrate was concentrated in vacuo to yield the title compound (0.040 g, 100%) as a solid, that was used without further purification. HRMS(ESI), 287.1308 (M+H)$^+$ calc, 287.1300 (M+H)$^+$ found.

E) 1-(3-Fluoro-4-(5-isopropyl-3,4-dihydropyrrolo[2,1-f][1,2,4]triazin-4-yloxy)phenyl)-3-(2-(4-fluorophenyl)acetyl)thiourea To a homogeneous solution of sodium thiocyanate (0.037 g, 0.46 mmol, 3.3 equiv) in ethyl acetate (1 mL), at room temperature under a nitrogen atmosphere, was added 4-fluorophenyl-acetyl chloride (0.048 ml, 0.35 mmol, 2.5 equiv). The mixture was stirred for 2 h before being added directly to a homogeneous solution of 3-fluoro-4-(5-isopropyl-3,4-dihydropyrrolo[2,1-f][1,2,4]triazin-4-yloxy)benzenamine (0.040 g, 0.139 mmol, 1.0 equiv) in anhydrous 1/1 THF/dichloromethane (3 mL), under a nitrogen atmosphere. The reaction mixture was stirred at ambient temperature for 16 h before being quenched with 1 N HCl. The solution was extracted with CH$_2$Cl$_2$ (3×50 ml), the combined organic fractions washed with 1 N NaOH (50 ml), dried (Na$_2$SO$_4$), filtered and concentrated in vacuo. Purification by silica gel (Merck KGaA, 230–400 mesh particle size) flash chromatography, eluting with 4/1 hexane/ethyl acetate, afforded the title compound (0.050 g, 75%). $^1$H NMR (CDCl$_3$) δ 12.34 (s, 1H), 8.47 (m, 1H), 7.65–7.78 (m, 2H), 7.63–7.64 (m, 1H), 7.19–7.32 (m, 4H) 703–7.08 (m, 2H), 6.66–6.67 (m, 1H), 3.65 (s, 2H), 3.40–3.50 (m, 1H), 1.28–1.30 (m, 6H); HRMS(ESI) 482.1462, calc, (M+H)$^+$ 482.1461 found. Elemental Analysis: C$_{24}$H$_{21}$N$_5$O$_2$SF$_2$. 0.23 H$_2$O. calc: C, 59.35; H, 4.45, N, 14.42, found. C, 59.36; H, 4.44; N, 14.03.

Examples 54 to 85

Examples 54 to 85 illustrated in Table 1 below were synthesized from 3-fluoro-4-(5-methylpyrrolo[2,1-f][1,2,4]triazin-4-yloxy)benzenamine (Compound B of Example 28)

using one equivalent of the corresponding carboxylic acid, (1 eq) PyBrOP (1 eq), DIEA (1 eq) in DMF. The reaction mixture was heated to 70° C. and the crude products were purified by preparative HPLC (H₂O/MeOH/0.1% TFA, gradient 35–90% MeOH over 10 min, 20×100 mm 5 μm YMC ODS-A column) utilizing mass-directed fractionation. The purified sample was reconstituted in 1:1/MeOH:DCE, transferred to a tared 2.5 mL plastic microtube, dried via centrifugal evaporation, weighed and analyzed by LCMS (H₂O/MeOH/0.1% TFA).

TABLE 1

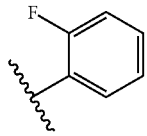

| Example # | R | Compound Name | LC/MS (M + H)⁺ |
|---|---|---|---|
| 54 | Ph | N-(3-Fluoro-4-(5-methylpyrrolo[2,1-f][1,2,4]triazin-4-yloxy)phenyl)benzamide | 363.4 |
| 55 | 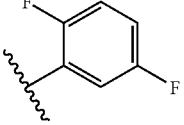 | 2-Fluoro-N-(3-fluoro-4-(5-methylpyrrolo[2,1-f][1,2,4]triazin-4-yloxy)phenyl)benzamide | 381.4 |
| 56 | 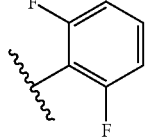 | 2,5-Difluoro-N-(3-fluoro-4-(5-methylpyrrolo[2,1-f][1,2,4]triazin-4-yloxy)phenyl)benzamide | 399.3 |
| 57 | 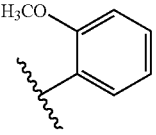 | 2,6-Difluoro-N-(3-fluoro-4-(5-methylpyrrolo[2,1-f][1,2,4]triazin-4-yloxy)phenyl)benzamide | 399.3 |
| 58 | 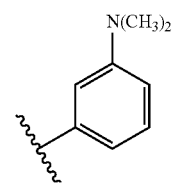 | N-(3-Fluoro-4-(5-methylpyrrolo[2,1-f][1,2,4]triazin-4-yloxy)phenyl)-2-methoxybenzamide | 393.4 |
| 59 | 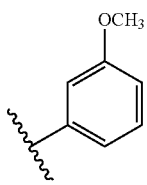 | 3-(Dimethylamino)-N-(3-fluoro-4-(5-methylpyrrolo[2,1-f][1,2,4]triazin-4-yloxy)phenyl)benzamide | 406.4 |
| 60 |  | N-(3-Fluoro-4-(5-methylpyrrolo[2,1-f][1,2,4]triazin-4-yloxy)phenyl)-3-methoxybenzamide | 393.4 |

TABLE 1-continued

| Example # | R | Compound Name | LC/MS (M + H)+ |
|---|---|---|---|
| 61 | 4-CN-phenyl | 4-Cyano-N-(3-fluoro-4-(5-methylpyrrolo[2,1-f][1,2,4]triazine-4-yloxy)phenyl)benzamide | 388.4 |
| 62 | 4-F-phenyl | 4-Fluoro-N-(3-fluoro-4-(5-methylpyrrolo[2,1-f][1,2,4]triazin-4-yloxy)phenyl)benzamide | 381.4 |
| 63 | 4-Cl-phenyl | 4-Chloro-N-(3-fluoro-4-(5-methylpyrrolo[2,1-f][1,2,4]triazin-4-yloxy)phenyl)benzamide | 397.8 |
| 64 | 4-N(CH$_3$)$_2$-phenyl | 4-(Dimethylamino)-N-(3-fluoro-4-(5-methylpyrrolo[2,1-f][1,2,4]triazin-4-yloxy)phenyl)benzamide | 406.4 |
| 65 | 4-SCH$_3$-phenyl | N-(3-Fluoro-4-(5-methylpyrrolo[2,1-f][1,2,4]triazin-4-yloxy)phenyl)-4-(methylthio)benzamide | 409.5 |
| 66 | furan-2-yl | N-(3-Fluoro-4-(5-methylpyrrolo[2,1-f][1,2,4]triazin-4-yloxy)phenyl)furan-2-carboxamide | 353.3 |
| 67 | naphthalen-1-yl | N-(3-Fluoro-4-(5-methylpyrrolo[2,1-f][1,2,4]triazin-4-yloxy)phenyl)-1-naphthamide | 413.4 |
| 68 | thiophen-3-yl | N-(3-Fluoro-4-(5-methylpyrrolo[2,1-f][1,2,4]triazin-4-yloxy)phenyl)thiophene-3-carboxamide | 369.4 |

TABLE 1-continued

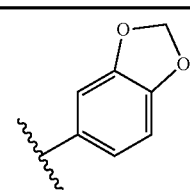

| Example # | R | Compound Name | LC/MS (M + H)+ |
|---|---|---|---|
| 69 | 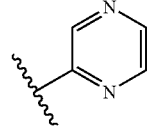 | N-(3-Fluoro-4-(5-methylpyrrolo[2,1-f][1,2,4]triazin-4-yloxy)phenyl)benzo[d][1,3]dioxide-5-carboxamide | 407.4 |
| 70 | 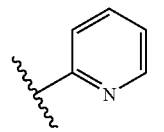 | N-(3-Fluoro-4-(5-methylpyrrolo[2,1-f][1,2,4]triazin-4-yloxy)phenyl)pyrazine-2-carboxamide | 365.3 |
| 71 | 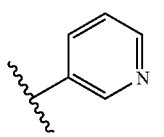 | N-(3-Fluoro-4-(5-methylpyrrolo[2,1-f][1,2,4]triazin-4-yloxy)phenyl)picolinamide | 364.4 |
| 72 | 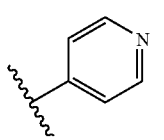 | N-(3-Fluoro-4-(5-methylpyrrolo[2,1-f][1,2,4]triazin-4-yloxy)phenyl)nicotinamide | 364.4 |
| 73 | 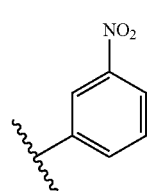 | N-(3-Fluoro-4-(5-methylpyrrolo[2,1-f][1,2,4]triazin-4-yloxy)phenyl)isonicotinamide | 364.4 |
| 74 | 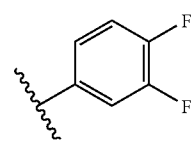 | N-(3-Fluoro-4-(5-methylpyrrolo[2,1-f][1,2,4]triazin-4-yloxy)phenyl)-3-nitrobenzamide | 408.4 |
| 75 | 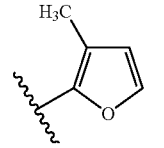 | 3,4-Difluoro-N-(3-fluoro-4-(5-methylpyrrolo[2,1-f][1,2,4]triazin-4-yloxy)phenyl)benzamide | 399.3 |
| 76 |  | N-(3-Fluoro-4-(5-methylpyrrolo[2,1-f][1,2,4]triazin-4-yloxy)phenyl)-3-methylfuran-2-carboxamide | 367.4 |

TABLE 1-continued

| Example # | R | Compound Name | LC/MS (M + H)+ |
|---|---|---|---|
| 77 | COCH₃ (3-acetylphenyl) | 3-Acetyl-N-(3-fluoro-4-(5-methylpyrrolo[2,1-f][1,2,4]triazin-4-yloxy)phenyl)benzamide | 405.4 |
| 78 | 3,5-dimethylisoxazol-4-yl | N-(3-Fluoro-4-(5-methylpyrrolo[2,1-f][1,2,4]triazin-4-yloxy)phenyl)-3,5-dimethylisoxazole-4-carboxamide | 382.4 |
| 79 | 2-(pyridin-3-yl)thiazol-4-yl | N-(3-Fluoro-4-(5-methylpyrrolo[2,1-f][1,2,4]triazin-4-yloxy)phenyl)-2-(pyridin-3-yl)triazole-4-carboxamide | 447.5 |
| 80 | 2-fluoro-5-methylphenyl | 2-Fluoro-N-(3-fluoro-4-(5-methylpyrrolo[2,1-f][1,2,4]triazin-4-yloxy)phenyl)-5-methylbenzamide | 395.4 |
| 81 | benzo[d]thiazol-6-yl | N-(3-Fluoro-4-(5-methylpyrrolo[2,1-f][1,2,4]triazin-4-yloxy)phenyl)benzo[d]thiazole-6-carboxamide | 420.4 |
| 82 | 5-methylisoxazol-3-yl | N-(3-Fluoro-4-(5-methylpyrrolo[2,1-f][1,2,4]triazin-4-yloxy)phenyl)-5-methylisoxazole-3-carboxamide | 368.3 |
| 83 | isoxazol-5-yl | N-(3-Fluoro-4-(5-methylpyrrolo[2,1-f][1,2,4]triazin-4-yloxy)phenyl)isoxazole-5-carboxamide | 354.3 |
| 84 | 3-(methylsulfonyl)phenyl (SO₂CH₃) | N-(3-Fluoro-4-(5-methylpyrrolo[2,1-f][1,2,4]triazin-4-yloxy)phenyl)-3-(methylsulfonyl)benzamide | 441.5 |

TABLE 1-continued

| Example # | R | Compound Name | LC/MS (M + H)+ |
|---|---|---|---|
| 85 | (3-methyl-4-fluorophenyl) | 4-Fluoro-N-(3-fluoro-4-(5-methylpyrrolo[2,1-f][1,2,4]triazin-4-yloxy)phenyl)-3-methylbenzamide | 395.4 |

Examples 86 to 130

Examples 86 to 130 illustrated in Table 2 below were synthesized from 3-fluoro-4-(5-methyl-6-(2-(4-methylpiperazin-1-yl)ethoxy)pyrrolo[2,1-f][1,2,4]triazin-4-yloxy)benzenamine (Compound B of Example 45). To an individual well of a 48-position MiniBlock® XT reactor was added 375 µL of a 0.2 M solution of the acid chloride in 1,2-dichloroethane (DCE) (0.075 mmol, 2.5 eq); 50 µL of pyridine (0.62 mmol; 20 eq); and 150 µL of a 0.2 M solution of the amine in DCE (0.03 mmol, 1 eq). The reactor was agitated via orbital shaker for 14 h. The crude product in DCE was diluted to a volume of 1 mL with methanol, then purified by standard preparative HPLC (H₂O/MeOH/0.1% TFA, gradient 35–90% MeOH over 10 min, 20×100 mm 5 µm YMC ODS-A column) utilizing mass-directed fractionation. The purified sample was constituted in 1:1/MeOH:DCE, transferred to a tared 2.5 mL plastic microtube, dried via centrifugal evaporation, weighed and analyzed by LCMS (H₂0/MeOH/0.1% TFA).

TABLE 2

| Example # | R | Compound Name | LC/MS (M + H)+ |
|---|---|---|---|
| 86 | (3-methoxyphenyl) | N-(3-Fluoro-4-(5-methyl-6-(2-(4-methylpiperazin-1-yl)ethoxy)pyrrolo[2,1-f][1,2,4]triazin-4-yloxy)phenyl)-3-methoxybenzamide | 535.6 |
| 87 | (2-fluoropyridin-3-yl) | 2-Fluoro-N-(3-fluoro-4-(5-methyl-6-(2-(4-methylpiperazin-1-yl)ethoxy)pyrrolo[2,1-f][1,2,4]triazin-4-yloxy)phenyl)nicotinamide | 524.6 |

TABLE 2-continued

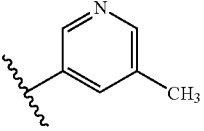

| Example # | R | Compound Name | LC/MS (M + H)+ |
|---|---|---|---|
| 88 | 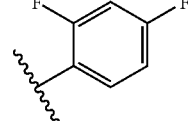 | N-(3-Fluoro-4-(5-methyl-6-(2-(4-methylpiperazin-1-yl)ethoxy)pyrrolo[2,1-f][1,2,4]triazin-4-yloxy)phenyl)-3-methylnicotinamide | 520.6 |
| 89 | 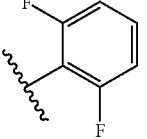 | 2,4-Difluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 541.6 |
| 90 | 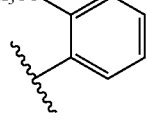 | 2,6-Difluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 541.6 |
| 91 | 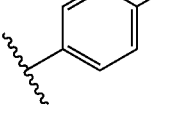 | N-(3-Fluoro-4-(5-methyl-6-(2-(4-methylpiperazin-1-yl)ethoxy)pyrrolo[2,1-f][1,2,4]triazin-4-yloxy)phenyl)-2-methoxybenzamide | 535.6 |
| 92 | 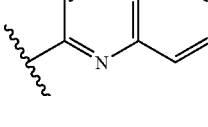 | N-(3-Fluoro-4-(5-methyl-6-(2-(4-methylpiperazin-1-yl)ethoxy)pyrrolo[2,1-f][1,2,4]triazin-4-yloxy)phenyl)-4-methylbenzamide | 519.6 |
| 93 | 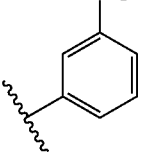 | N-(3-Fluoro-4-(5-methyl-6-(2-(4-methylpiperazin-1-yl)ethoxy)pyrrolo[2,1-f][1,2,4]triazin-4-yloxy)phenyl)quinoxaline-2-carboxamide | 557.6 |
| 94 | 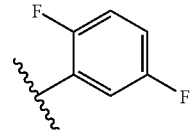 | N-(3-Fluoro-4-(5-methyl-6-(2-(4-methylpiperazin-1-yl)ethoxy)pyrrolo[2,1-f][1,2,4]triazin-4-yloxy)phenyl)-3-nitrobenzamide | 550.6 |
| 95 | | 2,5-Difluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 541.6 |

TABLE 2-continued

| Example # | R | Compound Name | LC/MS (M + H)+ |
|---|---|---|---|
| 96 | 2,3-difluorophenyl | 2,5-Difluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 541.6 |
| 97 | 4-(trifluoromethoxy)phenyl | N-(3-Fluoro-4-(5-methyl-6-(2-(4-methylpiperazin-1-yl)ethoxy)pyrrolo[2,1-f][1,2,4]triazin-4-yloxy)phenyl)-4-(trifluoromethoxy)benzamide | 589.6 |
| 98 | pyridin-2-yl | N-(3-Fluoro-4-(5-methyl-6-(2-(4-methylpiperazin-1-yl)ethoxy)pyrrolo[2,1-f][1,2,4]triazin-4-yloxy)phenyl)picolinamide | 506.6 |
| 99 | 2,4,5-trifluorophenyl | 2,4,5-Trifluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 559.5 |
| 100 | 2-chloropyridin-4-yl | 2-Chloro-N-(3-fluoro-4-(5-methyl-6-(2-(4-methylpiperazin-1-yl)ethoxy)pyrrolo[2,1-f][1,2,4]triazin-4-yloxy)phenyl)isonicotinamide | 541.0 |
| 101 | 2,5-dichloropyridin-3-yl | 2,5-Dichloro-N-(3-fluoro-4-(5-methyl-6-(2-(4-methylpiperazin-1-yl)ethoxy)pyrrolo[2,1-f][1,2,4]triazin-4-yloxy)phenyl)nicotinamide | 575.4 |
| 102 | 2,5-dimethylfuran-3-yl | N-(3-Fluoro-4-(5-methyl-6-(2-(4-methylpiperazin-1-yl)ethoxy)pyrrolo[2,1-f][1,2,4]triazin-4-yloxy)phenyl)-2,5-dimethylfuran-3-carboxamide | 523.6 |
| 103 | 5-chloro-2-fluorophenyl | 5-Chloro-2-fluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 558.0 |

TABLE 2-continued

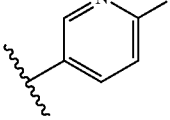

| Example # | R | Compound Name | LC/MS (M + H)+ |
|---|---|---|---|
| 104 | 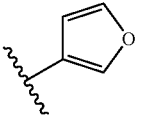 | N-(3-Fluoro-4-(5-methyl-6-(2-(4-methylpiperazin-1-yl)ethoxy)pyrrolo[2,1-f][1,2,4]triazin-4-yloxy)phenyl)-6-(trifluoromethyl)nicotinamide | 574.6 |
| 105 | 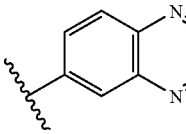 | N-(3-Fluoro-4-(5-methyl-6-(2-(4-methylpiperazin-1-yl)ethoxy)pyrrolo[2,1-f][1,2,4]triazin-4-yloxy)phenyl)furan-3-carboxamide | 495.5 |
| 106 | 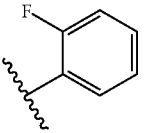 | N-(3-Fluoro-4-(5-methyl-6-(2-(4-methylpiperazin-1-yl)ethoxy)pyrrolo[2,1-f][1,2,4]triazin-4-yloxy)phenyl)quinoxaline-6-carboxamide | 557.6 |
| 107 | 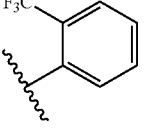 | 2-Fluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 523.6 |
| 108 | 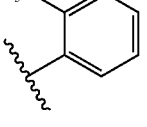 | N-(3-Fluoro-4-(5-methyl-6-(2-(4-methylpiperazin-1-yl)ethoxy)pyrrolo[2,1-f][1,2,4]triazin-4-yloxy)phenyl)-2-(trifluoromethyl)benzamide | 573.6 |
| 109 | 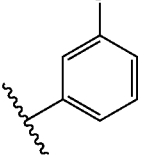 | N-(3-Fluoro-4-(5-methyl-6-(2-(4-methylpiperazin-1-yl)ethoxy)pyrrolo[2,1-f][1,2,4]triazin-4-yloxy)phenyl)-2-methylbenzamide | 519.6 |
| 110 | 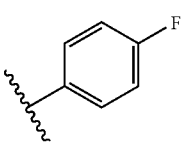 | 3-Fluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 523.6 |
| 111 | | 4-Fluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 523.6 |

TABLE 2-continued

| Example # | R | Compound Name | LC/MS (M + H)+ |
|---|---|---|---|
| 112 | 2-furyl | N-(3-Fluoro-4-(5-methyl-6-(2-(4-methylpiperazin-1-yl)ethoxy)pyrrolo[2,1-f][1,2,4]triazin-4-yloxy)phenyl)furan-2-carboxamide | 495.5 |
| 113 | 1-naphthyl | N-(3-Fluoro-4-(5-methyl-6-(2-(4-methylpiperazin-1-yl)ethoxy)pyrrolo[2,1-f][1,2,4]triazin-4-yloxy)phenyl)-1-naphthamide | 555.6 |
| 114 | 2-thienyl | N-(3-Fluoro-4-(5-methyl-6-(2-(4-methylpiperazin-1-yl)ethoxy)pyrrolo[2,1-f][1,2,4]triazin-4-yloxy)phenyl)thiophene-2-carboxamide | 511.6 |
| 115 | 3,4-difluorophenyl | 3,4-Difluoro-N-(3-fluoro-4-(5-methyl-6-(2-(4-methylpiperazin-1-yl)ethoxy)pyrrolo[2,1-f][1,2,4]triazin-4-yloxy)phenyl)benzamide | 541.6 |
| 116 | benzo[d][1,3]dioxol-5-yl | N-(3-Fluoro-4-(5-methyl-6-(2-(4-methylpiperazin-1-yl)ethoxy)pyrrolo[2,1-f][1,2,4]triazin-4-yloxy)phenyl)benzo[d][1,3]dioxole-5-carboxamide | 549.6 |
| 117 | 2,4-dimethoxyphenyl | N-(3-Fluoro-4-(5-methyl-6-(2-(4-methylpiperazin-1-yl)ethoxy)pyrrolo[2,1-f][1,2,4]triazin-4-yloxy)phenyl)-2,4-dimethoxybenzamide | 565.6 |
| 118 | 2-chloropyridin-3-yl | 2-Chloro-N-(3-fluoro-4-(5-methyl-6-(2-(4-methylpiperazin-1-yl)ethoxy)pyrrolo[2,1-f][1,2,4]triazin-4-yloxy)phenyl)nicotinamide | 541.0 |
| 119 | 2-(methylthio)pyridin-3-yl | N-(3-Fluoro-4-(5-methyl-6-(2-(4-methylpiperazin-1-yl)ethoxy)pyrrolo[2,1-f][1,2,4]triazin-4-yloxy)phenyl)-2-(methylthio)nicotinamide | 552.7 |

TABLE 2-continued

| Example # | R | Compound Name | LC/MS (M + H)+ |
|---|---|---|---|
| 120 | (6-chloropyridin-3-yl) | 6-Chloro-N-(3-fluoro-4-(5-methyl-6-(2-(4-methylpiperazin-1-yl)ethoxy)pyrrolo[2,1-f][1,2,4]triazin-4-yloxy)phenyl)nicotinamide | 541.0 |
| 121 | (2-phenoxypyridin-3-yl) | N-(3-Fluoro-4-(5-methyl-6-(2-(4-methylpiperazin-1-yl)ethoxy)pyrrolo[2,1-f][1,2,4]triazin-4-yloxy)phenyl)-2-phenoxynicotinamide | 598.7 |
| 122 | (2-chloro-6-methylpyridin-4-yl) | 2-Chloro-N-(3-fluoro-4-(5-methyl-6-(2-(4-methylpiperazin-1-yl)ethoxy)pyrrolo[2,1-f][1,2,4]triazin-4-yloxy)phenyl)-6-methylisonicotinamide | 555.0 |
| 123 | (4-fluoro-2-(trifluoromethyl)phenyl) | 4-Fluoro-N-(3-fluoro-4-(5-methyl-6-(2-(4-methylpiperazin-1-yl)ethoxy)pyrrolo[2,1-f][1,2,4]triazin-4-yloxy)phenyl)-2-(trifluoromethyl)benzamide | 591.6 |
| 124 | (3-chlorothiophen-2-yl) | 3-Chloro-N-(3-fluoro-4-(5-methyl-6-(2-(4-methylpiperazin-1-yl)ethoxy)pyrrolo[2,1-f][1,2,4]triazin-4-yloxy)phenyl)thiophene-2-carboxamide | 546.0 |
| 125 | (5-methyl-2-(trifluoromethyl)furan-3-yl) | N-(3-Fluoro-4-(5-methyl-6-(2-(4-methylpiperazin-1-yl)ethoxy)pyrrolo[2,1-f][1,2,4]triazin-4-yloxy)phenyl)-5-methyl 2-(trifluoromethyl)furan-3-carboxamide | 577.6 |
| 126 | (4-fluoro-3-methylphenyl) | 4-Fluoro-N-(3-fluoro-4-(5-methyl-6-(2-(4-methylpiperazin-1-yl)ethoxy)pyrrolo[2,1-f][1,2,4]triazin-4-yloxy)phenyl)-3-methylbenzamide | 537.6 |
| 127 | (2-fluoro-4-(trifluoromethyl)phenyl) | 2-Fluoro-N-(3-fluoro-4-(5-methyl-6-(2-(4-methylpiperazin-1-yl)ethoxy)pyrrolo[2,1-f][1,2,4]triazin-4-yloxy)phenyl)-4-(trifluoromethyl)benzamide | 591.6 |

TABLE 2-continued

| Example # | R | Compound Name | LC/MS (M + H)+ |
|---|---|---|---|
| 128 | F, CF3 (aryl) | 2-Fluoro-N-(3-fluoro-4-(5-methyl-6-(2-(4-methylpiperazin-1-yl)ethoxy)pyrrolo[2,1-f][1,2,4]triazin-4-yloxy)phenyl)-5-(trifluoromethyl)benzamide | 591.6 |
| 129 | F, pyridyl | 3-Fluoro-N-(3-fluoro-4-(5-methyl-6-(2-(4-methylpiperazin-1-yl)ethoxy)pyrrolo[2,1-f][1,2,4]triazin-4-yloxy)phenyl)isonicotinamide | 524.6 |
| 130 | Cl, pyridyl, Cl | 3,5-Dichloro-N-(3-fluoro-4-(5-methyl-6-(2-(4-methylpiperazin-1-yl)ethoxy)pyrrolo[2,1-f][1,2,4]triazin-4-yloxy)phenyl)isonicotinamide | 575.5 |

Example 131

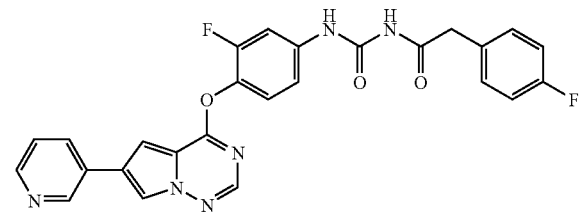

1-(3-Fluoro-4-(6-(pyridin-3-yl)pyrrolo[2,1-f][1,2,4]triazin-4-yloxy)phenyl)-3-(2(4-fluorophenyl)acetyl)urea, trifluroacetic acid salt

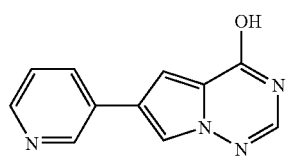

A) 6-(Pyridin-3-yl)pyrrolo[2,1-f][1,2,4]triazin-4-ol

A solution of 6-bromopyrrolo[2,1-f][1,2,4]triazin-4-ol (100 mg, 0.47 mmol, prepared from methyl 4-bromo-1H-pyrrole-2-carboxylate: see, generally, Kitamura, C. and Yamashita, Y. *J. Chem. Soc. Perkin Trans.* 1, 1997, 1443, the disclosure of which is herein incorporated by reference, using a similar procedure outlined in the PCT Appl. WO 00/71129) and pyridin-3-ylboronic acid (172 mg, 1.40 mmol) in 2 mL of DMF and 2 mL of saturated aqueous K$_2$CO$_3$ was degassed and then Pd(PPh$_3$)$_4$ (57 mg, 0.05 mmol) was added. The mixture was then heated to 120° C. for 3 h. LC-MS analysis indicated the disappearance of starting material. The mixture was cooled down and the solution was filtered. The filtrate was purified on preparative HPLC to afford the title compound (100 mg, 65%) as a TFA salt. MS(ESI$^+$) m/z 213.2 (M+H)$^+$.

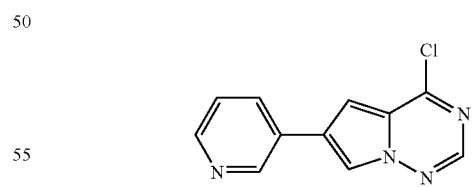

B) 4-Chloro-6-(pyridin-3-yl)pyrrolo[2,1-f][1,2,4]triazine

To a suspension of 6-(pyridin-3-yl)pyrrolo[2,1-f][1,2,4]triazin-4-ol (100 mg, 0.30 mmol) in 10 mL of toluene were added POCl$_3$ (0.18 mL, 1.88 mmol) and DIEA (0.09 mL, 0.5 mmol). The suspension was heated at 100° C. for 7 h. After cooling down, the excess POCl$_3$ was removed under reduced pressure. The residue was suspended in EtOAc, and then neutralized with sat. NaHCO₃. The organic layer was then washed with brine and dried over MgSO₄. After filtration and concentration, the residue was purified by flash column chromatography to afford the title compound (23 mg, 33%). MS(ESI⁺) m/z 231.2/233.2 (M+H)⁺.

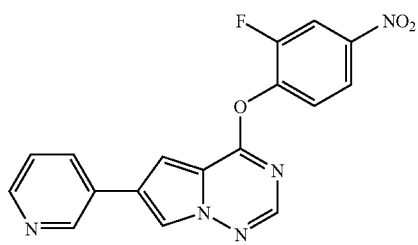

C) 4-(2-Fluoro-4-nitrophenoxy)-6-(pyridin-3-yl)pyrrolo[2,1-f][1,2,4]triazine

Following a procedure similar to the that for the synthesis of Compound B of Example 2,4-chloro-6-(pyridin-3-yl)pyrrolo[2,1-f][1,2,4]triazine (23 mg, 0.1 mmol) was converted to the title compound (35 mg, 95%). MS(ESI⁺) m/z 352.3 (M+H)⁺.

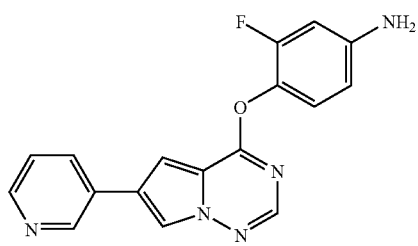

D) 3-Fluoro-4-(6-(pyridin-3-yl)pyrrolo[2,1-f][1,2,4]triazin-4-yloxy)benzenamine

Following a procedure similar to that for the synthesis of Compound C of Example 36, 4-(2-fluoro-4-nitrophenoxy)-6-(pyridin-3-yl)pyrrolo[2,1-f][1,2,4]triazine (35 mg, 0.10 mmol) was converted to the title compound (15 mg, 46%). MS(ESI⁺) m/z 322.3 (M+H)⁺.

E) 1-(3-Fluoro-4-(6-(pyridin-3-yl)pyrrolo[2,1-f][1,2,4]triazin-4-yloxy)phenyl)-3(2-(4-fluorophenyl)acetyl)urea, trifluoroaacetic acid salt The title compound was prepared using following a procedure similar to that for the synthesis of Example 46, 3-fluoro-4-(6-(pyridin-3-yl)pyrrolo[2,1-f][1,2,4]triazin-4-yloxy)benzenamine (15 mg, 0.046 mmol) was converted to the title compound (5.0 mg, 18%) as a TFA salt. ¹H NMR (DMSO-d₆) δ 10.99 (s, 1H), 10.53 (s, 1H), 9.12 (s, 1H), 8.75 (s, 1H), 8.50 (m, 1H), 8.30 (m, 1H), 8.12 (s, 1H), 7.67 (m, 2H), 7.30–7.50 (m, 5H), 7.12 (m, 2H), 3.69 (s, 2H); MS(ESI⁺) m/z 501.2 (M+H)⁺.

Example 132

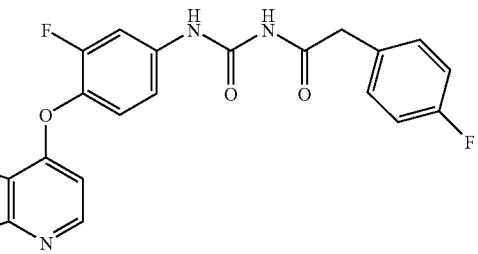

1-(4-(1H-Pyrrolo[2,3-b]pyridin-4-yloxy)-3-fluorophenyl)-3-(2-(4-fluorophenyl) acetyl)urea, hydrochloride salt

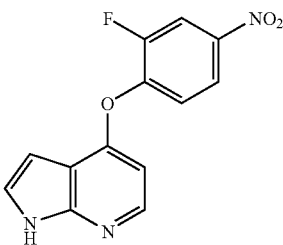

A) 4-(2-Fluoro-4-nitrophenoxy)-1H-pyrrolo[2,3-b]pyridine

A mixture of 4-chloro-1H-pyrrolo[2,3-b]pyridine (457 mg, 3.0 mmol, prepared according to Thibault, C. et al. *Org. Lett.* 2003, 5, 5023) and 2-fluoro-4-nitrophenol (706 mg, 4.5 mmol), and N,N-diisopropylethylamine (580 mg, 4.5 mmol) in 1-methyl-2-prolidinone (NMP) (3 mL) was heated at 200° C. under microwave irradiation for 1.0 h. The mixture was diluted with ethyl acetate (150 mL), washed with sat. aq. KH₂PO₄ solution, and Na₂CO₃ (aq. 1 M), dried over Na₂SO₄. The product was purified by flash column chromatography (silica gel, eluting with CH₂Cl₂ to 30% EtOAc/CH₂Cl₂) to afford a brown solid (350 mg, 43%). MS(ESI⁺) m/z 274 (M+H)⁺.

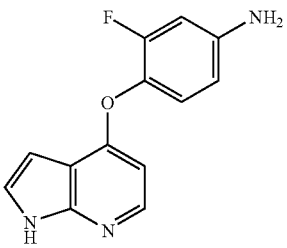

B) 4-(1H-Pyrrolo[2,3-b]pyridin-4-yloxy)-3-fluorobenzenamine

To a suspension of 4-(2-fluoro-4-nitrophenoxy)-1H-pyrrolo[2,3-b]pyridine (300 mg, 1.1 mmol) in tetrahydrofuran

113

(5 mL) and methanol (10 mL), were added zinc powder (350 mg, 5.5 mmol) and ammonium chloride (294 mg, 5.5 mmol). The mixture was stirred at rt overnight. The mixture was filtered through a pad of Celite®, rinsed with methanol. The filtrate was concentrated. The product was purified by flash column chromatography (silica gel, 1–5% MeOH in CH$_2$Cl$_2$) to afford the desired product (205 mg, 77%) as an off-white solid. MS(ESI$^+$) m/z 244 (M+H)$^+$.

C) 1-(4-(1H-Pyrrolo[2,3-b]pyridin-4-yloxy)-3-fluorophenyl)-3-(2-(4-fluorophenyl)acetyl)urea, hydrochloride salt A mixture of 4-(1H-pyrrolo[2,3-b]pyridin-4-yloxy)-3-fluorobenzenamine (30 mg, 0.12 mmol) and 2-(4-fluorophenyl)acetyl isocyanate, (Compound C, Example 4) (0.25 M in toluene, 0.18 mmol) in THF (0.5 mL) was stirred at rt for 1 h. The mixture was concentrated in vacuo, purified by preparative HPLC. The desired fractions were lyophilized to give a white TFA salt, which was dissolved in small amount of MeOH/H$_2$O with 1 N HCl (0.2 mL). This solution was then lyophilized to afford the title compound (15 mg, 27%) as a white solid. $^1$H NMR (CDCl$_3$) δ 11.74 (s, 1H), 8.12 (d, 1H, J=6.4 Hz), 7.73 (dd, 1H, J=2.4, 13.0 Hz), 7.39 (d, 1H, J=3.6 Hz), 6.90–7.3 (m, 6H), 6.65 (d, 1H, J=6.4 Hz), 6.50 (d, 1H, J=3.2 Hz), 3.68 (s, 2H); MS(ESI$^+$) m/z 423 (M+H)$^+$.

Example 133

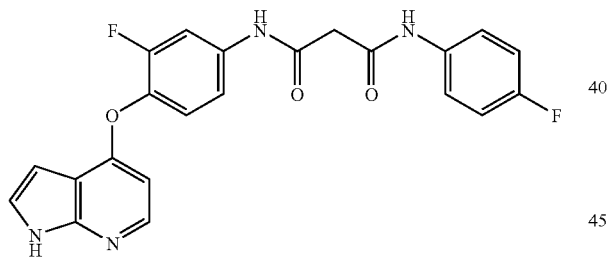

N$^1$-(4-(1H-Pyrrolo[2,3-b]pyridin-4-yloxy)-3-fluorophenyl)-N$^3$-(4-fluorophenyl) malonamide, trifluoroacetic acid salt To a solution of 4-(1H-pyrrolo[2,3-b]pyridin-4-yloxy)-3-fluorobenzenamine (Compound B, Example 132; 25 mg, 0.10 mmol) and 3-(4-fluorophenylamino)-3-oxopropanoic acid, Compound A, Example 25 (25 mg, 1.27 mmol) in DMF (0.5 mL), was added TBTU (48 mg, 0.15 mmol), followed by DIPEA (0.1 mL). The resulting mixture was stirred at rt for 2 h. The product was purified by preparative HPLC to afford the title compound (TFA salt, 26 mg, 62%) as a white solid. $^1$H NMR (CDCl$_3$) δ 7.94 (d, 1H, J=6.4 Hz), 7.66 (dd, 1H, J=2.4, 13.0 Hz), 7.54 (m, 2H), 6.90–7.25 (m, 5H), 6.31 (d, 2H, J=2.8 Hz), 3.37 (s, 2H); MS(ESI$^+$) m/z 423 (M+H)$^+$.

114

Example 134

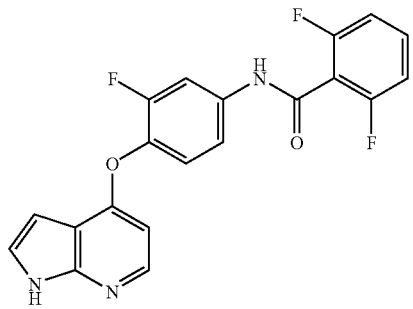

N-(4-(1H-Pyrrolo[2,3-b]pyridin-4-yloxy)-3-fluorophenyl)-2,6-difluorobenzamide

To a solution of 4-(1H-pyrrolo[2,3-b]pyridin-4-yloxy)-3-fluorobenzenamine (Compound B, Example 132; 20 mg, 0.08 mmol) in DMF (0.5 mL), was added 2,6-difluorobenzoyl chloride (20 mg, 0.11 mmol), followed by DIPEA (0.1 mL). The mixture was stirred at rt for 2 h and the product was purified by preparative HPLC. The desired fractions were lyophilized to give a white TFA salt, which was neutralized with sat. aq. sodium bicarbonate solution. The mixture was extracted with EtOAc (3×5 mL). The organic layers were dried and concentrated in vacuo to afford the title compound (14 mg, 37%) as a white solid. $^1$H NMR (CD$_3$OD) δ 8.15 (d, 1H, J=6.4 Hz), 7.87 (d, 1H, J=2.4, 12.8 Hz), 7.40 (m, 4H), 7.04 (m, 2H), 6.69 (d, 2H, J=7.6 Hz), 6.52 (m, 1H); MS(ESI$^+$) m/z 384 (M+H)$^+$.

Example 135

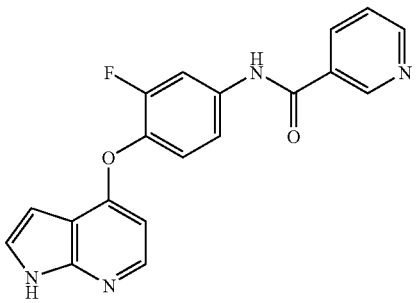

N-(4-(1H-Pyrrolo[2,3-b]pyridin-4-yloxy)-3-fluorophenyl)nicotinamide

In a similar manner as described for the preparation of Example 134, the title compound was isolated as a TFA salt and was prepared using commercially available nicotinyl chloride and 4-(1H-pyrrolo[2,3-b]pyridin-4-yloxy)-3-fluorobenzenamine (Compound B, Example 132). Yield: 55%. $^1$H NMR (CD$_3$OD) δ 9.09 (s, 1H), 8.73 (d, 1H, J=4.4 Hz), 8.44 (d, 1H, J=8.0 Hz), 8.22 (d, 1H, J=6.8 Hz), 8.22 (dd, 1H, J=2.4, 12.4 Hz), 7.40–7.80 (m, 4H), 6.79 (d, 1H, J=6.8 Hz), 6.59 (d, 1H, J=3.6 Hz); MS(ESI$^+$) m/z 349 (M+H)$^+$.

Example 136

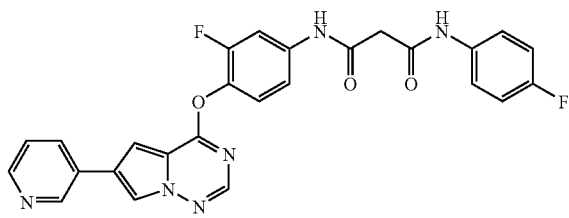

N¹-(3-Fluoro-4-(6-(pyridin-3-yl)pyrrolo[2,1-f][1,2,4]triazin-4-yloxy)phenyl)-N³-(4-fluorophenyl)malonamide, trifluoroacetic acid salt To a homogeneous solution of 3-fluoro-4-(6-(pyridin-3-yl)pyrrolo[2,1-f][1,2,4]triazin-4-yloxy)benzenamine (32 mg, 0.10 mmol, Compound D of Example 131) and 3-(4-fluorophenylamino)-3-oxopropanoic acid (20 mg, 0.10 mmol, Compound A of Example 25) in anhydrous DMF (3 mL), at room temperature under nitrogen atmosphere, was added diisopropylethylamine (26 µL, 0.15 mmol). The mixture was stirred for five minutes before o-benzotriazol-1-yl-N,N,N',N'-tetramethyluronium tetrafluoroborate (48 mg, 0.15 mmol) was added in one portion. The mixture was stirred for sixty-three hours before being partitioned between chloroform and brine. The aqueous layer was extracted three times with chloroform, and the combined organic layers were dried over anhydrous magnesium sulfate, filtered and concentrated in vacuo to remove volatiles. The resultant residue was purified by preparative HPLC (YMC S10 ODS, 30×500 mm, 30 minute gradient from 58% to 90% aqueous methanol with 0.1% TFA). The appropriate fractions were combined and lyophilized to afford the title compound (18 mg, 30%) as an off-white solid. $^1$H NMR (CDCl$_3$) δ 10.35 (br s, 1H), 9.49 (s, 1H), 9.18 (s, 1H), 8.80–8.65 (m, 2H), 8.36–8.29 (m, 1H), 8.17 (s, 1H), 8.04 (s, 1H), 7.83–7.68 (m, 2H), 7.55–7.49 (m, 2H), 7.35–7.23 (m, 2H), 7.10–7.00 (m, 2H), 3.58 (s, 2H); HRMS(ESI), 501.1487 (M+H)$^+$ calc, 501.1491 (M+H)$^+$ found.

Example 137

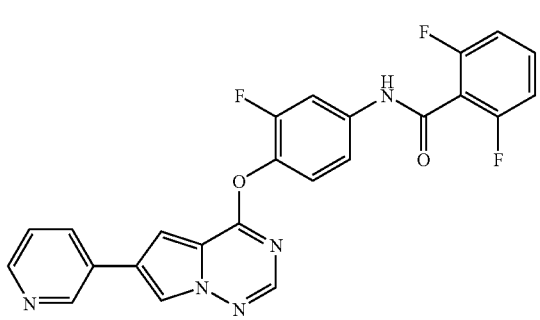

2,6-Difluoro-N-(3-fluoro-4-(6-(pyridin-3-yl)pyrrolo[2,1-f][1,2,4]triazin-4-yloxy)phenyl)benzamide, trifluoroacetic acid salt To a homogeneous solution of 3-fluoro-4-(6-(pyridin-3-yl)pyrrolo[2,1-f][1,2,4]triazin-4-yloxy)benzenamine (64 mg, 0.20 mmol, Compound D of Example 131) in anhydrous chloroform (5 mL), at room temperature under nitrogen atmosphere, was added diisopropylethylamine (49 µL, 0.28 mmol). The mixture was stirred for five minutes before 2,6-difluorobenzoyl chloride (33 µL, 0.26 mmol, Aldrich) was added. The mixture was stirred for eighty-seven hours before being partitioned between chloroform and saturated aqueous sodium bicarbonate. The organic layer was washed once with saturated aqueous sodium bicarbonate and once with brine, before the combined organic layers were dried over anhydrous magnesium sulfate, filtered and concentrated in vacuo to remove volatiles. The resultant residue was purified by preparative HPLC (YMC S10 ODS, 30×500 mm, 30 minute gradient from 58% to 90% aqueous methanol with 0.1% TFA). The appropriate fractions were combined and lyophilized to afford the title compound (24 mg, 21%) as a white solid. $^1$H NMR (CD$_3$OD) δ 9.20 (s, 1H), 8.85–8.78 (m, 1H), 8.65–8.60 (m, 1H), 8.51 (d, 1H, J=1.6 Hz), 8.00 (s, 1H), 7.98–7.90 (m, 1H), 7.81–7.74 (m, 1H), 7.58 (d, 1H, J=1.8 Hz), 7.51–7.27 (m, 3H), 7.00–7.10 (m, 2H); HRMS(ESI), 462.1178 (M+H)$^+$ calc, 462.1168 (M+H)$^+$ found.

Example 138

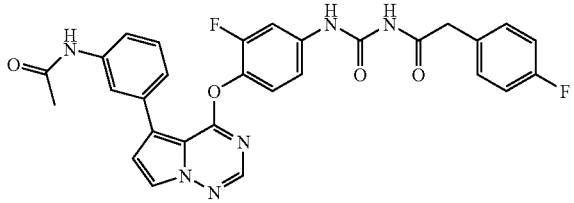

1-(4-(5-(3-Acetamidophenyl)pyrrolo[2,1-f][1,2,4]triazin-4-yloxy)-3-fluorophenyl)-3-(2-(4-fluorophenyl)acetyl)urea

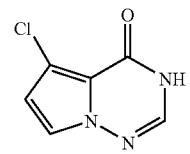

A) 5-Chloropyrrolo[2,1-f][1,2,4]triazin-4 (3H)-one

A solution of methyl 1-amino-3-chloro-1H-pyrrole-2-carboxylate (10.0 g, 57.3 mmol, WO 03/099286: Compound A of Example 9) in formamide (40 mL) was heated at 170° C. for 1 h and then at 190° C. for 1 h. Upon cooling to room temperature, the mixture solidified. The product was purified by recrystallization from ethyl acetate to give the title compound (6.53 g, 67%) as a white solid. $^1$H NMR (CDCl$_3$) δ 10.24 (br s, 1H), 7.48 (d, 1H, J=3.6 Hz), 7.29 (d, 1H, J=2.8 Hz), 6.47 (d, 1H, J=2.8 Hz); MS(ESI$^+$) m/z 170.1 (M+H)$^+$.

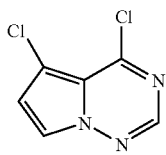

B) 4,5-Dichloropyrrolo[2,1-f][1,2,4]triazine

To a solution of 5-chloropyrrolo[2,1-f][1,2,4]triazin-4 (3H)-one (5.00 g, 29.5 mmol) in toluene (100 mL) at rt under nitrogen was added diisopropylethylamine (5.14 mL, 29.5 mmol) followed by phosphorus(III) oxychloride (8.25 mL, 88.5 mmol). The mixture was heated at 100° C. for 20 h and was then cooled to rt. The reaction was slowly added to saturated aqueous sodium bicarbonate solution (500 mL) at 0° C. After the addition was complete, the mixture was stirred at rt for 30 min. The aqueous phase was extracted with ethyl acetate (3×500 mL), dried over anhydrous MgSO$_4$, and concentrated in vacuo to give the crude product (3.73 g, 67%) as a yellow solid which was used without further purification. $^1$H NMR (CDCl$_3$) δ 8.03 (s, 1H), 7.70 (d, 1H, J=2.8 Hz), 6.84 (d, 1H, J=2.8 Hz); MS(ESI$^+$) m/z 188.1 (M+H)$^+$.

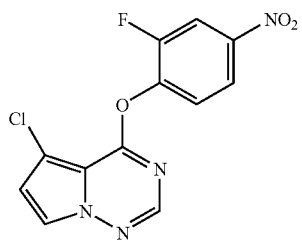

C) 5-Chloro-4-(2-fluoro-4-nitrophenoxy)pyrrolo[2,1-f][1,2,4]triazine

A mixture of 4,5-dichloropyrrolo[2,1-f][1,2,4]triazine (3.73 g, 19.8 mmol), 2-fluoro-4-nitrophenol (3.43 g, 21.8 mmol) and potassium carbonate (5.47 g, 39.6 mmol) in DMF (100 mL) was stirred at 60° C. for 1 h. After cooling to rt, the reaction was filtered through a short plug of silica gel with ethyl acetate and then concentrated in vacuo. The crude product was purified by recrystallization from ethyl acetate/hexanes (1:1) to give the title compound (4.37 g, 71%) as a white solid. $^1$H NMR (CDCl$_3$) δ 8.22–8.17 (m, 2H), 7.92 (s, 1H), 7.77 (d, 1H, J=2.8 Hz), 7.58 (t, 1H, J=7.2 Hz), 6.87 (d, 1H, J=3.2 Hz); MS(ESI$^+$) m/z 309.3 (M+H)$^+$.

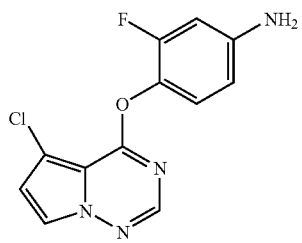

D) 4-(5-Chloropyrrolo[2,1-f][1,2,4]triazin-4-yloxy)-3-fluorobenzenamine

To a solution of 5-chloro-4-(2-fluoro-4-nitrophenoxy)pyrrolo[2,1-f][1,2,4]triazine (2.00 g, 6.48 mmol) in THF (50 mL)/MeOH (80 mL) was added zinc dust (2.12 g, 32.4 mmol) followed by ammonium chloride (1.73 g, 32.4 mmol). After stirring at rt for 8 h, the reaction mixture was filtered through Celite® with MeOH and then concentrated in vacuo. The residue was taken up in ethyl acetate (200 mL) and washed with water (2×100 mL) then brine (1×100 mL). The organic phase was dried over anhydrous Na$_2$SO$_4$ and concentrated in vacuo. The crude product was purified by flash chromatography on silica gel (50% EtOAc/hexanes) to give the title compound (1.51 g, 84%) as a pale yellow solid. $^1$H NMR (CDCl$_3$) δ 7.95 (s, 1H), 7.69 (d, 1H, J=2.8 Hz), 7.09 (t, 1H, J=8.4 Hz), 6.79 (d, 1H, J=2.8 Hz), 6.58 (dd, 1H, J=11.6, 2.6 Hz), 6.51 (d, 1H, J=8.7 Hz), 3.92 (br s, 2H); MS(ESI$^+$) m/z 279.2 (M+H)$^+$.

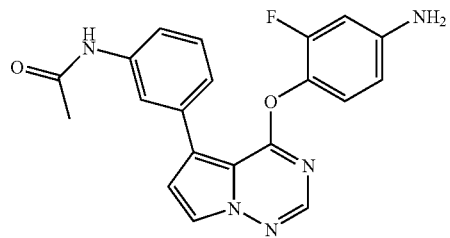

E) N-(3-(4-(4-Amino-2-fluorophenoxy)pyrrolo[2,1-f][1,2,4]triazin-5-yl)phenyl)acetamide A flask was charged with palladium acetate (4.5 mg, 0.02 mmol), X-Phos ligand (24 mg, 0.05 mmol, Strem), 4-(5-chloropyrrolo[2,1-f][1,2,4]triazin-4-yloxy)-3-fluorobenzenamine (56 mg, 0.20 mmol), 3-acetamidobenzene boronic acid (72 mg, 0.40 mmol, Lancaster), and potassium phosphate (127 mg, 0.60 mmol) in that order. The flask was flushed with nitrogen and then t-BuOH was added (0.40 mL). The mixture was heated at 80° C. for 8 h. Additional shots of palladium acetate (4.5 mg, 0.02 mmol), X-Phos ligand (24 mg, 0.05 mmol), and 3-acetamidobenzene boronic acid (72 mg, 0.40 mmol) were added and the reaction was stirred an additional 9 h at 80° C. After cooling to rt, the reaction was filtered using MeOH to remove the potassium phosphate and then concentrated in vacuo. The crude product was purified by reverse phase prep HPLC and the appropriate fractions were concentrated in vacuo to remove MeOH. The resulting aqueous layer was made basic with saturated sodium bicarbonate solution and extracted with ethyl acetate. The combined organic extracts were dried over anhydrous sodium sulfate and concentrated in vacuo to give the title compound (20 mg, 26%) as a white solid. $^1$H NMR (CD$_3$OD) δ 7.84–7.94 (m, 2H), 7.44–7.41 (m, 1H), 7.34–7.19 (m, 3H), 6.92 (t, 1H, J=8.8 Hz), 6.87 (d, 1H, J=2.8 Hz), 6.50 (dd, 1H, J=12.4, 2.4 Hz), 6.46–6.43 (m, 1H), 2.04 (s, 3H); MS(ESI$^+$) m/z 378.3 (M+H)$^+$.

F) 1-(4-(5-(3-Acetamidophenyl)pyrrolo[2,1-f][1,2,4]triazin-4-yloxy)-3-fluorophenyl)-3-(2-(4-fluorophenyl)acetyl)urea To a solution of N-(3-(4-(4-amino-2-fluorophenoxy)pyrrolo[2,1-f][1,2,4]triazin-5-yl)phenyl)acetamide (20 mg, 0.053 mmol) in dichloromethane (0.5 mL) at rt under nitrogen was added 2-(4-fluorophenyl)acetyl isocyanate (250 μL, 0.064 mmol, 0.25 M in toluene, Compound C of Example 4). The reaction was stirred at rt for 1 h and was then concentrated in vacuo. The residue was suspended in methanol and filtered to collect 14 mg (47%) of the title compound as a white solid. $^1$H NMR (DMSO-d$_6$) δ 11.09 (s, 1H), 10.63 (s, 1H), 10.04 (s, 1H), 8.25–8.21 (m, 2H), 8.05 (s, 1H), 7.78 (d, 1H, J=13.2 Hz), 7.51–7.38 (m, 7H), 7.23 (t, 2H, J=8.4 Hz), 7.13 (s, 1H), 3.81 (s, 2H), 2.10 (s, 3H); MS(ESI$^+$) m/z 557.4 (M+H)$^+$.

Examples 139–144 Were Prepared in a Manner Similar to Example 138.

Example 139

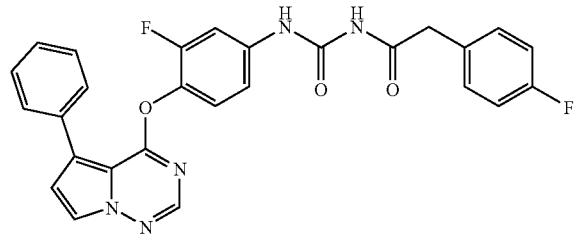

1-(3-Fluoro-4-(5-phenylpyrrolo[2,1-f][1,2,4]triazin-4-yloxy)phenyl)-3-(2-(4-fluorophenyl)acetyl)urea $^1$H NMR (DMSO-d$_6$) δ 10.56 (s, 1H), 8.55 (s, 1H), 7.89 (s, 1H), 7.77 (d, 1H, J=2.8 Hz), 7.62–7.57 (m, 3H), 7.33 (t, 2H, J=7.7 Hz), 7.26–7.19 (m, 4H), 7.10 (m, 1H), 7.02 (t, 2H, J=8.6 Hz), 6.88 (d, 1H, J=2.7 Hz), 3.65 (s, 2H); MS(ESI$^+$) m/z 500.3 (M+H)$^+$.

Example 140

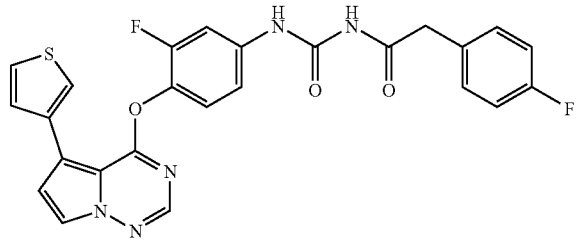

1-(3-Fluoro-4-(5-(thiophen-3-yl)pyrrolo[2,1-f][1,2,4]triazin-4-yloxy)phenyl)-3-(2-(4-fluorophenyl)acetyl)urea $^1$H NMR (DMSO-d$_6$) δ 11.05 (s, 1H), 10.59 (s, 1H), 8.16 (d, 1H, J=2.8 Hz), 8.12 (s, 1H), 7.81 (d, 1H, J=1.6 Hz), 7.75 (dd, 1H, J=12.4, 2 Hz), 7.62–7.49 (m, 3H), 7.39–7.36 (m, 3H), 7.21–7.16 (m, 3H), 3.76 (s, 2H); MS(ESI$^+$) m/z 506.3 (M+H)$^+$.

Example 141

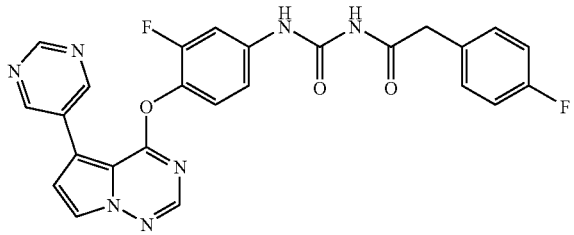

1-(3-Fluoro-4-(5-(pyrimidin-5-yl)pyrrolo[2,1-f][1,2,4]triazin-4-yloxy)phenyl)-3-(2-(4-fluorophenyl)acetyl)urea $^1$H NMR (DMSO-d$_6$) δ 11.10 (s, 1H), 10.65 (s, 1H), 9.21 (s, 2H), 9.18 (s, 1H), 8.37 (d, 1H, J=2.4 Hz), 8.31 (s, 1H), 7.80 (dd, 1H, J=12.4, 2 Hz), 7.58 (t, 1H, J=8.8 Hz), 7.44–7.40 (m, 4H), 7.23 (t, 2H, J=8.4 Hz), 3.80 (s, 2H); MS(ESI$^+$) m/z 502.3 (M+H)$^+$;

Example 142

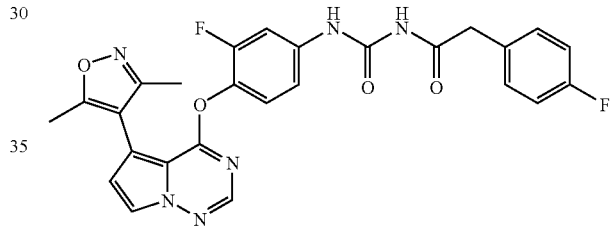

1-(4-(5-(3,5-Dimethylisoxazol-4-yl)pyrrolo[2,1-f][1,2,4]triazin-4-yloxy)-3-fluorophenyl)-3-(2-(4-fluorophenyl)acetyl)urea $^1$H NMR (DMSO-d$_6$) δ 11.04 (s, 1H), 10.58 (s, 1H), 8.24 (d, 1H, J=2.4 Hz), 8.17 (s, 1H), 7.42 (dd, 1H, J=13.2, 2 Hz), 7.38–7.35 (m, 4H), 7.18 (t, 2H, J=7.6 Hz), 7.06 (d, 1H, J=2.8 Hz), 3.75 (s, 2H), 2.37 (s, 3H), 2.20 (s, 3H); MS(ESI$^+$) m/z 519.3 (M+H)$^+$.

Example 143

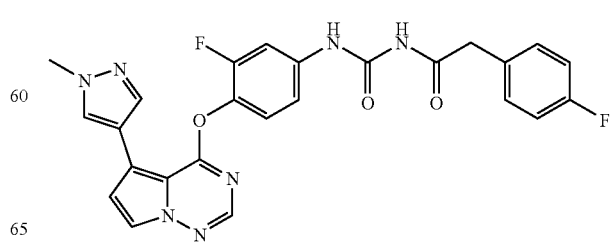

121

1-(3-Fluoro-4-(5-(1-methyl-1H-pyrazol-4-yl)pyrrolo[2,1-f][1,2,4]triazin-4-yloxy)phenyl)-3-(2-(4-fluorophenyl)acetyl)urea $^1$H NMR (DMSO-$d_6$) δ 11.04 (s, 1H), 10.59 (s, 1H), 8.11 (d, 1H, J=2.8 Hz), 8.05 (d, 2H, J=2.4 Hz), 7.85 (s, 1H), 7.76 (dd, 1H, J=12.4, 2 Hz), 7.52 (t, 1H, J=8.4 Hz), 7.39–7.36 (m, 3H), 7.18 (t, 2H, J=8.8 Hz), 7.12 (d, 1H, J=2.8 Hz), 3.86 (s, 3H), 3.76 (s, 2H); MS(ESI$^+$) m/z 504.3 (M+H)$^+$.

Example 144

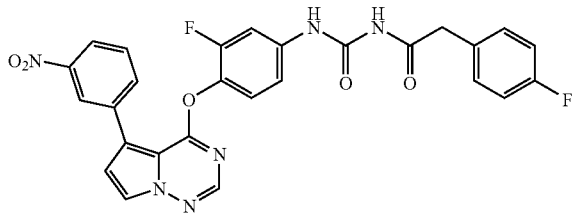

1-(3-Fluoro-4-(5-(3-nitrophenyl)pyrrolo[2,1-f][1,2,4]triazin-4-yloxy)phenyl)-3-(2-(4-fluorophenyl)acetyl)urea $^1$H NMR (DMSO-$d_6$) δ 11.03 (s, 1H), 10.57 (s, 1H), 8.62 (s, 1H), 8.27 (d, 1H, J=2.4 Hz), 8.23 (s, 1H), 8.20–8.16 (m, 2H), 7.76–7.72 (m, 2H), 7.49 (t, 1H, J=8.8 Hz), 7.39–7.34 (m, 4H), 7.18 (t, 2H, J=9.2 Hz), 3.75 (s, 2H); MS(ESI$^+$) m/z 545.2 (M+H)$^+$.

Example 145

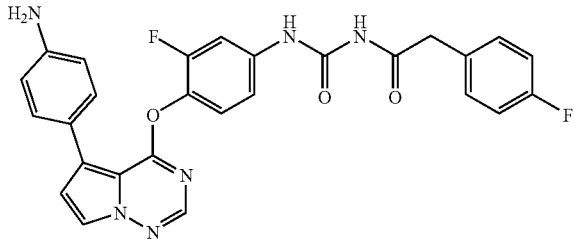

122

1-(4-(5-(4-Aminophenyl)pyrrolo[2,1-f][1,2,4]triazin-4-yloxy)-3-fluorophenyl)-3-(2-(4-fluorophenyl)acetyl)urea

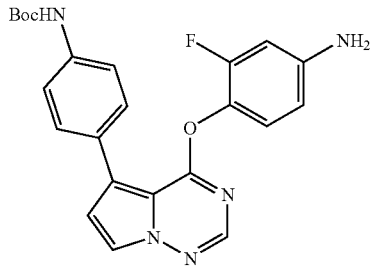

A) tert-Butyl 4-(4-(4-amino-2-fluorophenoxy)pyrrolo[2,1-f][1,2,4]triazin-5-yl)phenylcarbamate Prepared in a similar manner as Step E of Example 138 to give the title compound (46%) as a yellow oil. $^1$H NMR (CDCl$_3$) δ 7.88 (s, 1H), 7.73 (d, 1H, J=4 Hz), 7.54 (d, 2H, J=8 Hz), 7.33–7.30 (m, 2H), 6.93 (t, 1H, J=7.6 Hz), 6.82 (d, 1H, J=4 Hz), 6.60–6.47 (m, 2H), 1.44 (s, 9H); MS(ESI$^+$) m/z 436.4 (M+H)$^+$.

B) 1-(4-(5-(4-Aminophenyl)pyrrolo[2,1-f][1,2,4]triazin-4-yloxy)-3-fluorophenyl)-3-(2-(4-fluorophenyl)acetyl)urea Prepared in a similar manner as Step F of Example 138 to give the Boc protected material (51%). The Boc protected material was suspended in ether (2 mL), cooled to 0° C., and charged with TFA (0.5 mL). After stirring at rt for 1 h, the reaction was concentrated in vacuo. The residue was suspended in ethyl acetate (10 mL), washed with saturated aqueous sodium bicarbonate solution (5 mL), dried over anhydrous sodium sulfate, and concentrated. The crude product was purified by flash chromatography on silica gel (60% EtOAc/hexanes). Lyophilization from acetonitrile (1 mL)/water (3 mL) gave the title compound (38%) as a light brown solid. $^1$H NMR (DMSO-$d_6$) δ 10.95 (s, 1H), 10.50 (s, 1H), 8.02 (d, 1H, J=2.8 Hz), 7.98 (s, 1H), 7.67 (dd, 1H, J=12.4, 2 Hz), 7.36 (t, 1H, J=8.8 Hz), 7.31–7.28 (m, 5H), 7.10 (t, 2H, J=8.8 Hz), 6.89 (d, 1H, J=2.8 Hz), 6.51 (d, 2H, J=8.8 Hz), 5.08 (s, 2H), 3.68 (s, 2H); MS(ESI$^+$) m/z 515.3 (M+H)$^+$.

Example 146

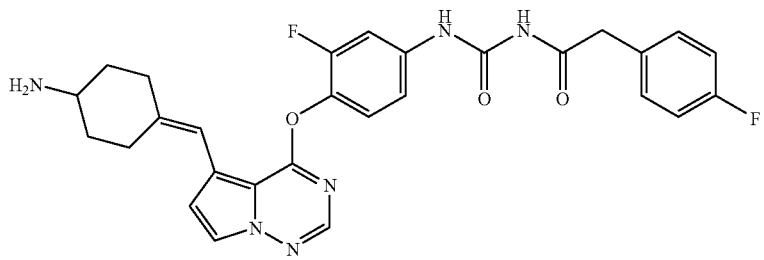

1-(4-(5-((4-Aminocyclohexylidene)methyl)pyrrolo[2,1-f][1,2,4]triazin-4-yloxy)-3-fluorophenyl)-3-(2-(4-fluorophenyl)acetyl)urea

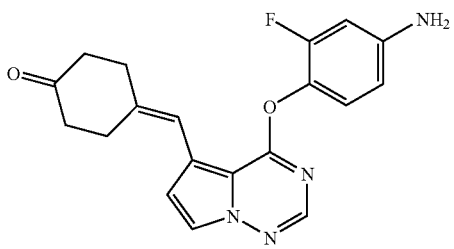

A) 4-((4-(4-Amino-2-fluorophenoxy)pyrrolo[2,1-f][1,2,4]triazin-5-yl)methylene)cyclohexanone Prepared in a similar manner as Step E of Example 138 using 4-((4,4,5,5-tetramethyl-1,3,2-dioxaborolan-2-yl)methylene)cyclohexanone (prepared according to the procedure of Morrill, C. and Grubbs, R. H. *J. Org. Chem.* 2003, 68, 6031–6034). to give the title compound (11%) as a yellow oil. $^1$H NMR (CD$_3$OD) δ 7.76 (s, 1H), 7.73 (d, 1H, J=2.8 Hz), 7.54–7.51 (m, 1H), 7.33 (d, 1H, J=2.8 Hz), 6.92 (t, 1H, J=7.6 Hz), 6.84 (d, 1H, J=2.8 Hz), 6.46–6.41 (m, 1H), 2.83 (t, 2H, J=6.8 Hz), 2.65 (t, 2H, J=6.8 Hz), 2.45–2.38 (m, 4H); MS(ESI$^+$) m/z 353.2 (M+H)$^+$.

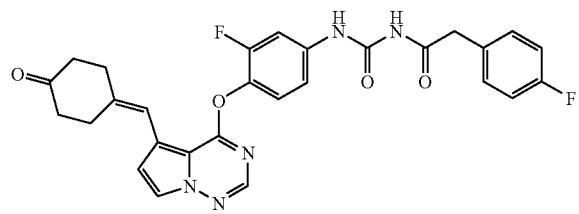

B) 1-(4-(5-(4-Aminophenyl)pyrrolo[2,1-f][1,2,4]triazin-4-yloxy)-3-fluorophenyl)-3-(2-(4-fluorophenyl)acetyl)urea Prepared in a similar manner as Step F of Example 138 to give the title compound (38%) as a yellow solid. $^1$H NMR (acetone-d$_6$) δ 10.62 (s, 1H), 9.87 (s, 1H), 7.80 (s, 1H), 7.79 (d, 1H, J=2.8 Hz), 7.70 (dd, 1H, J=12.8, 2.4 Hz), 7.33–7.19 (m, 4H), 6.96–6.93 (m, 3H), 6.16 (m, 1H), 3.75 (s, 2H), 2.82 (t, 2H, J=6.8 Hz), 2.62 (t, 2H, J=6.8 Hz), 2.37 (t, 2H, J=6.8 Hz), 2.30 (t, 2H, J=6.8 Hz); MS(ESI$^+$) m/z 532.2 (M+H)$^+$.

C) 1-(4-(5-((4-Aminocyclohexylidene)methyl)pyrrolo[2,1-f][1,2,4]triazin-4-yloxy)-3-fluorophenyl)-3-(2-(4-fluorophenyl)acetyl)urea A solution of 1-(4-(5-(4-aminophenyl)pyrrolo[2,1-f][1,2,4]triazin-4-yloxy)-3-fluorophenyl)-3-(2-(4-fluorophenyl)acetyl)urea (21 mg, 0.040 mmol) in methanol (0.5 mL) and THF (0.5 mL) at 0° C. was charged with ammonium acetate (30 mg, 0.40 mmol) followed by sodium cyanoborohydride (2.5 mg, 0.040 mmol). After stirring at 0° C. for 1 h, the reaction was concentrated in vacuo. The crude product was purified by reverse phase prep HPLC and the appropriate fractions were concentrated in vacuo. Toluene was added (2×5 mL) and concentrated to remove excess TFA. Lyophilization from acetonitrile (1 mL)/water (3 mL) gave the TFA salt of the title compound (19%) as a white solid. $^1$H NMR (CD$_3$OD) δ 7.77 (s, 1H), 7.76 (d, 1H, J=2.8 Hz), 7.63 (dd, 1H, J=12.8, 2.4 Hz), 7.29–7.14 (m, 4H), 7.03–6.93 (m, 2H), 6.91 (d, 1H, J=2.8 Hz), 6.67 (s, 1H), 3.62 (s, 2H), 3.15–3.08 (m, 1H), 2.50–2.30 (m, 2H), 2.21–2.05 (m, 2H), 1.46–1.30 (m, 4H); MS(ESI$^+$) m/z 533.2 (M+H)$^+$.

Example 147

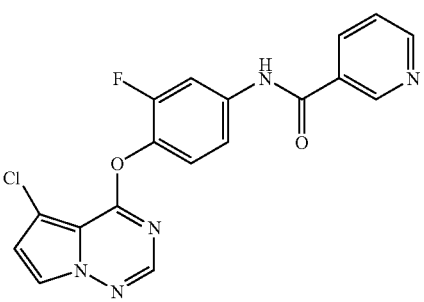

N-(4-(5-Chloropyrrolo[2,1-f][(1,2,4]triazin-4-yloxy)-3-fluorophenyl)nicotinamide To 4-(5-chloropyrrolo[2,1-f][1,2,4]triazin-4-yloxy)-3-fluorobenzenamine (100 mg, 0.359 mmol, Compound D of Example 138) in DMF (2 mL) was added nicotinic acid (53 mg, 0.431 mmol, Aldrich), DIPEA (300 μL, 1.80 mmol), followed by TBTU (173 mg, 0.539 mmol, Fluka). After stirring at rt overnight, the reaction was diluted with 20 mL of EtOAc, washed with 10% aqueous lithium chloride solution (2×10 mL) followed by brine (1×10 mL), dried over anhydrous sodium sulfate, and concentrated in vacuo. The crude product was purified by flash chromatography on silica gel (10% MeOH/EtOAc) to give the title compound (125 mg, 91%) as a white solid. $^1$H NMR (DMSO-d$_6$) δ 10.75 (s, 1H), 9.14 (d, 1H, J=2 Hz), 8.80 (dd, 1H, J=4.8, 1.2 Hz), 8.34–8.31 (m, 1H), 8.18 (d, 1H, J=2.8 Hz), 8.17 (s, 1H), 7.96 (dd, 1H, J=12.8, 2 Hz), 7.66–7.60 (m, 2H), 7.54 (t, 1H, J=8.8 Hz), 7.10 (d, 1H, J=2.8 Hz); MS(ESI$^+$) m/z 383.9 (M+H)$^+$.

Example 148

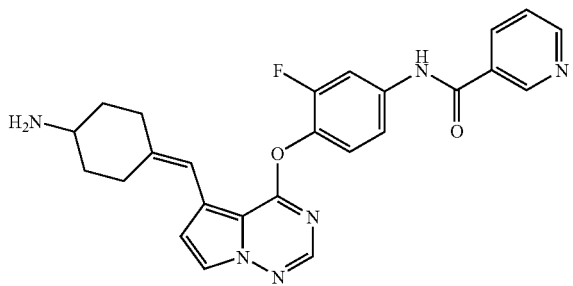

N-(4-(5-((4-Aminocyclohexylidene)methyl)pyrrolo[2,1-f][1,2,4]triazin-4-yloxy)-3-fluorophenyl)nicotinamide

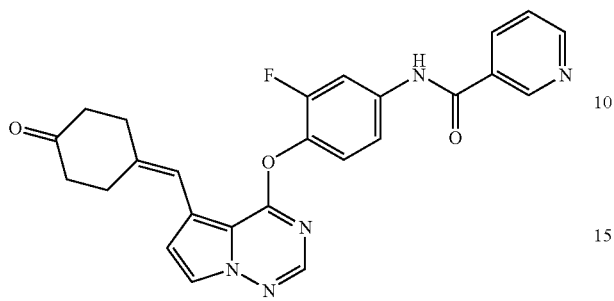

A) N-(3-Fluoro-4-(5-((4-oxocyclohexylidene)methyl)pyrrolo[2,1-f][1,2,4]triazin-4-yloxy)phenyl)nicotinamide Prepared in a similar manner as Step E of Example 138 to give the title compound (66%) as a yellow solid. $^1$H NMR (DMSO-$d_6$) δ 10.75 (s, 1H), 9.14 (d, 1H, J=2 Hz), 8.82 (dd, 1H, J=4.8, 1.2 Hz), 8.36–8.33 (m, 1H), 8.13 (d, 1H, J=2.8 Hz), 8.10 (s, 1H), 7.99–7.93 (m, 1H), 7.68–7.63 (m, 1H), 7.54 (t, 1H, J=8.8 Hz) 7.07 (d, 1H, J=2.8 Hz), 6.92 (s, 1H), 2.90 (t, 2H, J=6.8 Hz), 2.74 (t, 2H, J=6.8 Hz), 2.51 (t, 2H, J=6.8 Hz), 2.42 (t, 2H, J=6.8 Hz); MS(ESI$^+$) m/z 458.2 (M+H)$^+$.

B) N-(4-(5-((4-Aminocyclohexylidene)methyl)pyrrolo[2,1-f][1,2,4]triazin-4-yloxy)-3-fluorophenyl)nicotinamide Prepared in a similar manner as Step C of Example 146 to give the TFA salt of the title compound (6%) as a pale yellow solid. $^1$H NMR (CD$_3$OD) δ 9.15 (s, 1H), 8.80 (s, 1H), 8.59 (d, 1H, J=8 Hz), 7.84–7.76 (m, 4H), 7.48 (d, 1H, J=8 Hz), 7.29 (t, 1H, J=8 Hz), 6.80 (d, 1H, J=4 Hz), 6.67 (s, 1H), 3.62 (s, 2H), 3.10–3.08 (m, 1H), 2.48–2.05 (m, 4H), 1.47–1.20 (m, 4H); MS(ESI$^+$) m/z 459.2 (M+H)$^+$.

Example 149

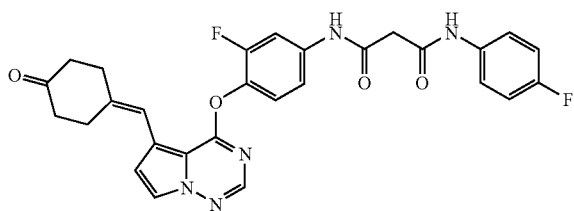

N$^1$-(3-Fluoro-4-(5-((4-oxocyclohexylidene)methyl)pyrrolo[2,1-f][1,2,4]triazin-4-yloxy)phenyl)-N$^3$-(4-fluorophenyl)malonamide Suzuki coupling in a similar manner as Step E of Example 138 followed by malonamide formation as in Step A of Example 133 gave the title compound (39%) as a yellow solid. $^1$H NMR(DMSO-$d_6$) δ 10.55 (s, 1H), 10.31 (s, 1H), 8.15 (d, 1H, J=2.4 Hz), 8.11 (s, 1H), 7.86 (dd, 1H, J=12.4, 2.8 Hz), 7.52 (t, 1H, J=8.8 Hz), 7.44–7.42 (m, 1H), 7.25–7.19 (m, 2H), 7.09 (d, 1H, J=2.8 Hz), 6.93 (s, 1H), 3.54 (s, 2H), 2.91 (t, 2H, J=6.8 Hz), 2.73 (t, 2H, J=6.4 Hz), 2.53 (t, 2H, J=6.8 Hz), 2.45 (t, 2H, J=6.8 Hz); MS(ESI$^+$) m/z 532.3 (M+H)$^+$.

Example 150

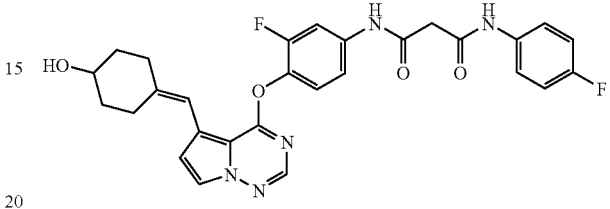

N$^1$-(3-Fluoro-4-(5-((4-hydroxycyclohexylidene)methyl)pyrrolo[2,1-f][1,2,4]triazin-4-yloxy)phenyl)-N$^3$-(4-fluorophenyl)malonamide To N$^1$-(3-fluoro-4-(5-((4-oxocyclohexylidene)methyl)pyrrolo[2,1-f][1,2,4]triazin-4-yloxy)phenyl)-N$^3$-(4-fluorophenyl)malonamide (80 mg, 0.15 mmol, Example 149) in methanol (2 mL) at 0° C. was added a spatula tip of sodium borohydride. The reaction was stirred at 0° C. for 30 min and was then quenched with saturated aqueous ammonium chloride solution (10 mL) and stirred at 0° C. for 5 min. The mixture was extracted with ethyl acetate (3×10 mL) and the combined organic extracts were dried over anhydrous sodium sulfate and concentrated in vacuo. The crude product was purified by flash chromatography on silica gel (10% MeOH/EtOAc) to give the title compound (30 mg, 37%) as an off-white solid. $^1$H NMR (DMSO-$d_6$) δ 10.57 (s, 1H), 10.34 (s, 1H), 8.11 (d, 1H, J=2.8 Hz), 8.10 (s, 1H), 7.86 (dd, 1H, J=12.8, 2.4 Hz), 7.71–7.68 (m, 2H), 7.53 (t, 1H, J=8.4 Hz), 7.46–7.43 (m, 1H), 7.25–7.21 (m, 2H), 6.99 (d, 1H, J=2.8 Hz), 6.64 (s, 1H), 4.65 (br s, 1H), 3.76–3.75 (m, 1H), 3.56 (s, 2H), 2.90–2.85 (m, 1H), 2.51–2.45 (m, 1H), 2.27–2.24 (m, 2H), 1.92–1.85 (m, 2H), 1.46–1.41 (m, 2H); MS(ESI$^+$) m/z 534.3 (M+H)$^+$.

Example 151

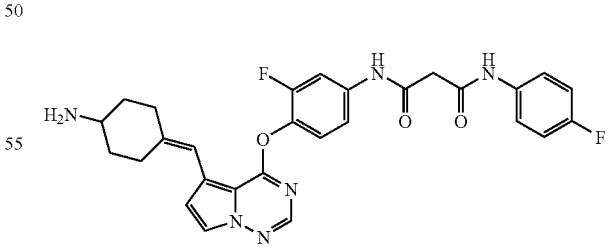

N$^1$-(4-(5-((4-Aminocyclohexylidene)methyl)pyrrolo[2,1-f][1,2,4]triazin-4-yloxy)-3-fluorophenyl)-N$^3$-(4-fluorophenyl)malonamide Prepared in a similar manner as Step C of Example 146 to give the TFA salt of the title compound (12%) as a white solid. ¹H NMR (DMSO-d₆) δ 10.51 (s, 1H), 10.26 (s, 1H), 8.02 (d, 1H, J=2.4 Hz), 7.99 (s, 1H), 7.74 (dd, 1H, J=12.8, 2 Hz), 7.59–7.55 (m, 2H), 7.38 (t, 1H, J=8.4 Hz), 7.32–7.35 (m, 1H), 7.13–7.08 (m, 2H), 6.90 (d, 1H, J=2.8 Hz), 6.59 (s, 1H), 3.44 (s, 2H), 2.95–3.00 (m, 1H), 2.20–2.41 (m, 2H), 1.96–2.11 (m, 2H), 1.32–1.39 (m, 2H), 1.17–1.13 (m, 2H); MS(ESI⁺) m/z 533.3 (M+H)⁺.

Example 152

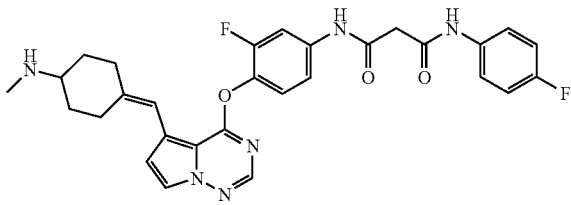

N¹-(3-Fluoro-4-(5-((4-(methylamino)cyclohexylidene)methyl)pyrrolo[2,1-f][1,2,4]triazin-4-yloxy)phenyl)-N³-(4-fluorophenyl)malonamide, trifluoroacetic acid salt To N'-(3-fluoro-4-(5-((4-oxocyclohexylidene)methyl)pyrrolo[2,1-f][,2,4]triazin-4-yloxy)phenyl)-N³-(4-fluorophenyl)malonamide (20 mg, 0.038 mmol, Example 149) in dichloroethane (1 mL) was added methylamine (23 μL, 0.045 mmol, 2 M THF), acetic acid (2.6 μL, 0.045 mmol), followed by sodium triacetoxyborohydride (13 mg, 0.056 mmol). After stirring at rt for 2 h, the reaction was quenched with 5% aqueous sodium bicarbonate solution (1 mL). The layers were separated and the organic layer was washed with brine, dried over anhydrous sodium sulfate, and concentrated in vacuo. The crude product was purified by reverse phase prep HPLC and the appropriate fractions were concentrated in vacuo. Toluene was added (2×4 mL) and concentrated to remove excess TFA. Lyophilization from acetonitrile (1 mL)/water (3 mL) gave the TFA salt of the title compound (11 mg, 44%) as a white solid. ¹H NMR (DMSO-d₆) δ 10.51 (s, 1H), 10.26 (s, 1H), 8.02 (d, 1H, J=2.8 Hz), 8.00 (s, 1H), 7.74 (dd, 1H, J=12.8, 2 Hz), 7.59–7.55 (m, 2H), 7.40 (t, 1H, J=8.4 Hz), 7.35–7.32 (m, 1H), 7.13–7.06 (m, 2H), 6.90 (d, 1H, J=2.8 Hz), 6.60 (s, 1H), 3.44 (s, 2H), 3.10–3.13 (m, 1H), 3.02–2.98 (m, 1H), 2.52–2.39 (m, 4H), 2.23–2.21 (m, 1H), 2.08–2.02 (m, 3H), 1.36–1.31 (m, 2H); MS(ESI⁺) m/z 547.1 (M+H)⁺.

Example 153

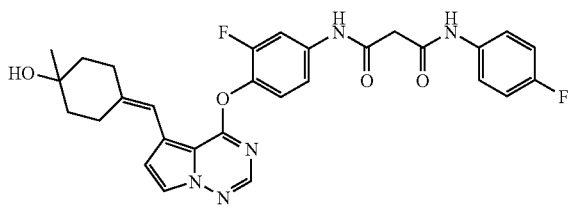

N¹-(3-Fluoro-4-(5-((4-hydroxy-4-methylcyclohexylidene)methyl)pyrrolo[2,1-f][1,2,4]triazin-4-yloxy)phenyl)-N³-(4-fluorophenyl)malonamide, trifluoroacetic acid salt To N¹-(3-fluoro-4-(5-((4-oxocyclohexylidene)methyl)pyrrolo[2,1-f][1,2,4]triazin-4-yloxy)phenyl)-N³-(4-fluorophenyl)malonamide (10 mg, 0.019 mmol, Example 149) in THF (1 mL) at 0° C. was added methyllithium (76 μL, 0.076 mmol, 1 M THF). After stirring at rt overnight, the reaction was quenched with brine (1 mL). The layers were separated and the organic layer was dried over anhydrous sodium sulfate and concentrated in vacuo. The crude product was purified by reverse phase prep HPLC and the appropriate fractions were concentrated in vacuo. Toluene was added (2×2 mL) and concentrated to remove excess TFA. Lyophilization from acetonitrile (1 mL)/water (3 mL) gave the TFA salt of the title compound (3 mg, 21%) as a pale yellow solid. ¹H NMR (DMSO-d₆) δ 10.45 (s, 1H), 10.21 (s, 1H), 7.98 (d, 1H, J=2.8 Hz), 7.96 (s, 1H), 7.74 (dd, 1H, J=12.8, 2 Hz), 7.58–7.55 (m, 2H), 7.40 (t, 1H, J=8 Hz), 7.33–7.31 (m, 1H), 7.13–7.08 (m, 2H), 6.87 (d, 1H, J=2.8 Hz), 6.51 (s, 1H), 4.20 (br s, 1H), 3.43 (s, 2H), 2.60–2.45 (m, 3H), 2.09–2.06 (m, 1H), 1.56–1.52 (m, 2H), 1.41–1.36 (m, 2H), 1.07 (s, 3H); MS(ESI⁺) m/z 548.3 (M+H)⁺.

Example 154

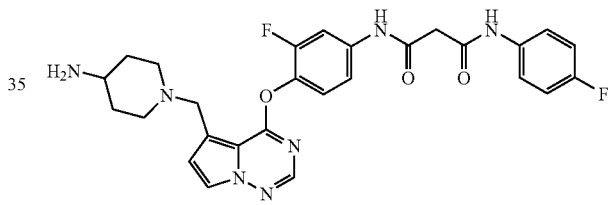

N¹-(4-(5-((4-Aminopiperidin-1-yl)methyl)pyrrolo[2,1-f][1,2,4]triazin-4-yloxy)-3-fluorophenyl)-N³-(4-fluorophenyl)malonamide, trifluoroacetic acid salt

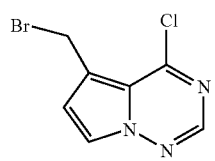

A) 5-Bromomethyl-4-chloro-pyrrolo[2,1-f][1,2,4]triazine

A mixture of 4-chloro-5-methyl-pyrrolo[2,1-f][1,2,4]triazine (2.0 g, 11.93 mmol, WO 03/042172) and AIBN (195 mg, 1.19 mmol) in CCl₄ (80 mL) under N₂ was heated to 100° C. for 5 min, NBS (2.55 g, 14.3 mmol) was added. The reaction mixture was stirred for 10 min, then cooled to rt, filtered. The CCl₄ layer was washed with dilute NaHCO₃ aqueous solution, dried (MgSO₄), filtered and concentrated to give the desired product (2.70 g, 92%).

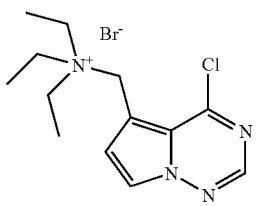

B) (4-Chloro-pyrrolo[2,1-f][1,2,4]triazin-5-ylmethyl)-triethylammonium bromide A mixture of 5-bromomethyl-4-chloro-pyrrolo[2,1-f][1,2,4]triazine (2.7 g, 11 mmol), Et$_3$N (5 mL, 36 mmol) in THF (20 mL) was stirred at rt for 12 h. The solid was filtered and rinsed with THF and Et$_2$O, dried to give the desired product (3.38 g, 89%). Analytical HPLC retention time=0.776 min. (Chromolith SpeedROD 4.6×50 mm, 10–90% aqueous methanol over 4 minutes containing 0.1% TFA, 4 mL/min, monitoring at 220 nm); MS(ESI$^+$) m/z 267 (M+H)$^+$.

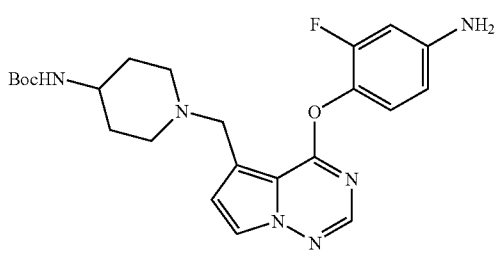

C) tert-Butyl 1-((4-(4-amino-2-fluorophenoxy)pyrrolo[2,1-f][1,2,4]triazin-5-yl)methyl)piperidin-4-ylcarbamate To 4-amino-2-fluorophenol (82 mg, 0.646 mmol) in THF (5 mL) at −78° C. under nitrogen was added NaHMDS (650 μL, 0.650 mmol, 1 M hexanes). After stirring at −78° C. for 20 min, the flask was transferred to a bath at 0° C. and solid N-((4-chloropyrrolo[2,1-f][1,2,4]triazin-5-yl)methyl)-triethylammonium bromide (200 mg, 0.807 mmol) was immediately added. The reaction was allowed to warm to rt and stirred for 2 h. DIPEA (280 μL, 1.6 mmol), tert-butyl piperidin-4-ylcarbamate (129 mg, 0.646 mmol, Aldrich), and DMF (2 mL) was added. The reaction was heated to 120° C. for 4 h. After cooling to rt, the reaction was concentrated in vacuo and the crude product was purified by reverse phase prep HPLC. The appropriate fractions were concentrated in vacuo. Toluene was added (2×2 mL) and concentrated to give the TFA salt of the title compound (100 mg, 27%) as a yellow solid. $^1$H NMR (CD$_3$OD) δ 8.09 (s, 1H), 8.03 (d, 1H, J=2.4 Hz), 7.23–7.13 (m, 2H), 6.83–6.61 (m, 2H), 4.73 (s, 2H), 3.67–3.64 (m, 1H), 3.30–3.19 (m, 2H), 2.31–2.24 (m, 2H), 1.76–1.63 (m, 2H), 1.49–1.45 (m, 2H), 1.45 (s, 9H); MS(ESI$^+$) m/z 457.5 (M+H)$^+$.

D) N$^1$-(4-(5-((4-Aminopiperidin-1-yl)methyl)pyrrolo[2,1-f][1,2,4]triazin-4-yloxy)-3-fluorophenyl)-N$^3$-(4-fluorophenyl)malonamide, trifluoroacetic acid salt Prepared in similar manner as Step A of Example 133. The resulting Boc protected material was dissolved in ether (1 mL) at 0° C. and charged with 4 N HCl in dioxane (3 mL). After stirring at 0° C. for 3 h, the reaction was concentrated in vacuo. The crude product was purified by reverse phase prep HPLC and the appropriate fractions were concentrated in vacuo. Toluene was added (2×2 mL) and concentrated to give the TFA salt of the title compound (4 mg, 12%) as a white solid. $^1$H NMR (DMSO-d$_6$) δ 10.49 (s, 1H), 10.22 (s, 1H), 8.18 (s, 1H), 7.90 (d, 1H, J=2.8 Hz), 7.76 (dd, 1H, J=12.8, 2.4 Hz), 7.57–7.56 (m, 2H), 7.43–7.36 (m, 2H), 7.13–7.09 (m, 3H), 4.57 (s, 2H), 3.51–3.48 (m, 1H), 3.44 (s, 2H), 3.09–3.06 (m, 2H), 2.53–2.50 (m, 2H), 2.00–1.97 (m, 2H), 1.72–1.67 (m, 2H); MS(ESI$^+$) m/z 536.5 (M+H)$^+$.

Example 155

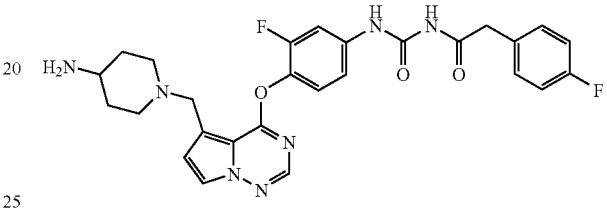

1-(4-(5-((4-Aminopiperidin-1-yl)methyl)pyrrolo[2,1-f][1,2,4]triazin-4-yloxy)-3-fluorophenyl)-3-(2-(4-fluorophenyl)acetyl)urea, trifluoroacetic acid salt To tert-butyl 1-((4-(4-amino-2-fluorophenoxy)pyrrolo[2,1-f][1,2,4]triazin-5-yl)methyl)piperidin-4-ylcarbamate (50 mg, 0.088 mmol, Compound C of Example 154) in dichloromethane (1 mL) at 0° C. was added 2-(4-fluorophenyl)acetyl isocyanate (290 uL, 0.088 mmol, 0.3 M in toluene, Compound C of Example 4). The reaction was stirred at 0° C. for 0.5 h and was purified directly by by flash chromatography on silica gel (10% MeOH/EtOAc) to give the Boc protected material (33 mg, 59%) as a colorless oil. The Boc protected material was suspended in ether (2 mL) at 0° C. and charged with 4 N HCl in dioxane (5 mL). After stirring at 0° C. for 1.5 h, the reaction was concentrated in vacuo. The crude product was purified by reverse phase prep HPLC and the appropriate fractions were concentrated in vacuo. Toluene was added (2×2 mL) and concentrated to give the TFA salt of the title compound (3 mg, 8%) as a white solid. $^1$H NMR (DMSO-d$_6$) δ 11.01 (s, 1H), 10.57 (s, 1H), 8.21–8.18 (m, 2H), 7.73 (dd, 1H, J=12.8, 2.4 Hz), 7.48–7.33 (m, 4H), 7.18–7.11 (m, 3H), 4.57 (m, 1H), 3.69 (s, 2H), 3.44 (s, 2H), 3.59–3.48 (m, 2H), 3.13–3.06 (m, 214), 2.05–1.98 (m, 2H), 1.71–1.55 (m, 2H); MS(ESI$^+$) m/z 535.3 (M+H)$^+$.

Example 156

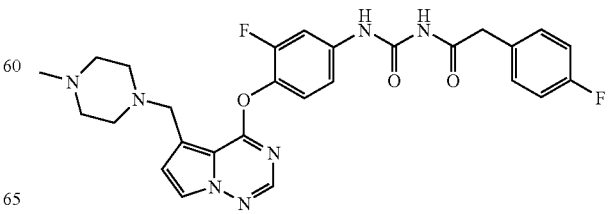

1-(3-Fluoro-4-(5-((4-methylpiperazin-1-yl)methyl)pyrrolo[2,1-f][1,2,4]triazin-4-yloxy)phenyl)-3-(2-(4-fluorophenyl)acetyl)urea

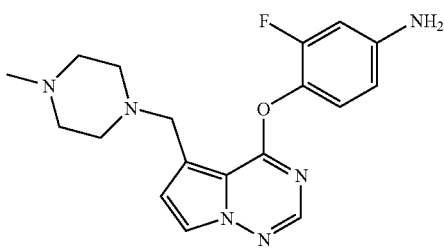

A) 1-(3-Fluoro-4-(5-((4-methylpiperazin-1-yl)methyl)pyrrolo[2,1-f][1,2,4]triazin-4-yloxy)phenyl)-3-(2-(4-fluorophenyl)acetyl)urea Prepared in a similar manner as Step C of Example 154 to give the TFA salt of the title compound (9%) as a brown solid. $^1$H NMR (CD$_3$OD) δ 7.90 (s, 1H), 7.85 (d, 1H, J=2.8 Hz), 7.17 (t, 1H, J=8.8 Hz), 6.94 (d, 1H, J=2.8 Hz), 6.75 (dd, 1H, J=11.6, 2.4 Hz), 6.72–6.69 (m, 1H), 4.39 (s, 2H), 3.40–3.31 (m, 8H), 2.79 (s, 3H); MS(ESI$^+$) m/z 357.3 (M+H)$^+$.

B) 1-(3-Fluoro-4-(5-((4-methylpiperazin-1-yl)methyl)pyrrolo[2,1-f][1,2,4]triazin-4-yloxy)phenyl)-3-(2-(4-fluorophenyl)acetyl)urea Prepared in similar manner as Example 155 to give the title compound (83%) as a white solid. $^1$H NMR (CD$_3$OD) δ 7.80 (s, 1H), 7.77 (d, 1H, J=2 Hz), 7.62 (dd, 1H, J=12.4, 2.4 Hz), 7.27–7.17 (m, 4H), 6.99–6.95 (m, 2H), 6.84 (d, 1H, J=2.4 Hz), 3.94 (s, 2H), 3.62 (s, 2H), 2.70–2.45 (m, 8H), 2.26 (s, 3H); MS(ESI$^+$) m/z 536.2 (M+H)$^+$.

Example 157

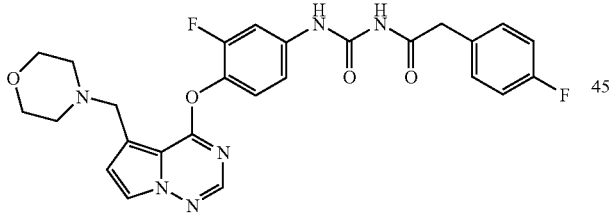

1-(3-Fluoro-4-(5-(morpholinomethyl)pyrrolo[2,1-f][1,2,4]triazin-4-yloxy)phenyl)-3-(2-(4-fluorophenyl)acetyl)urea

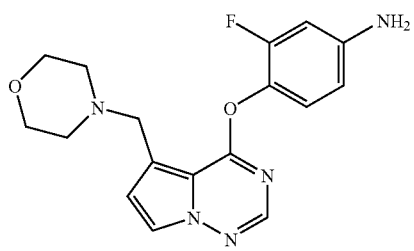

A) 3-Fluoro-4-(5-(morpholinomethyl)pyrrolo[2,1-f][1,2,4]triazin-4-yloxy)benzenamine Prepared in a similar manner as Step C of Example 154 to give the TFA salt of the title compound (10%) as a light brown solid. $^1$H NMR (CD$_3$OD) δ 7.98 (s, 1H), 7.91 (d, 1H, J=2.8 Hz), 7.11 (t, 1H, J=8.4 Hz), 7.02 (d, 1H, J=2.8 Hz), 6.62 (dd, 1H, J=12.4, 2.8 Hz), 6.60–6.57 (m, 1H), 4.67 (s, 2H), 4.00–3.94 (m, 2H), 3.68–3.61 (m, 2H), 3.43–3.40 (m, 2H), 3.22–3.20 (m, 2H); MS(ESI$^+$) m/z 344.3 (M+H)$^+$.

B) 1-(3-Fluoro-4-(5-(morpholinomethyl)pyrrolo[2,1-f][1,2,4]triazin-4-yloxy)phenyl)-3-(2-(4-fluorophenyl)acetyl)urea Prepared in similar manner as Example 155 to give the title compound (83%) as a white solid. $^1$H NMR (CD$_3$OD) δ 7.89 (s, 1H), 7.85 (d, 1H, J=2.8 Hz), 7.67 (dd, 1H, J=12.4, 2.4 Hz), 7.30–7.19 (m, 4H), 7.01–6.94 (m, 3H), 4.28 (s, 2H), 3.70–3.76 (m, 4H), 3.62 (s, 2H), 2.88–2.80 (m, 2H); MS(ESI$^+$) m/z 523.2 (M+H)$^+$.

Example 158

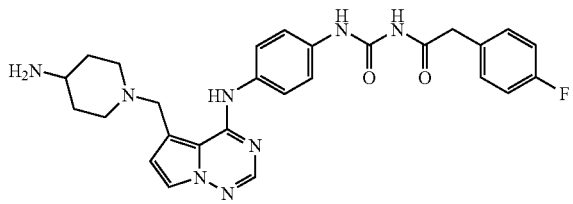

1-(4-(5-((4-Aminopiperidin-1-yl)methyl)pyrrolo[2,1-f][1,2,4]triazin-4-ylamino)phenyl)-3-(2-(4-fluorophenyl)acetyl)urea

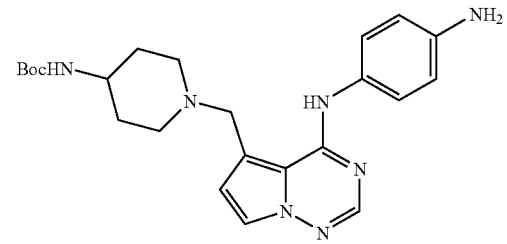

A) tert-Butyl 1-((4-(4-aminophenylamino)pyrrolo[2,1-f][1,2,4]triazin-5-yl)methyl)piperidin-4-ylcarbamate Prepared in a similar manner as Step C of Example 154 to give the TFA salt of the title compound (38%) as a yellow oil. $^1$H NMR (CD$_3$OD) δ 7.57 (s, 1H), 7.33 (d, 1H, J=2.4 Hz), 7.24–7.21 (m, 2H), 6.71–6.68 (m, 2H), 6.45 (d, 1H, J=2.8 Hz), 3.67 (s, 2H), 3.34–3.28 (m, 1H), 2.95–2.90 (m, 2H), 1.80–1.77 (m, 2H), 1.41–1.33 (m, 2H), 1.32 (s, 9H); MS(ESI$^+$) m/z 438.3 (M+H)$^+$.

B) 1-(4-(5-((4-Aminopiperidin-1-yl)methyl)pyrrolo[2,1-f][1,2,4]triazin-4-ylamino)phenyl)-3-(2-(4-fluorophenyl)acetyl)urea Prepared in similar manner as Example 155 to give the title compound (47%) as an off-white solid. $^1$H NMR (DMSO-$d_6$) δ 11.01 (s, 1H), 10.53 (s, 1H), 8.00–7.89 (m, 2H), 7.61–7.59 (m, 3H), 7.45–7.41 (m, 2H), 7.26–7.22 (m, 4H), 3.77 (s, 2H), 3.63 (s, 2H), 3.35–3.32 (m, 1H), 3.20–3.14 (m, 2H), 2.19–1.90 (m, 6H); MS(ESI$^+$) m/z 517.3 (M+H)$^+$.

Example 159

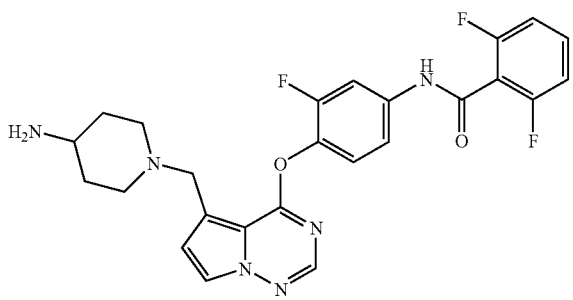

N-(4-(5-((4-Aminopiperidin-1-yl)methyl)pyrrolo[2,1-f][1,2,4]triazin-4-yloxy)-3-fluorophenyl)-2,6-difluorobenzamide Prepared in a similar manner as Example 147 to give the TFA salt of the title compound (5%) as a white solid. $^1$H NMR (DMSO-$d_6$) δ 11.10 (s, 1H), 8.19–8.17 (m, 2H), 7.82 (dd, 1H, J=12.8, 2.4 Hz), 7.49 (t, 1H, J=8.8 Hz), 7.49–7.47 (m, 2H), 7.25–7.21 (m, 2H), 7.14–7.09 (m, 1H), 4.59 (s, 2H), 3.54–3.48 (m, 3H), 3.15–3.08 (m, 2H), 2.08–2.00 (m, 2H), 1.74–1.66 (m, 2H); MS(ESI$^+$) m/z 497.2 (M+H)$^+$.

Example 160

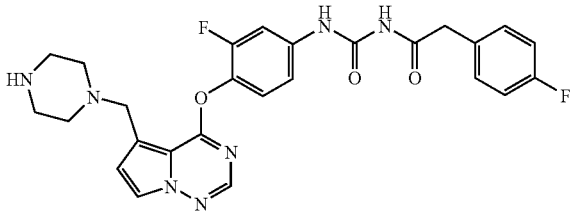

1-(3-Fluoro-4-(5-(piperazin-1-ylmethyl)pyrrolo[2,1-f][1,2,4]triazin-4-yloxy)phenyl)-3-(2-(4-fluorophenyl)acetyl)urea

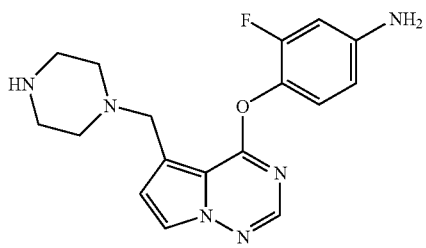

A) 3-Fluoro-4-(5-(piperazin-1-ylmethyl)pyrrolo[2,1-f][1,2,4]triazin-4-yloxy)benzenamine Prepared in a similar manner as Step C of Example 154 to give the title compound as a yellow oil. MS(ESI$^+$) m/z 443.3 (M+H)$^+$.

B) 1-(3-Fluoro-4-(5-(piperazin-1-ylmethyl)pyrrolo[2,1-f][1,2,4]triazin-4-yloxy)phenyl)-3-(2-(4-fluorophenyl)acetyl)urea Prepared in similar manner as Example 155 to give the title compound (6%) as a white solid. $^1$H NMR (DMSO-$d_6$) δ 11.00 (s, 1H), 10.55 (s, 1H), 8.12 (s, 1H), 8.11 (d, 1H, J=2.8 Hz), 7.71 (dd, 1H, J=12.8, 2.4 Hz), 7.42 (t, 1H, J=8.8 Hz), 7.35–7.28 (m, 3H), 7.11 (t, 2H, J=9.2 Hz), 7.03 (m, 1H), 4.58 (s, 2H), 3.69 (s, 2H), 3.66–3.59 (m, 4H), 3.32–3.05 (m, 4H); MS(ESI$^+$) m/z 522.3 (M+H)$^+$.

Example 161

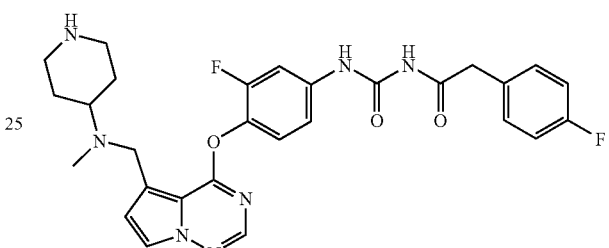

1-(3-Fluoro-4-(5-((methyl(piperidin-4-yl)amino)methyl)pyrrolo[2,1-f][1,2,4]triazin-4-yloxy)phenyl)-3-(2-(4-fluorophenyl)acetyl)urea

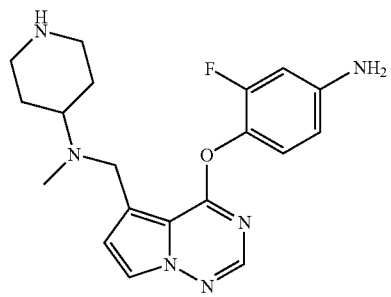

A) N-((4-(4-Amino-2-fluorophenoxy)pyrrolo[2,1-f][1,2,4]triazin-5-yl)methyl)-N-methylpiperidin-4-amine Prepared in a similar manner as Step C of Example 154 to give the title compound (38%) as a yellow oil. MS(ESI$^+$) m/z 471.3 (M+H)$^+$.

B) 1-(3-Fluoro-4-(5-((methyl(piperidin-4-yl)amino)methyl)pyrrolo[2,1-f][1,2,4]triazin-4-yloxy)phenyl)-3-(2-(4-fluorophenyl)acetyl)urea Prepared in similar manner as Example 155 to give the title compound (32%) as a white solid. $^1$H NMR (DMSO-$d_6$) δ 11.00 (s, 1H), 10.55 (s, 1H), 8.19 (s, 1H), 8.16 (d, 1H, J=2.4 Hz), 7.71 (dd, 1H, J=12.4, 2 Hz), 7.42–7.34 (m, 2H), 7.32–7.28 (m, 2H), 7.16–7.06 (m, 3H), 4.44 (s, 2H), 3.69 (s, 2H), 3.64–3.59 (m, 4H), 2.87–2.84 (m, 1H), 2.72 (s, 3H), 2.19–2.15 (m, 2H), 1.87–1.82 (m, 2H); MS(ESI$^+$) m/z 550.3 (M+H)$^+$.

Example 162

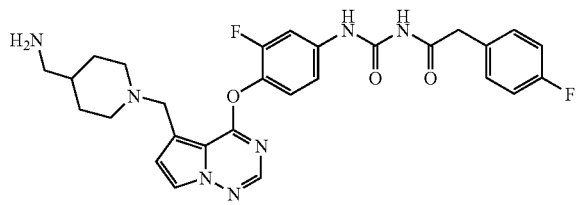

1-(4-(5-((4-(Aminomethyl)piperidin-1-yl)methyl)
pyrrolo[2,1-f][1,2,4]triazin-4-yloxy)-3-fluorophe-
nyl)-3-(2-(4-fluorophenyl)acetyl)urea

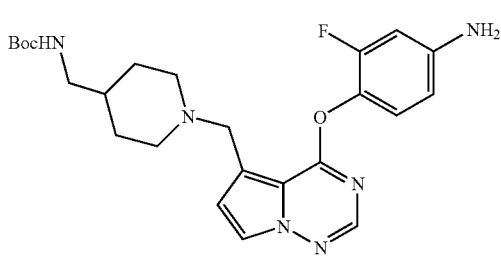

A) tert-Butyl (1-((4-(4-amino-2-fluorophenoxy)pyr-
rolo[2,1-f][1,2,4]triazin-5-yl)methyl)piperidin-4-yl)
methylcarbamate Prepared in a similar manner as Step C of Example 154 to give the title compound (29%) as a yellow oil. MS(ESI$^+$) m/z 471.3 (M+H)$^+$.

B) 1-(4-(5-((4-(Aminomethyl)piperidin-1-yl)methyl)
pyrrolo[2,1-f][1,2,4]triazin-4-yloxy)-3-fluorophe-
nyl)-3-(2-(4-fluorophenyl)acetyl)urea Prepared in similar manner as Example 155 to give the title compound (26%) as a white solid. $^1$H NMR (DMSO-d$_6$) δ 11.01 (s, 1H), 10.53 (s, 1H), 7.99 (s, 1H), 7.97 (d, 1H, J=2.4 Hz), 7.66 (dd, 1H, J=13.2, 2.4 Hz), 7.36–7.28 (m, 4H), 7.09 (t, 2H, J=8.8 Hz), 6.82 (d, 1H, J=2.4 Hz), 3.77 (s, 2H), 3.68 (s, 2H), 3.84–3.82 (m, 2H), 2.38–2.36 (m, 1H), 1.88 (t, 2H, J=10 Hz), 1.58–1.55 (m, 2H), 1.20–1.01 (m, 4H); MS(ESI$^+$) m/z 550.2 (M+H)$^+$.

Example 163

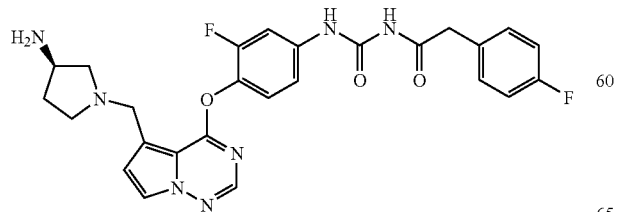

(R)-1-(4-(5-((3-Aminopyrrolidin-1-yl)methyl)pyr-
rolo[2,1-f][1,2,4]triazin-4-yloxy)-3-fluorophenyl)-3-
(2-(4-fluorophenyl)acetyl)urea

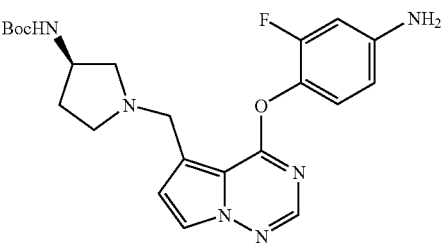

A) (R)-tert-Butyl 1-((4-(4-amino-2-fluorophenoxy)
pyrrolo[2,1-f][1,2,4]triazin-5-yl)methyl)pyrrolidin-3-
ylcarbamate Prepared in a similar manner as Step C of Example 154 to give the title compound (30%) as a yellow oil. MS(ESI$^+$) m/z 443.3 (M+H)$^+$.

B) (R)-1-(4-(5-((3-Aminopyrrolidin-1-yl)methyl)
pyrrolo[2,1-f][1,2,4]triazin-4-yloxy)-3-fluorophe-
nyl)-3-(2-(4-fluorophenyl)acetyl)urea Prepared in similar manner as Example 155 to give the title compound (11%) as a white solid. $^1$H NMR (DMSO-d$_6$) δ 10.54 (s, 1H), 10.21 (s, 1H), 7.99 (s, 1H), 7.98 (d, 1H, J=2.4 Hz), 7.67 (dd, 1H, J=12.4, 2 Hz), 7.40–7.26 (m, 3H), 7.13–7.07 (m, 3H), 6.84 (d, 1H, J=2.8 Hz), 3.90 (s, 2H), 3.68 (s, 2H), 2.67–2.41 (m, 3H), 2.20–2.16 (m, 2H), 1.96–1.91 (m, 1H), 1.32–1.29 (m, 1H); MS(ESI$^+$) m/z 522.2 (M+H)$^+$.

Example 164

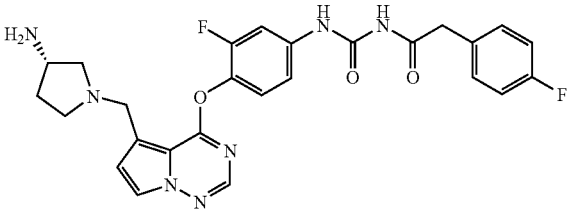

(S)-1-(4-(5-((3-Aminopyrrolidin-1-yl)methyl)pyrrolo
[2,1-f][1,2,4]triazin-4-yloxy)-3-fluorophenyl)-3-(2-
(4-fluorophenyl)acetyl)urea

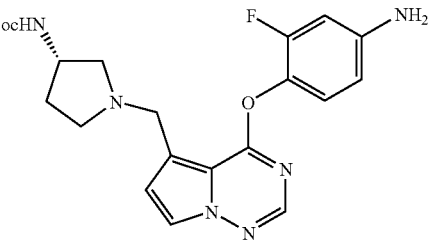

A) (S)-tert-Butyl 1-((4-(4-amino-2-fluorophenoxy)
pyrrolo[2,1-f][1,2,4]triazin-5-yl)methyl)pyrrolidin-3-
ylcarbamate Prepared in a similar manner as Step C of Example 154 to give the title compound (30%) as a yellow oil. MS(ESI$^+$) m/z 443.3 (M+H)$^+$.

B) (S)-1-(4-(5-((3-Aminopyrrolidin-1-yl)methyl)pyrrolo[2,1-f][1,2,4]triazin-4-yloxy)-3-fluorophenyl)-3-(2-(4-fluorophenyl)acetyl)urea Prepared in similar manner as Example 155 to give the title compound (7%) as a white solid. $^1$H NMR (DMSO-d$_6$) δ 10.54 (s, 1H), 10.21 (s, 1H), 7.99 (s, 1H), 7.98 (d, 1H, J=2.4 Hz), 7.67 (dd, 1H, J=12.4, 2 Hz), 7.40–7.26 (m, 3H), 7.13–7.07 (m, 3H), 6.84 (d, 1H, J=2.8 Hz), 3.90 (s, 2H), 3.68 (s, 2H), 2.67–2.41 (m, 3H) 2.20–2.16 (m, 2H), 1.96–1.91 (m, 1H), 1.32–1.29 (m, 1H); MS(ESI$^+$) m/z 522.2 (M+H)$^+$.

Example 165

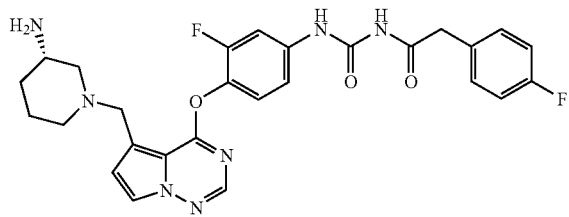

(S)-1-(4-(5-((3-Aminopiperidin-1-yl)methyl)pyrrolo[2,1-f][1,2,4]triazin-4-yloxy)-3-fluorophenyl)-3-(2-(4-fluorophenyl)acetyl)urea

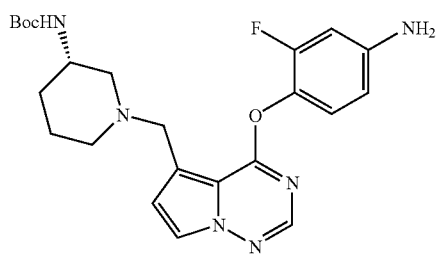

A) (S)-tert-Butyl 1-((4-(4-amino-2-fluorophenoxy)pyrrolo[2,1-f][1,2,4]triazin-5-yl)methyl)piperidin-3-ylcarbamate Prepared in a similar manner as Step C of Example 154 to give the title compound (40%) as a yellow oil. MS(ESI$^+$) m/z 457.3 (M+H)$^+$.

B) (S)-1-(4-(5-((3-Aminopiperidin-1-yl)methyl)pyrrolo[2,1-f][1,2,4]triazin-4-yloxy)-3-fluorophenyl)-3-(2-(4-fluorophenyl)acetyl)urea Prepared in similar manner as Example 155 to give the TFA salt of the title compound (29%) as a white solid. $^1$H NMR (DMSO-d$_6$) δ 11.00 (s, 1H), 10.55 (s, 1H), 8.15 (m, 2H), 7.71 (dd, 1H, J=12.4, 2 Hz), 7.41 (t, 1H, J=8.4 Hz), 7.35–7.28 (m, 3H), 7.11 (t, 2H, J=8.8 Hz), 7.05 (d, 1H, J=2.8 Hz), 4.58 (s, 2H), 3.69 (s, 2H), 3.66–3.30 (m, 5H), 1.95–1.83 (m, 2H), 1.67–1.53 (m, 1H), 1.40–1.32 (m, 1H); MS(ESI$^+$) m/z 536.2 (M+H)$^+$.

Example 166

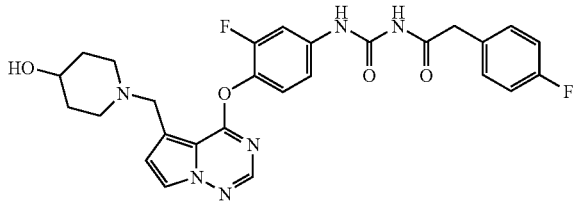

1-(3-Fluoro-4-(5-((4-hydroxypiperidin-1-yl)methyl)pyrrolo[2,1-f][1,2,4]triazin-4-yloxy)phenyl)-3-(2-(4-fluorophenyl)acetyl)urea, trifluoroacetic acid salt

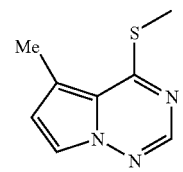

A) 5-Methyl-4-methylsulfanyl-pyrrolo[2,1-f][1,2,4]triazine

To a solution of 4-chloro-5-methyl-pyrrolo[2,1-f][1,2,4]triazine (4.02 g, 24.0 mmol, WO 03/042172) in dry THF (200 mL) sparged with N$_2$ at 0° C. was added NaSMe (1.85 g, 26.3 mmol). The sparging was continued for 5 min. The reaction mixture was then stirred at rt overnight, concentrated in vacuo to about 50 mL volume, diluted with H$_2$O (280 mL) and stirred at 0° C. The solid was filtered, washed with cold water, dried to give the desired product (3.91 g, 91%). Analytical HPLC retention time=3.38 min. (YMC S5 ODS column 4.6×50 mm, 10–90% aqueous methanol over 4 minutes containing 0.2% phosphoric acid, 4 ml/min, monitoring at 220 nm); MS(ESI$^+$) m/z 180 (M+H)$^+$.

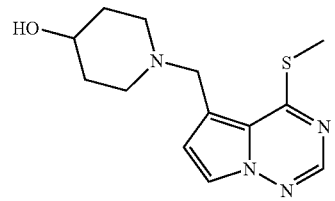

B) 1-((4-(Methylthio)pyrrolo[2,1-f][1,2,4]triazin-5-yl)methyl)piperidin-4-ol

A solution of 5-methyl-4-methylsulfanyl-pyrrolo[2,1-f][1,2,4]triazine (200 mg, 1.12 mmol), NBS (218 mg, 1.23 mmol), and AIBN (spatula tip) in carbon tetrachloride (4 mL) was heated at 80° C. for 1 h. After cooling to rt, the solution was filtered to remove succinimide. To the filtrate was added 4-hydroxypiperidine (126 mg, 1.34 mmol, Aldrich) and DIPEA (214 µL, 1.23 mmol). The reaction was stirred at rt overnight and was then concentrated in vacuo.

The residue was suspended in methanol and filtered. The filtrate was concentrated and the crude product was purified by flash chromatography on silica gel (20% MeOH/EtOAc) to give the title compound (229 mg, 74%) as a colorless solid. ¹H NMR (DMSO-d₆) δ 8.25 (s, 1H), 7.88 (d, 1H, J=2 Hz), 6.81 (d, 1H, J=2 Hz), 4.54 (br s, 1H), 3.76 (s, 2H), 3.48–3.44 (m, 1H), 2.75–2.71 (m, 2H), 2.62 (s, 3H), 2.10–2.08 (m, 2H), 1.70–1.68 (m, 2H), 1.38–1.36 (m, 2H); MS(ESI⁺) m/z 279.3 (M+H)⁺.

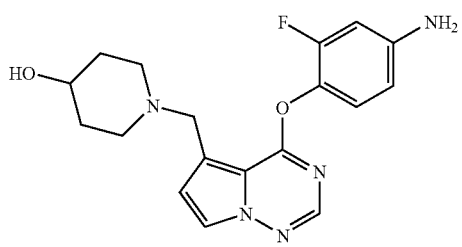

C) 1-((4-(4-Amino-2-fluorophenoxy)pyrrolo[2,1-f][1,2,4]triazin-5-yl)methyl)piperidin-4-ol To 1-((4-(methylthio)pyrrolo[2,1-f][1,2,4]triazin-5-yl)methyl)piperidin-4-ol (188 mg, 0.675 mmol) in dichloromethane (7 mL) at 0° C. was added TFA (78 μL, 1.01 mmol) followed by m-CPBA (166 mg, 0.675 mmol, ~70% pure). After stirring at 0° C. for 1 h, the mixture was concentrated in vacuo. Ether (20 mL) was added and then decanted off to remove the benzoic acid. The resulting crude sulfoxide was dried under high vacuum. 4-Amino-2-fluorophenol (343 mg, 2.7 mmol) was dissolved in THF (10 mL), cooled to −78° C., and charged with NaHMDS (2.7 mL, 2.7 mmol, 1 M in THF). After stirring at 0° C. for 5 min, the crude sulfoxide in THF (3 mL) was added. The reaction was stirred at 0° C. for 30 min and was then concentrated in vacuo. The residue was suspended in EtOAc (20 mL), washed with water (10 mL), dried over anhydrous sodium sulfate, and concentrated in vacuo. The crude product was purified by reverse phase prep HPLC and the appropriate fractions were concentrated in vacuo to remove methanol. The resulting aqueous solution was made basic with 5% aqueous sodium bicarbonate solution and extracted with EtOAc (3×10 mL). The combined extracts were dried over anhydrous sodium sulfate and concentrated in vacuo to give 36 mg (15%) of the title compound as a white solid. ¹H NMR (DMSO-d₆) δ 8.04 (s, 1H), 8.00 (d, 1H, J=2.8 Hz), 7.02 (t, 1H, J=8.8 Hz), 6.88 (d, 1H, J=2.8 Hz), 6.51 (dd, 1H, J=12.8, 2.8 Hz), 6.46–6.42 (m, 1H), 5.45 (br s, 2H), 3.83 (s, 2H), 3.18 (m, 1H), 2.76–2.71 (m, 2H), 2.12–2.06 (m, 2H), 1.72–1.67 (m, 2H), 1.41–1.38 (m, 2H); MS(ESI⁺) m/z 358.4 (M+H)⁺.

D) 1-(3-Fluoro-4-(5-((4-hydroxypiperidin-1-yl)methyl)pyrrolo[2,1-f][1,2,4]triazin-4-yloxy)phenyl)-3-(2-(4-fluorophenyl)acetyl)urea, trifluoroacetic acid salt Prepared in similar manner as Example 155 to give the TFA salt of the title compound (12%) as a white solid. ¹H NMR (DMSO-d₆) δ 11.00 (s, 1H), 10.55 (s, 1H), 8.18 (s, 1H), 8.16–8.14 (m, 1H), 7.71 (d, 1H, J=12.4 Hz), 7.41–7.28 (m, 4H), 7.11–7.08 (m, 3H), 4.59–4.54 (m, 2H), 3.68 (s, 2H), 3.60–3.00 (m, 5H), 1.92–1.87 (m, 1H), 1.81–1.68 (m, 2H), 1.53–1.48 (m, 1H); MS(ESI⁺) m/z 537.2 (M+H)⁺.

Example 167

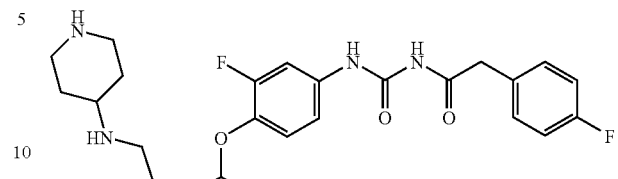

1-(3-Fluoro-4-(5-((piperidin-4-ylamino)methyl)pyrrolo[2,1-f][1,2,4]triazin-4-yloxy)phenyl)-3-(2-(4-fluorophenyl)acetyl)urea

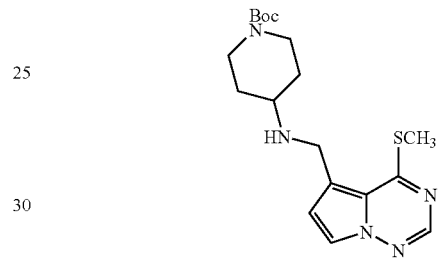

A) tert-Butyl 4-((4-(methylthio)pyrrolo[2,1-f][1,2,4]triazin-5-yl)methylamino)piperidine-1-carboxylate Prepared in a similar manner as Step A of Example 166 to give the title compound (50%) as a colorless oil. ¹H NMR (CD₃OD) δ 8.14 (s, 1H), 7.73 (d, 1H, J=2.8 Hz), 6.91 (d, 1H, J=2.8 Hz), 4.21 (s, 2H), 4.10–4.07 (m, 2H), 2.83–2.77 (m, 3H), 2.71 (s, 3H), 1.99–1.97 (m, 2H), 1.48 (s, 9H), 1.34–1.31 (m, 2H); MS(ESI⁺) m/z 378.3 (M+H)⁺.

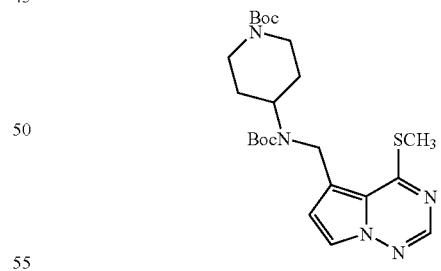

B) 4-[tert-Butoxycarbonyl-(4-methylsulfanyl-pyrrolo[2,1-f][1,2,4]triazin-5-ylmethyl)-amino]-piperidine-1-carboxylic acid tert-butyl ester tert-Butyl 4-((4-(methylthio)pyrrolo[1,2-f][1,2,4]triazin-5-yl)methylamino)piperidine-1-carboxylate (210 mg, 0.556 mmol) was dissolved in dichloromethane (5 mL) and triethylamine (120 μL, 0.834 mmol) followed by di-tert-butyl dicarbonate (134 mg, 0.612 mmol) was added. After stirring at rt for 8 h, the reaction was diluted with methylene chloride (20 mL), washed with saturated aqueous ammonium chloride solution (10 mL), dried over anhydrous sodium sulfate, and concentrated in vacuo. The crude product was purified by flash chromatography on silica gel (20% EtOAc/hexanes) to give the title compound (207 mg, 78%) as a colorless oil. $^1$H NMR (CDCl$_3$) δ 8.01 (s, 1H), 7.51 (d, 1H, J=2.8 Hz), 6.57 (d, 1H, J=2.8 Hz), 4.71 (s, 2H), 4.06–4.04 (m, 3H), 2.68–2.61 (m, 2H), 2.61 (s, 3H), 1.60–1.57 (m, 2H), 1.46–1.36 (m, 2H), 1.35 (s, 18H); MS(ESI$^+$) m/z 478.2 (M+H)$^+$.

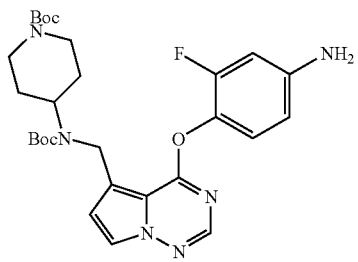

C) 4-{[4-(4-Amino-2-fluoro-phenoxy)-pyrrolo[2,1-f][1,2,4]triazin-5-ylmethyl]-tert-butoxycarbonyl-amino}-piperidine-1-carboxylic acid tert-butyl ester Prepared in a similar manner as Step C of Example 166 to give the title compound (43%) as a colorless oil. $^1$H NMR (CDCl$_3$) δ 7.84 (s, 1H), 7.62 (d, 1H, J=2.8 Hz), 6.98 (t, 1H, J=8.8 Hz), 6.70 (d, 1H, J=2.8 Hz), 6.47–6.41 (m, 2H), 4.72 (s, 2H), 4.10–4.04 (m, 2H), 3.77–3.75 (m, 1H), 2.62–2.60 (m, 2H), 1.71–1.38 (m, 4H), 1.35 (s, 18H); MS(ESI$^+$) m/z 557.2 (M+H)$^+$.

D) 1-(3-Fluoro-4-(5-((piperidin-4-ylamino)methyl)pyrrolo[2,1-f][1,2,4]triazin-4-yloxy)phenyl)-3-(2-(4-fluorophenyl)acetyl)urea Prepared in a similar manner as Example 155 to give the title compound (34%) as a white solid. $^1$H NMR (DMSO-d$_6$) δ 11.01 (s, 1H), 10.55 (s, 1H), 8.16 (s, 1H), 8.12 (d, 1H, J=2.4 Hz), 7.71 (dd, 1H, J=12.4, 2 Hz), 7.42–7.28 (m, 4H), 7.18–7.08 (m, 3H), 4.51 (s, 2H), 3.69 (s, 2H), 3.50–3.29 (m, 3H), 2.88–2.85 (m, 2H), 2.23–2.18 (m, 2H), 1.72–1.64 (m, 2H); MS(ESI$^+$) m/z 536.2 (M+H)$^+$.

Example 168

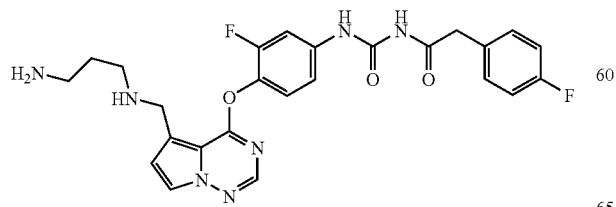

1-(4-(5-((3-Aminopropylamino)methyl)pyrrolo[2,1-f][1,2,4]triazin-4-yloxy)-3-fluorophenyl)-3-(2-(4-fluorophenyl)acetyl)urea

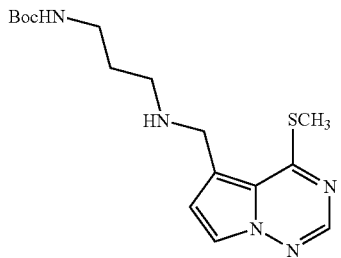

A) tert-Butyl 3-((4-(methylthio)pyrrolo[2,1-f][1,2,4]triazin-5-yl)methylamino)propylcarbamate Prepared in a similar manner as Step B of Example 166 to give the title compound (51%) as a yellow solid. $^1$H NMR (CD$_3$OD) δ 8.16 (s, 1H), 7.75 (d, 1H, J=2.4 Hz), 6.94 (d, 1H, J=2.8 Hz), 4.30 (s, 2H), 3.14 (t, 2H, J=6.4 Hz), 2.83 (t, 2H, J=7.2 Hz), 2.72 (s, 3H), 1.82–1.75 (m, 2H), 1.40 (s, 9H); MS(ESI$^+$) m/z 352.3 (M+H)$^+$.

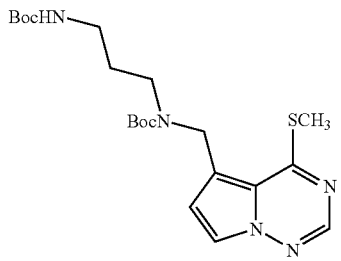

B) {3-[tert-Butoxycarbonyl-(4-methylsulfanyl-pyrrolo[2,1-f][1,2,4]triazin-5-ylmethyl)-amino]-propyl}-carbamic acid tert-butyl ester Prepared in a similar manner to Step B of Example 167 to give the title compound (77%) as a pale yellow oil. $^1$H NMR (CDCl$_3$) δ 8.14 (s, 1H), 7.73 (d, 1H, J=2.4 Hz), 6.75 (d, 1H, J=2 Hz), 4.88 (s, 2H), 3.29–3.25 (m, 2H), 3.04–3.02 (m, 2H), 2.71 (s, 3H), 1.72–1.68 (m, 2H), 1.54 (s, 9H), 1.42 (s, 9H); MS(ESI$^+$) m/z 452.2 (M+H)$^+$.

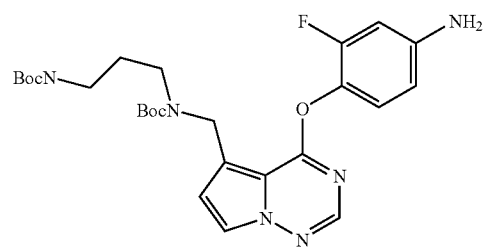

C) (3-{[4-(4-Amino-2-fluoro-phenoxy)-pyrrolo[2,1-f][1,2,4]triazin-5-ylmethyl]-tert-butoxycarbonyl-amino}-propyl)-carbamic acid tert-butyl ester Prepared in a similar manner as Step C of Example 166 to give the title compound (29%) as a colorless oil. $^1$H NMR (CDCl$_3$) δ 7.85 (s, 1H), 7.64 (d, 1H, J=2.8 Hz), 7.00 (t, 1H, J=8.8 Hz), 6.82–6.78 (m, 1H), 6.62 (dd, 1H, J=12.8, 2.4 Hz), 6.54–6.51 (m, 1H), 4.72 (m, 2H), 3.28–3.23 (m, 2H), 3.02–3.00 (m, 2H), 1.58–1.55 (m, 2H), 1.43 (s, 9H), 1.35 (s, 9H); MS(ESI⁺) m/z 531.2 (M+H)⁺.

D) 1-(4-(5-((3-Aminopropylamino)methyl)pyrrolo[2,1-f][1,2,4]triazin-4-yloxy)-3-fluorophenyl)-3-(2-(4-fluorophenyl)acetyl)urea Prepared in a similar manner as Example 155 to give the title compound (17%) as a white solid. ¹H NMR (DMSO-d₆) δ 11.01 (s, 1H), 10.52 (s, 1H), 8.00 (s, 1H), 7.98 (d, 1H, J=2.8 Hz), 7.68 (dd, 1H, J=12.8, 2.4 Hz), 7.34–7.28 (m, 4H), 7.13 (t, 2H, J=9.2 Hz), 6.84 (d, 1H, J=2.4 Hz), 3.68 (s, 2H), 3.52 (s, 2H), 2.90–2.85 (m, 2H), 2.28–2.20 (m, 2H), 1.35–1.30 (m, 2H); MS(ESI⁺) m/z 510.2 (M+H)⁺.

Example 169

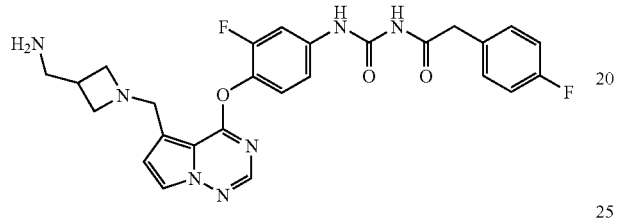

1-(4-(5-((3-(Aminomethyl)azetidin-1-yl)methyl)pyrrolo[2,1-f][1,2,4]triazin-4-yloxy)-3-fluorophenyl)-3-(2-(4-fluorophenyl)acetyl)urea

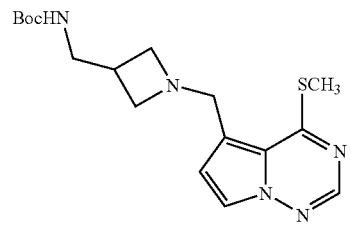

A) tert-Butyl (1-((4-(methylthio)pyrrolo[2,1-f][1,2,4]triazin-5-yl)methyl)azetidin-3-yl)methylcarbamate Prepared in a similar manner as Step B of Example 166 to give the title compound (31%) as a white solid. ¹H NMR (CD₃OD) δ 8.12 (s, 1H), 7.72 (d, 1H, J=2.4 Hz), 6.81 (d, 1H, J=2.8 Hz), 4.07 (s, 2H), 3.46 (t, 2H, J=8 Hz), 3.34–3.33 (m, 1H), 3.20–3.18 (m, 2H), 3.08 (t, 2H, J=7.6 Hz), 2.65 (s, 3H), 1.44 (s, 9H); MS(ESI⁺) m/z 364.3 (M+H)⁺.

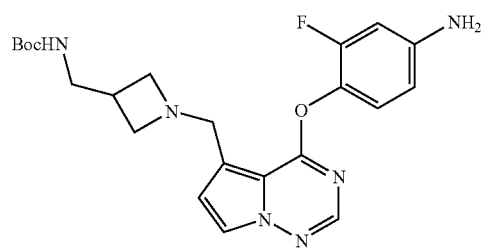

B) tert-Butyl (1-((4-(4-amino-2-fluorophenoxy)pyrrolo[2,1-f][1,2,4]triazin-5-yl)methyl)azetidin-3-yl)methylcarbamate Prepared in a similar manner as Step C of Example 166 to give the title compound (33%) as a brown solid. MS(ESI⁺) m/z 443.2 (M+H)⁺.

C) 1-(4-(5-((3-(Aminomethyl)azetidin-1-yl)methyl)pyrrolo[2,1-f][1,2,4]triazin-4-yloxy)-3-fluorophenyl)-3-(2-(4-fluorophenyl)acetyl)urea Prepared in a similar manner as Example 155 to give the title compound (4%) as a white solid. ¹H NMR (DMSO-d₆) δ 11.02 (s, 1H), 10.56 (s, 1H), 8.18–8.15 (m, 2H), 7.68 (dd, 1H, J=12.8, 2.4 Hz), 7.45–7.28 (m, 4H), 7.18–7.08 (m, 3H), 4.67 (s, 2H), 4.44–4.41 (m, 2H), 4.05–3.98 (m, 2H), 3.69 (s, 2H), 3.10–2.97 (m, 3H); MS(ESI⁺) m/z 522.3 (M+H)⁺.

Example 170

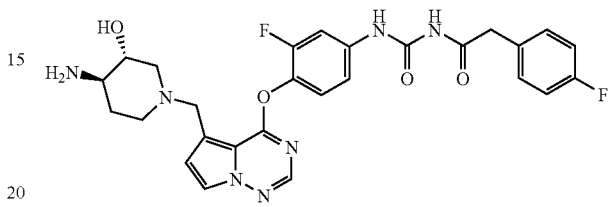

1-(4-(5-(((3R,4R)-4-Amino-3-hydroxypiperidin-1-yl)methyl)pyrrolo[2,1-f][1,2,4]triazin-4-yloxy)-3-fluorophenyl)-3-(2-(4-fluorophenyl)acetyl)urea

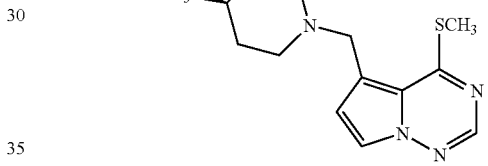

A) (3R,4R)-4-Azido-1-((4-(methylthio)pyrrolo[2,1-f][1,2,4]triazin-5-yl)methyl)piperidin-3-ol Prepared in a similar manner as Step B of Example 166 to give the title compound (65%) as a yellow foam. ¹H NMR (CD₃OD) δ 8.36 (s, 1H), 7.99 (d, 1H, J=2.4 Hz), 6.93 (d, 1H, J=2.8 Hz), 3.92–3.88 (m, 2H), 3.35–3.30 (m, 1H), 3.08–2.90 (m, 2H), 2.72 (s, 3H), 2.14–2.10 (m, 2H), 2.00–1.91 (m, 2H), 1.47–1.44 (m, 1H); MS(ESI⁺) m/z 320.2 (M+H)⁺.

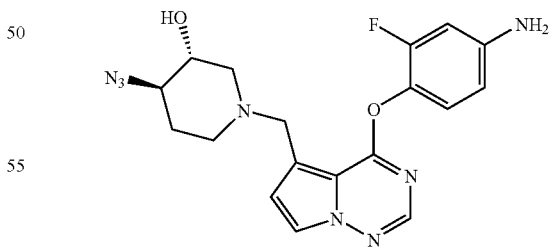

B) (3R,4R)-1-((4-(4-Amino-2-fluorophenoxy)pyrrolo[2,1-f][1,2,4]triazin-5-yl)methyl)-4-azidopiperidin-3-ol Prepared in a similar manner as Step C of Example 166 to give the title compound (24%) as a brown solid. MS(ESI⁺) m/z 399.2 (M+H)⁺.

C) 1-(4-(5-(((3R,4R)-4-Amino-3-hydroxypiperidin-1-yl)methyl)pyrrolo[2,1-f][1,2,4]triazin-4-yloxy)-3-fluorophenyl)-3-(2-(4-fluorophenyl)acetyl)urea The acylurea was prepared in a similar manner as Example 155 to give the corresponding azide (48%). MS(ESI+) m/z 578.16 (M+H)+. The azide (35 mg, 0.06 mmol) was then dissolved in ethyl acetate (1 mL) at 0° C. and charged with trimethylphosphine (0.11 mL, 0.11 mmol) followed by water (1 drop). After stirring at rt for 3 h, the reaction was concentrated in vacuo and purified by reverse phase prep HPLC. The appropriate fractions were concentrated in vacuo and toluene was added (2×2 mL) and concentrated to give the TFA salt of the title compound (8 mg, 17%) as a white solid. $^1$H NMR (DMSO-$d_6$) δ 11.00 (s, 1H), 10.55 (s, 1H), 8.18–8.16 (m, 2H), 7.72 (dd, 1H, J=12.8, 2.4 Hz), 7.36–7.28 (m, 4H), 7.14–7.09 (m, 3H), 4.62 (s, 2H), 3.69 (s, 2H), 3.22–2.85 (m, 6H), 2.03–1.98 (m, 1H), 1.68–1.65 (m, 1H); MS(ESI+) m/z 510.2 (M+H)+.

Example 171

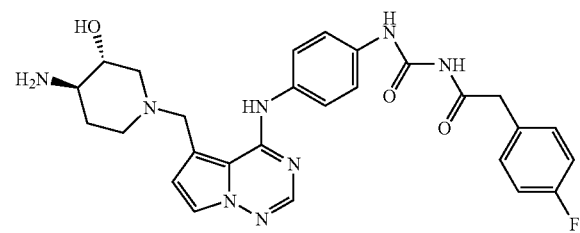

1-(4-(5-(((3R,4R)-4-Amino-3-hydroxypiperidin-1-yl)methyl)pyrrolo[2,1-f][1,2,4]triazin-4-ylamino)phenyl)-3-(2-(4-fluorophenyl)acetyl)urea

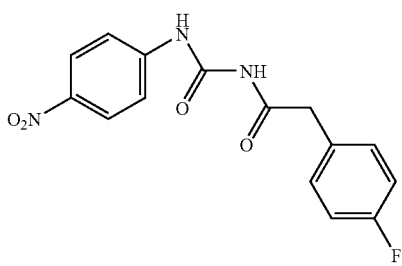

A) 1-(2-(4-Fluorophenyl)acetyl)-3-(4-nitrophenyl)urea

To a stirred solution of p-nitroaniline (200 mg, 1.45 mmol) in tetrahydrofuran (1 mL) at room temperature was added 2-(4-fluorophenyl)acetyl isocyanate (2 mL, 0.32 M in toluene, Compound C of Example 4). After 18 h, the mixture was concentrated in vacuo and the residue was dissolved in ethyl acetate (5 mL). The solution was slowly concentrated on rotary evaporator without heating. When a precipitate started to form, the flask was removed from the rotary evaporator and allowed to sit for 2 h. The solid formed was filtered and washed with small amount of ethyl acetate and dried in vacuo to afford light yellow crystalline compound (200 mg, 44%). MS(ESI+) m/z 318.3 (M+H)+.

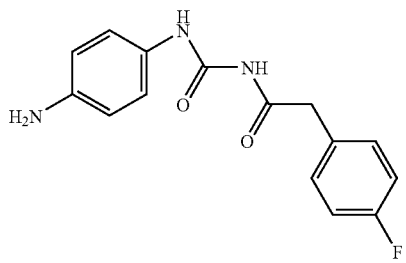

B) 1-(4-Aminophenyl)-3-(2-(4-fluorophenyl)acetyl)urea

To a solution of 1-(2-(4-fluorophenyl)acetyl)-3-(4-nitrophenyl)urea (200 mg, 0.63 mmol) in ethyl acetate (10 mL) was added 10% palladium on carbon (15 mg) and the flask was filled with hydrogen using a balloon. The mixture was stirred for 18 h, filtered and the catalyst was washed with ethyl acetate. The filtrate was concentrated in vacuo to give a solid which was was triturated with small amount of ether and dried in vacuo to obtain the desired compound (180 mg) as pale yellow solid. MS(ESI+) m/z 287.4 (M+H)+.

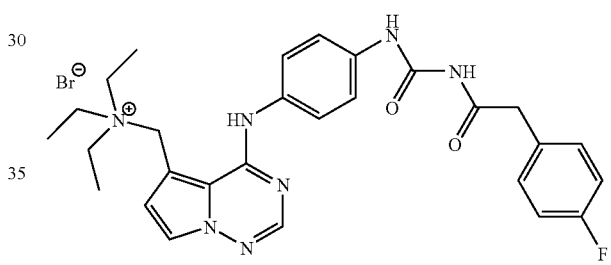

C) N,N-diethyl-N-((4-(4-(3-(2-(4-fluorophenyl)acetyl)ureido)phenylamino)pyrrolo[2,1-f][1,2,4]triazin-5-yl)methyl)ethanaminium bromide To a solution of (4-chloro-pyrrolo[2,1-f][1,2,4]triazin-5-ylmethyl)-triethylammonium bromide (75 mg, 0.22 mmol, Compound B of Example 154) in chloroform (1.5 mL) was added 1-(4-aminophenyl)-3-(2-(4-fluorophenyl)acetyl)urea (50 mg, 0.17 mmol) and the mixture was heated at reflux for 6 h. The mixture was cooled to room temperature, concentrated in vacuo and the residue was triturated with acetonitrile. The resulting solid was used in the next step without purification.

D) 1-(4-(5-(((3R,4R)-4-Azido-3-hydroxypiperidin-1-yl)methyl)pyrrolo[2,1-f][1,2,4]triazin-4-ylamino)phenyl)-3-(2-(4-fluorophenyl)acetyl)urea To a solution of crude N,N-diethyl-N-((4-(4-(3-(2-(4-fluorophenyl)acetyl)ureido)phenylamino)pyrrolo[2,1-f][1,2,4]triazin-5-yl)methyl)ethanaminium bromide in chloroform (3 mL), were added (3R,4R)-4-azidopiperidin-3-ol (0.28 mg, 0.2 mmol, WO 04/058144) and triethylamine (0.2 mL). The reaction mixture was stirred at 60° C. for 2 h, cooled to room temperature and was then washed with Water. The aqueous layer was extracted with chloroform (3×8 mL). The combined organic extracts were concentrated in vacuo to give the crude product as a yellow solid.

The above crude solid was dissolved in tetrahydrofuran (3 mL), triphenylphosphine (80 mg) and water (0.02 mL) were added and the resulting reaction mixture was heated to reflux for 2 h. The reaction mixture was cooled to room temperature, concentrated in vacuo and the crude product was purified by preparative reverse phase HPLC. The appropriate fractions were collected, concentrated and treated with 1 N HCl (2 mL). The solution was concentrated in vacuo, dissolved in water and lyophilized to obtain the title compound (48 mg, 47% over three steps) as a white solid. $^1$H NMR (CD$_3$OD) δ 7.87 (s, 1H), 7.77 (s, 1H), 7.65 (d, 2H, J=8.4 Hz), 7.46 (d, 2H, J=8.3 Hz), 7.28 (dd, 2H, J=5.4, 8.4 Hz), 7.06 (s, 1H), 6.98 (t, 2H, J=8.7 Hz), 4.7 (br s, 2H), 3.9 (br s, 2H), 3.63 (s, 2H), 3.56 (br s, 2H), 3.20–3.10 (br s, 2H), 2.99–2.87 (br s, 1H), 2.96 (br d, 1H, J=10.8 Hz), 1.91 (br t, J=10.8 Hz); MS(ESI$^+$) m/z 533.4 (M+H)$^+$.

Example 172

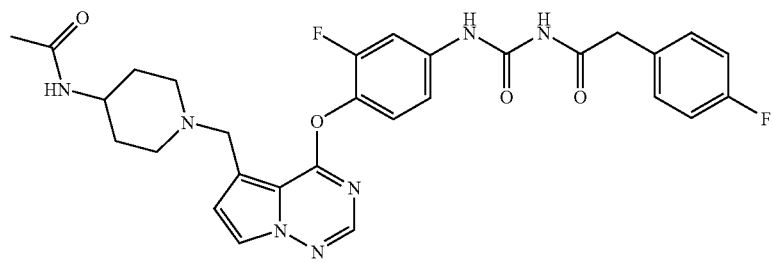

1-(4-(5-((4-Acetamidopiperidin-1-yl)methyl)pyrrolo[2,1-f][1,2,4]triazin-4-yloxy)-3-fluorophenyl)-3-(2-(4-fluorophenyl)acetyl)urea To 1-(4-(5-((4-aminopiperidin-1-yl)methyl)pyrrolo[2,1-f][1,2,4]triazin-4-yloxy)-3-fluorophenyl)-3-(2-(4-fluorophenyl)acetyl)urea (30 mg, 0.056 mmol, Example 155) in methylene chloride (1 mL) was added pyridine (6 μL, 0.067 mmol) followed by acetyl chloride (5 μL, 0.067 mmol). DMF (0.5 mL) was added to solubilize the reaction. After stirring at rt for 2 h, a second shot of pyridine (6 μL) and acetyl chloride (5 μL) was added. After stirring at rt for 1 h, the reaction was diluted with ethyl acetate (10 mL), washed with 10% aqueous lithium chloride solution followed by brine (1×5 mL each), dried over anhydrous sodium sulfate, and concentrated in vacuo. The crude product was purified by reverse phase prep hplc. The appropriate fractions were concentrated in vacuo and toluene was added (2×2 mL) and concentrated to give the TFA salt of the title compound (15 mg, 39%) as a white solid. $^1$H NMR (DMSO-d$_6$) δ 11.00 (s, 1H), 10.55 (s, 1H), 8.19 (s, 1H), 8.14 (d, 1H, J=2.8 Hz), 7.89 (d, 1H, J=7.2 Hz), 7.71 (dd, 1H, J=12.4, 2.4 Hz), 7.43–7.28 (m, 4H), 7.14–7.07 (m, 3H), 4.54 (s, 2H), 3.68 (s, 2H), 3.45–2.42 (m, 3H), 3.12–3.10 (m, 2H), 1.88–1.85 (m, 2H), 1.73 (s, 3H), 1.52–1.50 (m, 2H); MS(ESI$^+$) m/z 578.2 (M+H)$^+$.

Example 173

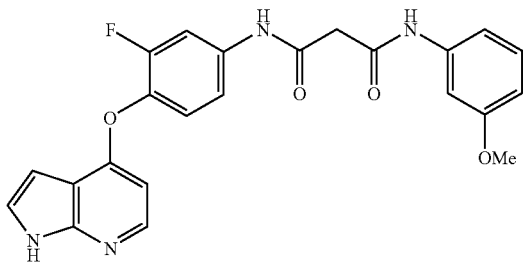

N$^1$-(4-(1H-Pyrrolo[2,3-b]pyridin-4-yloxy)-3-fluorophenyl)-N$^3$-(3-methoxyphenyl)malonamide, trifluoroacetic acid salt

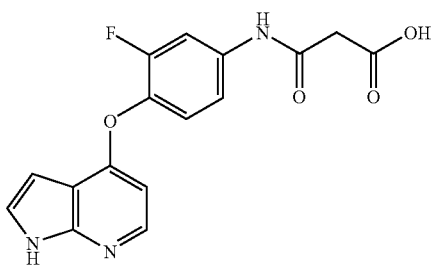

A) 3-(4-(1H-Pyrrolo[2,3-b]pyridin-4-yloxy)-3-fluorophenylamino)-3-oxopropanoic acid To a solution of 4-(1H-pyrrolo[2,3-b]pyridin-4-yloxy)-3-fluorobenzenamine (900 mg, 3.7 mmol, Compound B of Example 132) in CH$_2$Cl$_2$ (30 mL) at −40° C., was added ethyl 3-chloro-3-oxopropanoate (555 mg, 3.7 mmol, Aldrich), followed by pyridine (1 mL). The resulting mixture was stirred at −40° C. for 1 h. The mixture was diluted with CH$_2$Cl$_2$, washed with sat. KH$_2$PO$_4$, and dried over MgSO$_4$. The mixture was filtered through a short pad of silica gel, eluting with 2% MeOH/EtOAc to give a brown oil (1.1 g). The ester was saponified in EtOH (15 mL) and NaOH (1 N in H$_2$O, 15 mL) at 0° C. for 1 h, neutralized with 1 N HCl to pH 4. EtOH was removed from the reaction mixture under reduced pressure and the solid was collected by filtration. The solid was then rinsed with H$_2$O and dried (MgSO$_4$) to afford the title compound (670 mg, 55%) as a beige solid. LC/MS(ESI$^+$) m/z 330 (M+H)$^+$.

B) N$^1$-(4-(1H-Pyrrolo[2,3-b]pyridin-4-yloxy)-3-fluorophenyl)-N$^3$-(3-methoxyphenyl)malonamide, trifluoroacetic acid salt To a stirred solution of 3-(4-(1H-pyrrolo[2,3-b]pyridin-4-yloxy)-3-fluorophenylamino)-3-oxopropanoic acid (16.5 mg, 0.05 mmol) in DMF (0.4 mL), was added HATU (38 mg, 0.1 mmol), followed by 3-methoxybenzenamine (18 mg, 0.15 mmol) and DMAP (3 mg). The mixture was heated at 45° C. for 4 h. The desired product was purified by prep-HPLC to give the title compound (17 mg, 62%) as a white solid. $^1$H NMR (CD$_3$OD) δ 8.15 (d, 1H, J=6.6 Hz), 7.80 (dd, 1H, J=11.8, 2.2 Hz), 7.41 (d, 1H, J=3.9 Hz), 7.29–7.38 (m, 2H), 7.23 (m, 1H), 7.12 (t, 1H, J=8,3 Hz), 7.00 (dd, 1H, J=8.3, 1.1 Hz), 6.69 (d, 1H, J=6.6 Hz), 6.60 (dd, 1H, J=8.3, 2.2 Hz), 6.51 (d, 1H, J=3.3 Hz), 3.90 (s, 3H); LCMS(ESI$^+$) m/z 435 (M+H)$^+$.

Examples 174–236

The examples 174–236 illustrated in Table 3 were prepared from 3-(4-(1H-pyrrolo[2,3-b]pyridin-4-yloxy)-3-fluorophenylamino)-3-oxopropanoic acid (Compound A of Example 173) and the corresponding amines, in the presence of HATU, DIPEA, and DMAP in DMF. The crude products were purified by prep-HPLC (H$_2$O/MeOH/0.1% TFA, gradient 35–90% MeOH over 10 min, 20×100 mm 5 μm YMC ODS-A column). The desired fraction(s) was/were centrifugally evaporated, weighed and analyzed by LCMS (H$_2$O/MeOH/0.1% TFA).

TABLE 3

| EXAMPLE # | NR$_1$R$_2$ | Compound Name | LC/MS (M + H)$^+$ |
|---|---|---|---|
| 174 | (4-fluorophenyl)(methyl)amino | N$^1$-(4-(1H-Pyrrolo[2,3-b]pyridin-4-yloxy)-3-fluorophenyl)-N$^3$-(4-fluorophenyl)-N$^3$-methylmalonamide | 437 |
| 175 | (pyridin-3-yl)amino | N$^1$-(4-(1H-Pyrrolo[2,3-b]pyridin-4-yloxy)-3-fluorophenyl)-N$^3$-(pyridin-3-yl)malonamide | 406 |
| 176 | (2,4-difluorophenyl)amino | N$^1$-(4-(1H-Pyrrolo[2,3-b]pyridin-4-yloxy)-3-fluorophenyl)-N$^3$-(2,4-difluorophenyl)malonamide | 441 |
| 177 | (pyridin-3-ylmethyl)amino | N$^1$-(4-(1H-Pyrrolo[2,3-b]pyridin-4-yloxy)-3-fluorophenyl)-N$^3$-(pyridin-3-ylmethyl)malonamide | 420 |
| 178 | allylamino | N$^1$-(4-(1H-Pyrrolo[2,3-b]pyridin-4-yloxy)-3-fluorophenyl)-N$^3$-allylmalonamide | 369 |
| 179 | cyclopropylamino | N$^1$-(4-(1H-Pyrrolo[2,3-b]pyridin-4-yloxy)-3-fluorophenyl)-N$^3$-cyclopropylmalonamide | 369 |

TABLE 3-continued

| EXAMPLE # | NR₁R₂ | Compound Name | LC/MS (M + H)⁺ |
|---|---|---|---|
| 180 | (2-hydroxypropyl amine) | N¹-(4-(1H-Pyrrolo[2,3-b]pyridin-4-yloxy)-3-fluorophenyl)-N³-(2-hydroxypropyl)malonamide | 387 |
| 181 | (2-amino-2-methylpropyl amine) | N¹-(4-(1H-Pyrrolo[2,3-b]pyridin-4-yloxy)-3-fluorophenyl)-N³-(2-amino-2-methylpropyl)malonamide | 400 |
| 182 | (4-fluorobenzyl amine) | N¹-(4-(1H-Pyrrolo[2,3-b]pyridin-4-yloxy)-3-fluorophenyl)-N³-(4-fluorobenzyl)malonamide | 437 |
| 183 | (cycloheptyl amine) | N¹-(4-(1H-Pyrrolo[2,3-b]pyridin-4-yloxy)-3-fluorophenyl)-N³-cycloheptylmalonamide | 425 |
| 184 | (2,5-dichlorophenyl amine) | N¹-(4-(1H-Pyrrolo[2,3-b]pyridin-4-yloxy)-3-fluorophenyl)-N³-(2,5-dichlorophenyl)malonamide | 474 |
| 185 | (2-chloro-6-methylphenyl amine) | N¹-(4-(1H-Pyrrolo[2,3-b]pyridin-4-yloxy)-3-fluorophenyl)-N³-(2-chloro-6-methylphenyl)malonamide | 453 |
| 186 | (2-chloro-6-fluorophenyl amine) | N¹-(4-(1H-Pyrrolo[2,3-b]pyridin-4-yloxy)-3-fluorophenyl)-N³-(2-chloro-6-fluorophenyl)malonamide | 457 |
| 187 | (3-tert-butylphenyl amine) | N¹-(4-(1H-Pyrrolo[2,3-b]pyridin-4-yloxy)-3-fluorophenyl)-N³-(3-tert-butylphenyl)malonamide | 461 |
| 188 | (azepan-1-yl) | N¹-(4-(1H-Pyrrolo[2,3-b]pyridin-4-yloxy)-3-fluorophenyl)-3-(azepan-1-yl)-3-oxopropanamide | 411 |

TABLE 3-continued

| EXAMPLE # | NR₁R₂ | Compound Name | LC/MS (M + H)⁺ |
|---|---|---|---|
| 189 | -NH-iPr | N¹-(4-(1H-Pyrrolo[2,3-b]pyridin-4-yloxy)-3-fluorophenyl)-N³-isopropylmalonamide | 371 |
| 190 | -NH-tBu | N¹-(4-(1H-Pyrrolo[2,3-b]pyridin-4-yloxy)-3-fluorophenyl)-N³-tert-butylmalonamide | 385 |
| 191 | -NH-cyclopentyl | N¹-(4-(1H-Pyrrolo[2,3-b]pyridin-4-yloxy)-3-fluorophenyl)-N³ cyclopentylmalonamide | 397 |
| 192 | -NH-cyclohexyl | N¹-(4-(1H-Pyrrolo[2,3-b]pyridin-4-yloxy)-3-fluorophenyl)-N³ cyclohexylmalonamide | 411 |
| 193 | -NH-phenyl | N¹-(4-(1H-Pyrrolo[2,3-b]pyridin-4-yloxy)-3-fluorophenyl)-N³-phenylmalonamide | 405 |
| 194 | -NH-(1H-pyrazol-3-yl) | N¹-(4-(1H-Pyrrolo[2,3-b]pyridin-4-yloxy)-3-fluorophenyl)-N³-(1H-pyrazol-3-yl)malonamide | 395 |
| 195 | -NH-(pyridin-2-yl) | N¹-(4-(1H-Pyrrolo[2,3-b]pyridin-4-yloxy)-3-fluorophenyl)-N³-(pyridin-2-yl)malonamide | 406 |
| 196 | -NH-(3-methylpyridin-2-yl) | N¹-(4-(1H-Pyrrolo[2,3-b]pyridin-4-yloxy)-3-fluorophenyl)-N³-(3-methylpyridin-2-yl)malonamide | 420 |
| 197 | -NH-CH₂CH₂C(CH₃)₃ | N¹-(4-(1H-Pyrrolo[2,3-b]pyridin-4-yloxy)-3-fluorophenyl)-N³-(3,3-dimethylbutyl)malonamide | 413 |

TABLE 3-continued

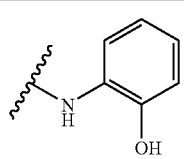

| EXAMPLE # | NR₁R₂ | Compound Name | LC/MS (M + H)⁺ |
|---|---|---|---|
| 198 | 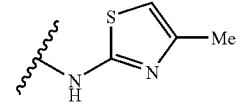 | N¹-(4-(1H-Pyrrolo[2,3-b]pyridin-4-yloxy)-3-fluorophenyl)-N³-(2-hydroxyphenyl)malonamide | 421 |
| 199 | 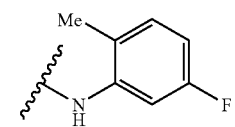 | N¹-(4-(1H-Pyrrolo[2,3-b]pyridin-4-yloxy)-3-fluorophenyl)-N³-(4-methylthiazol-2-yl)malonamide | 426 |
| 200 | 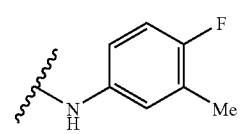 | N¹-(4-(1H-Pyrrolo[2,3-b]pyridin-4-yloxy)-3-fluorophenyl)-N³-(5-fluoro-2-methylphenyl)malonamide | 437 |
| 201 | 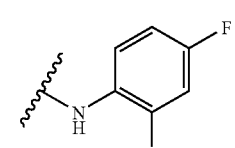 | N¹-(4-(1H-Pyrrolo[2,3-b]pyridin-4-yloxy)-3-fluorophenyl)-N³-(4-fluoro-3-methylphenyl)malonamide | 437 |
| 202 | 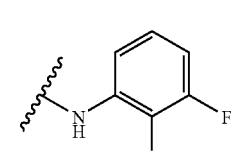 | N¹-(4-(1H-Pyrrolo[2,3-b]pyridin-4-yloxy)-3-fluorophenyl)-N³-(4-fluoro-2-methylphenyl)malonamide | 437 |
| 203 | 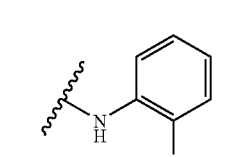 | N¹-(4-(1H-Pyrrolo[2,3-b]pyridin-4-yloxy)-3-fluorophenyl)-N³-(3-fluoro-2-methylphenyl)malonamide | 437 |
| 204 | 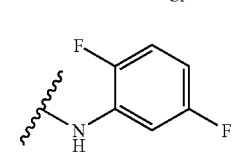 | N¹-(4-(1H-Pyrrolo[2,3-b]pyridin-4-yloxy)-3-fluorophenyl)-N³-(2-chlorophenyl)malonamide | 439 |
| 205 | | N¹-(4-(1H-Pyrrolo[2,3-b]pyridin-4-yloxy)-3-fluorophenyl)-N³-(2,5-difluorophenyl)malonamide | 441 |

TABLE 3-continued

| EXAMPLE # | NR₁R₂ | Compound Name | LC/MS (M + H)⁺ |
|---|---|---|---|
| 206 | [5-aminoindole structure] | N¹-(4-(1H-Pyrrolo[2,3-b]pyridin-4-yloxy)-3-fluorophenyl)-N³-(1H-indol-5-yl)malonamide | 444 |
| 207 | [2-isopropylaniline structure] | N¹-(4-(1H-Pyrrolo[2,3-b]pyridin-4-yloxy)-3-fluorophenyl)-N³-(2-isopropylphenyl)malonamide | 447 |
| 208 | [3-chloro-2-methylaniline structure] | N¹-(4-(1H-Pyrrolo[2,3-b]pyridin-4-yloxy)-3-fluorophenyl)-N³-(3-chloro-2-methylphenyl)malonamide | 453 |
| 209 | [benzylamine structure] | N¹-(4-(1H-Pyrrolo[2,3-b]pyridin-4-yloxy)-3-fluorophenyl)-N³-benzylmalonamide | 419 |
| 210 | [2-methoxy-6-methylaniline structure] | N¹-(4-(1H-Pyrrolo[2,3-b]pyridin-4-yloxy)-3-fluorophenyl)-N³-(2-methoxy-6-methylphenyl)malonamide | 449 |
| 211 | [phenethylamine structure] | N¹-(4-(1H-Pyrrolo[2,3-b]pyridin-4-yloxy)-3-fluorophenyl)-N³-phenethylmalonamide | 433 |
| 212 | [4-aminopyridine structure] | N¹-(4-(1H-Pyrrolo[2,3-b]pyridin-4-yloxy)-3-fluorophenyl)-N³-(pyridin-4-yl)malonamide | 406 |
| 213 | [5-aminoindazole structure] | N¹-(4-(1H-Pyrrolo[2,3-b]pyridin-4-yloxy)-3-fluorophenyl)-N³-(1H-indazol-5-yl)malonamide | 445 |

TABLE 3-continued

| EXAMPLE # | NR₁R₂ | Compound Name | LC/MS (M + H)⁺ |
|---|---|---|---|
| 214 | (2-carboxamido-phenyl)amino | 2-(3-(4-(1H-Pyrrolo[2,3-b]pyridin-4-yloxy)-3-fluorophenylamino)-3-oxopropanamido)benzamide | 448 |
| 215 | (3-phenylpropyl)amino | $N^1$-(4-(1H-Pyrrolo[2,3-b]pyridin-4-yloxy)-3-fluorophenyl)-$N^3$-(3-phenylpropyl)malonamide | 447 |
| 216 | (2-biphenyl)amino | $N^1$-(4-(1H-Pyrrolo[2,3-b]pyridin-4-yloxy)-3-fluorophenyl)-$N^3$-(2-biphenyl)malonamide | 481 |
| 217 | (4-biphenyl)amino | $N^1$-(4-(1H-Pyrrolo[2,3-b]pyridin-4-yloxy)-3-fluorophenyl)-$N^3$-(4-biphenyl)malonamide | 481 |
| 218 | (3-phenoxyphenyl)amino | $N^1$-(4-(1H-Pyrrolo[2,3-b]pyridin-4-yloxy)-3-fluorophenyl)-$N^3$-(3-phenoxyphenyl)malonamide | 497 |
| 219 | (3-benzylphenyl)amino | $N^1$-(4-(1H-Pyrrolo[2,3-b]pyridin-4-yloxy)-3-fluorophenyl)-$N^3$-(3-benzylphenyl)malonamide | 495 |
| 220 | (3-cyanophenyl)amino | $N^1$-(4-(1H-Pyrrolo[2,3-b]pyridin-4-yloxy)-3-fluorophenyl)-$N^3$-(3-cyanophenyl)malonamide | 430 |
| 221 | (2-cyanophenyl)amino | $N^1$-(4-(1H-Pyrrolo[2,3-b]pyridin-4-yloxy)-3-fluorophenyl)-$N^3$-(2-cyanophenyl)malonamide | 430 |

TABLE 3-continued

| EXAMPLE # | NR₁R₂ | Compound Name | LC/MS (M + H)⁺ |
|---|---|---|---|
| 222 | (4-cyanophenyl)NH- | N¹-(4-(1H-Pyrrolo[2,3-b]pyridin-4-yloxy)-3-fluorophenyl)-N³-(4-cyanophenyl)malonamide | 430 |
| 223 | (2,3-dihydro-1H-inden-5-yl)NH- | N¹-(4-(1H-Pyrrolo[2,3-b]pyridin-4-yloxy)-3-fluorophenyl)-N³-(2,3-dihydro-1H-inden-5-yl)malonamide | 445 |
| 224 | (2,6-dichlorophenyl)NH- | N¹-(4-(1H-Pyrrolo[2,3-b]pyridin-4-yloxy)-3-fluorophenyl)-N³-(2,6-dichlorophenyl)malonamide | 474 |
| 225 | (3,4-difluorophenyl)NH- | N¹-(4-(1H-Pyrrolo[2,3-b]pyridin-4-yloxy)-3-fluorophenyl)-N³-(3,4-difluorophenyl)malonamide | 441 |
| 226 | (R)-(2-amino-2-oxo-1-phenylethyl)NH- | (R)-N¹-(4-(1H-Pyrrolo[2,3-b]pyridin-4-yloxy)-3-fluorophenyl)-N³-(2-amino-2-oxo-1-phenylethyl)malonamide | 462 |
| 227 | (2-hydroxy-2,3-dihydro-1H-inden-1-yl)NH- | N¹-(4-(1H-Pyrrolo[2,3-b]pyridin-4-yloxy)-3-fluorophenyl)-N³-(2-hydroxy-2,3-dihydro-1H-inden-1-yl)malonamide | 461 |
| 228 | (5-chloro-2-fluorophenyl)NH- | N¹-(4-(1H-Pyrrolo[2,3-b]pyridin-4-yloxy)-3-fluorophenyl)-N³-(5-chloro-2-fluorophenyl)malonamide | 457 |
| 229 | (2-(cyanomethyl)phenyl)NH- | N¹-(4-(1H-Pyrrolo[2,3-b]pyridin-4-yloxy)-3-fluorophenyl)-N³-(2-(cyanomethyl)phenyl)malonamide | 444 |

TABLE 3-continued

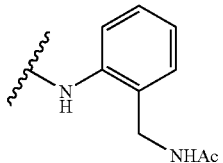

| EXAMPLE # | NR₁R₂ | Compound Name | LC/MS (M + H)⁺ |
|---|---|---|---|
| 230 | 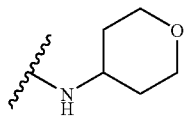 | $N^1$-(4-(1H-Pyrrolo[2,3-b]pyridin-4-yloxy)-3-fluorophenyl)-$N^3$-(2-acetamidophenyl)malonamide | 462 |
| 231 | 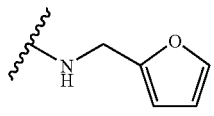 | $N^1$-(4-(1H-Pyrrolo[2,3-b]pyridin-4-yloxy)-3-fluorophenyl)-$N^3$-(tetrahydro-2H-pyran-4-yl)malonamide | 413 |
| 232 | 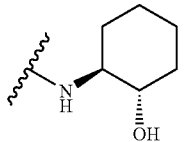 | $N^1$-(4-(1H-Pyrrolo[2,3-b]pyridin-4-yloxy)-3-fluorophenyl)-$N^3$-(furan-2-ylmethyl)malonamide | 409 |
| 233 | 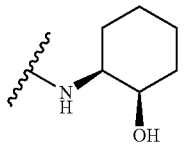 | $N^1$-(4-(1H-Pyrrolo[2,3-b]pyridin-4-yloxy)-3-fluorophenyl)-$N^3$-(trans-2-hydroxycyclohexyl)malonamide | 427 |
| 234 | 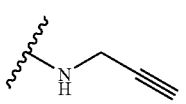 | $N^1$-(4-(1H-Pyrrolo[2,3-b]pyridin-4-yloxy)-3-fluorophenyl)-$N^3$-(cis-2-hydroxycyclohexyl)malonamide | 427 |
| 235 | 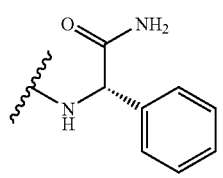 | $N^1$-(4-(1H-Pyrrolo[2,3-b]pyridin-4-yloxy)-3-fluorophenyl)-$N^3$-(prop-2-ynyl)malonamide | 367 |
| 236 |  | (S)-$N^1$-(4-(1H-Pyrrolo[2,3-b]pyridin-4-yloxy)-3-fluorophenyl)-$N^3$-(2-amino-2-oxo-1-phenylethyl)malonamide | 462 |

Example 237

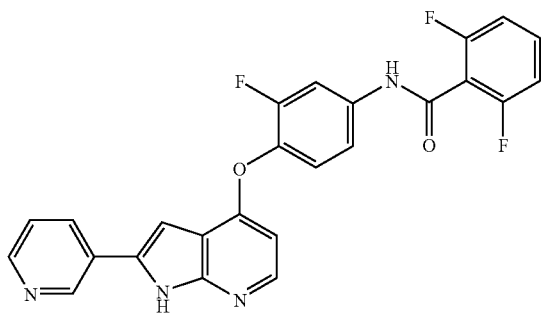

2,6-Difluoro-N-(3-fluoro-4-(2-(pyridin-3-yl)-1H-pyrrolo[2,3-b]pyridin-4-yloxy)phenyl)benzamide, hydrochloride salt

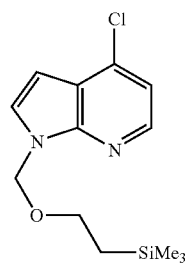

A) 4-Chloro-1-((2-(trimethylsilyl)ethoxy)methyl)-1H-pyrrolo[2,3-b]pyridine

To a solution of 4-chloro-1H-pyrrolo[2,3-b]pyridine (3.05 g, 20 mmol, prepared according to Thibault, C. et al. *Org. Lett.* 2003, 5, 5023) in DMF (50 mL) at −40° C. under $N_2$, was added NaH (60% in mineral oil, 880 mg, 22 mmol). The mixture was stirred at rt for 15 min, then cooled to −40° C. To this solution was added (2-(chloromethoxy)ethyl)trimethylsilane (3.67 g, 22 mmol). The resulting mixture was stirred at rt overnight. The mixture was diluted with EtOAc, washed twice with 10% LiCl, and dried over $MgSO_4$. The title compound was purified by flash column chromatography (silica gel, eluding with hexane, followed by $Et_2O$) to give the desired product (5.6 g, quantitiatve yield) as an oil. LC/MS(ESI+) m/z 283 (M+H)+.

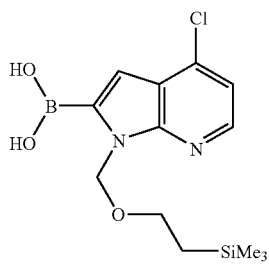

B) 4-Chloro-1-((2-(trimethylsilyl)ethoxy)methyl)-1H-pyrrolo[2,3-b]pyridin-2-ylboronic acid To a solution of 4-chloro-1-((2-(trimethylsilyl)ethoxy)methyl)-1H-pyrrolo[2,3-b]pyridine (565 mg, 2 mmol) in THF (5 mL) at −40° C. under $N_2$, was added n-BuLi (2.0 M in cyclohexane, Aldrich, 2.4 mmol). The reaction mixture was stirred at −40° C. for 1 h and then treated with triisopropylborate (489 mg, 2.6 mmol). The mixture was slowly warmed to rt and stirred overnight. To this solution was added 1 N HCl in $H_2O$ (20 mL), and the mixture was stirred for 20 min., neutralized with saturated aq. $K_2HPO_4$ solution and extracted with ether. The organic layer was dried over $Na_2SO_4$. After filtration and concentration under reduced pressure, the title compound was obtained as a light beige solid (640 mg, quantitative yield). LC/MS(ESI+) m/z 327 (M+H)+.

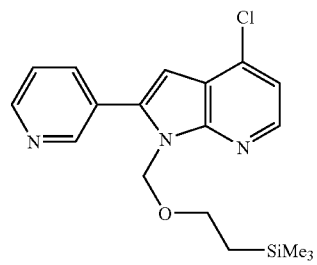

C) 4-Chloro-2-(pyridin-3-yl)-1-((2-(trimethylsilyl)ethoxy)methyl)-1H-pyrrolo[2,3-b]pyridine Argon was bubbled through a mixture of 4-chloro-1-((2-(trimethylsilyl)ethoxy)methyl)-1H-pyrrolo[2,3-b]pyridin-2-ylboronic acid (5.55 g, 17 mmol), 3-iodopyridine (6.97 g, 34 mmol), Pd(OAc)$_2$, 2-dicyclohexylphosphino-2',4',6'-tri-1-propyl-1,1'-biphenyl (405 mg, 0.85 mmol), and $K_3PO_4$ (2 M in $H_2O$, 34 mmol) in DME (50 mL) for 10 min and then heated at reflux overnight. The reaction mixture was diluted with EtOAc and washed with saturated aq. $K_2HPO_4$ solution. The title compound was purified by flash column chromatography (silica gel, 20% EtOAc/$CH_2Cl_2$) to afford the desired product (3.2 g, 52% yield) as an oil. LC/MS (ESI+) m/z 361 (M+H)+.

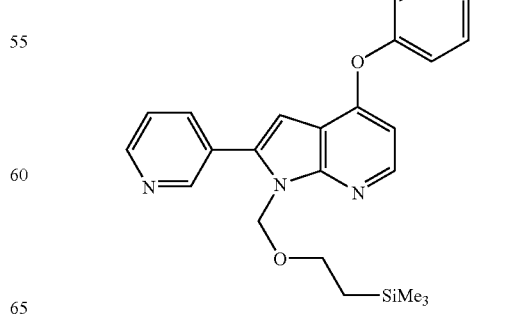

D) 3-Fluoro-4-(2-(pyridin-3-yl)-1-((2-(trimethylsilyl)ethoxy)methyl)-1H-pyrrolo[2,3-b]pyridin-4-yloxy)benzenamine A mixture of 4-chloro-2-(pyridin-3-yl)-1-((2-(trimethylsilyl)ethoxy)methyl)-1H-pyrrolo[2,3-b]pyridine (3.2 g, 8.9 mmol), 2-fluoro-4-nitrophenol (2.79 g, 17.8 mmol), and DIPEA (3.5 mL, 20 mmol) in NMP (15 mL) was heated in a sealed tube at 185° C. for 3 days. The mixture was diluted with EtOAc and filtered through a short pad of Celite® (EtOAc). The filtrate was washed with 5% aq. Na$_2$CO$_3$ solution and dried over MgSO$_4$. The title compound was purified by flash column chromatography (silica gel, 100% CH$_2$Cl$_2$ to 50% EtOAc/CH$_2$Cl$_2$) to afford the desired product (295 mg, 7.4%) as a light brown solid. LC/MS(ESI$^+$) m/z 451 (M+H)$^+$.

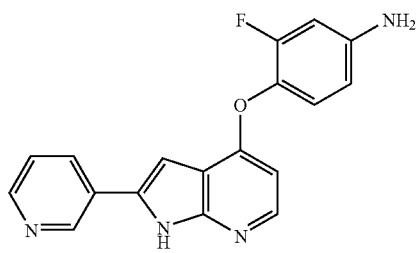

E) 3-Fluoro-4-(2-(pyridin-3-yl)-1H-pyrrolo[2,3-b]pyridin-4-yloxy)benzenamine A mixture of 3-fluoro-4-(2-(pyridin-3-yl)-1-((2-(trimethylsilyl)ethoxy)methyl)-1H-pyrrolo[2,3-b]pyridin-4-yloxy)benzenamine (275 mg, 0.61 mmol), tetrabutylammonium fluoride (1 M in THF, 4 mL), and 1,2-diaminoethane (0.2 mL) in THF (4 mL) was heated at 65° C. for 24 h. The solvent was removed in vacuo. The residue was purified by flash column chromatography (silica gel, 5% MeOH/EtOAc) to afford the desired product (180 mg, 92%) as a yellow solid. LC/MS(ESI$^+$) m/z 321 (M+H)$^+$.

F) 2,6-Difluoro-N-(3-fluoro-4-(2-(pyridin-3-yl)-1H-pyrrolo[2,3-b]pyridin-4-yloxy)phenyl)benzamide, hydrochloride salt To a solution of 3-fluoro-4-(2-(pyridin-3-yl)-1H-pyrrolo[2,3-b]pyridin-4-yloxy)benzenamine (15 mg, 0.047 mmol) and pyridine (0.1 mmol) in THF at 0° C. was added 2,6-difluorobenzoyl chloride (10 mg, 0.056 mmol). The reaction mixture was stirred at 0° C. for 1 h, concentrated in vacuo, and the resulting residue was purified by preparative HPLC. The desired fractions were lyophilized to give a white TFA salt, which was dissolved in small amount of MeOH/H$_2$O with 1 N HCl (0.2 mL). This solution was then lyophilized to afford the title compound (HCl salt, 12 mg, 48%) as a yellow solid. $^1$H NMR (CD$_3$OD) δ 9.29 (s, 1H), 8.85 (d, 1H, J=9.6 Hz), 8.74 (d, 1H, J=5.2 Hz), 8.26 (d, 1H, J=6.8 Hz), 8.01 (dd, 1H, J=8.4, 5.6 Hz), 7.88 (dd, 1H, J=12.4, 2.4 Hz), 7.50–7.35 (m, 4H), 7.10–7.00 (m, 2H), 6.73 (d, 1H, J=6.4 Hz); LC/MS(ESI$^+$) m/z 461 (M+H)$^+$.

Example 238

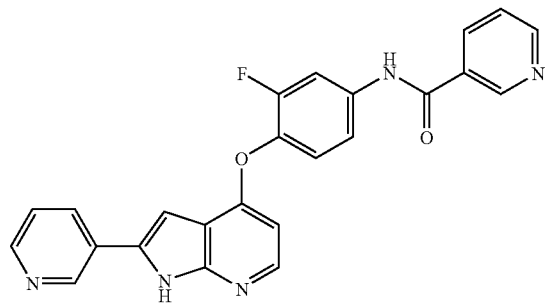

N-(3-Fluoro-4-(2-(pyridin-3-yl)-1H-pyrrolo[2,3-b]pyridin-4-yloxy)phenyl)nicotinamide Prepared in a similar manner as Example 237. $^1$H NMR (CD$_3$OD) δ 9.36 (s, 1H), 9.33 (s, 1H), 9.00–8.90 (m, 3H), 8.79 (d, 1H, J=5.2 Hz), 8.31 (d, 1H, J=6.8 Hz), 8.12–8.05 (m, 2H), 7.99 (dd, 1H, J=12.8, 2.4 Hz), 7.63 (d, 1H, J=8.8 Hz), 7.52 (s, 1H), 7.48–7.40 (m, 2H), 6.78 (d, 1H, J=6.4 Hz); LC/MS(ESI$^+$) m/z 461 (M+H)$^+$.

Example 239

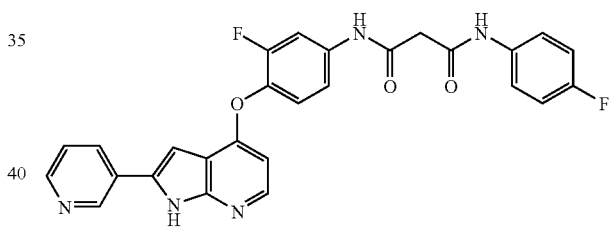

N$^1$-(3-Fluoro-4-(2-(pyridin-3-yl)-1H-pyrrolo[2,3-b]pyridin-4-yloxy)phenyl)-N$^3$-(4-fluorophenyl)malonamide, hydrochloride salt To a stirred solution of 3-fluoro-4-(2-(pyridin-3-yl)-1H-pyrrolo[2,3-b]pyridin-4-yloxy)benzenamine (16 mg, 0.05 mmol, Compound E of Example 237), 3-(4-fluorophenylamino)-3-oxopropanoic acid (19.7 mg, 0.1 mmol, Compound A of Example 25), and HATU (38 mg, 0.1 mmol) in DMF (0.5 mL) was added DIPEA (0.1 mL). The mixture was stirred at rt for 2 h, concentrated in vacuo, and the residue was purified by preparative HPLC. The desired fractions were lyophilized to give a white TFA salt, which was dissolved in small amount of MeOH/H$_2$O with 1 N HCl (0.2 mL) and lyophilized to afford the title compound (HCl salt, 12 mg, 42%) as a yellow solid. $^1$H NMR (CD$_3$OD) δ 9.25 (s, 1H), 8.81 (d, 1H, J=8.7 Hz), 8.72 (d, 1H, J=5.4 Hz), 8.25 (d, 1H, J=6.7 Hz), 8.00 (dd, 1H, J=8.1, 6.1 Hz), 7.82 (dd, 1H, J=12.1, 1.3 Hz), 7.53–7.48 (m, 2H), 7.40–7.32 (m, 3H), 7.00–6.95 (m, 2H), 6.71 (d, 1H, J=6.72 Hz), 3.48 (s, 2H); LC/MS(ESI$^+$) m/z 500 (M+H)$^+$.

Example 240

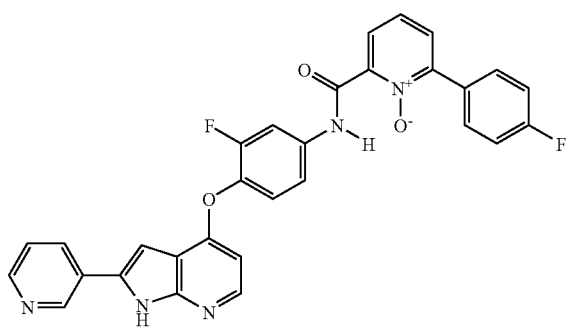

6-(4-Fluoro-phenyl)-1-oxy-pyridine-2-carboxylic acid [3-fluoro-4-(2-pyridin-3-yl-1H-pyrrolo[2,3-b]pyridin-4-yloxy)-phenyl]-amide, trifluoroacetic acid salt

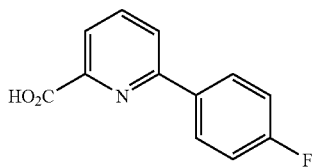

A) 6-(4-Fluorophenyl)picolinic acid

A solution of 2-bromo-picolinic acid (2.02 g, 10 mmol, Aldrich) in DME containing 4 mL of 10% aq. $Na_2CO_3$ was purged with Ar gas, treated with $Pd(PPh_3)_4$ followed by 2-(4-fluorophenyl)-5,5-dimethyl-1,3,2-dioxaborinane (2.40 g, 11.5 mmol, Aldrich) and EtOH (20 mL). This mixture was then also purged with Ar gas. The reaction mixture was heated at 100° C. for 2.5 h in a sealed tube. Additional 2-bromo-picolinic acid (900 mg) and $Pd(PPh_3)_4$ was added, and after purging with Ar gas it was heated at 100° C. for 4.5 h. Trifluoroacetic acid (20 mL) was added to the reaction and the mixture was concentrated in vacuo. MeOH (150 mL) was added to the residue and the insoluble material was filtered. The filtrate was concentrated in vacuo, and the resulting residue was purified by flash column chromatography on silica gel eluting with EtOAc/MeOH (9:1) followed by EtOAc/MeOH/HOAc (14:30:1) to afford the desired product (1.0 g, 40% based on borinane starting material) as a white solid. $^1$H NMR ($CD_3OD$) δ 8.01 (d, 1H, J=7.7 Hz), 7.94–7.87 (m, 3H), 7.73 (d, 1H, J=7.7 Hz), 7.13 (t, 2H, J=8.8 Hz); MS(ESI$^+$) m/z 234 (M+H)$^+$.

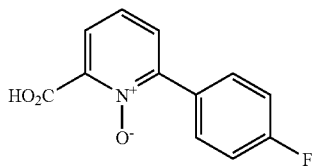

B) 6-(4-Fluorophenyl)picolinic acid-N-oxide

A mixture of the picolinic acid derivative above (1.0 g, 4.6 mmol), $Na_2HPO_4$ (1.2 g) and m-CPBA (1.1 g, ~70% from Aldrich) in $CH_2ClCH_2Cl$ (30 mL) was stirred at rt for 2 h. Additional $Na_2HPO_4$ (0.8 g) and m-CPBA (1.0 g) were added to the reaction mixture and it was stirred for 3 h at rt. $Na_2HPO_4$ (0.5 g) and m-CPBA (0.5 g) were again added to the reaction mixture and it was stirred at rt overnight. $CHCl_3$ (160 mL) and 2 N aq. HCl solution (50 mL) were added to the mixture and the organic layer was separated, dried over $MgSO_4$ and concentrated in vacuo. The residue was purified by flash column chromatography on silica gel eluting with EtOAc/MeOH/HOAc (70:24:6) to obtain the desired product which was contaminated with m-CPBA. This impure material was purified by preparative HPLC to obtain the desired product (175 mg, 16%) as a white solid. $^1$H NMR (DMF-d$_7$) 8.45 (dd, 1H, J=8.3, 2.2 Hz), 8.15 (d, 1H, J=2.2 Hz), 8.13–8.00 (m, 4H), 7.45 (t, 2H, J=8.7 Hz).

C) 6-(4-Fluoro-phenyl)-1-oxy-pyridine-2-carboxylic acid [3-fluoro-4-(2-pyridin-3-yl-1H-pyrrolo[2,3-b]pyridin-4-yloxy)-phenyl]-amide, trifluoroacetic acid salt To a solution of 6-(4-fluorophenyl)picolinic acid N-oxide (30 mg, 0.13 mmol), HOBT (16 mg), and EDCI.HCl (50 mg, 0.26 mmol) in DMF (4 mL) at room temperature was added 3-fluoro-4-(2-(pyridin-3-yl)-1H-pyrrolo[2,3-b]pyridin-4-yloxy)benzenamine (40 mg, 0.12 mmol, Compound E of Example 237). The reaction mixture was stirred at room temperature overnight and concentrated under reduced pressure. The residue was purified by preparative HPLC to afford the desired product (20 mg, 24%) as a beige solid. $^1$H NMR (DMF-d$_7$) δ 14.07 (br s, 1H), 12.64 (br s, 1H), 9.35 (s, 1H), 8.65 (d, 1H, J=4.4 Hz), 8.53 (d, 1H, J=7.7 Hz), 8.49 (dd, 1H, J=8.2, 2.2 Hz), 8.23 (d, 1H, J=5.5 Hz), 8.19 (dd, 1H, J=13.2, 2.8 Hz), 8.02–7.62 (m, 6H), 7.55 (t, 1H, J=8.8 Hz), 7.43 (t, 2H, J=8.8 Hz), 7.22 (s, 1H), 6.55 (d, 1H, J=5.5 Hz); MS(ESI$^+$) m/z 459.1 (M+H)$^+$.

Example 241

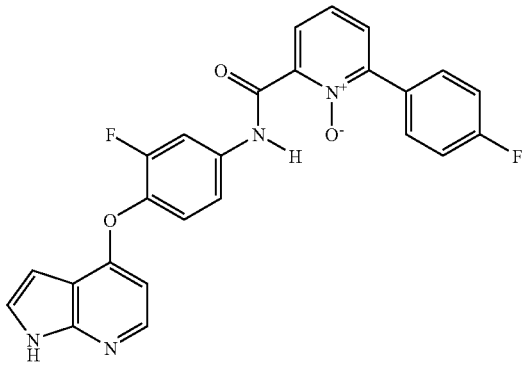

6-(4-Fluoro-phenyl)-1-oxy-pyridine-2-carboxylic acid [3-fluoro-4-(1H-pyrrolo[2,3-b]pyridin-4-yloxy)-phenyl]-amide, trifluoroacetic acid salt To a solution of 6-(4-fluorophenyl)picolinic acid N-oxide (47 mg, 0.20 mmol, Compound B of Example 240), HOBT (20 mg), and EDCI.HCl (60 mg, 0.31 mmol) in DMF (4 mL) at room temperature was added 4-(1H-pyrrolo[2,3-b]pyridin-4-yloxy)-3-fluorobenzenamine (50 mg, 0.20 mmol, Compound B of Example 132). The mixture was stirred at room temperature overnight and concentrated under reduced pressure. The resulting residue was purified by preparative HPLC to afford the desired product (68 mg, 12%) as a white solid. $^1$H NMR (DMF-d$_7$) δ 14.07 (br s, 1H), 12.14 (br s, 1H), 8.49 (dd, 1H, J=7.7, 1.7 Hz), 8.26 (d, 1H, J=6.1 Hz), 8.18 (dd, 1H, J=12.7, 1.7 Hz), 8.02–7.96 (m, 3H), 7.84 (t, 1H, J=8.3 Hz), 7.67 (d, 1H, J=8.8 Hz), 7.57–7.52 (m, 2H), 7.43 (d, 2H, J=8.8 Hz), 6.62 (d, 1H, J=6.0 Hz), 6.46 (d, 1H, J=2.8 Hz); MS(ESI$^+$) m/z 536.1 (M+H)$^+$.

Example 242

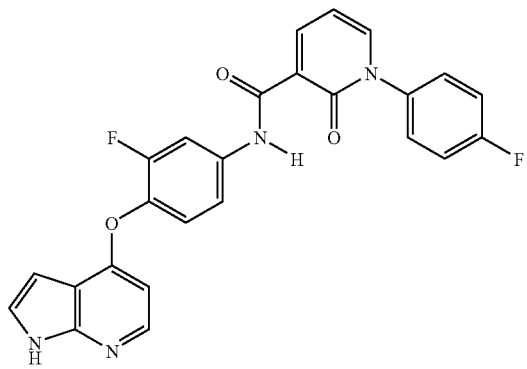

N-(4-(1H-Pyrrolo[2,3-b]pyridin-4-yloxy)-3-fluorophenyl)-1-(4-fluorophenyl)-2-oxo-1,2-dihydropyridine-3-carboxamide, trifluoroacetic acid salt

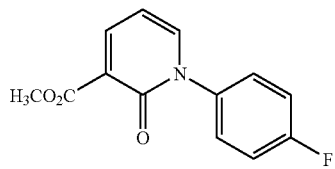

A) Methyl 1-(4-fluorophenyl)-2-oxo-1,2-dihydropyridine-3-carboxylate

To a solution of methyl 2-oxo-2H-pyran-3-carboxylate (2.31 g, 15 mmol, Aldrich) in THF (40 mL) and DMF (10 mL) at rt was added 4-fluoroaniline (1.67 g, 15 mmol), and the reaction mixture was stirred for 2.5 h. To the 4-fluoroaniline intermediate formed via a Michael addition was added EDCI.HCl (3.85 g, 20 mmol) and DMAP (120 mg) at rt. The reaction mixture was stirred at rt overnight. To the reaction mixture were added 1 N aq. HCl (50 mL) and EtOAc (150 mL). The EtOAc layer was separated, and the aqueous layer was washed with EtOAc (150 mL). The combined EtOAc layers were dried over MgSO$_4$ and concentrated in vacuo to obtain a semi-solid material (~4.4 g). The crude product was dissolved in ether (100 mL) and methanol (15 mL), and the solid which formed after stirring was filtered off. The filtrate was concentrated in vacuo to afford the desired product (2.95 g, 80%) as a semi-solid, which was sufficiently pure to use in the next step without further purification. $^1$H NMR (DMSO-d$_6$) δ 8.23 (dd, 1H, J=7.2, 2.2 Hz), 7.57 (dd, 1H, J=6.6, 1.7 Hz), 7.32–7.34 (m, 2H), 7.17 (t, 2H, J=8.8 Hz), 6.32 (t, 1H, J=7.1 Hz), 3.89 (s, 3H); MS(ESI$^+$) m/z 248.2 (M+H)$^+$.

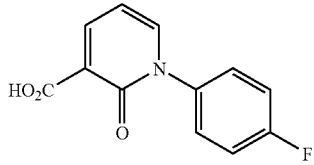

B) 1-(4-Fluorophenyl)-2-oxo-1,2-dihydropyridine-3-carboxylic acid

A mixture of methyl 1-(4-fluorophenyl)-2-oxo-1,2-dihydropyridine-3-carboxylate (crude 2.45 g, 12 mmol) and 6 N aq. NaOH (2.5 mL) in methanol (60 mL) was stirred at rt for 4 h. To the reaction mixture was added conc. HCl (1 mL) slowly with stirring at rt. The precipitate which formed was filtered, washed with a small amount water and dried to obtain the desired acid product (2.1 g) as a yellow solid. The filtrate was concentrated in vacuo. The residue was mixed with water (50 mL) and washed with EtOAc (2×130 mL). The EtOAc layers were dried over MgSO$_4$ and concentrated in vacuo. The residue was triturated with a small amount of ether to obtain a 2$^{nd}$ crop of product (195 mg, total 2.30 g, 82%). $^1$H NMR (DMSO-d$_6$) δ 8.47 (dd, 1H, J=7.2, 2.2 Hz), 8.19 (dd, 1H, J=6.6, 1.7 Hz), 7.62–7.60 (m, 2H), 7.42 (t, 2H, J=8.8 Hz), 6.78 (t, 1H, J=7.1 Hz); MS(ESI$^+$) m/z 234.2 (M+H)$^+$.

C) N-(4-(1H-Pyrrolo[2,3-b]pyridin-4-yloxy)-3-fluorophenyl)-1-(4-fluorophenyl)-2-oxo-1,2-dihydropyridine-3-carboxamide, trifluoroacetic acid salt To a solution of 1-(4-fluorophenyl)-2-oxo-1,2-dihydropyridine-3-carboxylic acid (70 mg, 0.30 mmol), HOBT (30 mg), and EDCI.HCl (200 mg, 1.04 mmol) in DMF (8 mL) at room temperature was added 4-(1H-pyrrolo[2,3-b]pyridin-4-yloxy)-3-fluorobenzenamine (70 mg, 0.29 mmol, Compound B of Example 132). The mixture was stirred at room temperature overnight and concentrated in vacuo. The resulting residue was purified by preparative HPLC to afford the desired product (71 mg, 43%) as a beige solid. $^1$H NMR (DMSO-d$_6$) δ 12.04 (br s, 1H), 11.96 (br s, 1H), 8.52 (dd, 1H, J=7.2, 2.2 Hz), 8.08 (t, 2H, J=5.5 Hz), 7.96 (dd, 1H, J=12.7, 2.2 Hz), 7.55–7.53 (m, 2H), 7.84 (t, 1H, J=8.3 Hz), 7.43 (dd, 1H, J=8.8, 1.7 Hz), 7.38–7.32 (m, 3H), 6.67 (t, 1H, J=7.2 Hz), 6.43 (d, 1H, J=6.1 Hz), 6.46 (dd, 1H, J=3.3, 1.4 Hz); MS(ESI$^+$) m/z 459.1 (M+H)$^+$.

Example 243

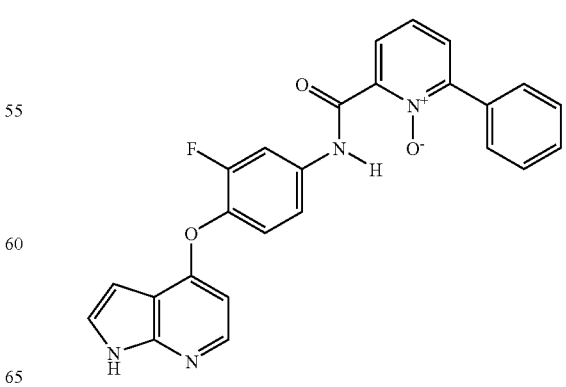

1-Oxy-6-phenyl-pyridine-2-carboxylic acid [3-fluoro-4-(1H-pyrrolo[2,3-b]pyridin-4-yloxy)-phenyl]-amide, trifluoroacetic acid salt

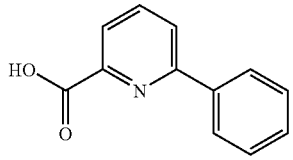

A) 6-Phenylpicolinic acid

A mixture of 6-bromopicolinic acid (2.02 g, 10 mmol), phenyboronic acid (1.22 g, 10 mmol), cesium carbonate (5.00 g) and $PdCl_2$ [(t-Bu)$_2$P(OH)]$_2$ (70 mg, CombiPhos Catalysts, Inc. Princeton, N.J.) in DMF (20 mL) and water (3 mL) was purged with Ar-gas and heated at 110° C. for 24 h. The reaction was incomplete and did not progress further. To the reaction mixture were added EtOAc (200 mL) and 1 N aq. HCl (40 mL). The EtOAc layer was separated, and the aqueous layer was washed with EtOAc (150 mL). The combined EtOAc layers were dried over $Na_2SO_4$ and concentrated in vacuo. The residue was purified by preparative HPLC to afford the desired product (350 mg, 18%) as a white solid. $^1$H NMR (CDCl$_3$) δ 10.45 (s, 1H), 8.18–7.96 (m, 5H), 7.51–7.53 (m, 3H).

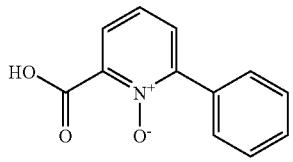

B) 6-Phenylpicolinic acid N-oxide

A mixture of 6-phenylpicolinic acid (150 mg, 0.75 mmol), $K_2HPO_4$ (600 mg) m-CPBA (300 mg, max 70% from Aldrich) in dichloroethane (8.0 mL) was heated at 60° C. for 1.5 h. Additional m-CPBA (2×300 mg) was added and the mixture was heated at 60° C. for 40 min. The reaction mixture was purified by preparative HPLC to afford the desired product (110 mg, 68%) as a white solid. $^1$H NMR (DMF-d$_7$) δ 8.57 (s, 1H), 8.43 (d, 1H, J=2.2 Hz), 8.10–7.88 (m, 5H), 7.59–7.57 (m, 3H).

C) 1-Oxy-6-phenyl-pyridine-2-carboxylic acid [3-fluoro-4-(1H-pyrrolo[2,3-b]pyridin-4-yloxy)-phenyl]-amide, trifluoroacetic acid salt To a solution of 6-phenylpicolinic acid N-oxide (25 mg, 0.12 mmol), HOBT (20 mg), and EDCI.HCl (120 mg, 1.14 mmol) in DMF (3.5 mL) at room temperature was added 4-(1H-pyrrolo[2,3-b]pyridin-4-yloxy)-3-fluorobenzenamine (40 mg, 0.16 mmol, Compound B of Example 132). The reaction mixture was stirred at room temperature overnight and concentrated in vacuo. The resulting residue was purified by preparative HPLC to afford the desired product (36 mg, 54%) as a white solid. $^1$H NMR (DMF-d$_7$) δ 14.12 (br s, 1H), 12.10 (br s, 1H), 8.48 (dd, 1H, J=7.9, 1.6 Hz), 8.24 (d, 1H, J=5.5 Hz), 8.18 (dd, 1H, J=14.8, 2.2 Hz), 7.95–7.89 (m, 3H), 7.83 (t, 1H, J=7.7 Hz), 7.67 (dd, 1H, J=8.6, 1.2 Hz), 7.61–7.51 (m, 5H), 6.60 (d, 1H, J=5.5 Hz), 6.44 (d, 1H, J=3.3 Hz); MS(ESI$^+$) m/z 441.1 (M+H)$^+$.

Example 244

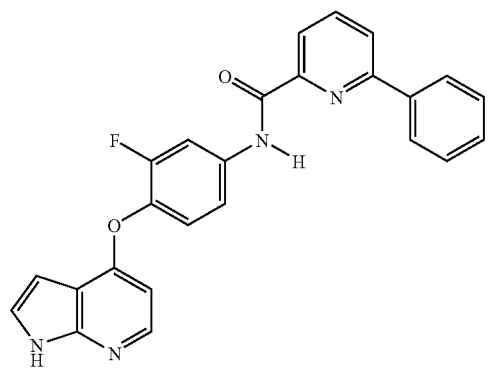

N-(4-(1H-Pyrrolo[2,3-b]pyridin-4-yloxy)-3-fluorophenyl)-6-phenylpicolinamide, trifluoroacetic acid salt To a solution of 6-phenylpicolinic acid (48 mg, 0.24 mmol, Compound A of Example 243), HOBT (25 mg), and EDCI.HCl (155 mg, 0.81 mmol) in DMF (3.5 mL) at room temperature was added 4-(1H-pyrrolo[2,3-b]pyridin-4-yloxy)-3-fluorobenzenamine (65 mg, 0.26 mmol, Compound B of Example 132). The mixture was stirred at room temperature overnight and concentrated in vacuo. The residue was purified by preparative HPLC to afford the desired product (25 mg, 19%) as a light brown solid. $^1$H NMR (DMF-d$_7$) δ 11.93 (br s, 1H), 11.01 (br s, 1H), 8.36 (dd, 2H, J=7.2, 1.6 Hz), 8.31–8.17 (m, 5H), 7.59–7.50 (m, 6H), 6.53 (d, 1H, J=5.5 Hz), 6.41 (d, 1H, J=2.8 Hz); MS(ESI$^+$) m/z 425.1 (M+H)$^+$.

Example 245

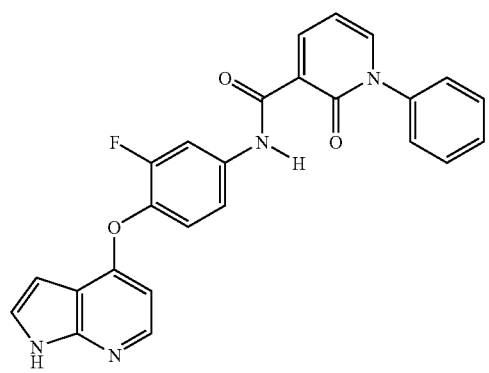

N-(4-(1H-Pyrrolo[2,3-b]pyridin-4-yloxy)-3-fluorophenyl)-2-oxo-1-phenyl-1,2-dihydropyridine-3-carboxamide, trifluoroacetic acid salt To a solution of 2-oxo-1-phenyl-1,2-dihydropyridine-3-carboxylic acid (30 mg, 0.14 mmol, prepared in a similar manner as Steps A and B of Example 242), HOBT (20 mg), and EDCI.HCl (80 mg, 0.42 mmol) in DMF (3.5 mL) at room temperature was added 4-(1H-pyrrolo[2,3-b]pyridin-4-yloxy)-3-fluorobenzenamine (31 mg, 0.13 mmol, Compound B of Example 132). The reaction mixture was stirred at room temperature overnight and concentrated in vacuo. The residue was purified by preparative HPLC to afford the desired product (10 mg, 14%) as a beige solid. $^1$H NMR (acetone-$d_6$) δ 13.40 (br s, 1H), 12.32 (br s, 1H), 8.66 (dd, 1H, J=7.1, 1.6 Hz), 8.43 (d, 1H, J=6.6 Hz), 8.18 (dd, 1H, J=13.2, 2.2 Hz), 8.03 (dd, 1H, J=6.6, 2.2 Hz), 7.67–7.49 (m, 8H), 6.89 (d, 1H, J=6.6 Hz), 6.75 (t, 1H, J=6.3 Hz), 6.58 (d, 1H, J=3.3 Hz); MS(ESI$^+$) m/z 441.1 (M+H)$^+$.

Example 246

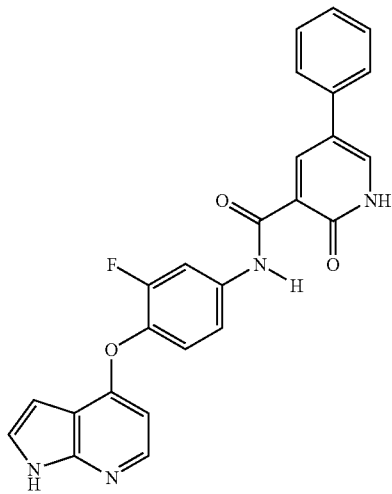

N-(4-(1H-Pyrrolo[2,3-b]pyridin-4-yloxy)-3-fluorophenyl)-2-oxo-5-phenyl-1,2-dihydropyridine-3-carboxamide, trifluoroacetic acid salt

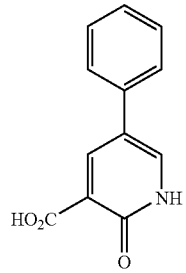

A) 2-Oxo-5-phenyl-1,2-dihydropyridine-3-carboxylic acid

A mixture of 5-bromo-2-hydroxynicotinic acid (436 mg, 2.00 mmol, *Syn. Comm.*, 19 (3&4), 553–559 (1989)), phenylboronic acid (248 mg, 2.03 mmol), Cs$_2$CO$_3$ (1.20 g) and PdCl$_2$ [(t-Bu)$_2$P(OH)]$_2$ (170 mg, CombiPhos Catalysts, Inc. Princeton, N.J.) in DMF (10 mL) and water (1.0 mL) was purged with Ar gas and heated at 110° C. for 6 h. Additional phenylboronic acid (75 mg) was added and the mixture was heated at 110° C. for 5 h. To the reaction was added TFA (3 mL), and the mixture was concentrated in vacuo to a volume of ~12 mL. The mixture was purified by preparative HPLC to afford the desired product (78 mg, 18%). $^1$H NMR (DMF-$d_7$) δ 14.8 (br s, 1H), 13.8 (br s, 1H), 8.73 (s, 1H), 8.46 (s, 1H), 7.74 (d, 1H, J=7.2 Hz), 7.53–7.42 (m, 3H), 5.81 (s, 1H).

B) N-(4-(1H-Pyrrolo[2,3-b]pyridin-4-yloxy)-3-fluorophenyl)-2-oxo-5-phenyl-1,2-dihydropyridine-3-carboxamide To a solution of 2-oxo-5-phenyl-1,2-dihydropyridine-3-carboxylic acid (35 mg, 0.16 mmol), HOBT (25 mg), and EDCI.HCl (80 mg, 0.42 mmol) in DMF (3.0 mL) at room temperature was added 4-(1H-pyrrolo[2,3-b]pyridin-4-yloxy)-3-fluorobenzenamine (30 mg, 0.12 mmol, Compound B of Example 132). The mixture was stirred at room temperature overnight and concentrated in vacuo. The residue was purified by preparative HPLC to afford the desired product (12 mg, 13%) as a light brown solid. $^1$H NMR (CD$_3$OD) δ 8.81 (d, 1H, J=2.8 Hz), 8.17 (d, 1H, J=6.6 Hz), 8.00 (dd, 1H, J=12.6, 2.2 Hz), 7.94 (d, 1H, J=3.3 Hz), 7.52–7.27 (m, 7H), 6.80 (d, 1H, J=9.3 Hz), 6.72 (d, 1H, J=6.6 Hz), 6.54 (d, 1H, J=3.8 Hz); MS(ESI$^+$) m/z 441.1 (M+H)$^+$.

Example 247

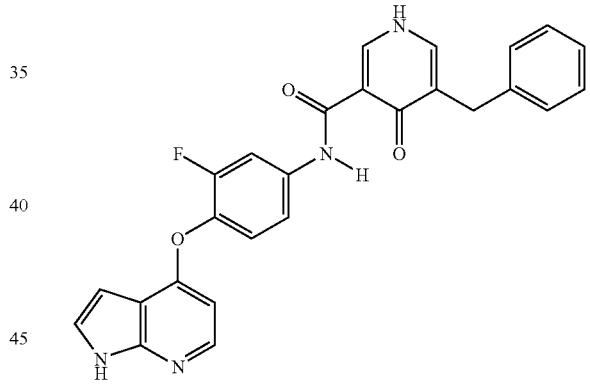

N-(4-(1H-Pyrrolo[2,3-b]pyridin-4-yloxy)-3-fluorophenyl)-5-benzyl-4-oxo-1,4-dihydropyridine-3-carboxamide, trifluoroacetic acid salt To a solution of 5-benzyl-4-oxo-1,4-dihydropyridine-3-carboxylic acid (35 mg, 0.15 mmol) and HOBt (30 mg) in DMF (2.5 mL) at rt was added EDCI.HCl (80 mg, 0.42 mmol) followed by 4-(1H-pyrrolo[2,3-b]pyridin-4-yloxy)-3-fluorobenzenamine (35 mg, 0.16 mmol, Compound B of Example 132). The reaction mixture was stirred at rt for 40 h and concentrated in vacuo. The resulting residue was purified by preparative HPLC to afford the desired product (38 mg, 45%) as a white solid. $^1$H NMR (DMSO-$d_6$) δ 13.21 (br s, 1H), 12.38 (s, 1H), 12.08 (br s, 1H), 8.59 (d, 1H, J=4.4 Hz), 8.17 (d, 1H, J=5.5 Hz), 8.03 (dd, 1H, J=13.2, 2.2 Hz), 7.80 (d, 1H, J=3.9 Hz), 7.48–7.19 (m, 8H), 6.52 (d, 1H, J=5.5 Hz), 6.34 (d, 1H, J=1.6 Hz 3.81 (s, 2H); MS(ESI$^+$) m/z 455.1 (M+H)$^+$.

Example 248

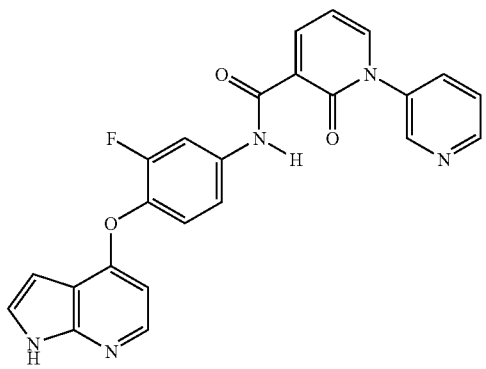

N-(4-(1H-Pyrrolo[2,3-b]pyridin-4-yloxy)-3-fluorophenyl)-2-oxo-1-(pyridin-3-yl)-1,2-dihydropyridine-3-carboxamide, trifluoroacetic acid salt

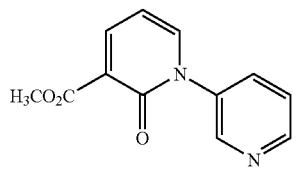

A) Methyl 2-oxo-1-(pyridin-3-yl)-1,2-dihydropyridine-3-carboxylate

To a solution of methyl 2-oxo-2H-pyran-3-carboxylate (462 mg, 3 mmol, Aldrich) in DMF (6 mL) at rt was added 3-aminopyridine (282 mg, 3 mmol). The reaction mixture was stirred overnight at rt, treated with EDCI.HCl (650 mg, 3.4 mmol) and DMAP (200 mg), stirred for an additional 24 h, and concentrated in vacuo. The residue was purified by preparative HPLC to afford the desired product (980 mg, 95%) as a beige solid. $^1$H NMR (CDCl$_3$) δ 13.00 (br s, 1H), 8.83 (br s, 1H), 8.74 (br s, 1H), 8.29 (dd, 1H, J=7.2, 1.7 Hz), 8.18 (d, 1H, J=8.3 Hz), 7.73 (dd, 1H, J=7.7, 5.0 Hz), 7.66 (dd, 1H, J=6.6, 1.6 Hz), 6.42 (t, 1H, J=7.1 Hz), 3.87 (s, 3H).

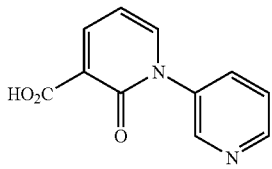

B) 2-Oxo-1-(pyridin-3-yl)-1,2-dihydropyridine-3-carboxylic acid

A mixture of methyl 2-oxo-1-(pyridin-3-yl)-1,2-dihydropyridine-3-carboxylate (980 mg, 2.85 mmol) and 6 N NaOH (1 mL) and methanol (20 mL) was stirred at rt overnight. To the reaction mixture was added 1 N aq. HCl (6 mL) and the mixture was concentrated in vacuo to obtain the acid (1.0 g, 100%) as a light yellow solid containing a small amount of NaCl. This material was used directly in the next step without further purification. $^1$H NMR (CD$_3$OD) δ 8.85 (d, 1H, J=1.7 Hz), 8.77 (d, 1H, J=4.9 Hz), 8.59 (dd, 1H, J=7.1, 1.7 Hz), 8.21 (d, 1H, J=8.2 Hz), 8.10 (dd, 1H, J=6.6, 2.2 Hz), 7.79 (dd, 1H, J=8.2, 5.0 Hz), 6.80 (t, 1H, J=6.6 Hz); MS(ESI$^+$) m/z 217.2 (M+H)$^+$.

C) N-(4-(1H-Pyrrolo[2,3-b]pyridin-4-yloxy)-3-fluorophenyl)-2-oxo-1-(pyridin-3-yl)-1,2-dihydropyridine-3-carboxamide, trifluoroacetic acid salt To a solution of 2-oxo-1-(pyridin-3-yl)-1,2-dihydropyridine-3-carboxylic acid (22 mg, 0.10 mmol) and HOBt (5 mg) in DMF (3 mL) at rt was added EDCI.HCl (24.5 mg, 0.13 mmol) followed by 4-(1H-pyrrolo[2,3-b]pyridin-4-yloxy)-3-fluorobenzenamine (24 mg, 0.10 mmol, Compound B of Example 132). The reaction mixture was stirred at rt overnight and concentrated in vacuo. The resulting residue was purified by preparative HPLC to afford the desired product (25 mg, 45%) as a beige solid. $^1$H NMR (DMF-d$_7$) δ 12.26 (br s, 1H), 12.18 (s, 1H), 8.90 (d, 1H, J=2.2 Hz), 8.78 (d, 1H, J=3.9 Hz), 8.71 (dd, 1H, J=7.1, 2.2 Hz), 8.28–8.15 (m, 4H), 7.72–7.48 (m, 4H), 6.87 (t, 1H, J=7.2 Hz), 6.64 (d, 1H, J=5.5 Hz), 6.47 (br s, 1H); MS(ESI$^+$) m/z 442.2 (M+H)$^+$.

Example 249

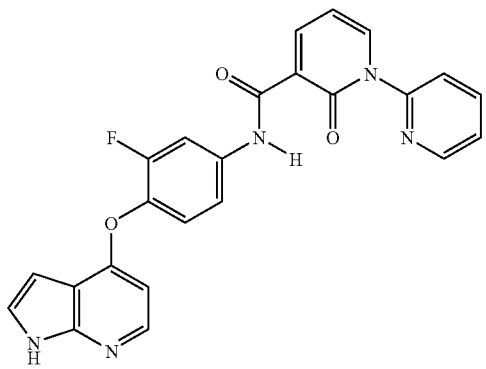

N-(4-(1H-Pyrrolo[2,3-b]pyridin-4-yloxy)-3-fluorophenyl)-2-oxo-1-(pyridin-2-yl)-1,2-dihydropyridine-3-carboxamide, trifluoroacetic acid salt

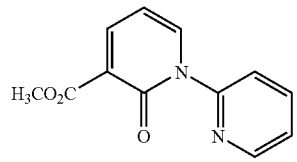

A) Methyl 2-oxo-1-(pyridin-2-yl)-1,2-dihydropyridine-3-carboxylate

To a solution of methyl 2-oxo-2H-pyran-3-carboxylate (462 mg, 3 mmol, Aldrich) in DMF (6 mL) at rt was added 3-aminopyridine (282 mg, 3 mmol). The reaction mixture was stirred at rt for 12 h and treated with EDCI.HCl (650 mg, 3.4 mmol) and DMAP (200 mg). The reaction mixture was stirred for 2.5 days at rt, and most of the DMF was removed in vacuo. The residue was purified by preparative HPLC to afford the desired product (500 mg, 72%) as a glassy material. $^1$H NMR (CDCl$_3$) δ 8.53 (d, 1H, J=5.0 Hz), 8.20 (dd, 1H, J=9.2, 2.2 Hz), 8.06 (dd, 1H, J=6.0, 1.1 Hz), 7.89–7.82 (m, 2H), 7.32 (dd, 1H, J=6.6, 5.0 Hz), 6.36 (t, 1H, J=6.6 Hz), 3.86 (s, 3H); MS(ESI$^+$) m/z 231.2 (M+H)$^+$.

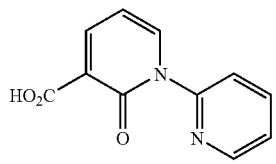

B) 2-Oxo-1-(pyridin-2-yl)-1,2-dihydropyridine-3-carboxylic acid

A mixture of methyl 2-oxo-1-(pyridin-2-yl)-1,2-dihydropyridine-3-carboxylate (500 mg, 2.17 mmol) and 3 N NaOH (1 mL) and methanol (10 mL) was stirred at rt overnight. To the reaction was added TFA (0.5 mL) and the mixture was concentrated in vacuo. The residue was dissolved in water (3 mL) and i-PrOH (10 mL). The solid which formed was filtered, washed with a small amount of water and i-PrOH, and dried to obtain the acid (260 mg, 55%) as a white solid. $^1$H NMR (DMF-$d_7$) δ 14.14 (br s, 1H), 8.72 (d, 1H, J=4.9 Hz), 8.62 (dd, 1H, J=7.7, 2.2 Hz), 8.47 (dd, 1H, J=6.6, 2.2 Hz), 8.18–7.98 (m, 2H), 7.67 (dd, 1H, J=7.2, 5.3 Hz), 6.97 (t, 1H, J=6.6 Hz); MS(ESI$^+$) m/z 217.2 (M+H)$^+$.

C) N-(4-(1H-Pyrrolo[2,3-b]pyridin-4-yloxy)-3-fluorophenyl)-2-oxo-1-(pyridin-2-yl)-1,2-dihydropyridine-3-carboxamide, trifluoroacetic acid salt To a solution of 2-oxo-1-(pyridin-2-yl)-1,2-dihydropyridine-3-carboxylic acid (200 mg, 0.93 mmol) and HOBt (100 mg) in DMF (5 mL) at rt was added EDCI.HCl (250 mg, 1.30 mmol) followed by 4-(1H-pyrrolo[2,3-b]pyridin-4-yloxy)-3-fluorobenzenamine (226 mg, 0.93 mmol, Compound B of Example 132) in DMF (4 mL). The reaction mixture was stirred at rt overnight and concentrated in vacuo. The residue was purified by preparative HPLC to afford the desired product (290 mg, 56%) as a white solid. $^1$H NMR (DMF-$d_7$) δ 12.16 (br s, 1H), 12.15 (br s, 1H), 11.99 (br s, 1H), 8.77–8.55 (m, 2H), 8.39–8.35 (m, 1H), 8.22–8.15 (m, 4H), 7.72–7.4 (m, 3H), 6.87 (t, 1H, J=7.2 Hz), 6.55 (t, 1H, J=5.5 Hz), 6.42 (d, 1H, J=2.3 Hz); MS(ESI$^+$) m/z 442.1 (M+H)$^+$.

Example 250

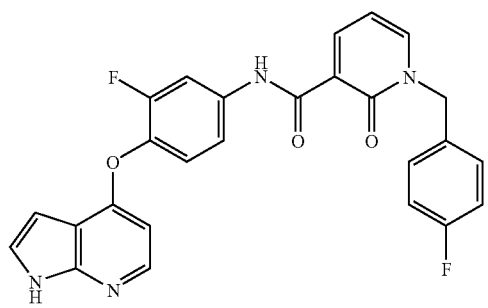

N-(4-(1H-Pyrrolo[2,3-b]pyridin-4-yloxy)-3-fluorophenyl)-1-(4-fluorobenzyl)-2-oxo-1,2-dihydropyridine-3-carboxamide, hydrochloride salt

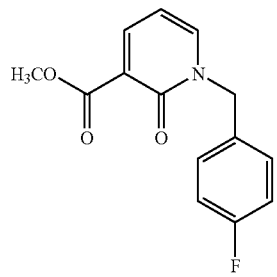

A) Methyl 1-(4-fluorobenzyl)-2-oxo-1,2-dihydropyridine-3-carboxylate

A heterogeneous mixture of methyl 2-oxo-2H-pyran-3-carboxylate (2.0 g, 13 mmol, 1.0 eq, Aldrich) and 4-fluorobenzylamine (1.5 mL, 13 mmol, 1.0 eq) in DMF (10 mL) was stirred at room temperature for 3 h. The reaction mixture was treated with EDCI (3.4 g, 18 mmol, 1.4 eq) and DMAP (0.11 g, 9.91 mmol, 0.07 eq) at room temperature and the resulting solution was stirred for 12 h. The reaction mixture was quenched with 1 N aqueous HCl and the solution was extracted with ethyl acetate (4×50 mL). The combined organic extracts were washed with 10% aqueous LiCl (3×70 mL), dried (Na$_2$SO$_4$), filtered and the filtrate concentrated in vacuo to afford the product (2.5 g, 73%) as a solid, which was used without further purification. $^1$H NMR (DMSO-$d_6$) δ 8.17–8.20 (m, 1H), 8.03–8.05 (m, 1H), 7.38–7.46 (m, 2H), 7.16–7.22 (m, 2H), 6.37 (dd, 1H, J=6.94 Hz), 5.13 (s, 2H), 3.73 (s, 3H); HRMS(ESI): calcd.: 262.0879, found: 262.0885.

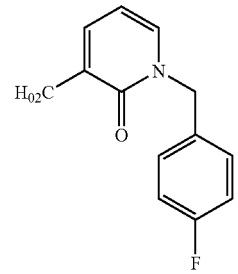

B) 1-(4-Fluorobenzyl)-2-oxo-1,2-dihydropyridine-3-carboxylic acid

A solution of methyl 1-(4-fluorobenzyl)-2-oxo-1,2-dihydropyridine-3-carboxylate (2.4 g, 9.2 mmol, 1.0 eq) in MeOH (25 ml) was treated with 5 N aqueous sodium hydroxide (4.6 mL, 24 mmol, 2.6 eq) at room temperature and the reaction mixture was stirred for 15 h. The reaction mixture was concentrated in vacuo, diluted with water and the solution was extracted with ethyl acetate (discarding the organic fraction). The aqueous fraction was cooled to 0° C. and acidified with concentrated HCl. The resulting solid was filtered, washed with water and the solid dried in vacuo to afford the product (1.6 g, 70%) which was sufficiently pure to use in the subsequent step without further purification. $^1$H NMR (DMSO-$d_6$) δ 8.44–8.39 (m, 2H), 7.46–7.42 (m, 2H), 7.24–7.18 (m, 2H), 6.78 (d, 1H, J=6.98 Hz), 5.31 (s, 2H); HRMS(ESI), calcd.: 248.0723, found: 248.0718.

C) N-(4-(1H-Pyrrolo[2,3-b]pyridin-4-yloxy)-3-fluorophenyl)-1-(4-fluorobenzyl)-2-oxo-1,2-dihydropyridine-3-carboxamide, hydrochloride salt A homogeneous solution of 1-(4-fluorobenzyl)-2-oxo-1,2-dihydropyridine-3-carboxylic acid (0.051 g, 0.21 mmol, 1.0 eq), 4-(1H-pyrrolo[2,3-b]pyridin-4-yloxy)-3-fluorobenzenamine (0.50 g, 0.21 mmol, 1.0 eq, Compound B of Example 132) and TBTU (0.086 g, 0.23 mmol, 1.1 eq) in DMF (1 mL) was treated with DIPEA (0.11 mL, 0.62 mmol, 3.0 eq) at room temperature. The reaction mixture was stirred for 12 h and quenched with 10% aqueous LiCl (15 mL). The resulting solution was extracted with ethyl acetate (4×40 mL). The combined organic extracts were washed with 10% aqueous LiCl (4×50 mL), dried ($Na_2SO_4$), filtered and the filtrate concentrated in vacuo. The residue was purified by flash chromatography ($SiO_2$, eluting 0–2.5% MeOH in $CHCl_3$) and the appropriate fractions were isolated and concentrated in vacuo. The free base was dissolved in THF, cooled to 0° C. and the homogeneous solution treated with anhydrous 4 N HCl in dioxane. The reaction mixture was warmed to room temperature, concentrated in vacuo and the residue triturated with diethyl ether. The solid was dried in vacuo to afford the title compound (0.062 g, 59%) as a HCl salt. $^1$H NMR (DMSO-$d_6$) δ 12.43 (s, 1H), 12.27 (s, 1H), 8.50–8.52 (m, 1H), 8.35–8.37 (m, 1H), 8.25–8.27 (m, 1H), 8.05–8.0 (m, 1H), 7.43–7.55 (m, 5H), 7.20–7.24 (m, 2H), 6.71 (t, 1H, J=6.89 Hz), 6.65 (d, 1H, J=6.03 Hz), 6.43 (s, 1H), 5.32 (s, 2H); HRMS(ESI$^+$): calcd: 473.1425, found: 473.1427.

was stirred at 0° C. for 30 min and treated with thionyl chloride (0.219 mL, 3.0 mmol, Aldrich). The reaction mixture was then stirred at 0° C. for another 30 min and a solution of 4-fluorobenzylamine (375 mg, 3.0 mmol, Aldrich) in 2 mL of THF was added. The reaction mixture was stirred at 0° C. for 2 h, diluted with 100 mL of ethyl acetate and extracted with 1 N NaOH (10 mL). The aqueous phase was acidified with 1 N HCl to pH 1–2. The solid that formed was collected by filtration (343 mg, 48%). MS(ESI$^+$) m/z 238.2 (M+H)$^+$.

B) N-(4-(1H-Pyrrolo[2,3-b]pyridin-4-yloxy)-3-fluorophenyl)-N-(4-fluorobenzyl)cyclopropane-1,1-dicarboxamide, trifluoroacetic acid salt To a solution of 4-(1H-pyrrolo[2,3-b]pyridin-4-yloxy)-3-fluorobenzenamine (45 mg, 0.1 mmol, Compound B of Example 132) and 1-((4-fluorobenzyl)carbamoyl)cyclopropanecarboxylic acid (24 mg, 0.1 mml) in DMF (0.5 mL) at room temperature was added HATU (57 mg., 0.15 mmol, Perseptive Biosystem) and DIEA (0.05 mL, 0.3 mmol, Aldrich). The reaction mixture was stirred at rt for 2 h, and then quenched by the addition of 2 mL of methanol. The reaction mixture was purified by preparative HPLC. The desired fractions were combined, concentrated under reduced pressure, and lyophilized to dryness to afford the desired product (39 mg, 67%) as a white solid. $^1$H NMR (DMSO-$d_6$) δ 11.99 (br s, 1H), 10.81 (s, 1H), 8.46 (t, 1H, J=5.8 Hz), 8.13 (d, 1H, J=6.1 Hz), 7.86 (dd, 1H, J=13.2, 2.2 Hz), 7.41–7.46 (m, 2H), 7.37 (t, 1H, J=9.1 Hz), 7.28–7.32 (m, 2H), 7.13 (t, 3H, J=9.1 Hz), 6.44 (d, 1H, J=6.1 Hz), 6.30 (s, 1H), 4.30 (d, 2H, J=5.5 Hz), 1.39 (d, 4H, J=2.2 Hz); MS(ESI$^+$) m/z 463.1 (M+H)$^+$.

Example 251

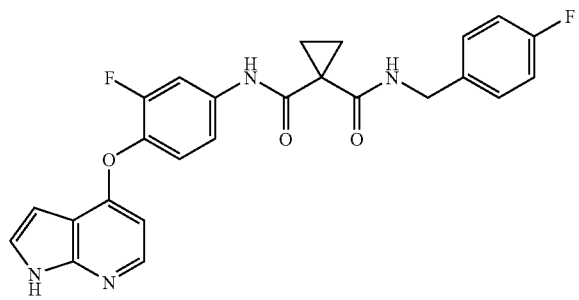

N-(4-(1H-Pyrrolo[2,3-b]pyridin-4-yloxy)-3-fluorophenyl)-N-(4-fluorobenzyl)cyclopropane-1,1-dicarboxamide, trifluoroacetic acid salt

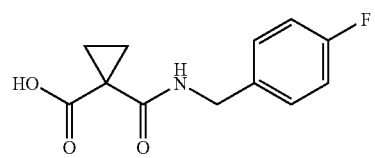

A) 1-((4-Fluorobenzyl)carbamoyl)cyclopropanecarboxylic acid

To a solution of 1,1-cyclopropanecarboxylic acid (390 mg, 3.0 mmol, Aldrich) in THF (5 mL) at 0° C. was added triethylamine (0.418 mL, 3.0 mmol). The reaction mixture

Example 252

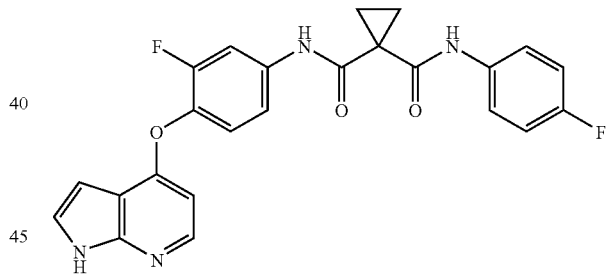

N-(4-(1H-Pyrrolo[2,3-b]pyridin-4-yloxy)-3-fluorophenyl)-N-(4-fluorophenyl)cyclopropane-1,1-dicarboxamide

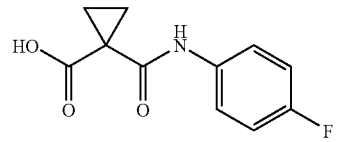

A) 1-((4-Fluorophenyl)carbamoyl)cyclopropanecarboxylic acid

To a solution of 1,1-cyclopropanecarboxylic acid (390 mg, 3.0 mmol, Aldrich) in THF (5 mL) at 0° C. was added triethylamine (0.418 mL, 3.0 mmol). The reaction mixture was stirred at 0° C. for 30 min and treated with thionyl chloride (0.219 mL, 3.0 mmol, Aldrich). The reaction mixture was stirred at 0° C. for an additional 30 min, and treated with a solution of 4-fluoroaniline (333 mg, 3.0 mmol, Aldrich) in 2 mL of THF. The reaction mixture was stirred at 0° C. for 2 h, then diluted with 100 mL of ethyl acetate and extracted with 1 N NaOH (10 mL). The aqueous phase was acidified with 1 N HCl to pH 1–2. The solid that formed was collected by filtration (508 mg, 76%). MS(ESI$^+$) m/z 224.2 (M+H)$^+$.

B) N-(4-(1H-Pyrrolo[2,3-b]pyridin-4-yloxy)-3-fluorophenyl)-N-(4-fluorophenyl)cyclopropane-1,1-dicarboxamide Prepared in a similar manner as Step B of Example 251 (41 mg, 73%). $^1$H NMR (DMSO-d$_6$) δ 11.97 (br s, 1H), 10.35 (s, 1H), 9.99 (s, 1H), 8.12 (d, 1H, J=5.5 Hz), 7.85 (d, 1H, J=13.2 Hz), 7.62 (m, 2H), 7.43 (m, 2H), 7.36 (t, 1H, J=9.4 Hz), 7.14 (t, 2H, J=9.1 Hz), 6.43 (d, 1H, J=5.5 Hz), 6.29 (s, 1H), 1.46 (, 4H, J=2.8 Hz); MS(ESI$^+$) m/z 449.1 (M+H)$^+$.

Example 253

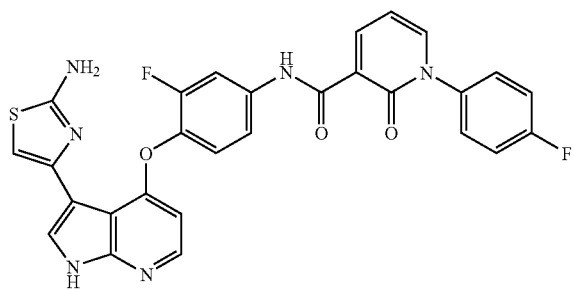

N-(4-(3-(2-Aminothiazol-4-yl)-1H-pyrrolo[2,3-b]pyridin-4-yloxy)-3-fluorophenyl)-1-(4-fluorophenyl)-2-oxo-1,2-dihydropyridine-3-carboxamide

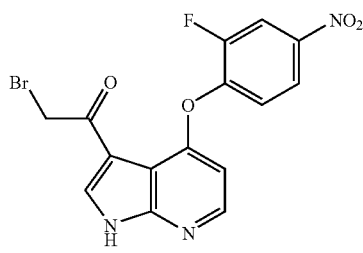

A) 2-Bromo-1-(4-(2-fluoro-4-nitrophenoxy)-1H-pyrrolo[2,3-b]pyridin-3-yl)ethanone To a solution of 4-(2-fluoro-4-nitrophenoxy)-1H-pyrrolo[2,3-b]pyridine (1.00 g, 3.66 mmol, Compound A of Example 132) in DCE (100 mL) at rt was added aluminum chloride (2.43 g, 18.3 mmol, Alfa Aesar). The reaction mixture was stirred at rt for 1 h and then treated with bromoacetyl chloride (7.32 mmol, Aldrich). The reaction mixture was then stirred at rt for 2 h and quenched by the addition of 100 mL of EtOAc, 30 mL of MeOH, and 30 mL of saturated aq. K$_2$HPO$_4$. This mixture was filtered through a pad of Celite®. The organic layer was washed with brine, dried (MgSO$_4$), and concentrated in vacuo. The residue was purified by flash chromatography (SiO$_2$, eluting with 2–5% MeOH in dichloromethane) to afford the desired product (1.12 g, 78%) as a light yellow solid. MS(ESI$^+$) m/z 393.9 (M+H)$^+$.

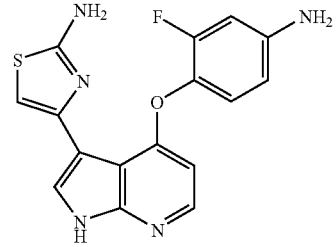

B) 4-(4-(4-Amino-2-fluorophenoxy)-1H-pyrrolo[2,3-b]pyridin-3-yl)thiazol-2-amine

To a solution of 2-bromo-1-(4-(2-fluoro-4-nitrophenoxy)-1H-pyrrolo[2,3-b]pyridin-3-yl)ethanone (392 mg, 1.0 mmol) in acetic acid (10 mL) was added thiourea (228 mg, 3.0 mmol, Aldrich). The reaction mixture was stirred at room temperature for 3 h, and then diluted with 50 mL of EtOAc. The reaction mixture was washed with saturated aq. NaHCO$_3$ solution and brine. The organic layer was dried (MgSO$_4$) and concentrated in vacuo to give a light yellow solid. The solid was dissolved in a mixed solvent (20 mL of THF and 40 mL of MeOH). Ammonium chloride (267 mg, 5.0 mmol, EMD) and Zn dust (327 mg, 5.0 mmol, Aldrich) were added then added to the resulting solution. The reaction mixture was stirred at room temperature overnight, diluted with 100 mL of EtOAc and filtered through a pad of Celite®. The filtrate was concentrated in vacuo and the resulting residue was purified by preparative HPLC. The desired fractions were combined, neutralized with saturated aq. NaHCO$_3$ solution, and concentrated under reduced pressure. The solid that formed was collected by filtration (194 mg, 57% over two steps). MS(ESI$^+$) m/z 342.2 (M+H)$^+$.

D) N-(4-(3-(2-Aminothiazol-4-yl)-1H-pyrrolo[2,3-b]pyridin-4-yloxy)-3-fluorophenyl)-1-(4-fluorophenyl)-2-oxo-1,2-dihydropyridine-3-carboxamide Prepared in a similar manner as Step C of Example 242 (5.6 mg, 12%). $^1$H NMR (CD$_3$OD) δ 8.60 (dd, 1H, J=5.5, 1.7 Hz), 8.08 (d, 1H, J=5.5 Hz), 7.90–7.88 (m, 2H), 7.67 (s, 1H), 7.45–7.42 (m, 2H), 7.29 (d, 1H, J=5.5 Hz), 7.25–7.18 (m, 4H), 6.65 (t, 1H, J=7.4 Hz), 6.43 (d, 1H, J=6.1 Hz); MS(ESI$^+$) m/z 557.1 (M+H)$^+$.

Example 254

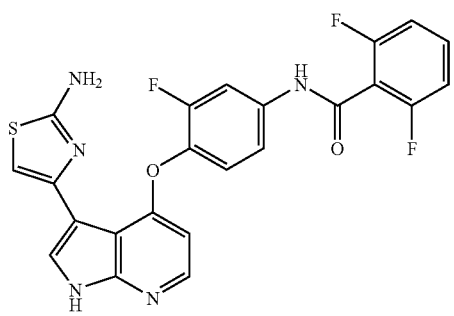

N-(4-(3-(2-Aminothiazol-4-yl)-1H-pyrrolo[2,3-b]pyridin-4-yloxy)-3-fluorophenyl)-2,6-difluorobenzamide, trifluoroacetic acid salt To a solution of 4-(4-(4-amino-2-fluorophenoxy)-1H-pyrrolo[2,3-b]pyridin-3-yl)thiazol-2-amine (20 mg, 0.06 mmol, Compound B of Example 253) in 0.5 mL of pyridine at –20° C. was added a solution of 2,6-difluorobenzoylchloride (10.6 mg, 0.06 mmol, Aldrich) in 0.3 mL of dichloromethane. The reaction mixture was stirred at –20° C. for 30 min and quenched by the addition of MeOH (0.5 mL). The reaction mixture was concentrated in vacuo and the resulting residue was purified by preparative HPLC. The desired fractions were combined, concentrated under reduced pressure, and lyophilized to afford the desired product (TFA salt, 9.2 mg, 22%) as a white solid. $^1$H NMR (CD$_3$OD) δ 8.10 (d, 1H, J=6.1 Hz), 7.68 (s, 1H), 7.48–7.37 (m, 2H), 7.24 (t, 1H, J=8.3 Hz), 7.05–7.01 (m, 3H), 6.86 (s, 1H), 6.46 (d, 1H, J=5.5 Hz); MS(ESI$^+$) m/z 482.1 (M+H)$^+$.

Example 255

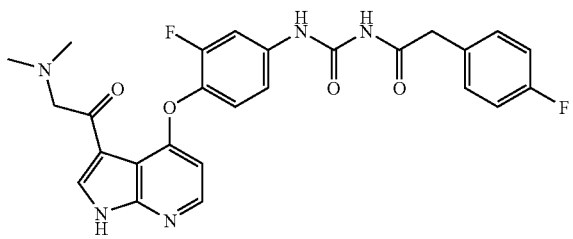

1-(4-(3-(2-(Dimethylamino)acetyl)-1H-pyrrolo[2,3-b]pyridin-4-yloxy)-3-fluorophenyl)-3-(2-(4-fluorophenyl)acetyl)urea B) 2-(Dimethylamino)-1-(4-(2-fluoro-4-nitrophenoxy)-1H-pyrrolo[2,3-b]pyridin-3-yl)ethanone To a solution of 2-bromo-1-(4-(2-fluoro-4-nitrophenoxy)-1H-pyrrolo[2,3-b]pyridin-3-yl)ethanone (96 mg, 0.24 mmol, Compound A of Example 253) in THF (5 mL) at 0° C. was added dimethylamine (1.0 M solution in THF, 0.72 mL, 0.72 mmol). The reaction mixture was stirred at 0° C. for 1 h and concentrated under reduced pressure to give the desired product (80 mg, 93%) as a light yellow solid, which was washed with cold water and air dried. MS(ESI$^+$) m/z 359.2 (M+H)$^+$.

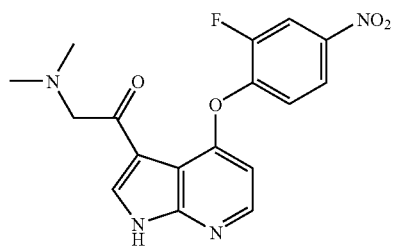

C) 1-(4-(4-Amino-2-fluorophenoxy)-1H-pyrrolo[2,3-b]pyridin-3-yl)-2-(dimethylamino)ethanone To a solution of 2-(dimethylamino)-1-(4-(2-fluoro-4-nitrophenoxy)-1H-pyrrolo[2,3-b]pyridin-3-yl)ethanone (80 mg, 0.22 mmol) in a mixed solvent (5 mL of THF and 5 mL of MeOH) were added ammonium chloride (64.2 mg, 1.2 mmol, EMD) and Zn dust (78.4 mg, 1.2 mmol, Aldrich). The reaction mixture was stirred at room temperature overnight, diluted with 30 mL of EtOAc and filtered through a pad of Celite®. The filtrate was concentrated in vacuo and the resulting residue was purified by preparative HPLC. The desired fractions were combined, neutralized with saturated aq. NaHCO$_3$ solution, and concentrated in vacuo. The solid that formed was collected by filtration (51 mg, 71%). MS(ESI$^+$) m/z 328.1 (M+H)$^+$.

ced 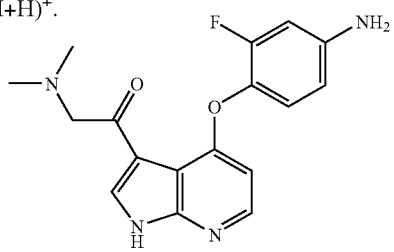

D) 1-(4-(3-(2-(Dimethylamino)acetyl)-1H-pyrrolo[2,3-b]pyridin-4-yloxy)-3-fluorophenyl)-3-(2-(4-fluorophenyl)acetyl)urea Prepared in a similar manner as Step C of Example 132 (5.7 mg, 11%). $^1$H NMR (CD$_3$OD) δ 10.67 (s, 1H), 8.27 (s, 1H), 8.08 (d, 1H, J=6.1 Hz), 7.65 (d, 1H, J=12.6 Hz), 7.24–7.16 (m, 4H), 6.96 (t, 2H, J=8.8 Hz), 6.45 (d, 1H, J=5.5 Hz), (s, 2H), 3.60 (s, 2H), 2.86 (s, 6H); MS(ESI$^+$) m/z 508.2 (M+H)$^+$.

Example 256

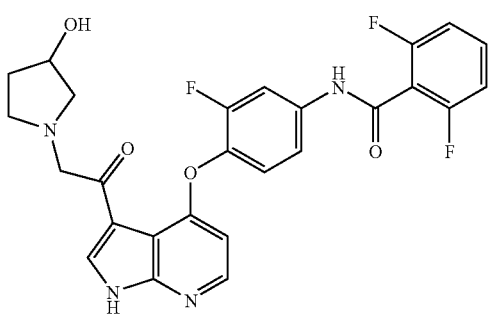

2,6-Difluoro-N-(3-fluoro-4-(3-(2-(3-hydroxypyrrolidin-1-yl)acetyl)-1H-pyrrolo[2,3-b]pyridin-4-yloxy)phenyl)benzamide Prepared in a similar manner as Example 254. $^1$H NMR (CD$_3$OD) δ 8.29 (d, 1H, J=6.6 Hz), 8.13 (d, 1H, J=5.5 Hz), 7.80 (dd, 1H, J=12.7, 2.2 Hz), 7.46–7.38 (m, 2H), 7.23 (t, 1H, J=9.1 Hz), 7.03 (t, 2H, J=8.3 Hz), 6.53 (d, 1H, J=5.5 Hz), 5.01–4.86 (m, 2H), 4.49–4.46 (m, 1H), 3.77–3.64 (m, 2H), 3.35–3.06 (m, 2H), 2.25–1.98 (m, 2H); MS(ESI$^+$) m/z 511.2 (M+H)$^+$.

Example 257

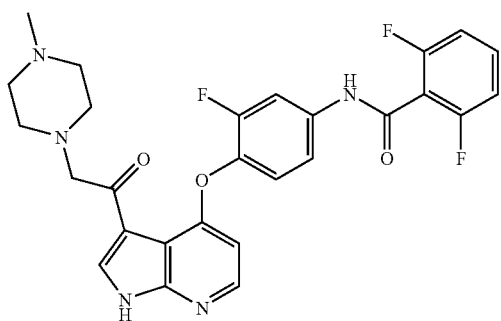

2,6-Difluoro-N-(3-fluoro-4-(3-(2-(4-methylpiperazin-1-yl)acetyl)-1H-pyrrolo[2,3-b]pyridin-4-yloxy)phenyl)benzamide Prepared in a similar manner as Example 254. $^1$H NMR (CD$_3$OD) δ 8.23 (s, 1H), 8.11 (d, 1H, J=5.5 Hz), 7.79 (dd, 1H, J=12.1, 2.2 Hz), 7.46–7.34 (m, 2H), 7.16(t, 1H, J=8.8 Hz), 7.03 (t, 2H, J=8.3 Hz), 6.53 (d, 1H, J=6.1 Hz), 4.11 (s, 2H), 3.21–2.92 (m, 8H), 2.76 (s, 3H); MS(ESI$^+$) m/z 524.3 (M+H)$^+$.

Example 258

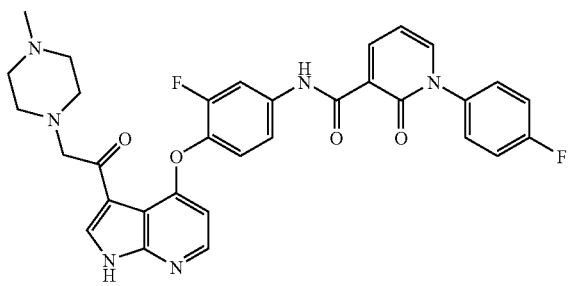

N-(3-Fluoro-4-(3-(2-(4-methylpiperazin-1-yl)acetyl)-1H-pyrrolo[2,3-b]pyridin-4-yloxy)phenyl)-1-(4-fluorophenyl)-2-oxo-1,2-dihydropyridine-3-carboxamide Prepared in a similar manner as Example 253. $^1$H NMR (CD$_3$OD) δ 8.59 (dd, 1H, J=7.2, 2.2 Hz), 8.53 (s, 1H), 8.08 (d, 1H, J=5.5 Hz), 7.89–7.85 (m, 2H), 7.44–7.41 (m, 2H), 7.28–7.18 (m, 3H), 7.15 (t, 1H, J=8.8 Hz), 6.65 (t, 1H, J=6.7 Hz), 6.48 (d, 1H, J=5.5 Hz), 4.13 (s, 2H), 3.21–2.89 (bm, 8), 2.76 (s, 3H); MS(ESI$^+$) m/z 599.2 (M+H)$^+$.

Example 259

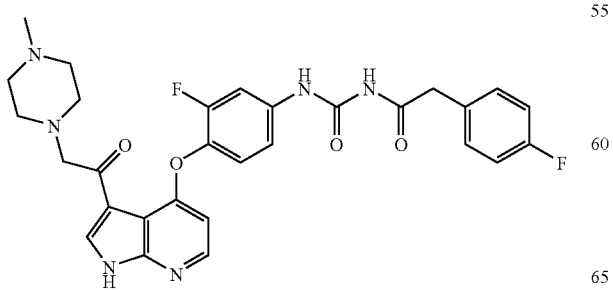

1-(3-Fluoro-4-(3-(2-(4-methylpiperazin-1-yl)acetyl)-1H-pyrrolo[2,3-b]pyridin-4-yloxy)phenyl)-3-(2-(4-fluorophenyl)acetyl)urea Prepared in a similar manner as Example 255. $^1$H NMR (CD$_3$OD) δ 8.28 (s, 1H), 8.12 (d, 1H, J=6.1 Hz), 7.66 (dd, 1H, J=10.1, 2.8 Hz), 7.28–7.16 (m, 4H), 6.97–6.92 (m, 3H), 6.51 (d, 1H, J=6.1 Hz), 4.43 (s, 2H), 3.88 (s, 2H), 3.49 (s, 2H), 3.37–3.20 (m, 4H), 2.82 (s, 3H); MS(ESI$^+$) m/z 563.2 (M+H)$^+$.

Example 260

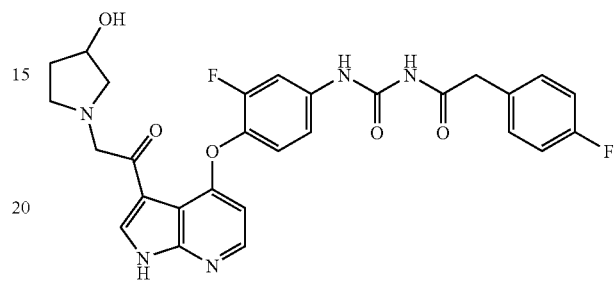

1-(3-Fluoro-4-(3-(2-(3-hydroxypyrrolidin-1-yl)acetyl)-1H-pyrrolo[2,3-b]pyridin-4-yloxy)phenyl)-3-(2-(4-fluorophenyl)acetyl)urea Prepared in a similar manner as Example 255. $^1$H NMR (CD$_3$OD) δ 10.69 (s, 1H), 8.27 (d, 1H, J=8.8 Hz), 8.09 (d, 1H, J=5.5 Hz), 7.66 (d, 1H, J=12.7 Hz), 7.27–7.16 (m, 4H), 6.98 (t, 2H, J=8.8 Hz), 6.47 (d, 1H, J=5.5 Hz), 4.99 (m, 1H), 4.49–4.44 (m, 2H), 3.90–3.68 (m, 2H), 3.62 (s, 2H), 3.37–3.09 (m, 2H), 2.15–1.92 (m, 2H); MS(ESI$^+$) m/z 550.1 (M+H)$^+$.

Example 261

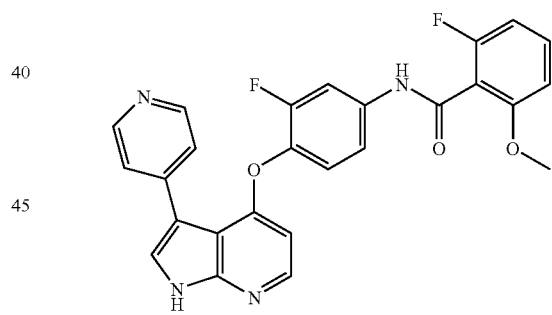

2-Fluoro-N-(3-fluoro-4-(3-(pyridin-4-yl)-1H-pyrrolo[2,3-b]pyridin-4-yloxy)phenyl)-6-methoxybenzamide

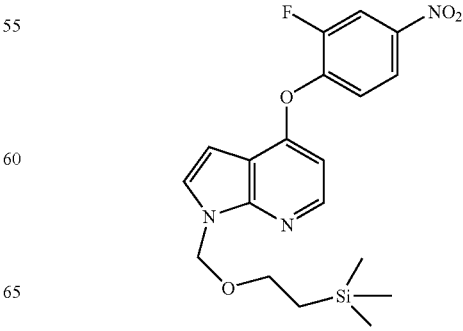

A) 4-(2-Fluoro-4-nitrophenoxy)-1-((2-(trimethylsilyl)ethoxy)methyl)-1H-pyrrolo[2,3-b]pyridine To a solution of 4-(2-fluoro-4-nitrophenoxy)-1H-pyrrolo[2,3-b]pyridine (1.68 g, 6.15 mmol, Compound A of Example 132) in 20 mL of DMF at −40° C. was added sodium hydride (271 mg, 6.77 mmol, 60% in mineral oil, Aldrich). The reaction mixture was stirred at 0° C. for 30 min, cooled to −40° C., and treated with 2-(trimethylsilyl)ethoxymethyl chloride (1.20 mL, 6.77 mmol, Aldrich). The reaction mixture was stirred at room temperature for 1 h, quenched by the addition of cold water (40 mL) and extracted with EtOAc (3×100 mL). The combined organic extracts were dried (MgSO$_4$) and concentrated in vacuo to give the desired product (2.40 g, 97%) as a brown solid. MS(ESI$^+$) m/z 404.2 (M+H)$^+$.

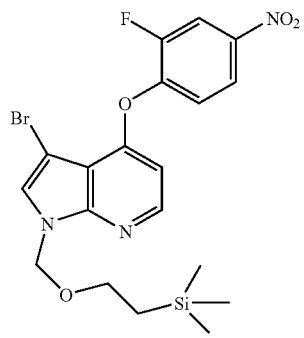

B) 3-Bromo-4-(2-fluoro-4-nitrophenoxy)-1-((2-(trimethylsilyl)ethoxy)methyl)-1H-pyrrolo[2,3-b]pyridine To a solution of 4-(2-fluoro-4-nitrophenoxy)-1-((2-(trimethylsilyl)ethoxy) methyl)-1H-pyrrolo[2,3-b]pyridine (2.40 g, 5.96 mmol) in 20 mL of acetonitrile at 0° C. was added a solution of NBS (1.01 g, 5.69 mmol, Aldrich) in 10 mL of acetonitrile. The reaction mixture was stirred at 0° C. for 30 min, quenched by the addition of cold water (50 mL), and extracted with EtOAc (3×120 mL). The combined organic extracts were dried (MgSO$_4$) and concentrated in vacuo. The residue was purified by flash chromatography (SiO$_2$, eluting with dichloromethane) to afford the desired product (2.70 g, 94%) as a light yellow oil. MS(ESI$^+$) m/z 482.9 (M+H)$^+$.

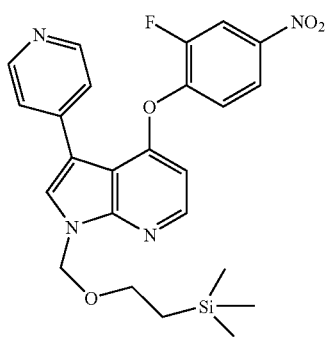

C) 4-(2-Fluoro-4-nitrophenoxy)-3-(pyridin-4-yl)-1-((2-(trimethylsilyl)ethoxy)methyl)-1H-pyrrolo[2,3-b]pyridine A sealed tube was charged with a solution of 3-bromo-4-(2-fluoro-4-nitrophenoxy)-1-((2-(trimethylsilyl) ethoxy)methyl)-1H-pyrrolo[2,3-b]pyridine (480 mg, 1.0 mmol) in toluene (5 mL), pyridin-4-ylboronic acid (246 mg, 2.0 mmol, Lancaster), 0.5 mL of ethanol, and potassium phosphate (1.0 mL, 2 M solution, 2.0 mmol). Argon was bubbled through the mixture for 15 minutes, and the reaction mixture was treated with tetrakis(triphenylphosphine)Pd(0)(58) mg, 0.05 mmol, Strem). the tube was sealed and the mixture was heated at 95 ° C. for 18 with vigorous stirring. The reaction mixture was then cooled to room temperature and diluted with EtOAc. The mixture ws washed with sasturated aq. NaHCO$_3$ solution and brine, dried (MgSO$_4$), and concentated in vacuo. The residue was purified by flash chromatography (SiO$_2$, eluting with 2% MeOH in dichloromethane) to give the desired product (237 mg, 49%) as a thick brown oil. MS(ESI$^+$) m/z 481.1 (M+H)$^+$.

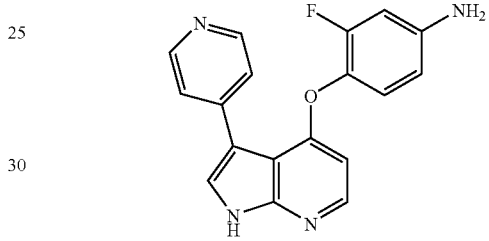

D) 3-Fluro-4-(3-(pyridin-4-yl)-1H-pyrrolo[2,3-b]Pyridin-4-yloxy)benzenamine

To a solution of 4-(2-fluoro-4-nitrophenoxy)-3-(pyridin-4-yl)-1-((2-(trimethylsilyl)ethoxy) methyl)-1-pyrolo[2,3-b]pyridine (237mg, 0.49 mmol) in a mixed solvent (8 mL of MeOH and 4 mL of THF) were added ammonium choride (131 mg, 2.49 mmol, EMC) and zinc dust (163 mg, 2.49 mmol, Aldrich). The reaction mixture was stirred at room temperature for 3 h, diluted with EtOAc (40 mL), and filered through a pad of Celite®. The filtrate was concentrated in vacuo to give a solid. MS(ESI$^+$) m/z 451.3 (M+H)$^+$. The solid was dissolved in 15 mL of THF and treated with TBAF (4 mL, 1.0 M solution i THF, Aldrich) and etane-1,2-diamine (0.4 mL, Aldrich). The reaction mixture was reflulxed for 16 h, cooled to room temperature, diluted with EtOAc, washedd with brine, dried (MgSO$_4$), and concentrated in vacuo. The residue was purified by flash chromatography (SiO$_2$, eluting with 2–5% MeOH in dechloromethane) to afford the desired product (127 mg, 81% for two steps). MS(ESI$^+$) m/z 321.2 (M+H)$^+$.

E) 2-Fluro-N-(3-fluro-4-(3-(pyridin-4-yl)-1H-pyrrolo[2,3-b]pyridin-4-yloxy)phenyl)-6-methoxybenzamide Prepared in a similar manner as Example 254 (3.2 mg, 7%). $^1$H NMR (DMSO-d$_6$) δ 12.92 (s, 1H), 10.80 (s, 1H), 8.72 (d, 2H, J=7.2 Hz), 8.44 (s, 1H), 8.31 (d, 2H, J=7.2 Hz), 8.16 (d, 2H, J=5.5 Hz), 7.94–7.86 (m, 1H), 7.55–7.41 (m, 2H), 6.97–6.91 (m, 1H), 6.88 (t, 1H, J=8.8 Hz), 6.45 (d, 1H, J=5.5 Hz), 3.78 (s, 3H); MS(ESI$^+$) m/z 473.1 (M+H)$^+$.

Example 262

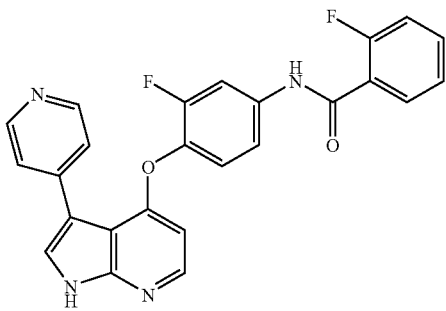

2-Fluoro-N-(3-fluoro-4-(3-(pyridin-4-yl)-1H-pyrrolo[2,3-b]pyridin-4-yloxy)phenyl)benzamide Prepared in a similar manner as Example 261. $^1$H NMR (DMSO-d$_6$) δ 12.97 (s, 1H), 10.76 (s, 1H), 8.78 (d, 2H, J=8.8 Hz), 8.50 (s, 1H), 8.36 (d, 2H, J=6.1 Hz), 8.23 (d, 1H, J=5.5 Hz), 7.96 (d, 1H, J=8.8 Hz), 7.70–7.54 (m, 4H), 7.39–7.35 (m, 2H), 6.50 (d, 1H, J=5.5 Hz); MS(ESI$^+$) m/z 443.1 (M+H)$^+$.

Example 263

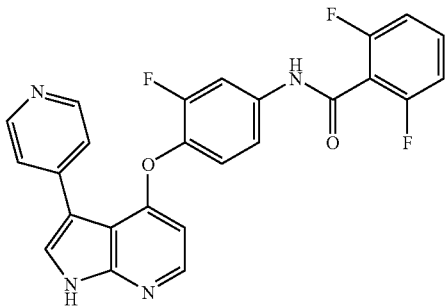

2,6-Difluoro-N-(3-fluoro-4-(3-(pyridin-4-yl)-1H-pyrrolo[2,3-b]pyridin-4-yloxy)phenyl)benzamide Prepared in a similar manner as Example 261. $^1$H NMR (DMSO-d$_6$) δ 12.89 (s, 1H), 11.10 (s, 1H), 8.70 (d, 2H, J=6.6 Hz), 8.42 (s, 1H), 8.27 (d, 2H, J=6.6 Hz), 8.16 (d, 1H, J=5.5 Hz), 7.86 (d, 1H, J=11.6 Hz), 7.58–7.48 (m, 3H), 7.23 (t, 2H, J=8.3 Hz), 6.45 (d, 1H, J=5.5 Hz); MS(ESI$^+$) m/z 461.1 (M+H)$^+$.

Example 264

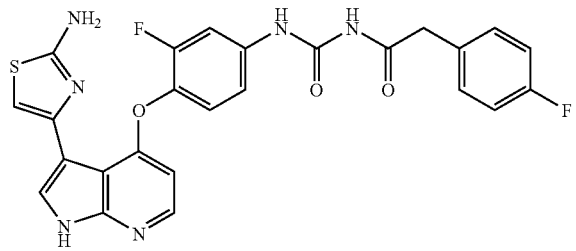

1-(4-(3-(2-Aminothiazol-4-yl)-1H-pyrrolo[2,3-b]pyridin-4-yloxy)-3-fluorophenyl)-3-(2-(4-fluorophenyl)acetyl)urea, trifluoroacetic acid salt To a solution of 4-(4-(4-amino-2-fluorophenoxy)-1H-pyrrolo[2,3-b]pyridin-3-yl)thiazol-2-amine (34 mg, 0.1 mmol, Compound B of Example 253) in a mixed solvent (0.5 mL of DMF and 0.5 mL of THF) at rt was added a solution of 2-(4-fluorophenyl)acetyl isocyanate in toluene (0.4 M, 0.25 ml, 0.1 mmol, Compound C of Example 4). The reaction mixture was stirred at rt for 1 h, concentrated in vacuo and the resulting residue was purified by preparative HPLC. The desired fractions were combined, concentrated under reduced pressure, and lyophilized to afford the desired product (TFA salt, 21.2 mg, 28%) as a white solid. $^1$H NMR (CD$_3$OD) δ 10.69 (s, 1H), 8.08 (d, 1H, J=5.5 Hz), 7.68 (s, 1H), 7.66 (d, 1H, J=12.1 Hz), 7.26–7.18 (m, 4H), 6.98 (t, 2H, J=8.8 Hz), 6.84 (s, 1H), 6.42 (d, 1H, J=6.1 Hz), 3.62 (s, 2H); MS(ESI$^+$) m/z 521.1 (M+H)$^+$.

Example 265

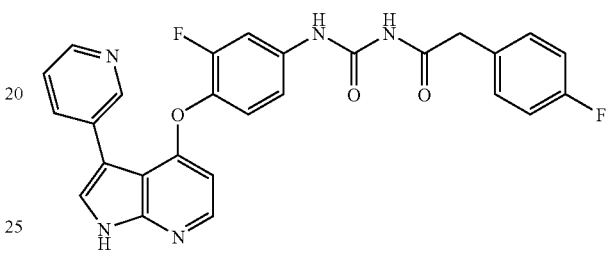

1-(3-Fluoro-4-(3-(pyridin-3-yl)-1H-pyrrolo[2,3-b]pyridin-4-yloxy)phenyl)-3-(2-(4-fluorophenyl)acetyl)urea Prepared in a similar manner as Example 264. $^1$H NMR (DMSO-d$_6$) δ 12.71 (s, 1H), 11.04 (s, 1H), 10.61 (s, 1H), 9.18 (s, 1H), 8.84 (d, 1H, J=8.3 Hz), 8.74 (d, 1H, J=5.5 Hz), 8.20 (d, 1H, J=5.5 Hz), 8.12 (s, 1H), 8.06 (dd, 1H, J=8.3, 2.8 Hz), 7.78 (dd, 1H, J=12.7, 2.2 Hz), 7.47 (t, 1H, J=8.8 Hz), 7.40–7.34 (m, 3H), 7.16 (t, 2H, J=8.8 Hz), 6.41 (d, 1H, J=5.5 Hz), 3.75 (s, 2H); MS(ESI$^+$) m/z 500.1 (M+H)$^+$.

Example 266

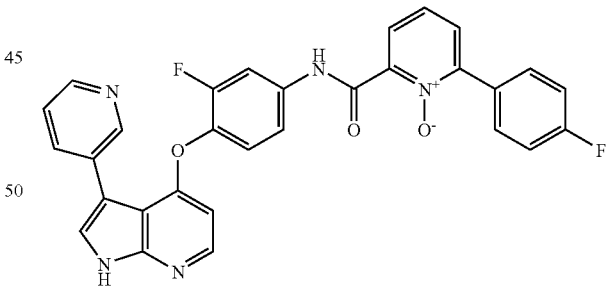

6-(4-Fluoro-phenyl)-1-oxy-pyridine-2-carboxylic acid [3-fluoro-4-(3-pyridin-3-yl-1H-pyrrolo[2,3-b]pyridin-4-yloxy)-phenyl]-amide Prepared in a similar manner as Example 241. $^1$H NMR (DMSO-d$_6$) δ 13.58 (s, 1H), 12.50 (s, 1H), 9.10 (s, 1H), 8.66 (d, 1H, J=5.5 Hz), 8.32 (dd, 1H, J=8.2, 2.2 Hz), 8.19 (d, 1H, J=5.5 Hz), 8.05–8.02 (m, 2H), 7.89–7.85 (m, 5H), 7.73 (t, 1H, J=7.7 Hz), 7.60 (t, 1H, J=8.8 Hz), 7.50 (t, 1H, J=8.8 Hz), 7.38 (t, 2H, J=8.8 Hz), 6.41 (d, 1H, J=6.5 Hz); MS(ESI$^+$) m/z 536.2 (M+H)$^+$.

Example 267

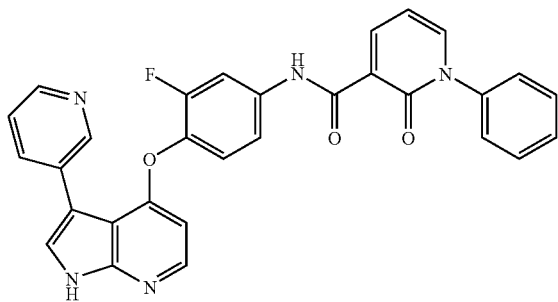

N-(3-Fluoro-4-(3-(pyridin-3-yl)-1H-pyrrolo[2,3-b]pyridin-4-yloxy)phenyl)-2-oxo-1-phenyl-1,2-dihydropyridine-3-carboxamide Prepared in a similar manner as Example 245. $^1$H NMR (DMSO-d$_6$) δ 12.48 (s, 1H), 12.15 (s, 1H), 9.09 (s, 1H), 8.65–8.59 (m, 3H), 8.18 (d, 1H, J=5.5 Hz), 8.15(dd, 1H, J=6.6, 2.2 Hz), 8.04–7.99 (m, 2H), 7.88 (m, 1H), 7.59–7.46 (m, 7H), 6.74 (t, 1H, J=7.2 Hz), 6.40 (d, 1H, J=5.5 Hz); MS(ESI$^+$) m/z 518.1 (M+H)$^+$.

Example 268

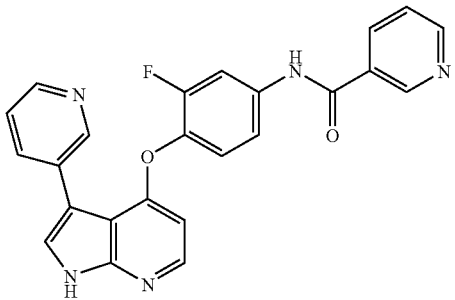

N-(3-Fluoro-4-(3-(pyridin-3-yl)-1H-pyrrolo[2,3-b]pyridin-4-yloxy)phenyl)nicotinamide Prepared in a similar manner as Example 254. $^1$H NMR (DMSO-d$_6$) δ 12.65 (s, 1H), 10.96 (s, 1H), 9.22 (s, 1H), 9.18 (s, 1H), 8.84 (t, 2H, J=5.0 Hz), 8.74 (d, 1H, J=5.5 Hz), 8.49 (d, 1H, J=8.3 Hz), 8.21 (d, 1H, J=5.5 Hz), 8.11 (d, 1H, J=1.7 Hz), 8.08–8.01 (m, 2H), 7.73–7.69 (m, 2H), 7.54 (t, 1H, J=8.8 Hz), 6.43 (d, 1H, J=5.5 Hz); MS(ESI$^+$) m/z 426.2 (M+H)$^+$.

Example 269

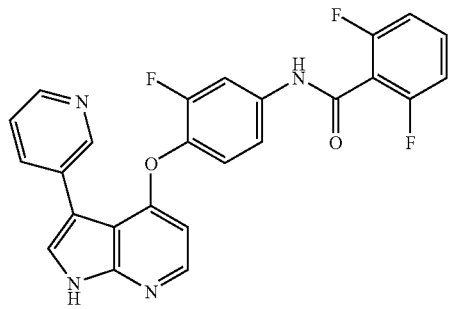

2,6-Difluoro-N-(3-fluoro-4-(3-(pyridin-3-yl)-1H-pyrrolo[2,3-b]pyridin-4-yloxy)phenyl)benzamide Prepared in a similar manner as Example 254. $^1$H NMR (DMSO-d$_6$) δ 11.23 (s, 1H), 9.20 (d, 1H, J=1.7 Hz), 8.87 (d, 1H, J=8.3 Hz), 8.77 (d, 1H, J=5.5 Hz), 8.23 (d, 1H, J=5.5 Hz), 8.55 (s, 1H), 8.08 (dd, 1H, J=8.2, 2.2 Hz), 7.90 (d, 1H, J=13.7 Hz), 7.62–7.55 (m, 3H), 7.27 (t, 2H, J=8.3 Hz), 6.50 (d, 1H, J=5.5 Hz); MS(ESI$^+$) m/z 461.1 (M+H)$^+$.

Example 270

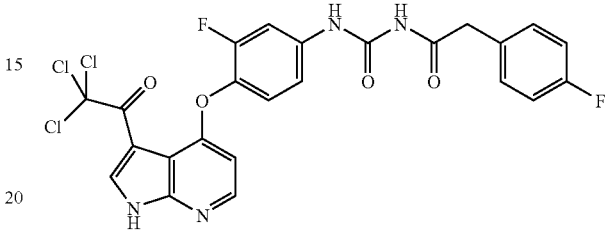

1-(3-Fluoro-4-(3-(2,2,2-trichloroacetyl)-1H-pyrrolo[2,3-b]pyridin-4yloxy)phenyl)-3-(2-(4-fluorophenyl)acetyl)urea

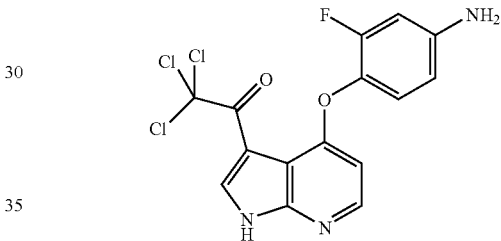

A) 1-(4-(4-Amino-2-fluorophenoxy)-1H-pyrrolo[2,3-b]pyridin-3-yl)-2,2,2-trichloroethanone To a solution of 4-(2-fluoro-4-nitrophenoxy)-1H-pyrrolo[2,3-b]pyridine (546 mg, 2.0 mmol, Compound A of Example 132) in 100 mL of dichloroethane at room temperature was added aluminum chloride (1.33 g, 10 mmol, Alfa Aesar). The reaction mixture was stirred at rt for 30 min, treated with trichloroacetyl chloride (0.34 mL, 3.0 mmol), and then stirred at 45° C. for 5 h. After cooling to 0° C., ice water (30 mL) was added to the mixture and the pH was adjusted to 7–8 with aq. K$_2$HPO$_4$ solution. The mixture was then filtered through a pad of Celite®. The organic layer was dried (MgSO$_4$), concentrated in vacuo and the resulting residue was purified by flash chromatography (SiO$_2$, eluting with 2–7% MeOH in dichloromethane) to afford 2,2,2-trichloro-1-(4-(2-fluoro-4-nitrophenoxy)-1H-pyrrolo[2,3-b]pyridin-3-yl)ethanone (498 mg, 60%). MS(ESI$^+$) m/z 417.9 (M+H)$^+$.

To a solution of the above intermediate (83 mg, 0.2 mmol) in a mixed solvent (3 mL of MeOH and 2 mL of THF) were added ammonium chloride (53.5 mg, 1.0 mmol, EMC) and zinc dust (65.4 mg, 1.0 mmol, Aldrich). The reaction mixture was stirred at room temperature for 3 h, diluted with EtOAc (10 mL), and filtered through a pad of Celite®. The filtrate was concentrated in vacuo to give the desired product (78 mg, 100%) as a solid. MS(ESI$^+$) m/z 390.1, 392.1 (M+H)$^+$.

C) 1-(3-Fluoro-4-(3-(2,2,2-trichloroacetyl)-1H-pyrrolo[2,3-b]pyridin-4-yloxy)phenyl)-3-(2-(4-fluorophenyl)acetyl)urea Prepared in a similar manner as Example 264 (33 mg, 37%). ¹H NMR (DMSO-d₆) δ 13.18 (s, 1H), 11.02 (s, 1H), 10.57 (s, 1H), 8.62 (s, 1H), 8.25 (d, 1H, J=5.5 Hz), 7.78 (dd, 1H, J=10.5, 2.2 Hz), 7.38–7.35 (m, 3H), 7.28 (t, 1H, J=9.4 Hz), 7.18 (t, 2H, J=8.8 Hz), 6.52 (d, 1H, J=5.5 Hz), 3.75 (s, 2H); MS(ESI⁺) m/z 567.05 (M+H)⁺.

Example 271

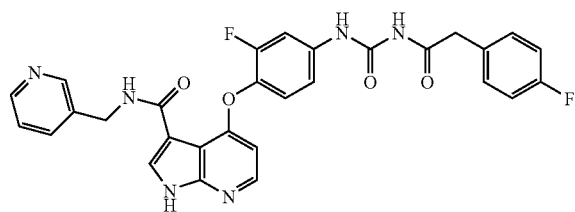

1-(4-(3-((Pyridin-3-ylmethyl)carbamoyl)-1H-pyrrolo[2,3-b]pyridin-4-yloxy)-3-fluorophenyl)-3-(2-(4-fluorophenyl)acetyl)urea To a solution of 1-(3-fluoro-4-(3-(2,2,2-trichloroacetyl)-1H-pyrrolo[2,3-b]pyridine 4-yloxy)phenyl)-3-(2-(4-fluorophenyl)acetyl)urea (7.0 mg, 0.012 mmol, Example 270) in 0.5 mL of DMF was added 3-(aminomethyl)pyridine (10 mg, 0.092 mmol, Aldrich). The reaction mixture was stirred at rt for 1 h, and quenched by the addition of 1 mL of cold water. The precipitate that formed was collected by filtration, washed with cold water (1 mL) and cold acetonitrile (1 mL) and dried under vacuum to afford the desired product (4.3 mg, 64%) as a white solid. ¹H NMR (DMSO-d₆) δ 12.38 (s, 1H), 11.03 (s, 1H), 10.57 (s, 1H), 8.48 (s, 1H), 8.40 (t, 1H, J=5.5 Hz), 8.34 (d, 1H, J=3.3 Hz), 8.11 (d, 1H, J=5.5 Hz), 8.00 (s, 1H), 7.73 (d, 1H, J 13.2 Hz), 7.65 (d, 1H, J=7.7 Hz), 7.37–7.29 (m, 4H), 7.16 (t, 3H, J=8.8 Hz), 6.34 (d, 1H, J=5.5 Hz), 4.48 (d, 2H, J=5.5 Hz), 3.74 (s, 2H); MS(ESI⁺) m/z 567.1 (M+H)⁺.

Example 272

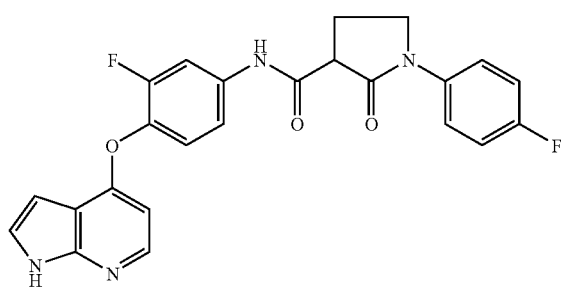

N-(4-(1H-Pyrrolo[2,3-b]pyridin-4-yloxy)-3-fluorophenyl)-1-(4-fluorophenyl)-2-oxopyrrolidine-3-carboxamide

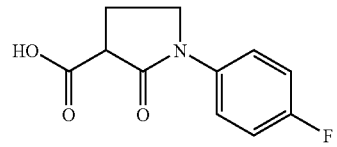

A)
1-(4-Fluorophenyl)-2-oxopyrrolidine-3-carboxylic acid

To a solution of 6,6-dimethyl-5,7-dioxaspiro[2,5]-octane-4,8-dione (1.02 g, 6.0 mmol, Aldrich) in 3 mL of DMF was added 4-fluorobenzenamine (666 mg, 6.0 mmol, Aldrich). The reaction mixture was stirred at rt overnight. The reaction mixture was poured into cold water (10 mL). The precipitate that formed was collected by filtration, washed with water, and dried under vacuum to afford the desired product (980 mg, 73%) as a tan solid. MS(ESI⁺) m/z 224.3 (M+H)⁺.

B) N-(4-(1H-Pyrrolo[2,3-b]pyridin-4-yloxy)-3-fluorophenyl)-1-(4-fluorophenyl)-2-oxopyrrolidine-3-carboxamide Prepared in a similar manner as Step B of Example 251 (98 mg, 49%). ¹H NMR (DMSO-d₆) δ 11.76 (s, 1H), 10.63 (s, 1H), 8.06 (d, 1H, J=5.5 Hz), 7.86 (dd, 1H, J=13.2, 2.2 Hz), 7.71–7.68 (m, 2H), 7.45–7.36 (m, 3H), 7.25 (t, 2H, J=8.8 Hz), 6.38 (d, 1H, J=6.5 Hz), 6.22 (dd, 1H, J=3.3, 2.2 Hz), 3.94–3.89 (m, 2H), 3.77 1H, J=8.5 Hz), 2.49–2.33 (m, 2H); MS(ESI⁺) m/z 449.2 (M+H)⁺.

Example 273

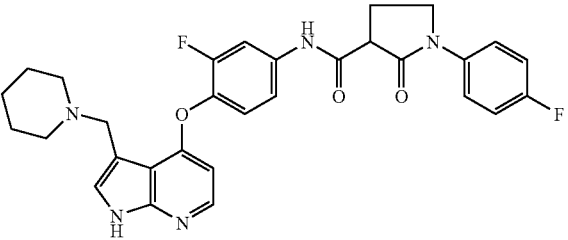

N-(3-Fluoro-4-(3-(piperidin-1-ylmethyl)-1H-pyrrolo[2,3-b]pyridin-4-yloxy)phenyl)-1-(4-fluorophenyl)-2-oxopyrrolidine-3-carboxamide, trifluoroacetic acid salt To a solution of N-(4-(1H-pyrrolo[2,3-b]pyridin-4-yloxy)-3-fluorophenyl)-1-(4-fluorophenyl)-2-oxopyrrolidine-3-carboxamide (22.4 mg, 0.05 mmol, Compound B of Example 272) and paraformaldehyde (2.4 mg, 0.08 mmol) in a mixed solvent (1 mL of isopropanol and 0.2 mL of DMF) was added piperidine (8.5 mg, 0.1 mmol). The reaction mixture was heated at 85° C. for 7 h, concentrated in vacuo, and the resulting residue was purified by preparative HPLC. The desired fractions were lyophilized to give the desired product (TFA salt, 3.4 mg, 13%) as a white solid. ¹H NMR (CD₃OD) δ 8.15 (d, 1H, J=5.5 Hz), 7.91 (dd, 1H, J=11.0, 2.2 Hz), 7.67–7.63 (m, 3H), 7.48–7.38 (m, 2H), 7.15 (t, 2H, J=8.8 Hz), 6.45 (d, 1H, J=5.5 Hz), 4.64 (s, 2H), 3.99–3.95 (m, 2H), 3.81 (t, 1H, J=8.8 Hz), 3.61–3.59 (m, 2H), 3.10–3.06 (m, 2H), 2.61–2.47 (m, 2H), 1.97–1.93 (m, 2H), 1.81–1.71 (m, 4H); MS(ESI⁺) m/z 546.2 (M+H)⁺.

Example 274

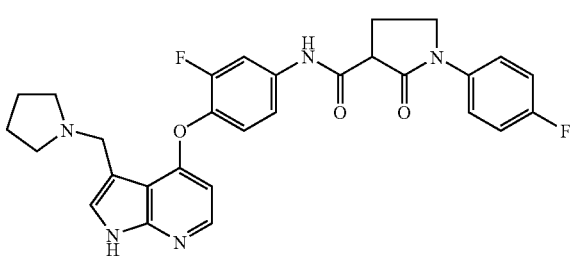

N-(3-Fluoro-4-(3-(pyrrolidin-1-ylmethyl)-1H-pyrrolo[2,3-b]pyridin-4-yloxy)phenyl)-1-(4-fluorophenyl)-2-oxopyrrolidine-3-carboxamide Prepared in a similar manner as Example 273. $^1$H NMR (DMSO-$d_6$) δ 12.13 (s, 1H), 10.62 (s, 1H), 8.04 (d, 1H, J=5.5 Hz), 7.84 (dd, 1H, J=13.2, 2.2 Hz), 7.65–7.62 (m, 3H), 7.43–7.39 (m, 2H), 7.19 (t, 2H, J=8.8 Hz), 6.25 (d, 1H, J=6.5 Hz), 4.54 (d, 2H, J=3.3 Hz), 3.91–3.85 (m, 2H), 3.72 (t, 1H, J=8.5 Hz), 3.38–3.37 (m, 2H), 3.20–3.77 (m, 2H), 2.38–2.31 (m, 2H), 1.95–1.91 (m, 2H), 1.81–1.76 (m, 2H); MS(ESI$^+$) m/z 532.2 (M+H)$^+$.

Example 275

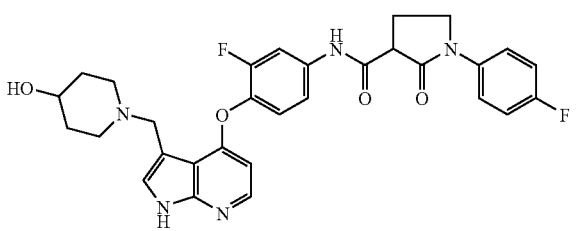

N-(3-Fluoro-4-(3-((4-hydroxypiperidin-1-yl)methyl)-1H-pyrrolo[2,3-b]pyridin-4-yloxy)phenyl)-1-(4-fluorophenyl)-2-oxopyrrolidine-3-carboxamide Prepared in a similar manner as Example 273. $^1$H NMR (DMSO-$d_6$) δ 11.71 (s, 1H), 10.88 (s, 1H), 8.00 (d, 1H, J=5.5 Hz), 7.79 (dd, 1H, J=12.7, 2.2 Hz), 7.67–7.64 (m, 2H), 7.30–7.35 (m, 3H), 7.20 (t, 2H, J=8.8 Hz), 6.30 (d, 1H, J=6.5 Hz), 6.16 (s, 1H), 4.51 (d, 1H, J=4.4 Hz), 3.83–3.79 (m, 2H), 3.38 (m, 1H), 3.70–2.69 (m, 5H), 2.28–2.19 (m, 3H), 1.65–1.62 (m, 2H), 1.37–1.26 (m, 2H); MS(ESI$^+$) m/z 562.2 (M+H)$^+$.

Example 276

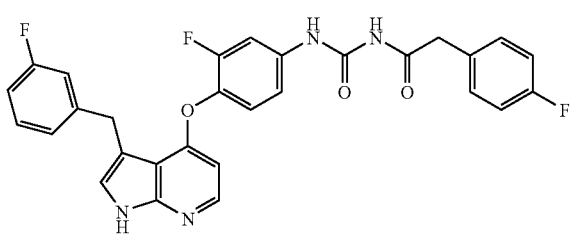

1-(4-(3-(3-Fluorobenzyl)-1H-pyrrolo[2,3-b]pyridin-4-yloxy)-3-fluorophenyl)-3-(2-(4-fluorophenyl)acetyl)urea

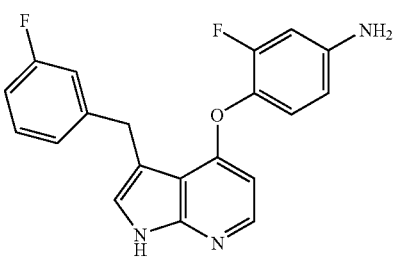

A) 4-(3-(3-Fluorobenzyl)-1H-pyrrolo[2,3-b]pyridin-4-yloxy)-3-fluorobenzenamine To a solution of 4-(1H-pyrrolo[2,3-b]pyridin-4-yloxy)-3-fluorobenzenamine (49 mg, 0.2 mmol, Compound B of Example 132) in 2 mL of methanol were added sodium hydroxide (40 mg, 1.0 mmol, EMD) and 3-fluorobenzaldehyde (62 mg, 0.5 mmol, Aldrich). The reaction mixture was stirred at rt for 16 h, poured into cold water (5 mL), and extracted with EtOAc (3×30 mL). The organic extracts were dried (MgSO$_4$) and concentrated in vacuo. The residue was dissolved in 2 mL of dichloromethane, and treated with 1 mL of TFA and 0.2 mL of triethylsilane (Aldrich). The reaction mixture was stirred for 1 h and concentrated under reduced pressure. The residue was purified by preparative HPLC and the desired fractions were combined, concentrated in vacuo, neutralized with saturated aq. NaHCO$_3$ solution, and extracted with dichloromethane. The organic extracts were dried (MgSO$_4$) and concentrated in vacuo to give the desired compound (12.1 mg, 35% over two steps). MS(ESI$^+$) m/z 351.4 (M+H)$^+$.

B) 1-(4-(3-(3-Fluorobenzyl)-1H-pyrrolo[2,3-b]pyridin-4-yloxy)-3-fluorophenyl)-3-(2-(4-fluorophenyl)acetyl)urea Prepared in a similar manner as Example 264 (3.4 mg, 11%). $^1$H NMR (DMSO-$d_6$) δ 11.58 (s, 1H), 10.96 (s, 1H), 10.49 (s, 1H), 7.95 (d, 1H, J=5.5 Hz), 7.67 (dd, 1H, J=11.6, 2.1 Hz), 7.31–6.67 (m, 12H), 6.10 (d, 1H, J=5.5 Hz), 4.09 (s, 2H), 3.68 (s, 2H); MS(ESI$^+$) m/z 531.2 (M+H)$^+$.

Example 277

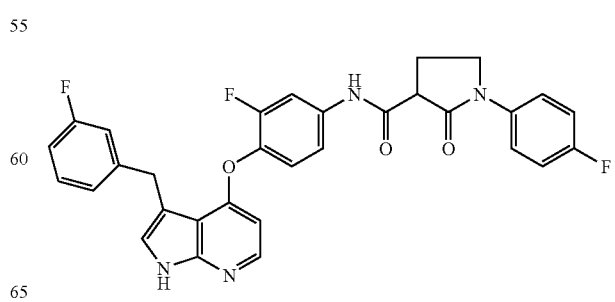

N-(4-(3-(3-Fluorobenzyl)-1H-pyrrolo[2,3-b]pyridin-4-yloxy)-3-fluorophenyl)-1-(4-fluorophenyl)-2-oxopyrrolidine-3-carboxamide Prepared in a similar manner as Example 273. $^1$H NMR (DMSO-$d_6$) δ 11.74 (s, 1H), 10.62 (s, 1H), 8.03 (d, 1H, J=5.5 Hz), 7.84 (dd, 1H, J=12.7, 2.2 Hz), 7.71–7.68 (m, 2H), 7.41 (d, 1H, J=8.8 Hz), 7.30 (d, 1H, J=1.7 Hz), 7.26–7.22 (m, 3H), 7.16 (t, 1H, J=8.5 Hz), 7.08 (d, 1H, J=7.7 Hz), 7.01 (d, 1H, J=10.4 Hz), 6.94 (t, 1H, J=8.8 Hz), 6.22 (d, 1H, J=5.5 Hz), 4.17 (s, 2H), 3.94–3.90 (m, 2H), 3.76 (t, 1H, J=8.5 Hz), 2.49–2.35 (m, 2H); MS(ESI$^+$) m/z 557.2 (M+H)$^+$.

Example 278

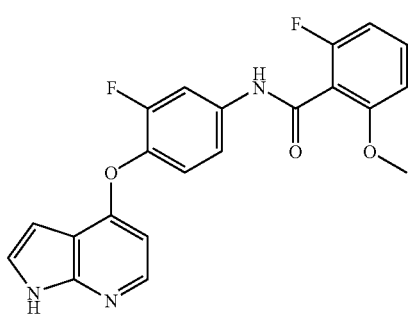

N-(4-(1H-Pyrrolo[2,3-b]pyridin-4-yloxy)-3-fluorophenyl)-2-fluoro-6-methoxybenzamide Prepared in a similar manner as Example 261 (12.1 mg, 31%). $^1$H NMR (DMSO-$d_6$) δ 11.97 (s, 1H), 10.86 (s, 1H), 8.14 (d, 1H, J=5.5 Hz), 7.92 (dd, 1H, J=13.2, 2.2 Hz), 7.54–7.42 (m, 4H), 7.03 (d, 1H, J=8.2 Hz), 6.95 (t, 1H, J=8.8 Hz), 6.48 (d, 1H, J=6.1 Hz), 6.35 (d, 1H, J=1.4 Hz); MS(ESI$^+$) m/z 396.2 (M+H)$^+$.

Example 279

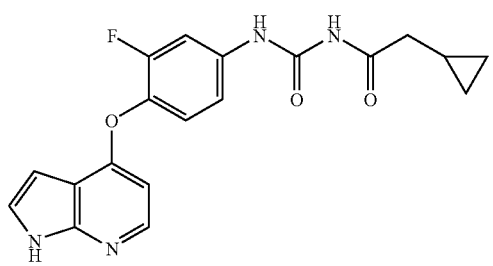

1-(4-(1H-Pyrrolo[2,3-b]pyridin-4-yloxy)-3-fluorophenyl)-3-(2-cyclopropylacetyl)urea

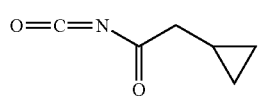

A) 2-Cyclopropylacetyl isocyanate

To a suspension of silver cyanate (435 mg, 3.0 mmol, Aldrich) in 10 mL of toluene was added cyclopropylacetyl chloride (313 mg, 3.0 mmol, Aldrich). The reaction mixture was refluxed for 2 h, cooled to rt and filtered. The filtrate was used as 0.3 M solution for next reaction.

B) 1-(4-(1H-Pyrrolo[2,3-b]pyridin-4-yloxy)-3-fluorophenyl)-3-(2-cyclopropylacetyl)urea Prepared in a similar manner as Example 264 (13.5 mg, 59%). $^1$H NMR (CD$_3$OD) δ 8.03 (d, 1H, J=5.5 Hz), 7.80–7.76 (m, 1H), 7.27–7.24 (m, 3H), 6.41 (d, 1H, J=5.5 Hz), 6.38 (d, 1H, J=3.9 Hz), 2.25 (d, 1H, J=7.2 Hz), 0.64–0.59 (m, 2H), 0.28–0.23 (m, 2H); MS(ESI$^+$) m/z 369.2 (M+H)$^+$.

Example 280

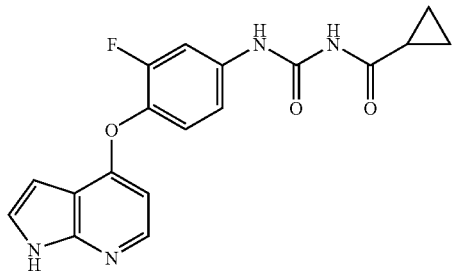

1-(4-(1H-Pyrrolo[2,3-b]pyridin-4-yloxy)-3-fluorophenyl)-3-(cyclopropanecarbonyl)urea

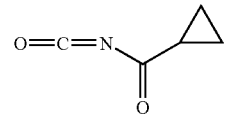

A) Cyclopropanecarbonyl isocyanate

Prepared in a similar manner as Step A of Example 279.

B) 1-(4-(1H-Pyrrolo[2,3-b]pyridin-4-yloxy)-3-fluorophenyl)-3-(cyclopropanecarbonyl)urea Prepared in a similar manner as Step B of Example 279 (17.2 mg, 60%). $^1$H NMR (CD$_3$OD) δ 7.93 (d, 1H, J=5.5 Hz), 7.57 (d, 1H, J=13.8 Hz), 7.12–7.08 (m, 3H), 6.31 (m, 2H), 1.02 (m, 2H), 0.90 (m, 2H); MS(ESI$^+$) m/z 355.19 (M+H)$^+$.

Example 281

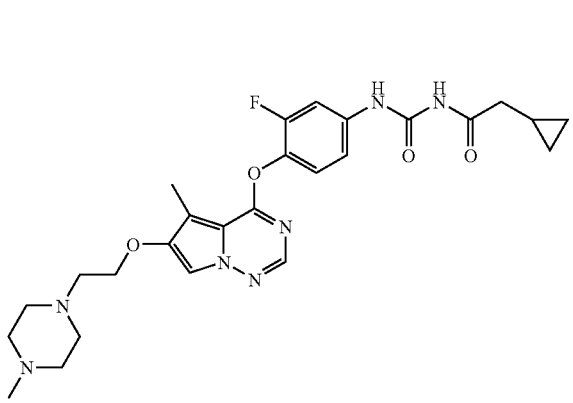

1-(2-Cyclopropylacetyl)-3-(3-fluoro-4-(5-methyl-6-(2-(4-methylpiperazin-1-yl)ethoxy)pyrrolo[2,1-f][1,2,4]triazin-4-yloxy)phenyl)urea Prepared in a similar manner as Example 264 using Compound B of Example and Compound A of Example 279 (21.0 mg, 81%). $^1$H NMR (CD$_3$OD) δ 7.81 (s, 1H), 7.74 (d, 1H, J=5.5 Hz), 7.25 (m, 3H), 4.18 (t, 2H, J=5.5 Hz), 3.35 (t, 2H, J=1.7 Hz), 2.90 (t, 2H, J=5.5 Hz), 2.74–2.54 (m, 4H), 2.45 (s, 3H), 2.33 (t, 4H, J=2.8 Hz), 1.12 (m, 1H), 0.67–0.64 (m, 2H), 0.29–0.25 (m, 2H); MS(ESI$^+$) m/z 529.3 (M+H)$^+$.

Example 282

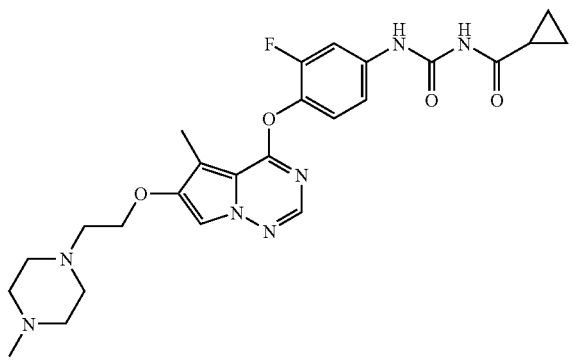

1-Cyclopropanecarbonyl-3-(3-fluoro-4-(5-methyl-6-(2-(4-methylpiperazin-1-yl)ethoxy)pyrrolo[2,1-f][1,2,4]triazin-4-yloxy)phenyl)urea Prepared in a similar manner as Example 264 using Compound B of Example 45 and Compound A of Example 280 (20.3 mg, 64%). $^1$H NMR (CD$_3$OD) δ 10.85 (s, 1H), 7.70 (s, 1H), 7.76–7.72 (m, 2H), 7.22–7.14 (m, 2H), 4.14 (t, 2H, J=5.5 Hz), 2.94 (t, 2H, J=5.5 Hz), 2.89–2.60 (m, 4H), 2.78 (s, 3H), 2.34 (s, 4H), 1.70–1.67 (m, 1H), 0.99–0.95 (m, 2H), 0.91–0.86 (m, 2H); MS(ESI$^+$) m/z 512.3 (M+H)$^+$.

Example 283

N-(4-(3-(3-(Dimethylamino)prop-1-ynyl)-1H-pyrrolo[2,3-]pyridin-4-yloxy)-3-fluorophenyl)-1-(4-fluorophenyl)-2-oxo-1,2-dihydropyridine-3-carboxamide, trifluoroacetic acid salt

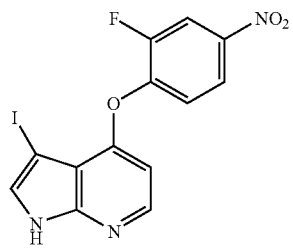

A) 4-(2-Fluoro-4-nitrophenoxy)-3-iodo-1H-pyrrolo[2,3-b]pyridine

A mixture of 4-(2-fluoro-4-nitrophenoxy)-1H-pyrrolo[2,3-b]pyridine (550 mg, 2 mmol, Compound A of Example 132) and N-iodosuccinimide (450 mg, 2 mmol) in CH$_2$Cl$_2$ (50 mL) was stirred at rt for 1 h. The mixture was washed with brine, dried over MgSO$_4$, and passed through a short pad of silica gel, eluting with EtOAc. The filtrate was concentrated in vacuo to give the desired product (quantitative yield) as a yellow solid. LC/MS(ESI$^+$) m/z 400 (M+H)$^+$.

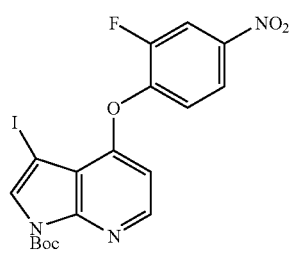

B) tert-Butyl 4-(2-fluoro-4-nitrophenoxy)-3-iodo-1H-pyrrolo[2,3-b]pyridine-1-carboxylate To a solution of 4-(2-fluoro-4-nitrophenoxy)-3-iodo-1H-pyrrolo[2,3-b]pyridine (400 mg, 1 mmol) in DMF (10 mL) at −40° C. under N$_2$ was added NaH (60% in mineral oil, 1.2 mmol). The mixture was stirred at 0° C. for 20 min, and cooled to −40° C. To this mixture, was added Boc$_2$O (330 mg, 1.5 mmol). The mixture was stirred at −40° C. for 1 h, diluted with 5% aq. sodium citrate solution, extracted with EtOAc. The organic layer was dried over MgSO$_4$ and concentrated in vacuo. The crude compound was purified by flash column chromatography (silica gel, 20% EtOAc/CH$_2$Cl$_2$) to give the desired compound (460 mg, 92%) as a yellow solid. LC/MS(ESI$^+$) m/z 500 (M+H)$^+$.

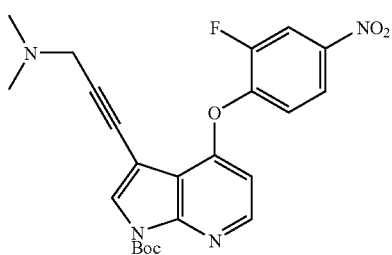

C) tert-Butyl 3-(3-(dimethylamino)prop-1-ynyl)-4-(2-fluoro-4-nitrophenoxy)-1H-pyrrolo[2,3-b]pyridine-1-carboxylate A stream of Ar was bubbled through a mixture of tert-butyl 4-(2-fluoro-4-nitrophenoxy)-3-iodo-1H-pyrrolo[2,3-b]pyridine-1-carboxylate (200 mg, 0.4 mmol), N,N-dimethylprop-2-yn-1-amine (66 mg, 0.8 mmol), Pd(dppf)$_2$Cl$_2$:CH$_2$Cl$_2$ (33 mg, 0.04 mmol), and CuI (20 mg) in triethylamine (0.4 mL) and THF (3 mL) for 5 min. The reaction mixture was heated in a sealed tube at 70° C. for 2 h and the solvent was removed in vacuo. The crude compound was purified by flash column chromatography (silica gel, 5% MeOH/EtOAc) to afford the desired product (170 mg, 95%) as a yellow oil. LC/MS(ESI$^+$) m/z 455 (M+H)$^+$.

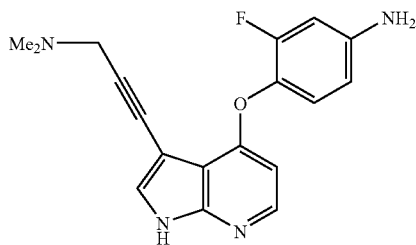

D) 4-(3-(3-(Dimethylamino)prop-1-ynyl)-1H-pyrrolo[2,3-b]pyridin-4-yloxy)-3-fluorobenzenamine To a mixture of tert-butyl 3-(3-(dimethylamino)prop-1-ynyl)-4-(2-fluoro-4-nitrophenoxy)-1H-pyrrolo[2,3-b]pyridine-1-carboxylate (170 mg, 0.374 mmol) in THF (10 mL) and MeOH (10 mL), was added Zn powder (<10 micron, 500 mg) and NH$_4$Cl (500 mg). The reaction mixture was stirred at rt for 2 h, diluted with EtOAc, and filtered through a pad of Celite®. The filtrate was washed with sat. aq. KH$_2$PO$_4$ solution, dried over MgSO$_4$, filtered, and concentrated in vacuo to afford the desired product (110 mg, 90%) as a yellow solid. LC/MS(ESI$^+$) m/z 325 (M+H)$^+$.

E) N-(4-(3-(3-(Dimethylamino)prop-1-ynyl)-1H-pyrrolo[2,3-]pyridin-4-yloxy)-3-fluorophenyl)-1-(4-fluorophenyl)-2-oxo-1,2-dihydropyridine-3-carboxamide, trifluoroacetic acid salt To a mixture of 4-(3-(3-(dimethylamino)prop-1-ynyl)-1H-pyrrolo[2,3-b]pyridin-4-yloxy)-3-fluorobenzenamine (33 mg, 0.1 mmol), 1-(4-fluorophenyl)-2-oxo-1,2-dihydropyridine-3-carboxylic acid (46 mg, 0.2 mmol, Compound B of Example 242), and HATU (Perseptive Biosystems, 76 mg, 0.2 mmol) in DMF (1 mL), was added DIPEA (0.1 mL). The reaction mixture was stirred at rt overnight and concentrated in vacuo. The crude compound was purified by preparative HPLC, and the appropriate fractions were lyophilized to afford the title compound (15 mg, TFA salt, 23%) as a yellow solid. $^1$H NMR (CD$_3$OD) δ 8.73 (dd, 1H, J=7.6, 2.4 Hz), 8.14 (d, 1H, J=5.6 Hz), 8.00–8.16 (m, 2H), 7.74 (s, 1H), 7.54–7.60 (m, 2H), 7.30–7.47 (m, 4H), 6.78 (dd, 1H, J=6.8, 6.8 Hz), 6.47 (d, 1H, J=5.6 Hz), 4.30 (s, 2H), 2.99 (s, 6H); LC/MS ESI$^+$) m/z 540 (M+H)$^+$.

Example 284

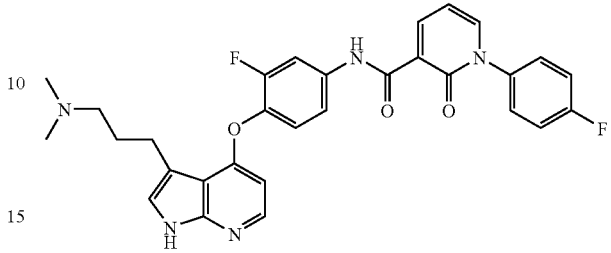

N-(4-(3-(3-(Dimethylamino)propyl)-1H-pyrrolo[2,3-b]pyridin-4-yloxy)-3-fluorophenyl)-1-(4-fluorophenyl)-2-oxo-1,2-dihydropyridine-3-carboxamide, trifluoroacetic acid salt A mixture of N-(4-(3-(3-(dimethylamino)prop-1-ynyl)-1-(1-(4-fluorophenyl)-2-oxo-1,2-dihydropyridine-3-carbonyl)-1H-pyrrolo[2,3-b]pyridin-4-yloxy)-3-fluorophenyl)-1-(4-fluorophenyl)-2-oxo-1,2-dihydropyridine-3-carboxamide (32 mg, TFA salt, 0.037 mmol, obtained as a byproduct in Step E of Example 283), and Pd/C (10%, 100 mg) in MeOH (5 mL) was hydrogenated under 1 atm for 1 h. The mixture was bubbled through a stream of N$_2$ for 5 min, filtered through a pad Celite®. The filtrate was purified by prep-HPLC to afford the title compound as a white solid (10 mg, TFA salt, 39% yield). $^1$H NMR (CD$_3$OD) δ 8.62 (dd, 1H, J=7.2, 2.0 Hz), 8.04 (d, 1H, J=6.4 Hz), 7.95 (dd, 1H, J=12.8, 1.2 Hz), 7.90 (dd, 1H, J=6.8, 2.4 Hz), 7.20–7.50 (m, 6H), 6.66 (t, 1H, J=7.20 Hz), 6.43 (d, 1H, J=6.4 Hz), 3.11 (t, 2H, J=8.0 Hz), 2.96 (t, 2H, J=7.2 Hz), 2.77 (s, 6H), 2.11 (m, 2H); LC/MS(ESI$^+$) m/z 544 (M+H)$^+$.

Example 285

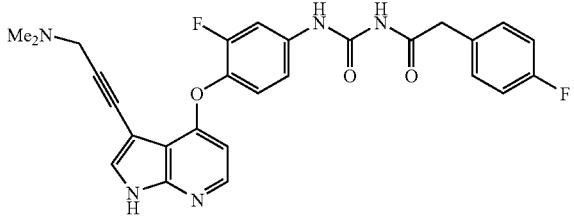

1-(4-(3-(3-(Dimethylamino)prop-1-ynyl)-1H-pyrrolo[2,3-b]pyridin-4-yloxy)-3-fluorophenyl)-3-(2-(4-fluorophenyl)acetyl)urea, trifluoroacetic acid salt To a solution of 4-(3-(3-(dimethylamino)prop-1-ynyl)-1H-pyrrolo[2,3-b]pyridin-4-yloxy)-3-fluorobenzenamine (15 mg, 0.046 mmol, Compound D of Example 283) in THF (1.5 mL) was added 2-(4-fluorophenyl)acetyl isocyanate (0.05 mmol, Compound C of Example 4) at rt. The mixture was stirred for 1 h and concentrated in vacuo. The crude compound was purified by preparative HPLC to give the desired product (TFA salt, 12 mg, 42% yield) as a white solid. $^1$H NMR (DMSO-d$_6$) δ 12.30 (s, 1H), 10.98 (s, 1H), 10.52 (s, 1H), 10.00 (s, 1H), 8.07 (d, 1H, J=5.6 Hz), 7.74 (d, 1H, J=2.4 Hz), 7.73 (dd, 1H, J=12.4, 2.4 Hz), 7.25–7.40 (m, 4H), 7.10 (m, 2H), 6.26 (d, 1H, J=5.2 Hz), 4.21 (s, 2H), 3.68 (s, 2H), 2.43 (s, 6H); LC/MS(ESI$^+$) m/z 504 (M+H)$^+$.

Example 286

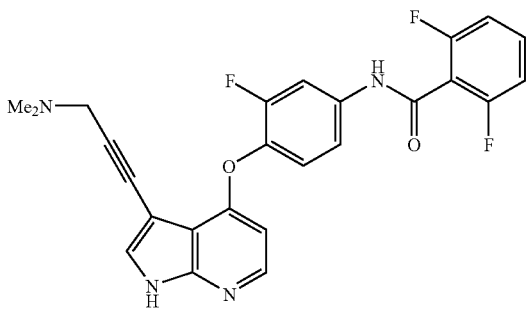

N-(4-(3-(3-(Dimethylamino)prop-1-ynyl)-1H-pyrrolo[2,3-b]pyridin-4-yloxy)-3-fluorophenyl)-2,6-difluorobenzamide, trifluoroacetic acid salt To a solution of 4-(3-(3-(dimethylamino)prop-1-ynyl)-1H-pyrrolo[2,3-b]pyridin-4-yloxy)-3-fluorobenzenamine (15 mg, 0.046 mmol, Compound D of Example 283) and pyridine (0.05 mL) in CH$_2$Cl$_2$ (1.0 mL) at 0° C., was added 2,6-difluorobenzoyl chloride (9 mg, 0.05 mmol). The mixture was stirred at 0° C. for 30 min and concentrated in vacuo. The crude compound was purified by preparative HPLC to give the desired product (TFA salt, 11 mg, 41%) as a white solid. $^1$H NMR (CD$_3$OD) δ 8.05 (d, 1H, J=5.6 Hz), 7.82 (dd, 1H, J=12.4, 2.4 Hz), 7.63 (s, 1H), 7.35–7.50 (m, 2H), 7.25 (t, 1H, J=8.8 Hz), 7.00–7.06 (m, 2H), 6.38 (d, 1H, J=5.6 Hz), 4.19 (s, 2H), 2.87 (s, 6H); LC/MS(ESI$^+$) m/z 465 (M+H)$^+$.

Example 287

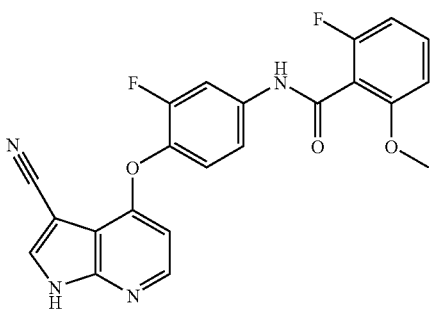

N-(4-(3-Cyano-1H-pyrrolo[2,3-b]pyridin-4-yloxy)-3-fluorophenyl)-2-fluoro-6-methoxybenzamide, hydrochloride salt

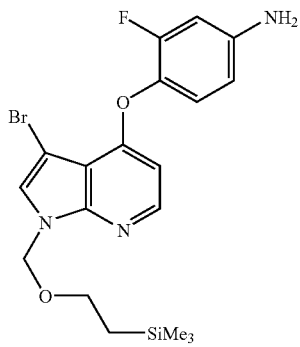

A) 4-(3-Bromo-1-((2-(trimethylsilyl)ethoxy)methyl)-1H-pyrrolo[2,3-b]pyridin-4-yloxy)-3-fluorobenzenamine A mixture of 3-bromo-4-(2-fluoro-4-nitrophenoxy)-1-((2-(trimethylsilyl)ethoxy)methyl)-1H-pyrrolo[2,3-b]pyridine (626 mg, 1.3 mmol, Compound B of Example 261), zinc powder (1.0 g), and ammonium chloride (1.0 g) in THF (25 mL) and MeOH (25 mL) was stirred at rt overnight. The mixture was diluted with CH$_2$Cl$_2$ and filtered through a short pad of Celite®. The resulting solution was then concentrated under reduced pressure, and the residue was purified by flash column chromatography (silica gel, eluting with 30% EtOAc/CH$_2$Cl$_2$) to give the desired product (420 mg, 71%) as a clear oil. LC/MS(ESI$^+$) m/z 453 (M+H)$^+$.

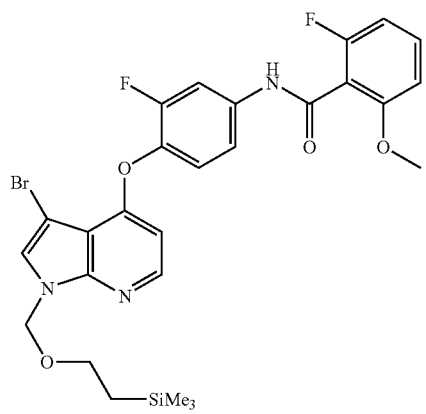

B) N-(4-(3-Bromo-1-((2-(trimethylsilyl)ethoxy)methyl)-1H-pyrrolo[2,3-b]pyridin-4-yloxy)-3-fluorophenyl)-2-fluoro-6-methoxybenzamide To a stirred solution of 4-(3-bromo-1-((2-(trimethylsilyl)ethoxy)methyl)-1H-pyrrolo[2,3-b]pyridin-4-yloxy)-3-fluorobenzenamine (400 mg, 0.85 mmol), 2-fluoro-6-methoxybenzoic acid (226 mg, 1.33 mmol), and HATU (641 mg, 1.33 mmol) in DMF (6 mL) was added DIPEA (387 mg, 3 mmol), followed by DMAP (50 mg). The resulting mixture was stirred at rt overnight, diluted with EtOAc, and washed with saturated aq. K$_2$HPO$_4$ solution and brine. The organic layer was dried over MgSO$_4$ and concentrated in vacuo. The residue was purified by flash column chromatography (silica gel, eluting with 30% EtOAc/CH$_2$Cl$_2$) to give the desired product (370 mg, 72%) as a white solid. LC/MS(ESI$^+$) m/z 605 (M+H)$^+$.

C) N-(4-(3-Cyano-1H-pyrrolo[2,3-b]pyridin-4-yloxy)-3-fluorophenyl)-2-fluoro-6-methoxybenzamide, hydrochloride salt A mixture of N-(4-(3-bromo-1-((2-(trimethylsilyl)ethoxy)methyl)-1H-pyrrolo[2,3-b]pyridin-4-yloxy)-3-fluorophenyl)-2-fluoro-6-methoxybenzamide (30 mg, 0.05 mmol), Zn(CN)$_2$ (17 mg, 0.15 mmol), Pd(dppf)$_2$Cl$_2$:CH$_2$Cl$_2$ (5 mg, Aldrich), Zn(OAc)$_2$ (1 mg) and zinc powder (1 mg) in DMF (0.6 mL) was heated in a sealed tube at 120° C. for 15 h. The mixture was diluted with CH$_2$Cl$_2$, filtered through a pad of Celite® (CH$_2$Cl$_2$). The filtrate was washed with brine, dried over MgSO$_4$, filtered, and concentrated under reduced pressure. The resulting residue was treated with TBAF (1 M in THF, 1.0 mmol) and ethane-1,2-diamine (30 μL) in THF (3 mL). The mixture was refluxed for 15 h and concentrated in vacuo. The residue was purified by preparative HPLC. The desired fractions were lyophilized to give a white TFA salt, which was dissolved in small amount of MeOH/H$_2$O with 1 N HCl (0.1 mL). This solution was then lyophilized to afford the title compound (HCl salt, 12 mg, 53%) as a white solid. $^1$H NMR (DMSO-d$_6$) δ 10.80 (s, 1H), 8.36 (d, 1H, J=2.8 Hz), 8.14 (d, 1H, J=5.6 Hz), 7.87 (dd, 1H, J=12.8, 2.0 Hz), 7.37 (m, 3H), 6.95 (d, 1H, J=8.4 Hz), 6.88 (t, 1H, J=8.8 Hz), 6.41 (d, 1H, J=5.2 Hz), 3.79 (s, 3H); LC/MS(ESI$^+$) m/z 421 (M+H)$^+$.

Example 288

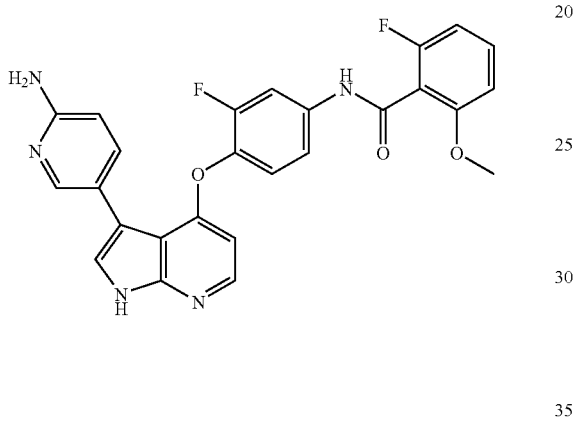

N-(4-(3-(6-Aminopyridin-3-yl)-1H-pyrrolo[2,3-b]pyridin-4-yloxy)-3-fluorophenyl)-2-fluoro-6-methoxybenzamide A mixture of N-(4-(3-bromo-1-((2-(trimethylsilyl)ethoxy)methyl)-1H-pyrrolo[2,3-b]pyridin-4-yloxy)-3-fluorophenyl)-2-fluoro-6-methoxybenzamide (50 mg, 0.08 mmol, Compound B of Example 287), 5-(4,4,5,5-tetramethyl-1,3-dioxolan-2-yl)pyridin-2-amine (36 mg, 0.16 mmol, Oakwood), Pd(PPh$_3$)$_4$ (10 mg), and K$_3$PO$_4$ (2 M in H$_2$O, 0.32 mmol) in toluene (1 mL), EtOH (0.2 mL), and DME (0.4 mL) was purged with Ar for 10 min. The reaction mixture was heated at 95° C. for 2 h, diluted with EtOAc, and washed with brine. The organic layer was dried over MgSO$_4$, filtered, and concentrated in vacuo to give a residue, which was treated with TBAF (1 M in THF, 1 mL), ethane-1,2-diamine (50 μL) in THF (3 mL) at reflux for 24 h. The mixture was diluted with EtOAc, washed with brine, dried with MgSO$_4$, and concentrated in vacuo. The residue was purified by flash column chromatography (silica gel, 5% 2 M NH$_3$ in MeOH/CH$_2$Cl$_2$) to give the desired product, which was converted to the HCl salt by lyophilization with 1 N HCl in H$_2$O (white solid, 10 mg, 26% yield). $^1$H NMR (CD$_3$OD) δ 8.32 (dd, 1H, J=9.2, 2.0 Hz), 8.21 (d, 1H, J=6.1 Hz), 8.15 (d, 1H, J=2.0 Hz), 7.94 (dd, 1H, J=12.7, 2.5 Hz), 7.70 (s, 1H), 7.44–7.50 (m, 2H), 7.36 (t, 1H, J=8.7 Hz), 7.08 (d, 1H, J=9.2 Hz), 6.98 (d, 1H, J=8.7 Hz), 6.85 (t, 1H, J=8.7 Hz), 6.56 (d, 1H, J=5.6 Hz), 3.92 (s, 3H); LC/MS(ESI$^+$) m/z 488 (M+H)$^+$.

Example 289

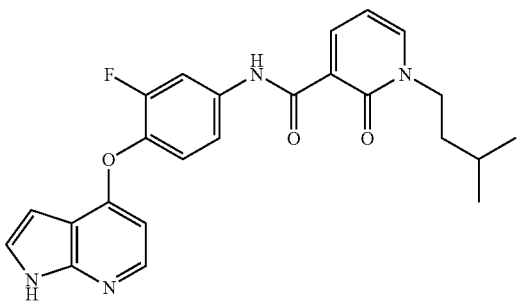

N-(4-(1H-Pyrrolo[2,3-b]pyridin-4-yloxy)-3-fluorophenyl)-1-isopentyl-2-oxo-1,2-dihydropyridine-3-carboxamide, trifluoroacetic acid salt

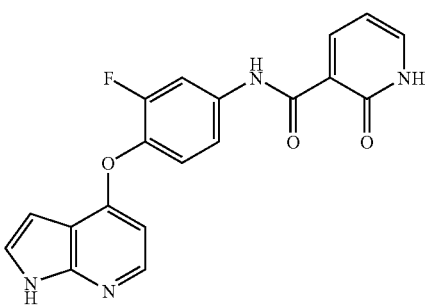

A) N-(4-(1H-Pyrrolo[2,3-b]pyridin-4-yloxy)-3-fluorophenyl)-2-oxo-1,2-dihydropyridine-3-carboxamide To a stirred solution of 4-(1H-pyrrolo[2,3-b]pyridin-4-yloxy)-3-fluorobenzenamine (24 mg, 0.1 mmol, Compound B of Example 132), 2-hydroxynicotinic acid (27 mg, 0.2 mmol), and HATU (76 mg, 0.2 mmol) in DMF (1 mL) was added DIPEA (0.1 mL) and DMAP (5 mg). The resulting mixture was stirred at rt for 2 h and concentrated in vacuo. The residue was was purified by preparative HPLC to give the desired product (8 mg, 22%) as a white solid. LC/MS (ESI$^+$) m/z 365 (M+H)$^+$.

B) N-(4-(1H-Pyrrolo[2,3-b]pyridin-4-yloxy)-3-fluorophenyl)-1-isopentyl-2-oxo-1,2-dihydropyridine-3-carboxamide, trifluoroacetic acid salt A mixture of N-(4-(1H-pyrrolo[2,3-b]pyridin-4-yloxy)-3-fluorophenyl)-2-oxo-1,2-dihydropyridine-3-carboxamide (8 mg, 0.02 mmol), Na$_2$CO$_3$ (50 mg), and 1-iodo-3-methylbutane (50 mg) in DMF (1 mL) was stirred at rt overnight. The reaction mixture was concentrated in vacuo and the residue was was purified by preparative HPLC to give the desired product (TFA salt, 5 mg, 42%) as a white solid. $^1$H NMR (CD$_3$OD) δ 12.50 (s, 1H), 8.46 (dd, 1H, J=7.1, 2.0 Hz), 8.16 (d, 1H, J=6.1 Hz), 7.90–8.00 (m, 2H), 7.38–7.44 (m, 2H), 7.33 (t, 1H, J=8.7 Hz), 6.70 (d, 1H, J=6.6 Hz), 6.51–6.57 (m, 2H), 4.08 (t, 2H, J=7.6 Hz), 1.51–1.53 (m, 3H), 0.92 (d, 6H, J=6.1 Hz); LC/MS(ESI$^+$) m/z 435 (M+H)$^+$.

Example 290

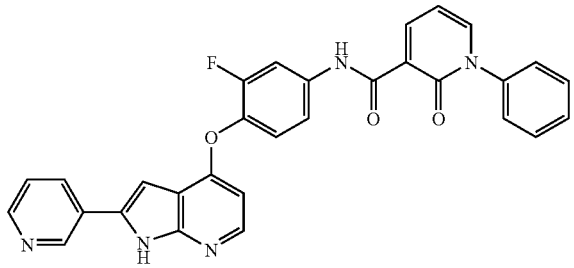

N-(3-Fluoro-4-(2-(pyridin-3-yl)-1H-pyrrolo[2,3-b]
pyridin-4-yloxy)phenyl)-2-oxo-1-phenyl-1,2-dihy-
dropyridine-3-carboxamide Prepared in a similar manner as Example 239 using 3-fluoro-4-(2-(pyridin-3-yl)-1H-pyrrolo[2,3-b]pyridin-4-yloxy)benzenamine (Compound E of Example 237) and 2-oxo-1-phenyl-1,2-dihydropyridine-3-carboxylic acid. $^1$H NMR (DMSO-d$_6$) δ 12.87 (s, 1H), 12.18 (s, 1H), 9.39 (s, 1H), 8.70–8.85 (m, 2H), 8.60 (d, 1H, J=7.1 Hz), 8.00–8.25 (m, 3H), 7.94 (s, 1H), 7.30–7.75 (m, 8H), 6.77 (t, 1H, J=6.6 Hz), 6.45 (d, 1H, J=4.6 Hz), 4.21 (s, 2H), 3.68 (s, 2H), 2.43 (s, 6H); LC/MS(ESI$^+$) m/z 518 (M+H)$^+$.

Example 291

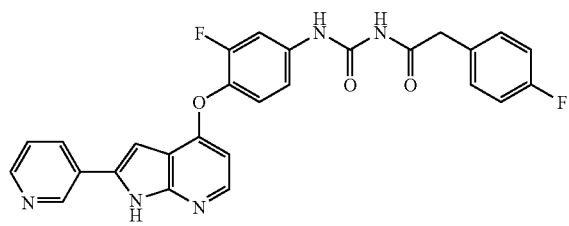

1-(3-Fluoro-4-(2-(pyridin-3-yl)-1H-pyrrolo[2,3-b]
pyridin-4-yloxy)phenyl)-3-(2-(4-fluorophenyl)
acetyl)urea, hydrochloride salt A mixture of 3-fluoro-4-(2-(pyridin-3-yl)-1H-pyrrolo[2,3-b]pyridin-4-yloxy)benzenamine (25 mg, 0.078 mmol, Compound E of Example 237) and 2-(4-fluorophenyl)acetyl isocyanate (0.09 mmol in toluene, Compound C of Example 4) in THF was stirred at rt for 1 h. The solvent was removed in vacuo and the residue was purified by preparative HPLC to afford the desired product (HCl salt, 18 mg, 40%) as a yellow solid. $^1$H NMR (CD$_3$OD) δ 10.76 (s, 1H), 9.19 (s, 1H), 8.70 (d, 1H, J=8.0 Hz), 8.66 (d, 1H, J=5.2 Hz), 8.18 (d, 1H, J=6.4 Hz), 8.00 (dd, 1H, J=8.4, 5.6 Hz), 7.75 (dd, 1H, J=13.2, 2.4 Hz), 7.10–7.35 (m, 4H), 6.90–7.03–7.40 (m, 3H), 6.6 (d, 1H, J=6.4 Hz); LC/MS(ESI$^+$) m/z 500 (M+H)$^+$.

Example 292

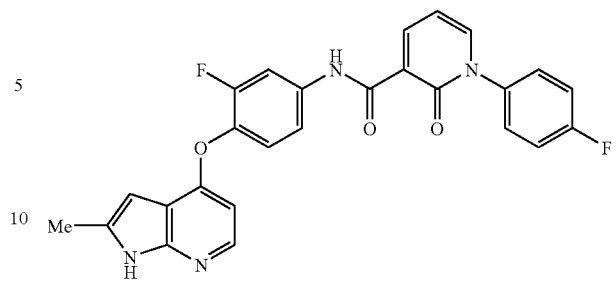

N-(3-Fluoro-4-(2-methyl-1H-pyrrolo[2,3-b]pyridin-
4-yloxy)phenyl)-1-(4-fluorophenyl)-2-oxo-1,2-dihy-
dropyridine-3-carboxamide

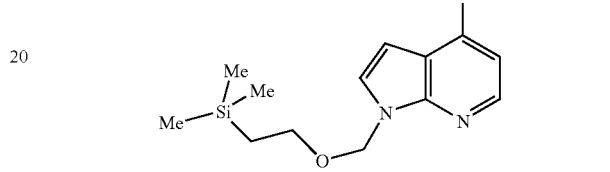

A) 4-Chloro-1-((2-(trimethylsilyl)ethoxy)methyl)-
1H-pyrrolo[2,3-b]pyridine

To a suspension of NaH (88 mg, 60% in mineral oil, 2.2 mmol) in DMF (1 mL) was added 4-chloro-1H-pyrrolo[2,3-b]pyridine (305 mg, 2 mmol, prepared according to Thibault, C. et al. *Org. Lett.* 2003, 5, 5023) at room temperature with stirring. The mixture was stirred for 5 min and trimethylsilylethyl chloromethyl ether (350 mg, 2.1 mmol, Aldrich) was added. The mixture was stirred at room temperature for 1 h, poured onto ice, and extracted with ethyl acetate (3×10 mL). The combined extracts were washed with brine, dried (MgSO$_4$) and concentrated under reduced pressure to give the crude product, which was purified by flash chromatograph (5% ethyl acetate in hexanes) to afford the title compound (300 mg, 1.06 mmol, 53%) as a liquid. $^1$H NMR (CDCl$_3$) δ 8.28 (d, 1H, J=5.5 Hz), 7.45 (d, 1H, J=3.6 Hz), 7.18 (d, 1H, J=5.5 Hz), 6.69 (d, 1H, J=3.6 Hz), 5.74 (s, 2H), 3.60 (t, 2H, J=6.8 Hz), 0.96 (t, 2H, J=6.8 Hz), 0.07 (s, 9H); MS(ESI$^+$) m/z 283 and 285 (M+H, 1 Cl)$^+$.

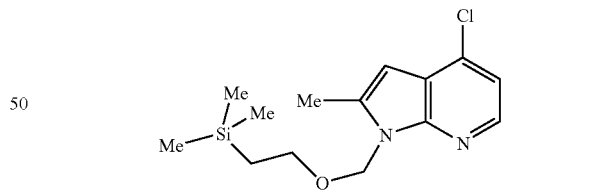

B) 4-Chloro-2-methyl-1-((2-(trimethylsilyl)ethoxy)
methyl)-1H-pyrrolo[2,3-b]pyridine To a solution of 4-chloro-1-((2-(trimethylsilyl)ethoxy) methyl)-1H-pyrrolo[2,3-b]pyridine (150 mg, 0.53 mmol) in THF (1 mL) at −78° C. under argon was added butyllithium (0.4 mL, 1.6 M in hexanes, 6.4 mmol) dropwise. The mixture was stirred at the same temperature for 5 min, and treated with iodomethane (0.1 mL). The mixture was warmed up to room temperature, quenched by the addition of saturated ammonium chloride solution, and extracted with ethyl acetate (3×10 mL). The combined extracts were washed with brine, dried (MgSO$_4$) and concentrated in vacuo to give the crude product (150 mg, 95%), which was used for the next reaction. ¹H NMR (CDCl₃) δ 8.19 (d, 1H, J=5.5 Hz), 7.14 (d, 1H, J=5.5 Hz), 6.42 (s, 1H), 5.74 (s, 2H), 3.60 (t, 2H, J=6.8 Hz), 2.61 (s, 3H), 0.96 (t, 2H, J=6.8 Hz), 0.07 (s, 9H); MS(ESI⁺) m/z 297 and 299 (M+H, 1 Cl)⁺.

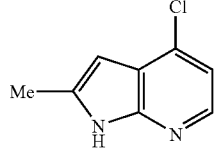

C) 4-Chloro-2-methyl-1H-pyrrolo[2,3-b]pyridine

A mixture of 4-chloro-2-methyl-1-((2-(trimethylsilyl)ethoxy)methyl)-1H-pyrrolo-[2,3-b]pyridine (296.5 mg, 1 mmol) and TBAF (5 mL, 1 M in THF, Aldrich) was refluxed overnight. The THF was removed under reduced pressure and the residue was diluted with water (5 mL). The precipitate that formed was collected, washed with water and dried (MgSO₄) to afford the title compound (101 mg, 60%). ¹H NMR (CD₃OD) δ 7.99 (d, 1H, J=5.5 Hz), 7.06 (d, 1H, J=5.5 Hz), 6.23 (s, 1H), 2.46 (s, 3H); MS(ESI⁺) m/z 167 and 169 (M+H, 1 Cl)⁺.

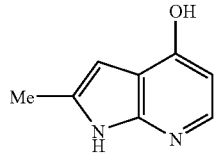

D) 2-Methyl-1H-pyrrolo[2,3-b]pyridin-4-ol

A mixture of 4-chloro-2-methyl-1H-pyrrolo[2,3-b]pyridine (120 mg, 0.72 mmol) and sodium acetate (150 mg, 1.83 mmol) in acetic acid (1.5 mL) was microwaved at 200° C. for 40 minutes. The mixture was purified by preparative HPLC and the appropriate fractions were concentrated in vacuo and lyophilized to afford the title compound (90 mg, 47%). ¹H NMR (CD₃OD) δ 8.09 (d, 1H, J=5.5 Hz), 6.80 (d, 1H, J=5.5 Hz), 6.49 (s, 1H), 2.46 (s, 3H); MS(ESI⁺) m/z 149 (M+H)⁺.

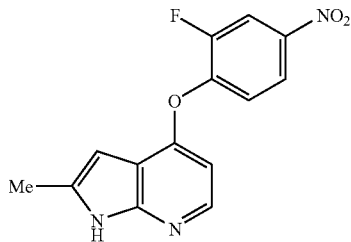

D) 4-(2-Fluoro-4-nitrophenoxy)-2-methyl-1H-pyrrolo[2,3-]pyridine

A mixture of 2-methyl-1H-pyrrolo[2,3-b]pyridin-4-ol (90 mg, TFA salt, 0.34 mmol), 3,4-difluoronitrobenzene (0.05 mL) and potassium carbonate (100 mg, 0.72 mmol) in DMF (1 mL) was stirred at 50° C. for 2 h. The mixture was diluted with water and extracted with ethyl acetate (3×5 mL). The combined extracts were washed with water, dried (MgSO₄) and concentrated in vacuo to afford the crude product, which was purified by preparative HPLC to give the title compound (45 mg, 46%). ¹H NMR (CD₃OD) δ 8.25 (dd, 2H, J=10.4, 2.6 Hz), 8.12 (m, 1H), 8.04 (d, 1H, J=5.5 Hz), 7.30 (t, 1H, J=8.3 Hz), 6.67 (d, 1H, J=5.5 Hz), 5.95 (s, 1H), 2.41 (s, 3H); MS(ESI⁺) m/z 288 (M+H)⁺.

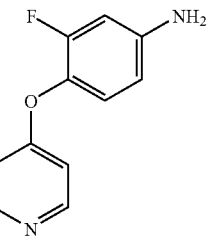

E) 3-Fluoro-4-(2-methyl-1H-pyrrolo[2,3-b]pyridin-4-yloxy)benzenamine

A mixture of 4-(2-fluoro-4-nitrophenoxy)-2-methyl-1H-pyrrolo[2,3-b]pyridine (43 mg, 0.15 mmol), zinc dust (50 mg, 0.75 mmol) and ammonium chloride (50 mg) in THF/Methanol (1/2, 0.6 mL) was stirred at room temperature for 1 h, filtered and concentrated in vacuo to afford the desired product (35 mg, 90%), which was sufficiently pure to use in the subsequent reaction. ¹H NMR (DMSO-d₆) δ 11.71 (s, 1H), 8.04 (d, 1H, J=5.5 Hz), 7.10 (t, 1H, J=8.4 Hz), 6.64 (dd, 1H, J=10.4, 2.6 Hz), 6.51 (m, 1H), 6.35 (d, 1H, J=5.5 Hz), 5.95 (s, 1H), 5.50 (s 2H), 2.41 (s, 3H); MS(ESI⁺) m/z 258 (M+H)⁺.

F) N-(3-Fluoro-4-(2-methyl-1H-pyrrolo[2,3-b]pyridin-4-yloxy)phenyl)-1-(4-fluorophenyl)-2-oxo-1,2-dihydropyridine-3-carboxamide A mixture of 3-fluoro-4-(2-methyl-1H-pyrrolo[2,3-b]pyridin-4-yloxy)benzenamine (17 mg, 0.066 mmol), 1-(4-fluorophenyl)-2-oxo-1,2-dihydropyridine-3-carboxylic acid (20 mg, 0.086 mmol) in DMF (0.5 mL) was stirred with BOP reagent (50 mg, 0.11 mmol) and triethylamine (0.01 mL) at 50° C. for 1 h. The reaction mixture was cooled to room temperature and diluted with water. The precipitate was collected and washed with water. The crude product was purified by preparative HPLC and the appropriate fractions were collected, neutralized and concentrated in vacuo to give the title compound (7.85 mg, 25%) as a solid. ¹H NMR (DMSO-d₆) δ 12.07 (s, 1H), 11.56 (s, 1H), 8.49 (d, 1H, J=6.2 Hz), 8.12 (d, 1H, J=6.2 Hz), 7.98 (dd, 1H, J=10.4, 2.6 Hz), 7.95 (d, 1H, J=5.5 Hz), 7.61 (m, 2H), 7.43 (m, 3H), 7.29 (t, 1H, J=8.40 Hz), 6.72 (t, 1H, J=6.2 Hz), 6.36 (d, 1H, J=5.5 Hz), 5.88 (s, 1H), 2.32 (s, 3H); MS(ESI⁺) m/z 473 (M+H)⁺.

Example 293

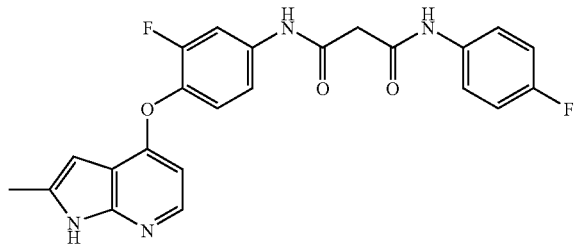

N¹-(3-Fluoro-4-(2-methyl-1H-pyrrolo[2,3-b]pyridin-4-yloxy)phenyl)-N³-(4-fluorophenyl)malonamide, hydrochloride salt To a mixture of 3-fluoro-4-(2-methyl-1H-pyrrolo[2,3-b]pyridin-4-yloxy)benzenamine (20 mg, 0.078 mmol, Compound E of Example 292), 3-(4-fluorophenylamino)-3-oxo-propanoic acid (20 mg, 1 mmol, Compound A of Example 25), and HATU (44 mg, 0.12 mmol) in DMF (0.5 mL) was added DIPEA (0.1 mL). The reaction mixture was stirred at rt for 2 h and concentrated in vacuo. The residue was purified by preparative HPLC to give the desired product (HCl salt, 12.5 mg, 34%) as a white solid. $^1$H NMR (CD$_3$OD) δ 8.05 (d, 1H, J=7.2 Hz), 7.79 (dd, 1H, J=12.7, 2.8 Hz), 7.50–7.53 (m, 2H), 7.27–7.36 (m, 2H), 6.97 (m, 2H), 6.70 (d, 1H, J=6.6 Hz), 6.20 (s, 1H), 3.47 (s, 2H), 2.40 (s, 3H); LC/MS(ESI$^+$) m/z 437 (M+H)$^+$.

Example 294

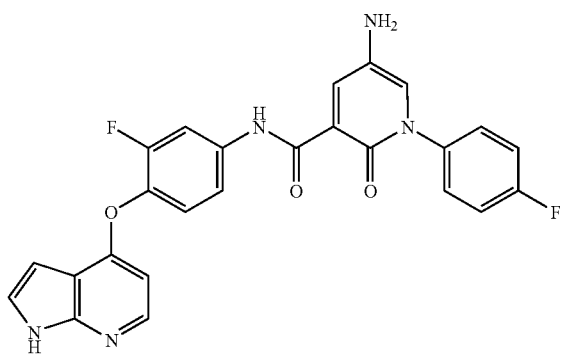

N-(4-(1H-Pyrrolo[2,3-b]pyridin-4-yloxy)-3-fluorophenyl)-5-amino-1-(4-fluorophenyl)-2-oxo-1,2-dihydropyridine-3-carboxamide, hydrochloride salt

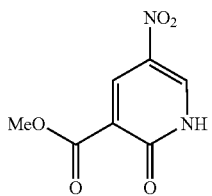

A) Methyl 5-nitro-2-oxo-1,2-dihydropyridine-3-carboxylate

To a solution of 2-hydroxy-5-nitronicotinic acid (0.80 g, 4.35 mmol, Combi-Blocks) in methanol (10 mL) at 0° C. was added thionyl chloride (1 mL) dropwise. The mixture was stirred at 0° C. for 1 h, then at 60° C. for 2 h. The excess methanol was removed under reduced pressure and the residue was neutralized with aqueous sodium bicarbonate solution. The solid was collected, washed with water and dried to afford the title compound (0.85 g, 99%). $^1$H NMR (DMSO-d$_6$) δ 8.44 (s, 1H), 8.34 (s, 1H), 3.67 (s, 3H); MS(ESI$^+$) m/z 199 (M+H)$^+$.

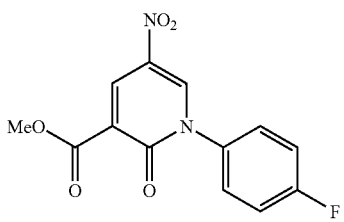

B) Methyl 1-(4-fluorophenyl)-5-nitro-2-oxo-1,2-dihydropyridine-3-carboxylate

A mixture of methyl 5-nitro-2-oxo-1,2-dihydropyridine-3-carboxylate (850 mg, 4.29 mmol), 4-fluorophenylboronic acid (1.40 g, 10 mmol, Combi-Blocks) and copper acetate (200 mg, 1.1 mmol) in pyridine (1 mL) and dioxane (20 mL) was stirred at 80° C. for 4 h. The reaction mixture was cooled to room temperature and diluted with a solution of ammonia. The solid was collected, washed with water and dried to afford the title compound (656 mg, 52%). $^1$H NMR (DMSO-d$_6$) δ 8.95 (d, 1H, J=3.2 Hz), 8.80 (d, 1H, J=3.2 Hz), 7.40 (m, 2H), 7.25 (m, 2H), 3.95 (s, 3H); MS(ESI$^+$) m/z 293 (M+H)$^+$.

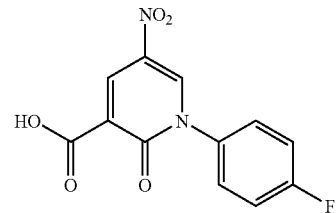

C) 1-(4-Fluorophenyl)-5-nitro-2-oxo-1,2-dihydropyridine-3-carboxylic acid

A mixture of methyl 1-(4-fluorophenyl)-5-nitro-2-oxo-1,2-dihydropyridine-3-carboxylate (75 mg, 0.245 mmol) and 2 N NaOH solution (1 mL) was stirred at 80° C. for 2 h. The reaction mixture was cooled to rt and acidified with 1 N HCl solution. The solid that formed was collected, washed with water and dried to afford the title compound (45 mg, 66%), which was used directly in the next reaction. $^1$H NMR (DMSO-d$_6$) δ 13.41 (s, 1H), 9.28 (d, 1H, J=3.2 Hz), 8.70 (d, 1H, J=3.2 Hz), 7.60 (m, 2H), 7.41 (m, 2H); MS(ESI$^+$) m/z 279 (M+H)$^+$.

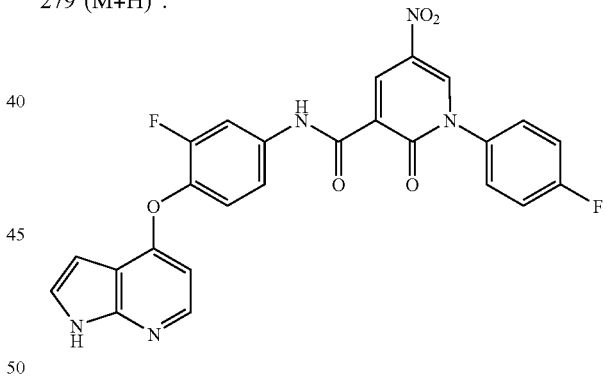

D) N-(4-(1H-Pyrrolo[2,3-b]pyridin-4-yloxy)-3-fluorophenyl)-1-(4-fluorophenyl)-5-nitro-2-oxo-1,2-dihydropyridine-3-carboxamide A mixture of 1-(4-fluorophenyl)-5-nitro-2-oxo-1,2-dihydropyridine-3-carboxylic acid (40 mg, 0.14 mmol) and 4-(1H-pyrrolo[2,3-b]pyridin-4-yloxy)-3-fluorobenzenamine (35 mg, 0.14 mmol, Compound B of Example 132) in DMF (1 mL) was stirred with BOP reagent (100 mg, 0.23 mmol) and triethylamine (0.1 mL) at 50° C. for 1 h. The reaction mixture was cooled to room temperature and diluted with water. The solid that formed was collected, washed with aqueous sodium bicarbonate solution, 1 N HCl solution, and water to afford the title compound (54 mg, 76%). $^1$H NMR (DMSO-d$_6$) δ 12.19 (s, 1H), 11.04 (s, 1H), 9.37 (d, 1H, J=2.6 Hz), 9.03 (d, 1H, J=2.6 Hz), 8.18 (d, 1H, J=5.5 Hz), 8.01 (dd, 1H, J=10.2, 2.6 Hz), 7.71 (m, 2H), 7.61 (m, 1H), 7.46 (m, 4H), 6.55 (d, 1H, J=5.5 Hz), 6.36 (s, 1 Hz); MS(ESI⁺) m/z 504 (M+H)⁺.

E) N-(4-(1H-Pyrrolo[2,3-b]pyridin-4-yloxy)-3-fluorophenyl)-5-amino-1-(4-fluorophenyl)-2-oxo-1,2-dihydropyridine-3-carboxamide, hydrochloride salt A solution of N-(4-(1H-pyrrolo[2,3-b]pyridin-4-yloxy)-3-fluorophenyl)-1-(4-fluorophenyl)-5-nitro-2-oxo-1,2-dihydropyridine-3-carboxamide (51 mg, 0.1 mmol) in DMF (1 mL) and ethanol (5 mL) was hydrogenated in the presence of Pd/C (10%, 10 mg) under hydrogen atmosphere for 4 h at room temperature. The reaction mixture was filtered and concentrated in vacuo. The residue was purified by preparative HPLC and the fraction containing the desired compound was collected and concentrated in vacuo. The product was converted to the HCl salt by adding 1 N HCl solution and lyophilizing to afford the title compound (7.6 mg, 15%) as a light yellow solid. ¹H NMR (CD₃OD) δ 8.56 (d, 1H, J=3.2 Hz), 8.31 (d, 1H, J=5.5 Hz), 8.08 (dd, 1H, J=10.4, 2.6 Hz), 7.78 (m, 1H), 7.56 (m, 5H), 7.48 (m, 2H), 7.35 (t, 1H, J=8.7 Hz), 6.90 (d, 1H, J=5.5 Hz), 6.69 (s, 1H); MS(ESI⁺) m/z 474 (M+H)⁺.

Example 295

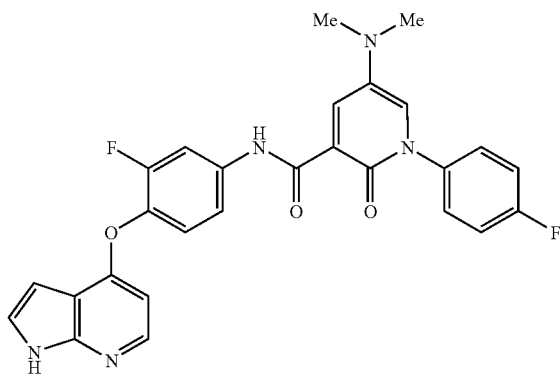

N-(4-(1H-Pyrrolo[2,3-b]pyridin-4-yloxy)-3-fluorophenyl)-5-(dimethylamino)-1-(4-fluorophenyl)-2-oxo-1,2-dihydropyridine-3-carboxamide

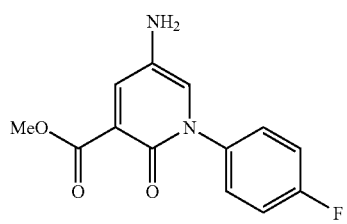

A) Methyl 5-amino-1-(4-fluorophenyl)-2-oxo-1,2-dihydropyridine-3-carboxylate

A mixture of methyl 1-(4-fluorophenyl)-5-nitro-2-oxo-1,2-dihydropyridine-3-carboxylate (1.46 g, 5 mmol, Compound B of Example 294), zinc dust (1.63 g, 25 mmol) and ammonium chloride (1.5 g, 28 mmol) in methanol/THF (1:1, 20 mL) was stirred at room temperature for 2 h. The reaction mixture was filtered and concentrated in vacuo to afford the desired product (1.30 g, 99%), which was used directly in the next reaction without purification. ¹H NMR (CD₃OD) δ 8.08 (s, 1H), 7.41 (m, 2H), 7.29 (m, 3H), 3.84 (s, 3H); MS(ESI⁺) m/z 263 (M+H)⁺.

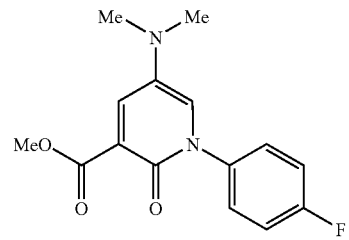

B) Methyl 5-(dimethylamino)-1-(4-fluorophenyl)-2-oxo-1,2-dihydropyridine-3-carboxylate To a solution of methyl 5-amino-1-(4-fluorophenyl)-2-oxo-1,2-dihydropyridine-3-carboxylate (30 mg, 0.11 mmol) and formalin (37%, 0.1 mL) in acetic acid (1 mL) was added sodium triacetoxyborohydride (50 mg, 0.23 mmol). The reaction mixture was stirred at room temperature for 1 h and purified by preparative HPLC. The fractions containing the desired product were collected, neutralized and concentrated in vacuo to afford a solid. The solid was collected, washed with water and dried to give the title compound (25 mg, 77%). ¹H NMR (CD₃OD) δ 8.31 (d, 1H, J=2.6 Hz), 7.41 (m, 2H), 7.26 (m, 3H), 3.89 (s, 3H), 2.79 (s, 6H); MS(ESI⁺) m/z 291 (M+H)⁺.

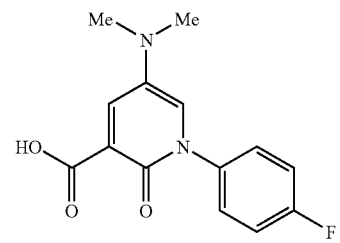

C) 5-(Dimethylamino)-1-(4-fluorophenyl)-2-oxo-1,2-dihydropyridine-3-carboxylic acid The title compound was prepared from methyl 5-(dimethylamino)-1-(4-fluorophenyl)-2-oxo-1,2-dihydropyridine-3-carboxylate (25 mg, 0.086 mmol) utilizing the procedure described in Step C of Example 294 (20 mg, 84%). ¹H NMR (CD₃OD) δ 8.31 (d, 1H, J=2.6 Hz), 7.41 (m, 2H), 7.26 (m, 3H), 2.70 (s, 6H); MS(ESI⁺) m/z 277 (M+H)⁺.

D) N-(4-(1H-Pyrrolo[2,3-b]pyridin-4-yloxy)-3-fluorophenyl)-5-(dimethylamino)-1-(4-fluorophenyl)-2-oxo-1,2-dihydropyridine-3-carboxamide The title compound was prepared from 5-(dimethylamino)-1-(4-fluorophenyl)-2-oxo-1,2-dihydropyridine-3-carboxylic acid (20 mg, 0.072 mmol) utilizing the procedure described in Step D of Example 294 (13.5 mg, 37%). ¹H NMR (DMSO-d₆) δ 12.54 (s, 1H), 11.79 (s, 1H), 8.45 (d, 1H, J=3.2 Hz), 8.10 (d, 1H, J=5.5 Hz), 8.01 (dd, 1H, J=10.4, 2.6 Hz), 7.62 (m, 1H), 7.44 (m, 6H), 6.40 (d, 1H, J=5.5 Hz), 6.24 (s, 1 Hz), 2.82 (s, 6H); MS(ESI⁺) m/z 502 (M+H)⁺.

Example 296

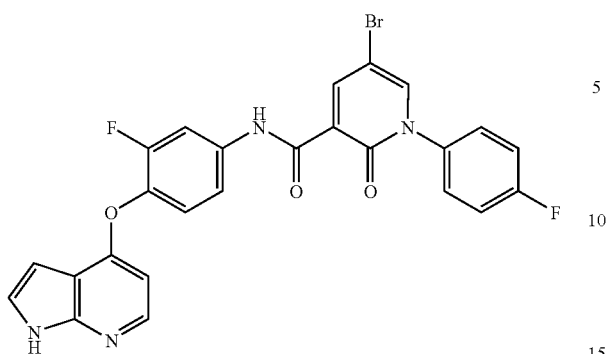

N-(4-(1H-Pyrrolo[2,3-b]pyridin-4-yloxy)-3-fluorophenyl)-5-bromo-1-(4-fluorophenyl)-2-oxo-1,2-dihydropyridine-3-carboxamide

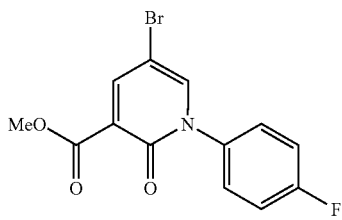

A) Methyl 5-bromo-1-(4-fluorophenyl)-2-oxo-1,2-dihydropyridine-3-carboxylate

The title compound was prepared from 5-bromo-2-hydroxynicotinic acid (Combi-Blocks) utilizing the procedures described in Steps A and B of Example 294 in 69% yield. $^1$H NMR (DMSO-$d_6$) δ 8.29 (d, 1H, J=3.2 Hz), 8.14 (d, 1H, J=3.2 Hz), 7.50 (m, 2H), 7.37 (m, 2H), 3.75 (s, 3H); MS(ESI$^+$) m/z 326 and 328 (M+H, 1 Br)$^+$.

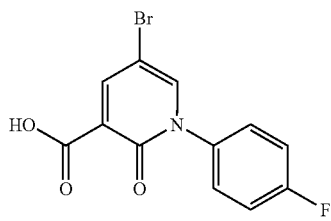

B) 5-Bromo-1-(4-fluorophenyl)-2-oxo-1,2-dihydropyridine-3-carboxylic acid

The title compound was prepared from methyl 5-bromo-1-(4-fluorophenyl)-2-oxo-1,2-dihydropyridine-3-carboxylate (65 mg, 0.2 mmol) utilizing the procedure described in Step C of Example 294 (55 mg, 88%). $^1$H NMR (DMSO-$d_6$) δ 8.58 (d, 1H, J=2.6 Hz), 8.44 (d, 1H, J=2.6 Hz), 7.69 (m, 2H), 7.43 (t, 2H, J=8.8 Hz); MS(ESI$^+$) m/z 312 and 314 (M+H, 1 Br)$^+$.

C) N-(4-(1H-Pyrrolo[2,3-b]pyridin-4-yloxy)-3-fluorophenyl)-5-bromo-1-(4-fluorophenyl)-2-oxo-1,2-dihydropyridine-3-carboxamide The title compound was prepared from 5-bromo-1-(4-fluorophenyl)-2-oxo-1,2-dihydropyridine-3-carboxylic acid (31.2 mg, 0.1 mmol) utilizing the procedure described in Step D of Example 294 (28 mg, 52%). $^1$H NMR (DMSO-$d_6$) δ 11.93 (s, 1H), 11.80 (s, 1H), 8.53 (m, 2H), 8.01 (dd, 1H, J=10.4, 2.6 Hz), 7.64 (m, 2H), 7.41 (m, 6H), 6.41 (br.s, 1H), 6.27 (s, 1H); MS(ESI$^+$) m/z 537 and 539 (M+H, 1 Br)$^+$.

Example 297

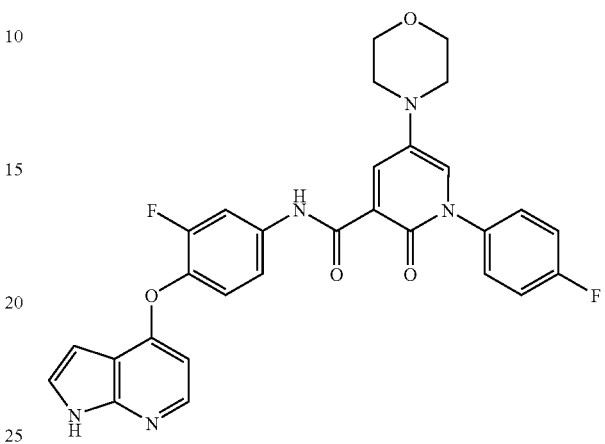

N-(4-(1H-Pyrrolo[2,3-b]pyridin-4-yloxy)-3-fluorophenyl)-1-(4-fluorophenyl)-5-morpholino-2-oxo-1,2-dihydropyridine-3-carboxamide A mixture of N-(4-(1H-pyrrolo[2,3-b]pyridin-4-yloxy)-3-fluorophenyl)-5-bromo-1-(4-fluorophenyl)-2-oxo-1,2-dihydropyridine-3-carboxamide (40 mg, 0.074 mmol, Example 296) and morpholine (0.1 mL) in dimethylacetamide (1 mL) was microwaved at 160° C. for 30 minutes. The reaction mixture was cooled to room temperature and purified by preparative HPLC. The fractions containing the desired product were collected, neutralized and concentrated in vacuo to afford a solid. The solid was collected, washed with water and dried to give the title compound (7.5 mg, 18%). $^1$H NMR (DMSO-$d_6$) δ 12.38 (s, 1H), 11.75 (s, 1H), 8.50 (d, 1H, J=2.6 Hz), 8.06 (d, 1H, J=5.5 Hz), 8.01 (dd, 1H, J=10.4, 2.6 Hz), 7.60 (m, 2H), 7.41 (m, 6H), 6.41 (d, 1H, J=5.5 Hz), 6.21 (s, 1H), 3.72 (m, 4H), 3.00 (m, 4H); MS(ESI$^+$) m/z 544 (M+H)$^+$.

Example 298

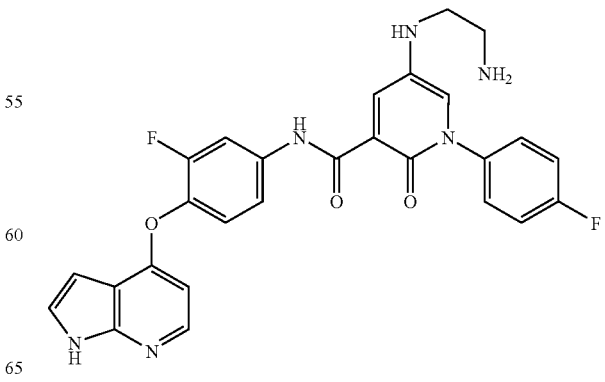

N-(4-(1H-Pyrrolo[2,3-b]pyridin-4-yloxy)-3-fluorophenyl)-5-(2-aminoethylamino)-1-(4-fluorophenyl)-2-oxo-1,2-dihydropyridine-3-carboxamide

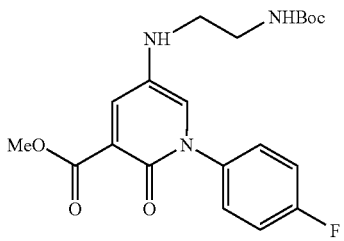

A) Methyl 5-(2-(tert-butoxycarbonyl)ethylamino)-1-(4-fluorophenyl)-2-oxo-1,2-dihydropyridine-3-carboxylate To a solution of methyl 5-bromo-1-(4-fluorophenyl)-2-oxo-1,2-dihydropyridine-3-carboxylate (131 mg, 0.5 mmol, Compound A of Example 296) and tert-butyl 2-oxoethylcarbamate (159 mg, 1 mmol, Aldrich) in acetic acid (1 mL) was added sodium triacetoxyborohydride (212 mg, 1 mmol). The reaction mixture was stirred at room temperature for 1 h, quenched by adding water, and extracted with ethyl acetate (3×10 mL). The combined organic extracts were washed with brine, aqueous sodium bicarbonate solution and dried. The solution was concentrated in vacuo and the residue was purified by flash column chromatography (SiO₂, 10% ethyl acetate in hexanes) to afford the title compound (60 mg, 30%) as a gel. $^1$H NMR (CDCl₃) δ 7.90 (d, 1H, J=2.6 Hz), 7.37 (m, 2H), 7.13 (m, 2H), 6.81 (d, 1H, J=2.6 Hz), 3.88 (s, 3H), 3.30 (m, 2H), 3.10 (m, 2H), 1.46 (s, 9H); MS(ESI⁺) m/z 406 (M+H)⁺.

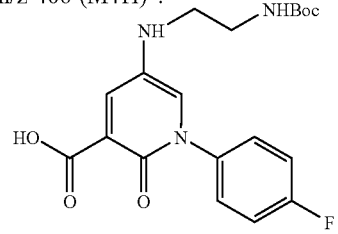

B) 5-(2-(tert-Butoxycarbonyl)ethylamino)-1-(4-fluorophenyl)-2-oxo-1,2-dihydropyridine-3-carboxylic acid The title compound was prepared from methyl 5-(2-(tert-butoxycarbonyl)ethylamino)-1-(4-fluorophenyl)-2-oxo-1,2-dihydropyridine-3-carboxylate (60 mg, 0.15 mmol) utilizing the procedure described in Step C of Example 294 (50 mg, 85%), which was used directly in the next reaction without further purification. $^1$H NMR (CDCl₃) δ 8.26 (d, 1H, J=2.6 Hz), 7.50 (m, 2H), 7.25 (m, 2H), 6.91 (d, 1H, J=2.6 Hz), 3.30 (m, 2H), 3.10 (m, 2H), 1.46 (s, 9H); MS(ESI⁺) m/z 392 (M+H)⁺.

C) N-(4-(1H-Pyrrolo[2,3-b]pyridin-4-yloxy)-3-fluorophenyl)-5-(2-aminoethylamino)-1-(4-fluorophenyl)-2-oxo-1,2-dihydropyridine-3-carboxamide A mixture of 5-(2-(tert-butoxycarbonyl)ethylamino)-1-(4-fluorophenyl)-2-oxo-1,2-dihydropyridine-3-carboxylic acid (50 mg, 0.13 mmol) and 4-(1H-pyrrolo[2,3-b]pyridin-4-yloxy)-3-fluorobenzenamine (40 mg, 0.16 mmol, Compound B of Example 132), BOP reagent (100 mg, 0.23 mmol) in DMF (1 mL) was stirred at 50° C. with triethylamine (0.1 mL) for 1 h. The reaction mixture was cooled to room temperature, diluted with water, and extracted with methylene chloride (3×10 mL). The combined organic extracts were washed with water, dried and concentrated in vacuo. The residue was stirred with TFA (1 mL) at room temperature for 30 minutes. The TFA was removed and the residue was purified by preparative HPLC. The fraction containing the desired product was collected and concentrated in vacuo. The residue was converted to the HCl salt by adding 1 N HCl solution and lyophilizing to give the title compound (20 mg, 27%). $^1$H NMR (CD₃OD) δ 8.35 (d, 1H, J=2.6 Hz), 8.26 (d, 1H, J=5.5 Hz), 8.01 (dd, 1H, J=10.4, 2.6 Hz), 7.48 (m, 2H), 7.41 (m, 6H), 6.81 (d, 1H, J=5.5 Hz), 6.60 (s, 1H), 3.26 (t, 2H, J=6.1 Hz), 3.07 (t, 2H, J=6.1 Hz); MS(ESI⁺) m/z 517 (M+H)⁺.

Example 299

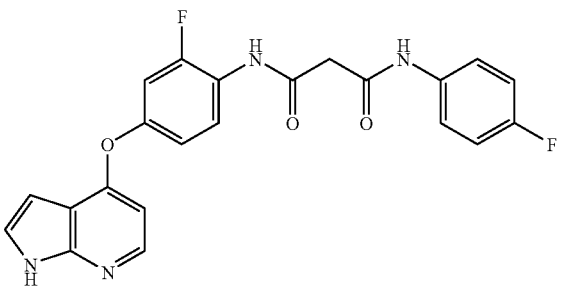

N¹-(4-(1H-Pyrrolo[2,3-b]pyridin-4-yloxy)-2-fluorophenyl)-N³-(4-fluorophenyl)malonamide, trifluoroacetic acid salt

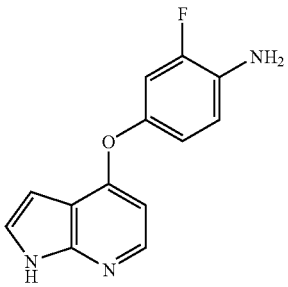

A) 4-(1H-Pyrrolo[2,3-b]pyridin-4-yloxy)-2-fluorobenzenamine

To a solution of 4-chloro-1H-pyrrolo[2,3-b]pyridine (50 mg, 0.33 mmol, prepared according to Thibault, C. et al. Org. Lett. 2003, 5, 5023) in NMP (0.5 mL) were added 4-amino-3-fluorophenol (51 mg, 0.40 mmol) and DIEA (0.1 mL, 0.57 mmol). The mixture was heated at 250° C. in a microwave oven for 1 h and then cooled to room temperature. To the mixture was added NaH (10 mg, 0.4 mmol) and the mixture was again heated at 250° C. for 3 h. After cooling, the mixture was diluted with H₂O and extracted with EtOAc. The organic layer was washed with H₂O, brine, and dried over MgSO₄. After filtration and concentration in vacuo, the residue was purified by flash column chromatography (ISCO RediSep® silica gel cartridge) to give the title compound (15 mg, 19%). MS (ESI) m/z 244.1 (M+H)⁺.

B) N¹-(4-(1H-Pyrollo[2,3-b]pyridin-4-yloxy)-2-fluorophenyl)-N³-(4-fluorophenyl)malonamide, trifluoroacetic acid To a solution of 4-(1H-pyrrolo[2,3-b]pyridin-4-yloxy)-2-fluorobenzenamine (14 mg, 0.058 mmol) and 3-(4-fluorophenylamino)-3-oxopropanoic acid (12 mg, 0.06 mmol, Compound A of Example 25) in DMF (1 mL) were added DIEA (0.04 mL, 0.23 mmol) and TBTU (22 mg, 0.07 mmol). The reaction mixture was stirred at room temperature for 2 d and concentrated in vacuo. The residue was purified by preparative HPLC to give the title compound (18 mg, 74%). $^1$H NMR (CD$_3$OD) δ 8.25 (d, 1H, J=7.5 Hz), 8.19 (t, 1H, J=7.5 Hz), 7.55 (m, 2H), 7.49 (d, 1H, J=3.5 Hz), 7.25 (d, 1H, J=8.0 Hz), 7.13 (d, 1H, J=7.0 Hz), 7.01 (m, 2H), 6.84 (d, 1H, J=7.0 Hz), 6.60 (d, 1H, J=3.5 Hz), 3.60 (s, 2H); MS(ESI) m/z 423.1 (M+H)$^+$.

Example 300

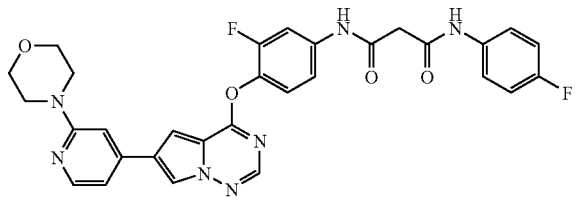

N¹-(3-Fluoro-4-(6-(2-morpholinopyridin-4-yl)pyrrolo[2,1-f][1,2,4]triazin-4-yloxy)phenyl)-N³-(4-fluorophenyl)malonamide

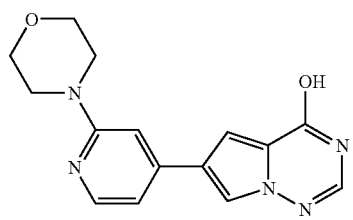

A) 6-(2-Morpholinopyridin-4-yl)pyrrolo[2,1-f][1,2,4]triazin-4-ol

To a solution of 6-bromopyrrolo[2,1-f][1,2,4]triazin-4-ol (100 mg, 0.47 mmol, prepared from methyl 4-bromo-1H-pyrrole-2-carboxylate: see, generally, Kitamura, C. and Yamashita, Y. *J. Chem. Soc. Perkin Trans.* 1, 1997, 1443, the disclosure of which is herein incorporated by reference, using a similar procedure outlined in the PCT Appl. WO 00/71129) and 4-(4-(4,4,5,5-tetramethyl-1,3,2-dioxaborolan-2-yl)pyridin-2-yl)morpholine (290 mg, 1.0 mmol) in DMF (2 mL) were added saturated aq. K$_2$CO$_3$ solution (2.0 mL) and Pd(PPh$_3$)$_4$ (60 mg, 0.05 mmol). The reaction mixture was purged with N$_2$ for 10 min and then was heated at 80° C. for 5 h and 100° C. for 12 h. After cooling, the mixture was diluted with H$_2$O and filtered to afford the crude product, which was triturated with DCM to provide the title compound (114 mg, 82% yield). MS(ESI) m/z 298.2 (M+H)$^+$.

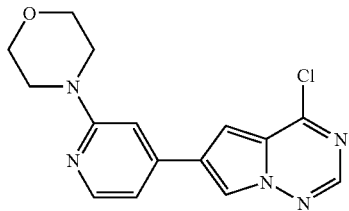

B) 4-Chloro-6-(2-morpholinopyridin-4-yl)pyrrolo[2,1-f][1,2,4]triazine

To a suspension of 6-(2-morpholinopyridin-4-yl)pyrrolo[2,1-f][1,2,4]triazin-4-ol (110 mg, 0.37 mmol) in toluene (100 mL) were added one drop of DMF and POCl$_3$ (30 mL). The flask was sealed and heated at 100° C. for 3 d. The reaction mixture was cooled to rt and concentrated in vacuo. The residue was then dissolved in DCM, neutralized with saturated aq. NaHCO$_3$ solution and the organic layer was separated. The aqueous layer was extracted with DCM (2×50 mL). The combined organic layers were dried over MgSO$_4$, filtered, and concentrated in vacuo to afford the desired product, which was used directly in the next step. MS(ESI) m/z 316.2/318.2 (M+H)$^+$.

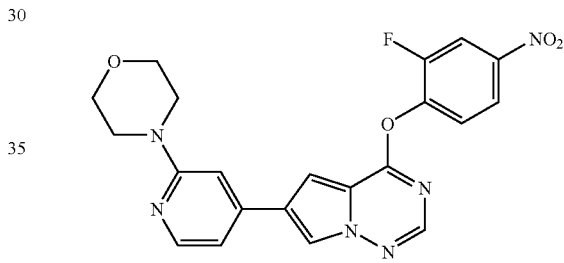

C) 4-(2-Fluoro-4-nitrophenoxy)-6-(2-morpholinopyridin-4-yl)pyrrolo[2,1-f][1,2,4]triazine To a suspension of the crude 4-chloro-6-(2-morpholinopyridin-4-yl)pyrrolo[2,1-f][1,2,4]triazine in MeCN (5 mL) were added 2-fluoro-4-nitrophenol (59 mg, 0.37 mmol) and DABCO (45 mg, 0.4 mmol). The reaction mixture was stirred at room temperature for 2 h. The solvent was removed in vacuo and the residue was purified by flash column chromatography (ISCO RediSep® silica gel cartridge) to give the desired compound (54 mg, 33% yield in two steps). MS(ESI) m/z 437.2 (M+H)$^+$.

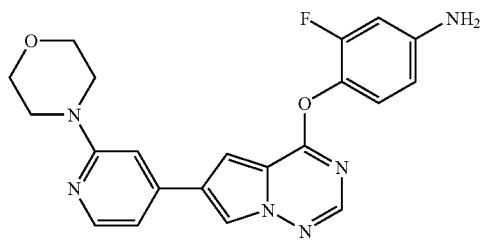

D) 3-Fluoro-4-(6-(2-morpholinopyridin-4-yl)pyrrolo[2,1-f][1,2,4]triazin-4-yloxy)benzenamine To a solution of 4-(2-fluoro-4-nitrophenoxy)-6-(2-morpholinopyridin-4-yl)pyrrolo[2,1-f][1,2,4]triazine (54 mg, 0.12 mmol) in a mixture of THF (2.0 mL) and MeOH (2.0 mL) were added NH$_4$Cl (127 mg, 2.4 mmol) and Zn dust (78 mg, 1.2 mmol). The reaction mixture was stirred at room temperature for 3 h, filtered and concentrated in vacuo. The residue was purified by preparative HPLC to provide the desired product (40 mg, 82% yield). MS(ESI) m/z 407.19 (M+H)$^+$.

E) N$^1$-(3-Fluoro-4-(6-(2-morpholinopyridin-4-yl)pyrrolo[2,1-f][1,2,4]triazin-4-yloxy)phenyl)-N$^3$-(4-fluorophenyl)malonamide To a solution of 3-fluoro-4-(6-(2-morpholinopyridin-4-yl)pyrrolo[2,1-f][1,2,4]triazin-4-yloxy)benzenamine (15 mg, 0.037 mmol) and 3-(4-fluorophenylamino)-3-oxopropanoic acid (8 mg, 0.04 mmol, Compound A of Example 25) in DMF (1 mL) were added DIEA (0.1 mL, 0.57 mmol) and TBTU (13 mg, 0.04 mmol). The reaction mixture was stirred at room temperature overnight and then purified using preparative HPLC. The fraction containing the desired product was collected and concentrated in vacuo. The residue was neutralized with 1 N NH$_4$OH and concentrated again. The solid that formed was filtered, washed with 1 N NH$_4$OH, dissolved in MeOH/H$_2$O, and lyophilized to give the title compound (8 mg, 37%). $^1$H NMR (DMSO-d$_6$) δ 10.49 (s, 1H), 10.23 (s, 1H), 8.63 (s, 1H), 8.55 (s, 1H), 8.06 (s, 1H), 8.00 (d, 1H, J=7.5 Hz), 7.70 (m, 1H), 7.50 (m, 2H), 7.30–7.45 (m, 3H), 7.04–7.17 (m, 3H), 6.85–6.92 (m, 2H), 3.36 (s, 4H), 3.44 (s, 6H); MS(ESI) m/z 586.2 (M+H)$^+$.

Example 301

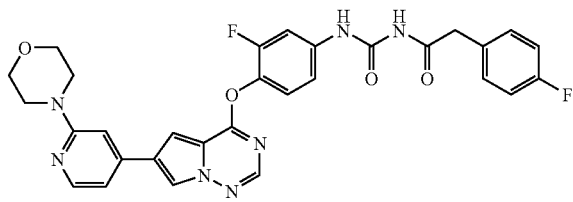

1-(3-Fluoro-4-(6-(2-morpholinopyridin-4-yl)pyrrolo[2,1-f][1,2,4]triazin-4-yloxy)phenyl)-3-(2-(4-fluorophenyl)acetyl)urea To a solution of 3-fluoro-4-(6-(2-morpholinopyridin-4-yl)pyrrolo[2,1-f][1,2,4]triazin-4-yloxy)benzenamine (15 mg, 0.037 mmol, Compound D of Example 300) in THF (1 mL) were added DIEA (0.1 mL, 0.57 mmol) and 2-(4-fluorophenyl)acetyl isocyanate (0.347 M, 0.21 mL, 0.074 mmol, Compound C of Example 4). The reaction mixture was stirred at room temperature for 1 h and the precipitate was collected on a Buchner funnel and washed with toluene to give the title compound (10 mg, 46%). $^1$H NMR (DMSO-d$_6$) δ 11.05 (s, 1H), 10.60 (s, 1H), 8.71 (s, 1H), 8.62 (s, 1H), 8.13 (s, 1H), 8.09 (d, 1H, J=7.5 Hz), 7.80 (d, 1H, J=8.0 Hz), 7.35–7.54 (m, 5H), 7.18 (t, 2H, J=7.5 Hz), 6.91 (d, 1H, J=8.0 Hz), 3.71–3.76 (m, 6H), 3.48–3.51 (m, 4H); MS(ESI) m/z 586.2 (M+H)$^+$.

Example 302

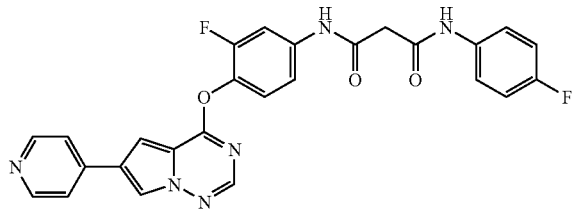

N$^1$-(3-Fluoro-4-(6-(pyridin-4-yl)pyrrolo[2,1-f][1,2,4]triazin-4-yloxy)phenyl)-N$^3$-(4-fluorophenyl)malonamide, trifluoroacetic acid salt

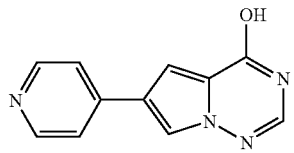

A) 6-(Pyridin-4-yl)pyrrolo[2,1-f][1,2,4]triazin-4-ol

Following a similar procedure as described in Step A of Example 300, 6-(pyridin-4-yl)pyrrolo[2,1-f][1,2,4]triazin-4-ol (100 mg, 0.47 mmol) was coupled with pyridin-4-ylboronic acid (172 mg, 1.40 mmol) to provide the title compound (72 mg, 72%). MS(ESI) m/z 213.2 (M+H)$^+$.

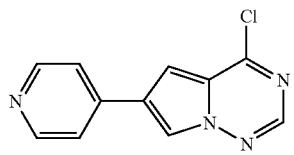

B) 4-Chloro-6-(pyridin-4-yl)pyrrolo[2,1-f][1,2,4]triazine

Following a similar procedure as described in Step B of Example 300, 6-(pyridin-4-yl)pyrrolo[2,1-f][1,2,4]triazin-4-ol (62 mg, 0.29 mmol) was converted to the title compound (30 mg, 45%). MS(ESI) m/z 231.1/233.1 (M+H)$^+$.

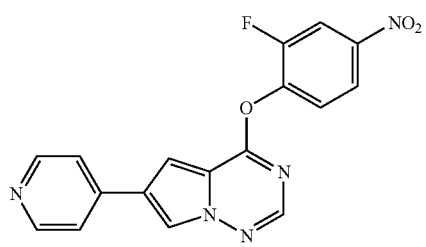

C) 4-(2-Fluoro-4-nitrophenoxy)-6-(pyridin-4-yl) pyrrolo[2,1-f][1,2,4]triazine Following a similar procedure as described in Step C of Example 300, 4-chloro-6-(pyridin-4-yl)pyrrolo[2,1-f][1,2,4]triazine (37 mg, 0.16 mmol) was converted to the desired compound (50 mg, 89%). MS(ESI) m/z 352.2 (M+H)+.

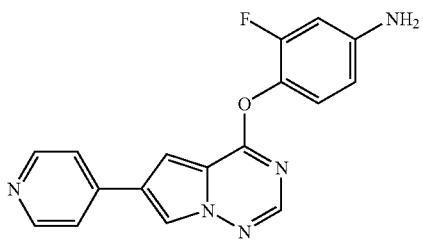

D) 3-Fluoro-4-(6-(pyridin-4-yl)pyrrolo[2,1-f][1,2,4]triazin-4-yloxy)benzenamine Following a similar procedure as described in Step D of example 300, 4-(2-fluoro-4-nitrophenoxy)-6-(pyridin-4-yl)pyrrolo[2,1-f][1,2,4]triazine (50 mg, 0.14 mmol) was converted to the desired compound (50 mg, quantitative yield). MS(ESI) m/z 322.3 (M+H)+.

E) N¹-(3-Fluoro-4-(6-(pyridin-4-yl)pyrrolo[2,1-f][1,2,4]triazin-4-yloxy)phenyl)-N³-(4-fluorophenyl)malonamide, trifluoroacetic acid salt Following a similar procedure as described in Step E of Example 300, 3-fluoro-4-(6-(pyridin-4-yl)pyrrolo[2,1-f][1,2,4]triazin-4-yloxy)benzenamine (20 mg, 0.06 mmol) was converted to the title compound (8.5 mg, 28%). ¹H NMR (DMSO-$d_6$) δ 10.53 (s, 1H), 10.27 (s, 1H), 9.06 (s, 1H), 8.80 (d, 2H, J=7.0 Hz), 8.30 (d, 2H, J=6.0 Hz), 8.24 (s, 1H), 7.98 (s, 1H), 7.80 (d, 1H, J=8.0 Hz), 7.60 (m, 2H), 7.35–7.45 (m, 2H), 7.16 (t, 2H, J=8.0 Hz), 3.49 (s, 2H); MS(ESI) m/z 501.2 (M+H)+.

Example 303

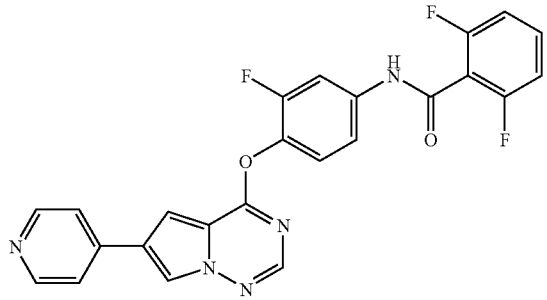

2,6-Difluoro-N-(3-fluoro-4-(6-(pyridin-4-yl)pyrrolo[2,1-f][1,2,4]triazin-4-yloxy)phenyl)benzamide, trifluoroacetic acid salt To a solution of 3-fluoro-4-(6-(pyridin-4-yl)pyrrolo[2,1-f][1,2,4]triazin-4-yloxy)benzenamine (20 mg, 0.06 mmol, Compound D of Example 302) in DCM (1 mL) were added DIEA (0.1 mL, 0.57 mmol) and a solution of 2,6-difluorobenzoyl chloride in DCM (0.5 M, 0.14 mL, 0.07 mmol) at room temperature. The reaction mixture was stirred for 0.5 h and quenched with 1 N NH₄OH. The solution was then concentrated in vacuo and the residue was purified by preparative HPLC to give the title compound (15 mg, 54%). ¹H NMR (DMSO-$d_6$) δ 11.09 (s, 1H), 8.96 (s, 1H), 8.70 (m, 2H), 8.18 (s, 1H), 8.10 (br. s, 2H), 7.90 (s, 1H), 7.80 (d, 1H, J=8.0 Hz), 7.45–7.55 (m, 3H), 7.23 (t, 2H, J=8.0 Hz); MS(ESI) m/z 462.2 (M+H)+.

Example 304

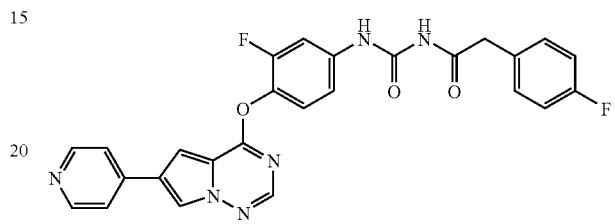

1-(3-Fluoro-4-(6-(pyridin-4-yl)pyrrolo[2,1-f][1,2,4]triazin-4-yloxy)phenyl)-3-(2-(4-fluorophenyl)acetyl)urea, trifluoroacetic acid salt Following a similar procedure as described in Example 301, 3-fluoro-4-(6-(pyridin-4-yl)pyrrolo[2,1-f][1,2,4]triazin-4-yloxy)benzenamine (16 mg, 0.05 mmol, Compound D of Example 302) was converted to the title compound (6.5 mg, 26%). ¹H NMR (DMSO-$d_6$) δ 10.99 (s, 1H), 10.55 (s, 1H), 9.04 (s, 1H), 8.78 (d, 2H, J=6.4 Hz), 8.31 (d, 2H, J=6.4 Hz), 8.20 (s, 1H), 7.96 (s, 1H), 7.72 (m, 1H), 7.09–7.44 (m, 6H), 3.69 (s, 2H); MS(ESI) m/z 501.2 (M+H)+.

Example 305

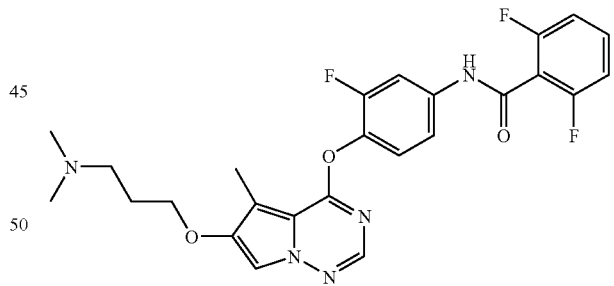

N-(4-(6-(3-(Dimethylamino)propoxy)-5-methylpyrrolo[2,1-f][1,2,4]triazin-4-yloxy)-3-fluorophenyl)-2,6-difluorobenzamide, hydrochloride salt Following a similar procedure as described in Example 134, 4-(6-(3-(dimethylamino)propoxy)-5-methylpyrrolo[2,1-f][1,2,4]triazin-4-yloxy)-3-fluorobenzenamine (36 mg, 0.1 mmol, Compound B of Example 32) was converted to the title compound (20 mg, 40%). ¹H NMR (DMSO-$d_6$) δ 11.17 (s, 1H), 10.40 (s, 1H), 8.00 (d, 2H, J=4.0 Hz), 7.86 (d, 1H, J=12.0 Hz), 7.65 (m, 1H), 7.51 (d, 2H, J=5.0 Hz), 7.29 (t, 2H, J=8.0 Hz), 4.15 (m, 2H), 3.24 (m, 2H), 2.80 (s, 6H), 2.40 (s, 3H), 2.18 (m, 2H); MS(ESI) m/z 500.3 (M+H)+.

Example 306

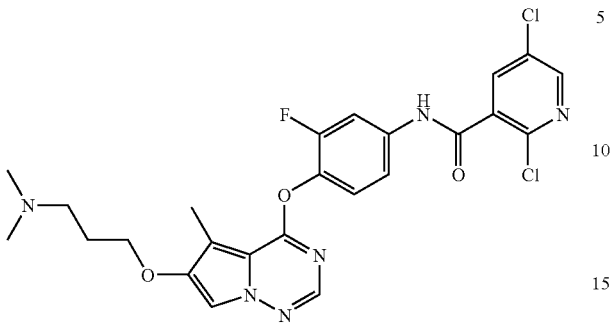

2,5-Dichloro-N-(4-(6-(3-(dimethylamino)propoxy)-5-methylpyrrolo[2,1-f][1,2,4]triazin-4-yloxy)-3-fluorophenyl)nicotinamide, hydrochloride salt Following a similar procedure as described in Example 134, 4-(6-(3-(dimethylamino)propoxy)-5-methylpyrrolo[2,1-f][1,2,4]triazin-4-yloxy)-3-fluorobenzenamine (36 mg, 0.1 mmol, Compound B of Example 32) was converted to the title compound (10 mg, 18%). $^1$H NMR (DMSO-$d_6$) δ 11.12 (s, 1H), 10.50 (s, 1H), 8.69 (s, 1H), 8.42 (s, 1H), 8.00 (s, 1H), 7.86 (d, 1H, J=12 Hz), 7.52 (s, 1H), 7.38 (s, 1H), 7.25 (s, 1H), 7.12 (s, 1H), 4.12 (m, 2H), 3.26 (m, 2H), 2.78 (s, 6H), 2.41 (s, 3H), 2.20 (m, 2H); MS(ESI) m/z 533.2 (M+H)$^+$.

Example 307

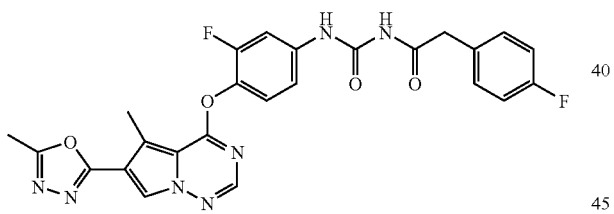

1-(3-Fluoro-4-(5-methyl-6-(5-methyl-1,3,4-oxadiazol-2-yl)pyrrolo[2,1-f][1,2,4]triazin-4-yloxy)phenyl)-3-(2-(4-fluorophenyl)acetyl)urea

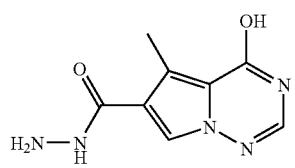

A) 4-Hydroxy-5-methylpyrrolo[2,1-f][1,2,4]triazine-6-carbohydrazide

Ethyl 4-hydroxy-5-methylpyrrolo[2,1-f][1,2,4]triazine-6-carboxylate (467 mg, 2.11 mmol, preparation: See U.S. Pat. No. 6,670,357) was dissolved in N$_2$H$_4$H$_2$O/EtOH (4:1, 5 mL). The solution was heated at 88° C. for 4 h, cooled to rt, and concentrated in vacuo to give the title compound (450 mg, >95%). MS(ESI) m/z 208.1 (M+H)$^+$.

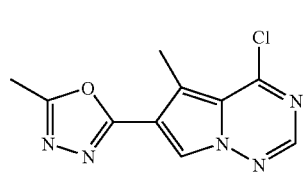

B) 4-Chloro-5-methyl-6-(5-methyl-1,3,4-oxadiazol-2-yl)pyrrolo[2,1-f][1,2,4]triazine To a suspension of 4-hydroxy-5-methylpyrrolo[2,1-f][1,2,4]triazine-6-carbohydrazide (100 mg, 0.48 mmol) in POCl$_3$ (5 mL) was added AcOH (50 mg, 0.83 mmol). The reaction mixture was heated at 80° C. for 3 d, cooled to rt, and concentrated in vacuo. The resulting residue was dissolved in EtOAc and treated with sat. aq. NaHCO$_3$ solution, brine, and dried over MgSO$_4$. Filtration, followed by concentration, provide the title compound, which was used directly in next step. MS (ESI) m/z 250.1/252.1 (M+H)$^+$.

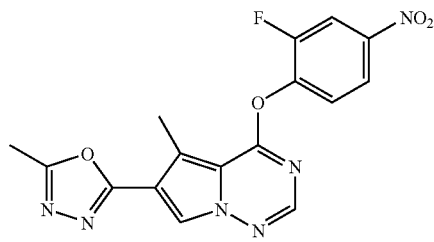

C) 4-(2-Fluoro-4-nitrophenoxy)-5-methyl-6-(5-methyl-1,3,4-oxadiazol-2-yl)pyrrolo[2,1-f][1,2,4]triazine Following a similar procedure as described in Step C of Example 300, 4-chloro-5-methyl-6-(5-methyl-1,3,4-oxadiazol-2-yl)pyrrolo[2,1-f][1,2,4]triazine was converted to the title compound (50 mg, 28% in two steps). MS(ESI) m/z 371.2 (M+H)$^+$.

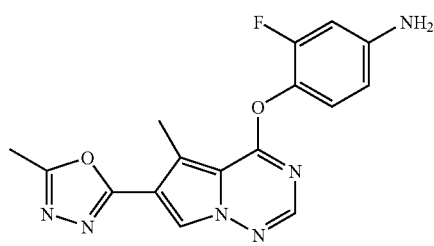

D) 3-Fluoro-4-(5-methyl-6-(5-methyl-1,3,4-oxadiazol-2-yl)pyrrolo[2,1-f][1,2,4]triazin-4-yloxy)benzenamine Following a similar procedure as described in Step D of Example 300, 4-(2-fluoro-4-nitrophenoxy)-5-methyl-6-(5- methyl-1,3,4-oxadiazol-2-yl)pyrrolo[2,1-f][1,2,4]triazine (50 mg, 0.13 mmol) was converted to the title compound (45 mg, >95%). MS(ESI) m/z 341.2 (M+H)+.

E) 1-(3-Fluoro-4-(5-methyl-6-(5-methyl-1,3,4-oxadiazol-2-yl)pyrrolo[2,1-f][1,2,4]triazin-4-yloxy)phenyl)-3-(2-(4-fluorophenyl)acetyl)urea Following a similar procedure as described for Example 301, 3-fluoro-4-(5-methyl-6-(5-methyl-1,3,4-oxadiazol-2-yl)pyrrolo[2,1-f][1,2,4]triazin-4-yloxy)benzenamine (20 mg, 0.06 mmol) was converted to the title compound (11 mg, 35%). $^1$H NMR (CDCl$_3$) δ 10.80 (s, 1H), 8.69 (s, 1H), 8.18 (s, 1H), 7.96 (s, 1H), 7.70 (m, 1H), 7.10–7.30 (m, 6H), 3.75 (s, 2H), 2.92 (s, 3H), 2.64 (s, 3H); MS(ESI) m/z 520.2 (M+H)+.

Example 308

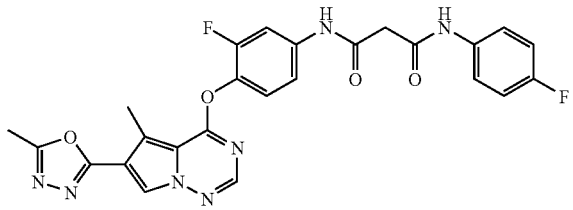

N$^1$-(3-Fluoro-4-(5-methyl-6-(5-methyl-1,3,4-oxadiazol-2-yl)pyrrolo[2,1-f][1,2,4]triazin-4-yloxy)phenyl)-N$^3$-(4-fluorophenyl)malonamide Following a similar procedure as described in Step E of Example 300, 3-fluoro-4-(5-methyl-6-(5-methyl-1,3,4-oxadiazol-2-yl)pyrrolo[2,1-f][1,2,4]triazin-4-yloxy)benzenamine (20 mg, 0.06 mmol) was converted to the title compound (8 mg, 26%). $^1$H NMR (CDCl$_3$) δ 9.26 (s, 1H), 8.47 (s, 1H), 8.21 (s, 1H), 7.96 (s, 1H), 7.80 (m, 1H), 7.50 (m, 2H), 7.10–7.30 (m, 4H), 3.60 (s, 2H), 2.93 (s, 3H), 2.69 (s, 3H); MS (ESI) m/z 520.1 (M+H)+.

Example 309

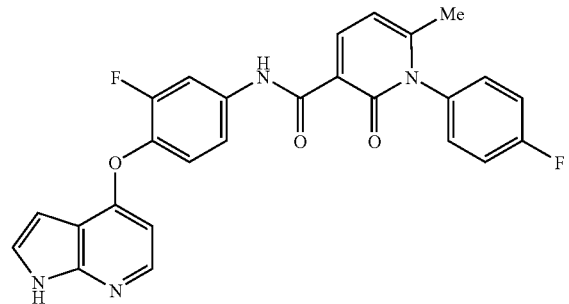

N-(4-(1H-Pyrollo[2,3-b]pyridin-4-yloxy)-3-fluorophenyl)-1-(4-fluorophenyl)-6-methyl-2-oxo-1,2-dihydropyridine-3-carboxamide

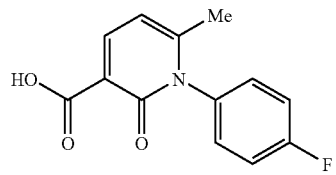

A) 1-(4-Fluorophenyl)-6-methyl-2-oxo-1,2-dihydropyridine-3-carboxylic acid

Prepared in a similar manner as Steps B and C of Example 294 using 2-hydroxy-6-methylnicotinic acid (Aldrich). $^1$H NMR (DMSO-d$_6$) δ 8.41 (d, 1H, J=6.5 Hz), 8.08 (s, 1H), 7.51–7.48 (m, 4H), 6.81 (d, 1H, J=6.5 Hz), 2.10 (s, 3H); MS(ESI+) m/z 248 (M+H)+.

B) N-(4-(1H-Pyrrolo[2,3-b]pyridin-4-yloxy)-3-fluorophenyl)-1-(4-fluorophenyl)-6-methyl-2-oxo-1,2-dihydropyridine-3-carboxamide Prepared in a similar manner as Step D of Example 294 (21% yield). $^1$H NMR (DMSO-d$_6$) δ 12.11 (s, 1H), 11.83 (s, 1H), 8.56 (d, 1H, J=6.5 Hz), 8.13 (d, 1H, J=5.5 Hz), 8.01 (dd, 1H, J=10.4, 2.6 Hz), 7.56–7.50 (m, 7H), 6.78 (d, 1H, J=6.5 Hz), 6.44 (d, 1H, J=5.5 Hz), 6.30 (s, 1H), 2.14 (s, 3H); MS(ESI+) m/z 473 (M+H)$^{30}$.

Example 310

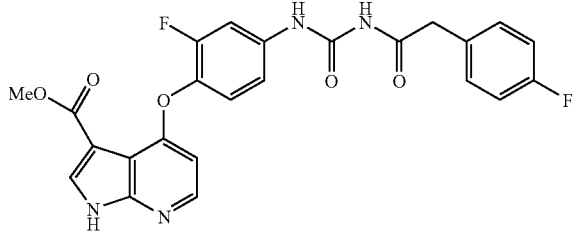

Methyl 4-(2-fluoro-4-(3-(2-(4-fluorophenyl)acetyl)ureido)phenoxy)-1H-pyrrolo[2,3-b]pyridine-3-carboxylate A) Methyl 4-(2-fluoro-4-nitrophenoxy)-1H-pyrrolo[2,3-b]pyridine-3-carboxylate To a solution of 2,2,2-trichloro-1-(4-(2-fluoro-4-nitrophenoxy)-1H-pyrrolo[2,3-b]pyridin-3-yl)ethanone (490 mg, 1.17 mmol, See: Step A of Example 270) in a mixed solvent (10 mL of MeOH and 10 mL of THF) was added 1 N NaOH (10 mL, 10 mmol). The reaction mixture was stirred at room temperature for 3 h, and diluted with EtOAc (30 mL). The organic layer was washed with sat. aq. NaHCO$_3$, solution, dried and concentrated in vacuo to give the desired product (235 mg, 61%) as a light brown solid. MS(ESI+) m/z 332.2 (M+H)+.

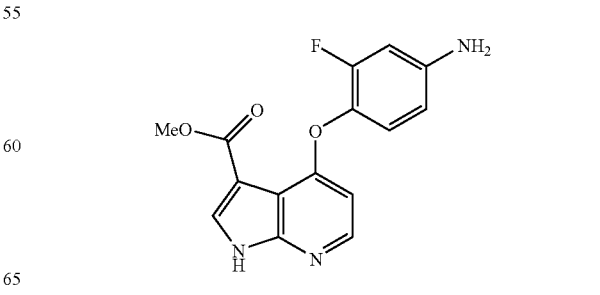

B) Methyl 4-(4-amino-2-fluorophenoxy)-1H-pyrrolo[2,3-b]pyridine-3-carboxylate

To a solution of methyl 4-(2-fluoro-4-nitrophenoxy)-1H-pyrrolo[2,3-b]pyridine-3-carboxylate (230 mg, 0.69 mmol) in a mixed solvent (10 mL of MeOH and 10 mL of THF) were added ammonium chloride (185 mg, 3.45 mmol) and zinc dust (226 mg, 3.45 mmol). The reaction mixture was stirred at room temperature overnight, diluted with EtOAc (50 ml), and filtered through a pad of Celite®. The filtrate was concentrated in vacuo to give the desired product (207 mg, 100%) as a yellow solid. MS(ESI+) m/z 302.2 (M+H)+.

C) Methyl 4-(2-fluoro-4-(3-(2-(4-fluorophenyl)acetyl)ureido)phenoxy)-1H-pyrrolo[2,3-b]pyridine-3-carboxylate Prepared in a similar manner as Step C of Example 132 (61 mg, 36%). $^1$H NMR (DMSO-d$_6$) δ 11.01 (s, 1H), 10.54 (s, 1H), 8.15 (s, 1H), 8.14 (d, 1H, J=5.5 Hz), 7.74 (dd, 1H, J=12.5, 2.2 Hz), 7.31–7.36 (m, 3H), 7.14–7.19 (m, 3H), 6.45 (d, 1H, J=5.5 Hz), 3.73 (s, 2H), 3.69 (s, 3H). MS(ESI+) m/z 481.1 (M+H)+.

Example 311

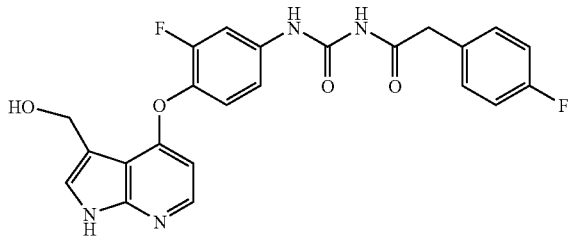

1-(3-Fluoro-4-(3-(hydroxymethyl)-1H-pyrrolo[2,3-h]pyridin-4-yloxy)phenyl)-3-(2-(4-fluorophenyl)acetyl)urea Example 312

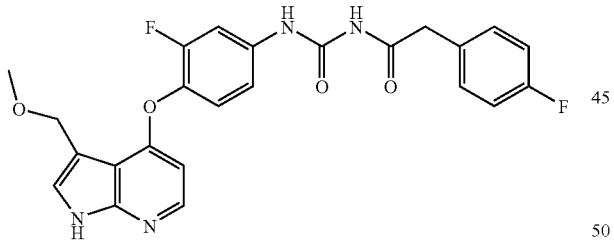

1-(3-Fluoro-4-(3-(methoxymethyl)-1H-pyrrolo[2,3-b]pyridin-4-yloxy)phenyl)-3-(2-(4-fluorophenyl)acetyl)urea To a solution of methyl 4-(2-fluoro-4-(3-(2-(4-fluorophenyl)acetyl)ureido) phenoxy)-1H-pyrrolo[2,3-b]pyridine-3-carboxylate (19.2 mg, 0.04 mmol, Compound C of Example 310) in THF (1 mL) at 0° C. was added DIBAL-H (1.5 M soln in toluene, 133 μL, 0.2 mmol, Aldrich). The reaction mixture was stirred at 0° C. for 2 h, and quenched by adding 2 mL of methanol. The reaction mixture was concentrated in vacuo and purified by preparative HPLC. The desired fractions were combined, concentrated in vacuo and lyophilized to give a white solid. LC/MS indicated that the solid contained two compounds. The solid was purified again by flash column chromatography (ISCO RediSep® silica gel cartridge, eluting with 1–10% MeOH in dichloromethane) to afford Examples 311 and 312. For 1-(3-fluoro-4-(3-(hydroxymethyl)-1H-pyrrolo[2,3-b]pyridin-4-yloxy)phenyl)-3-(2-(4-fluorophenyl)acetyl)urea (Example 311, 7.47 mg, 42%): $^1$H NMR (DMSO-d$_6$) δ 11.47 (s, 1H), 10.94 (s, 1H), 10.49 (s, 1H), 7.92 (d, 1H, J=5.5 Hz), 7.68 (dd, 1H, J=13.2, 2.2 Hz), 7.31–7.19 (m, 5H), 7.09 (t, 2H, J=8.8 Hz), 6.10 (d, 1H, J=5.5 Hz), 4.68 (q, 1H, J=5.5 Hz), 4.65 (d, 1H, J=5.5 Hz), 3.67 (s, 2H); MS(ESI+) m/z 453.3 (M+H)+. For 1-(3-Fluoro-4-(3-(methoxymethyl)-1H-pyrrolo[2,3-b]pyridin-4-yloxy)phenyl)-3-(2-(4-fluorophenyl)acetyl)urea (Example 312): $^1$H NMR (DMSO-d$_6$) δ 11.67 (s, 1H), 10.97 (s, 1H), 10.64 (s, 1H), 7.96 (d, 1H, J=5.5 Hz), 7.68 (d, 1H, J=12.5), 7.34–7.28 (m, 5H), 7.23 (t, 1H, J=8.8 Hz), 7.01 (t, 2H, J=8.8 Hz), 6.16 (d, 1H, J=5.5 Hz), 4.54 (s, 2H), 3.70 (s, 2H), 3.18 (s, 3H); MS(ESI+) m/z 467.2 (M+H)+.

Example 313

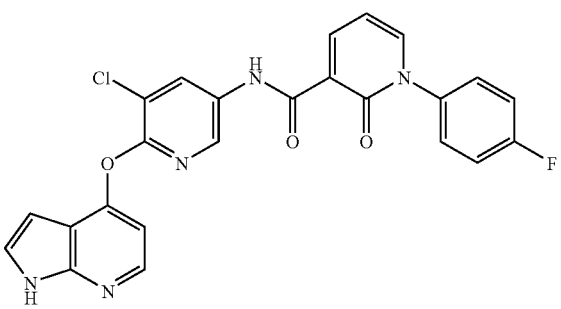

N-(6-(1H-Pyrollo[2,3-b]pyridin-4-yloxy)-5-chloropyridin-3-yl)-1-(4-fluorophenyl)-2-oxo-1,2-dihydropyridine-3-carboxamide, trifluoroacetic acid salt

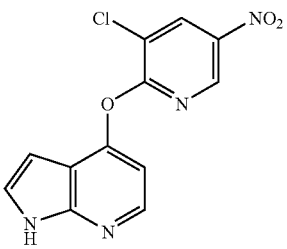

A) 4-(3-Chloro-5-nitropyridin-2-yloxy)-1H-pyrrolo[2,3-b]pyridine

To a solution of 1H-pyrrolo[2,3-b]pyridin-4-ol (210 mg, 1.56 mmol, see: Thibault, C. et al. Org. Lett. 2003, 5, 5023) in 3 mL of MeCN was added K$_2$CO$_3$ (240 mg, 1.74 mmol). The suspension was stirred for 10 min and treated with 2,3-dichloro-5-nitropyridine (270 mg, 1.40 mmol, see: Koch, V. and Schnatterer, S. Synthesis, 1990, 499). The reaction mixture was stirred for 12 h and quenched with 20 mL of H$_2$O. The solution was extracted with EtOAc and the organic layer was washed with brine, and dried over MgSO$_4$. After filtration and concentration in vacuo, the residue was purified by flash column chromatography (ISCO RediSep® silica gel cartridge) to give the title compound (220 mg, 54%). MS (ESI) m/z 291.1 (M+H)+.

233

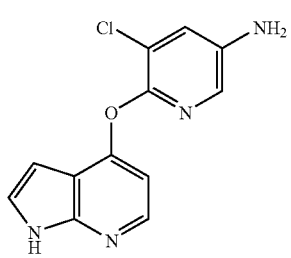

B) 6-(1H-Pyrrolo[2,3-b]pyridin-4-yloxy)-5-chloro-pyridin-3-amine

Following a similar procedure as described in Step B of Example 132, 4-(3-chloro-5-nitropyridin-2-yloxy)-1H-pyrrolo[2,3-b]pyridine (140 mg, 0.48 mmol) was reduced to the title compound (90 mg, 72%). MS(ESI) m/z 261.1 (M+H)$^+$.

C) N-(6-(1H-Pyrrolo[2,3-b]pyridin-4-yloxy)-5-chloropyridin-3-yl)-1-(4-fluorophenyl)-2-oxo-1,2-dihydropyridine-3-carboxamide, trifluoroacetic acid salt Following a similar procedure as described in Step C of Example 242, 6-(1H-pyrrolo[2,3-b]pyridin-4-yloxy)-5-chloropyridin-3-amine, dihydrochloride (14 mg, 0.042 mmol) was converted to the title compound (5.0 mg, 20%). $^1$H NMR (DMSO-d$_6$) δ 12.08 (s, 1H), 11.86 (s, 1H), 8.67 (d, 1H, J=2.0 Hz), 8.57 (dd, 1H, J=7.0. 2.0 Hz), 8.41 (d, 1H, J=2.0 Hz), 8.18 (d, 1H, J=5.5 Hz), 8.14 (dd, 1H, J=6.5, 2.0 Hz), 7.60 (dd, 2H, J=9.0, 5.0 Hz), 7.38–7.43 (m, 3H), 6.76 (d, 1H, J=5.5 Hz), 6.73 (t, 1H, J=7.0 Hz), 6.08 (m, 1H); MS(ESI) m/z 476.2 (M+H)$^+$.

Example 314

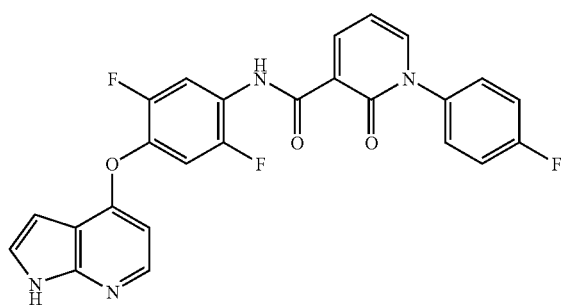

N-(4-(1H-Pyrrolo[2,3-b]pyridin-4-yloxy)-2,5-difluorophenyl)-1-(4-fluorophenyl)-2-oxo-1,2-dihydropyridine-3-carboxamide, trifluoroacetic acid salt

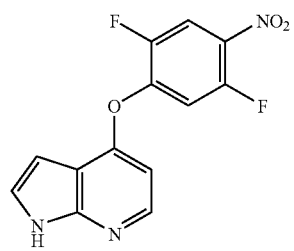

A) 4-(2,5-Difluoro-4-nitrophenoxy)-1H-pyrrolo[2,3-b]pyridine

Following a similar procedure as described in Step A of Example 313 and using 1,2,4-trifluoro-5-nitrobenzene,

234

1H-pyrrolo[2,3-b]pyridin-4-ol (268 mg, 2.0 mmol) was converted to the title compound (230 mg, 40%). MS(ESI) m/z 292.2 (M+H)$^+$.

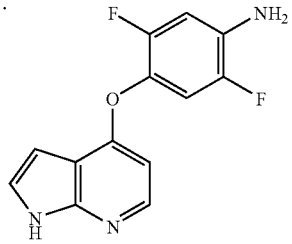

B) 4-(1H-Pyrrolo[2,3-b]pyridin-4-yloxy)-2,5-difluorobenzenamine

Following a similar procedure as described in Step B of Example 132, 4-(2,5-difluoro-4-nitrophenoxy)-1H-pyrrolo[2,3-b]pyridine (230 mg, 0.79 mmol) was converted to the title compound (34 mg, 17%). MS(ESI) m/z 262.2 (M+H)$^+$.

C) N-(4-(1H-pyrrolo[2,3-b]pyridin-4-yloxy)-2,5-difluorophenyl)-1-(4-fluorophenyl)-2-oxo-1,2-dihydropyridine-3-carboxamide, trifluoroacetic acid Following a similar procedure as described in Step C of Example 242, 4-(1H-pyrrolo[2,3-b]pyridin-4-yloxy)-2,5-difluorobenzenamine, dihydrochloride (14 mg, 0.042 mmol) was converted to the title compound (4.5 mg, 18%). $^1$H NMR (DMSO-d$_6$) δ 12.42 (s, 1H); 11.86 (s, 1H), 8.61 (dd, 1H, J=7.0, 2.0 Hz), 8.55 (dd, 1H, J=12.5, 7.0 Hz), 8.15 (dd, 1H, J=6.5, 2.0 Hz), 8.10 (d, 1H, J=6.5 Hz), 7.57–7.62 (m, 3H), 7.40–7.44 (m, 3H), 6.75 (t, 1H, J=7.0 Hz), 6.47 (d, 1H, J=5.5 Hz), 6.29 (m, 1H); MS(ESI) m/z 477.2 (M+H)$^+$.

Example 315

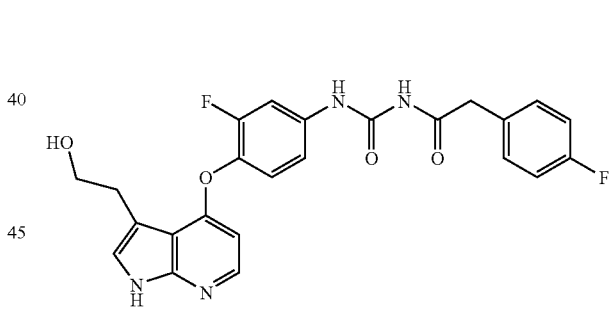

1-(3-Fluoro-4-(3-(2-hydroxyethyl)-1H-pyrrolo[2,3-b]pyridin-4-yloxy)phenyl)-3-(2-(4-fluorophenyl)acetyl)urea

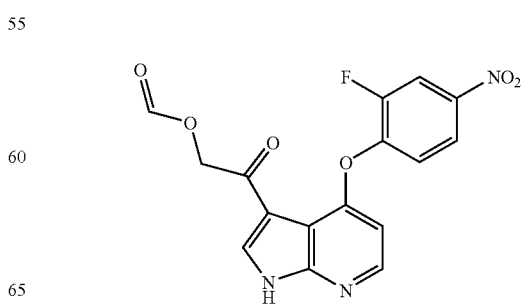

A) 2-(4-(2-Fluoro-4-nitrophenoxy)-1H-pyrrolo[2,3-b]pyridin-3-yl)-2-oxoethyl formate To a solution of 2-bromo-1-(4-(2-fluoro-4-nitrophenoxy)-1H-pyrrolo[2,3-b]pyridin-3-yl)ethanone (100 mg, 0.25 mmol, Compound A of Example 253) in 1 mL of DMF was added sodium formate (52 mg, 0.75 mmol, Aldrich). The reaction mixture was stirred at room temperature for 4 h, and diluted with sat. aq. $K_2HPO_4$ (2 mL). The precipitate that formed was collected by filtration, washed with cold $H_2O$ (2 mL) and ether (5 mL), and dried under vacuum to afford the desired product (81 mg, 90%) as a light brown solid. $MS(ESI^+)$ m/z 360.16 $(M+H)^+$.

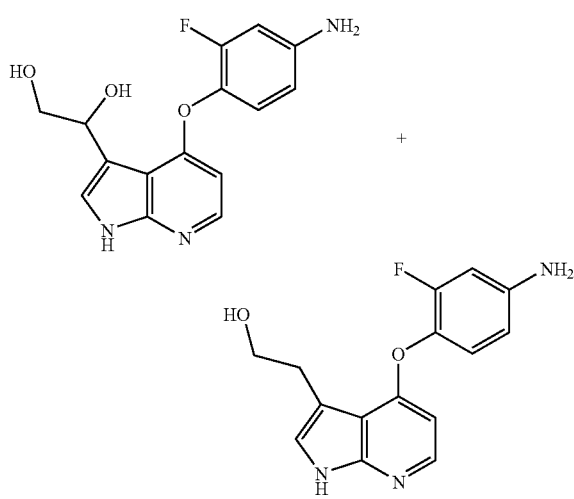

B) 1-(4-(4-Amino-2-fluorophenoxy)-1H-pyrrolo[2,3-b]pyridin-3-yl)ethane-1,2-diol and 2-(4-(4-Amino-2-fluorophenoxy)-1H-pyrrolo[2,3-b]pyridin-3-yl)ethanol To a suspension of anhydrous aluminum hydride (266 mg, 2.0 mmol, Alfa Aesar) in 5 mL of 1,2 dimethoxyethane at 0° C. was added lithium aluminum hydride (1 M soln. in THF, 1.0 mL, 1.0 mmol). A solution of 2-(4-(2-fluoro-4-nitrophenoxy)-1H-pyrrolo[2,3-b]pyridin-3-yl)-2-oxoethyl formate (72 mg, 0.2 mmol) in 5 mL of 1,2-dimethoxyethane was added dropwise. The reaction mixture was stirred at rt for 2 h and quenched by the addition of 5 mL of cold water. The mixture was extracted with EtOAc (3×30 mL) and the combined organic extracts were dried ($MgSO_4$), concentrated in vacuo and purified by flash column chromatography (ISCO RediSep® silica gel cartridge, etuting with 2–10% MeOH in dichloromethane) to give 1-(4-(4-amino-2-fluorophenoxy)-1H-pyrrolo[2,3-b]pyridin-3-yl)ethane-1,2-diol (27 mg, 45%): $MS(ESI^+)$ m/z 304.3 (M+H)+ and 2-(4-(4-amino-2-fluorophenoxy)-1H-pyrrolo[2,3-b]pyridin-3-yl)ethanol (10 mg, 18%): $MS(ESI^+)$ m/z 288.3 $(M+H)^+$.

C) 1-(3-Fluoro-4-(3-(2-hydroxyethyl)-1H-pyrrolo[2,3-b]pyridin-4-yloxy)phenyl)-3-(2-(4-fluorophenyl)acetyl)urea Prepared from 2-(4-(4-amino-2-fluorophenoxy)-1H-pyrrolo[2,3-b]pyridin-3-yl)ethanol using a similar procedure as described for Example 264 (4.5 mg, 28%). $^1H$ NMR ($CD_3OD$) δ 10.74 (s, 1H), 8.06 (d, 1H, J=5.5 Hz), 7.74 (d, 1H, J=12.1 Hz), 7.29–7.25 (m, 4H), 7.00–6.96 (m, 3H), 6.51 (d, 1H, J=5.5 Hz), 3.80 (t, 2H, J=6.6 Hz), 3.62 (s, 2H), 3.06 (t, 2H, J=6.6 Hz); $MS(ESI^+)$ m/z 467.3 $(M+H)^+$.

Example 316

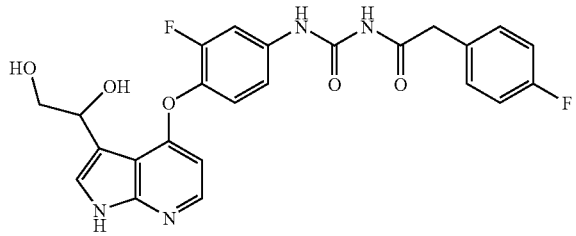

1-(4-(3-(1,2-Dihydroxyethyl)-1H-pyrrolo[2,3-b]pyridin-4-yloxy)-3-fluorophenyl)-3-(2-(4-fluorophenyl)acetyl)urea

Example 317

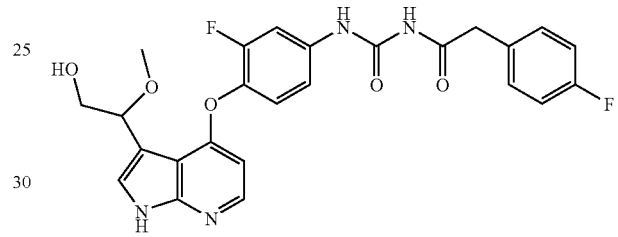

1-(3-Fluoro-4-(3-(2-hydroxy-1-methoxyethyl)-1H-pyrrolo[2,3-b]pyridin-4-yloxy)phenyl)-3-(2-(4-fluorophenyl)acetyl)urea Examples 316 and 317 were prepared from 1-(4-(4-amino-2-fluorophenoxy)-1H-pyrrolo[2,3-b]pyridin-3-yl)ethane-1,2-diol (see: Step B of Example 315) using a similar procedure as described for Example 264. The reaction mixture was concentrated in vacuo and purified by preparative HPLC. The desired fractions were combined, concentrated in vacuo and lyophilized to give a white solid. LC/MS indicated that the solid contained 1-(4-(3-(1,2-dihydroxyethyl)-1H-pyrrolo[2,3-b]pyridin-4-yloxy)-3-fluorophenyl)-3-(2-(4-fluorophenyl)acetyl)urea and 1-(3-fluoro-4-(3-(2-hydroxy-1-methoxyethyl)-1H-pyrrolo[2,3-b]pyridin-4-yloxy)phenyl)-3-(2-(4-fluorophenyl)acetyl)urea. The solid was purified again by flash column chromatography (ISCO RediSep® silica gel cartridge, eluting with 1–10% MeOH in dichloromethane) to afford two products: For 1-(4-(3-(1,2-dihydroxyethyl)-1H-pyrrolo[2,3-b]pyridin-4-yloxy)-3-fluorophenyl)-3-(2-(4-fluorophenyl)acetyl)urea (6.3 mg, 16%); $^1H$ NMR (DMSO-$d_6$) δ 11.57 (s, 1H), 11.03 (s, 1H), 10.59 (s, 1H), 7.99 (d, 1H, J=5.5 Hz), 7.77 (dd, 1H, J=12.6, 2.2 Hz), 7.41–7.32 (m, 4H), 7.28 (d, 1H, J=2.2 Hz), 7.18 (t, 1H, J=8.8 Hz), 7.01 (t, 2H, J=8.8 Hz), 6.15 (d, 1H, J=5.5 Hz), 5.05 (m, 1H), 4.91 (d, 1H, J=4.4 Hz), 4.60 (t, 1H, J=5.8 Hz), 3.79–3.75 (m, 1H), 3.75 (s, 2H), 3.47–3.44 (m, 1H); $MS(ESI^+)$ m/z 483.3 $(M+H)^+$. For 1-(3-fluoro-4-(3-(2-hydroxy-1-methoxyethyl)-1H-pyrrolo[2,3-b]pyridin-4-yloxy)phenyl)-3-(2-(4-fluorophenyl)acetyl)urea (3.2 mg, 8%); $^1H$ NMR ($CD_3OD$) δ 8.05 (d, 1H, J=5.5 Hz), 7.71 (d, 1H, J=12.1 Hz), 7.37 (s, 1H), 7.28–6.25 (m, 4H), 6.98 (t, 1H, J=8.2 Hz), 6.45 (d, 1H, J=5.5 Hz), 3.81 (m, 1H), 3.73–3.71 (m, 2H), 3.63 (s, 2H), 3.34 (s, 3H); $MS(ESI^+)$ m/z 497.2 $(M+H)^+$.

Example 318

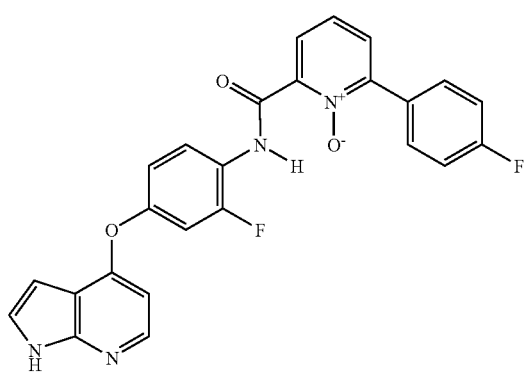

6-(4-Fluoro-phenyl)-1-oxy-pyridine-2-carboxylic acid [2-fluoro-4-(1H-pyrrolo[2,3-b]pyridin-4-yloxy)-phenyl]-amide Prepared in a similar manner as Example 241. HPLC $t_R$=3.328 min (YMC S5 ODS 4.6×50 mm, 10–90% aqueous methanol containing 0.2% $H_3PO_4$, 4 min gradient, monitored at 220 nm); MS(ESI$^+$) m/z 459.2 (M+H)$^+$.

Example 319

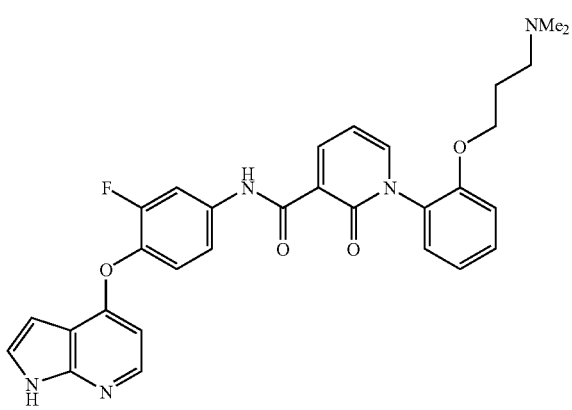

N-(4-(1H-Pyrrolo[2,3-b]pyridin-4-yloxy)-3-fluorophenyl)-1-(2-(3-(dimethylamino)propoxy)phenyl)-2-oxo-1,2-dihydropyridine-3-carboxamide, hydrochloride salt

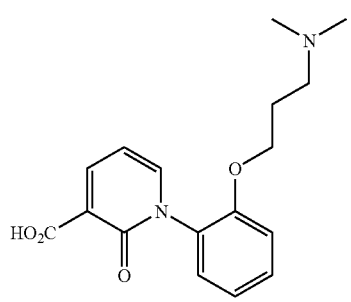

A) 1-(2-(3-(Dimethylamino)propoxy)phenyl)-2-oxo-1,2-dihydropyridine-3-carboxylic acid Prepared in a similar manner as Steps A and B of Example 242. $^1$H NMR (DMSO-$d_6$) δ 10.53 (br m, 1H), 8.51–8.53 (m, 1H), 8.18–8.20 (m, 1H), 7.48–7.51 (m, 2H), 7.30 (d, 1H, J=7.96 Hz), 7.13–7.17 (m, 1H), 6.82 (t, 1H, J=6.95 Hz), 4.11–4.18 (m, 2H), 2.66–2.68 (m, 2H), 2.67 (s, 6H), 1.98–2.05 (m, 2H); HRMS(ESI), calculated: 317.1501, found: 317.1490.

B) N-(4-(1H-Pyrrolo[2,3-b]pyridin-4-yloxy)-3-fluorophenyl)-1-(2-(3-(dimethylamino)propoxy)phenyl)-2-oxo-1,2-dihydropyridine-3-carboxamide, hydrochloride salt Prepared in a similar manner as Step C of Example 242. $^1$H NMR (CD$_3$OD) δ 8.62–8.65 (m, 1H), 8.23 (d, 1H, J=6.90 Hz), 7.98–8.01 (m, 1H), 7.83–7.85 (m, 1H), 7.39–7.50 (m, 2H), 7.31–7.49 (m, 3H), 7.20 (d, 1H, J=7.93), 7.10–7.13 (m, 1H), 6.80 (d, 1H, J=6.72 Hz), 6.69 (t, 1H, J=6.75 Hz), 6.59–6.60 (m, 1H), 4.12 (t, 2H, J=5.61 Hz), 3.02–3.06 (m, 2H), 2.70 (s, 6H), 2.03–2.04 (m, 2H); HRMS(ESI), calculated: 542.2204, found: 542.2194.

Example 320

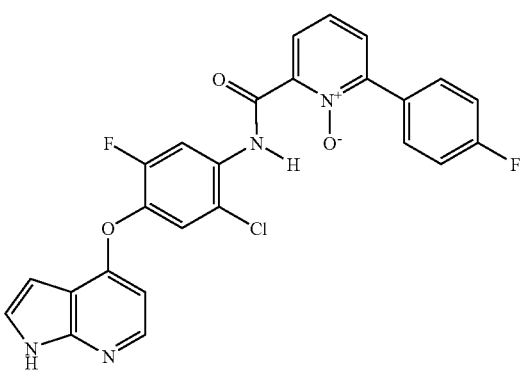

6-(4-Fluoro-phenyl)-1-oxy-pyridine-2-carboxylic acid [2-chloro-5-fluoro-4-(1H-pyrrolo[2,3-b]pyridin-4-yloxy)-phenyl]-amide Prepared in a similar manner as Example 241. HPLC $t_R$=3.293 min (Chromolith SpeedROD 4.6×50 mm, 10–90% aqueous methanol containing 0.1% TFA, 4 min gradient, monitored at 220 nm); MS(ESI$^+$) m/z 493 (M+H)$^+$.

Example 321

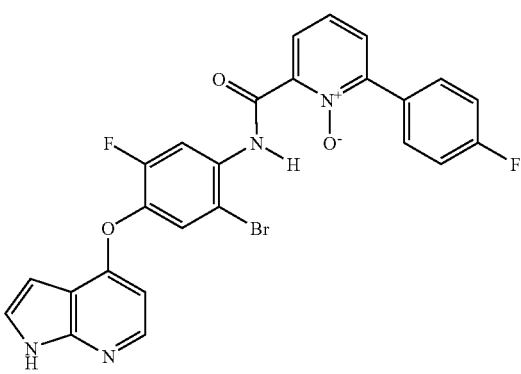

6-(4-Fluoro-phenyl)-1-oxy-pyridine-2-carboxylic acid [2-bromo-5-fluoro-4-(1H-pyrrolo[2,3-b]pyridin-4-yloxy)-phenyl]-amide Prepared in a similar manner as Example 241. HPLC $t_R$=3.371 min (Chromolith SpeedROD 4.6×50 mm, 10–90% aqueous methanol containing 0.1% TFA, 4 min gradient, monitored at 220 nm); MS(ESI$^+$) m/z 537 (M+H)$^+$.

Example 322

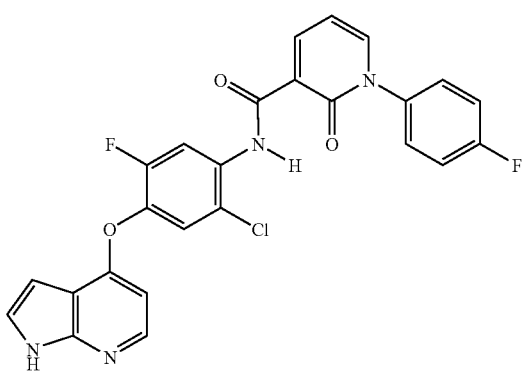

N-(4-(1H-Pyrrolo[2,3-b]pyridin-4-yloxy)-2-chloro-5-fluorophenyl)-1-(4-fluorophenyl)-2-oxo-1,2-dihydropyridine-3-carboxamide Prepared in a similar manner as Step C of Example 242. HPLC $t_R$=3.070 min (Chromolith SpeedROD 4.6×50 mm, 10–90% aqueous methanol containing 0.1% TFA, 4 min gradient, monitored at 220 nm); MS(ESI⁺) m/z 493 (M+H)⁺.

Example 323

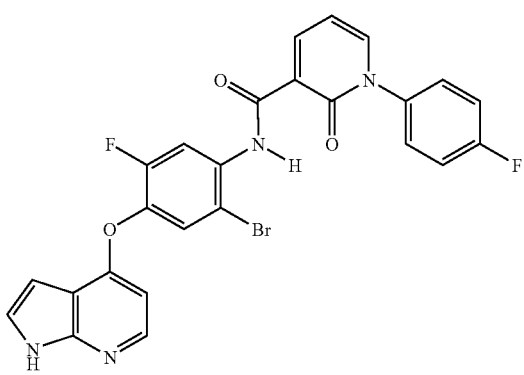

N-(4-(1H-Pyrrolo[2,3-b]pyridin-4-yloxy)-2-bromo-5-fluorophenyl)-1-(4-fluorophenyl)-2-oxo-1,2-dihydropyridine-3-carboxamide Prepared in a similar manner as Step C of Example 242. HPLC $t_R$=3.115 min (Chromolith SpeedROD 4.6×50 mm, 10–90% aqueous methanol containing 0.1% TFA, 4 min gradient, monitored at 220 nm); MS(ESI⁺) m/z 538 (M+H)⁺.

Example 324

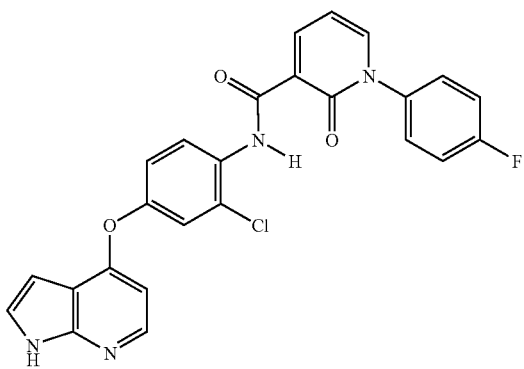

N-(4-(1H-Pyrrolo[2,3-b]pyridin-4-yloxy)-2-chlorophenyl)-1-(4-fluorophenyl)-2-oxo-1,2-dihydropyridine-3-carboxamide Prepared in a similar manner as Step C of Example 242. HPLC $t_R$=2.946 min (Chromolith SpeedROD 4.6×50 mm, 10–90% aqueous methanol containing 0.1% TFA, 4 min gradient, monitored at 220 nm); MS(ESI⁺) m/z 475 (M+H)⁺.

Example 325

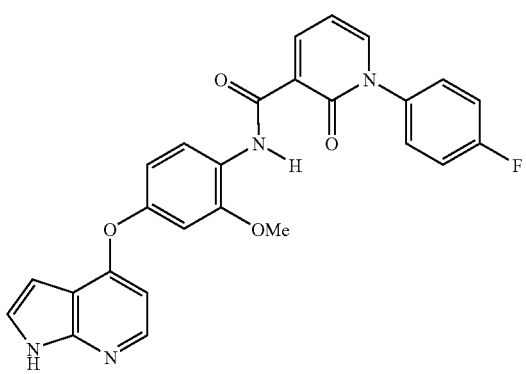

N-(4-(1H-Pyrrolo[2,3-b]pyridin-4-yloxy)-2-methoxyphenyl)-1-(4-fluorophenyl)-2-oxo-1,2-dihydropyridine-3-carboxamide Prepared in a similar manner as Step C of Example 242. HPLC $t_R$=2.795 min (Chromolith SpeedROD 4.6×50 mm, 10–90% aqueous methanol containing 0.1% TFA, 4 min gradient, monitored at 220 nm); MS(ESI⁺) m/z 471 (M+H)⁺.

Example 326

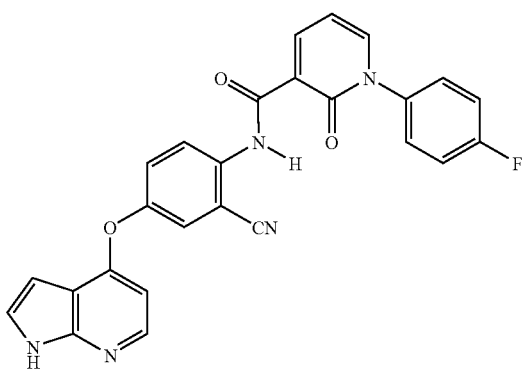

N-(4-(1H-Pyrollo[2,3-b]pyridin-4-yloxy)-2-cyanophenyl)-1-(4-fluorophenyl)-2-oxo-1,2-dihydropyridine-3-carboxamide Prepared in a similar manner as Step C of Example 242. HPLC $t_R$=2.618 min (Chromolith SpeedROD 4.6×50 mm, 10–90% aqueous methanol containing 0.1% TFA, 4 min gradient, monitored at 220 nm); MS(ESI⁺) m/z 466 (M+H)⁺.

Example 327

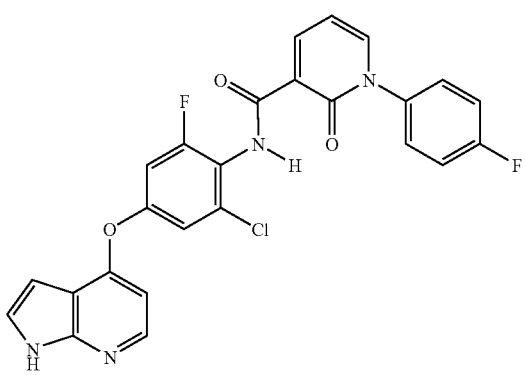

N-(4-(1H-Pyrrolo[2,3-b]pyridin-4-yloxy)-2-chloro-6-fluorophenyl)-1-(4-fluorophenyl)-2-oxo-1,2-dihydropyridine-3-carboxamide Prepared in a similar manner as Step C of Example 242. HPLC $t_R$=2.805 min (Chromolith SpeedROD 4.6×50 mm, 10–90% aqueous methanol containing 0.1% TFA, 4 min gradient, monitored at 220 nm); MS(ESI$^+$) m/z 493 (M+H)$^+$.

Example 328

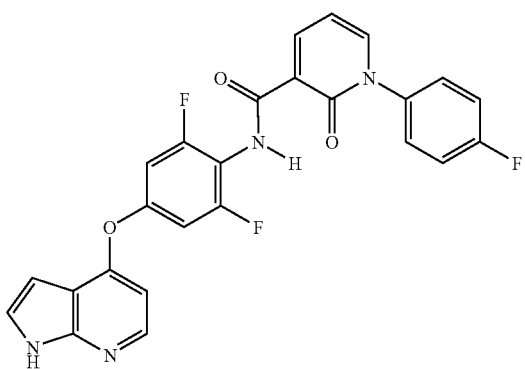

N-(4-(1H-Pyrrolo[2,3-b]pyridin-4-yloxy)-2,6-difluorophenyl)-1-(4-fluorophenyl)-2-oxo-1,2-dihydropyridine-3-carboxamide Prepared in a similar manner as Step C of Example 242. HPLC $t_R$=2.653 min (Chromolith SpeedROD 4.6×50 mm, 10–90% aqueous methanol containing 0.1% TFA, 4 min gradient, monitored at 220 nm); MS(ESI$^+$) m/z 477 (M+H)$^+$.

Example 329

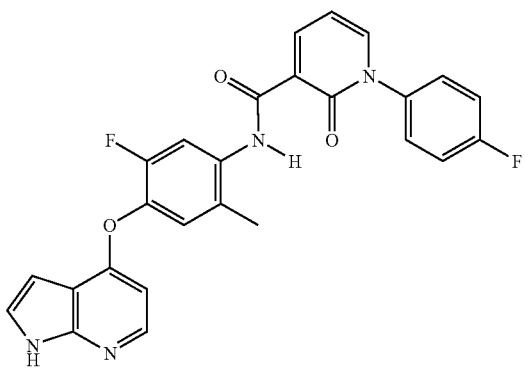

N-(4-(1H-Pyrrolo[2,3-b]pyridin-4-yloxy)-2-methyl-4-fluorophenyl)-1-(4-fluorophenyl)-2-oxo-1,2-dihydropyridine-3-carboxamide Prepared in a similar manner as Step C of Example 242. HPLC $t_R$=3.010 min (Chromolith SpeedROD 4.6×50 mm, 10–90% aqueous methanol containing 0.1% TFA, 4 min gradient, monitored at 220 nm); MS(ESI$^+$) m/z 473 (M+H)$^+$.

Example 330

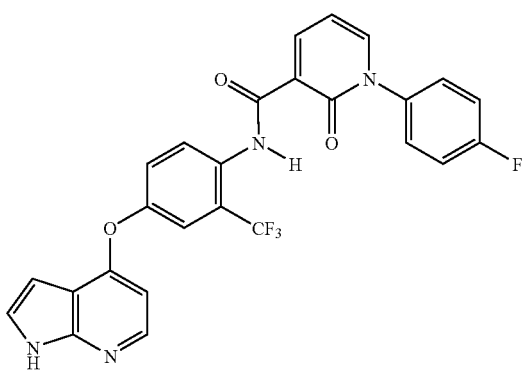

N-(4-(1H-Pyrrolo[2,3-b]pyridin-4-yloxy)-2-trifluoromethyl-phenyl)-1-(4-fluorophenyl)-2-oxo-1,2-dihydropyridine-3-carboxamide Prepared in a similar manner as Step C of Example 242. HPLC $t_R$=2.943 min (Chromolith SpeedROD 4.6×50 mm, 10–90% aqueous methanol containing 0.1% TFA, 4 min gradient, monitored at 220 nm); MS(ESI$^+$) m/z 509 (M+H)$^+$.

Example 331

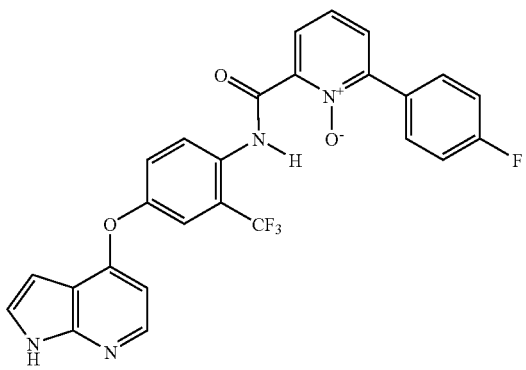

6-(4-Fluoro-phenyl)-1-oxy-pyridine-2-carboxylic acid [2-trifluoromethyl-4-(1H-pyrrolo[2,3-b]pyridin-4-yloxy)-phenyl]-amide Prepared in a similar manner as Example 241. HPLC $t_R$=3.205 min (Chromolith SpeedROD 4.6×50 mm, 10–90% aqueous methanol containing 0.1% TFA, 4 min gradient, monitored at 220 nm); MS(ESI$^+$) m/z 509 (M+H)$^+$.

Example 332

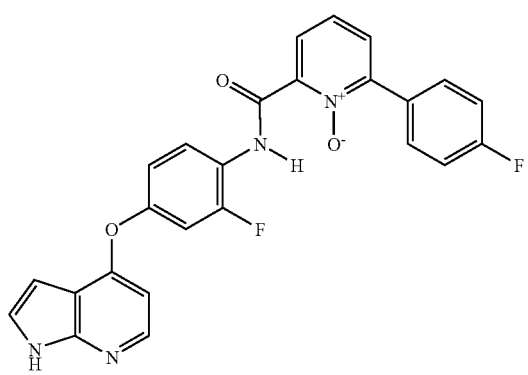

6-(4-Fluoro-phenyl)-1-oxy-pyridine-2-carboxylic acid [2-fluoro-4-(1H-pyrrolo[2,3-b]pyridin-4-yloxy)-phenyl]-amide Prepared in a similar manner as Example 241. HPLC $t_R$=1.103 min (YMC S5 ODS 4.6×50 mm, 10–90% aqueous methanol containing 0.1% $H_3PO_4$, 4 min gradient, monitored at 220 nm); MS(ESI$^+$) m/z 459 (M+H)$^+$.

Example 333

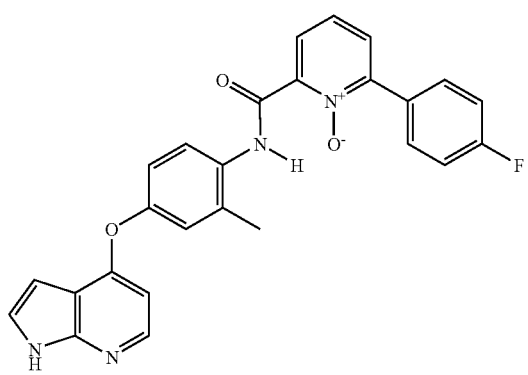

6-(4-Fluoro-phenyl)-1-oxy-pyridine-2-carboxylic acid [2-methyl-4-(1H-pyrrolo[2,3-b]pyridin-4-yloxy)-phenyl]-amide Prepared in a similar manner as Example 241. HPLC $t_R$=3.120 min (Chromolith SpeedROD 4.6×50 mm, 10–90% aqueous methanol containing 0.1% TFA, 4 min gradient, monitored at 220 nm); MS(ESI$^+$) m/z 455 (M+H)$^+$.

Example 334

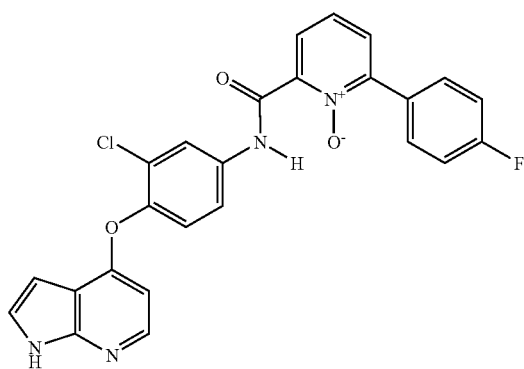

6-(4-Fluoro-phenyl)-1-oxy-pyridine-2-carboxylic acid [5-chloro-4-(1H-pyrrolo[2,3-b]pyridin-4-yloxy)-phenyl]-amide Prepared in a similar manner as Example 241. HPLC $t_R$=3.200 min (Chromolith SpeedROD 4.6×50 mm, 10–90% aqueous methanol containing 0.1% TFA, 4 min gradient, monitored at 220 nm); MS(ESI$^+$) m/z 475 (M+H)$^+$.

Example 335

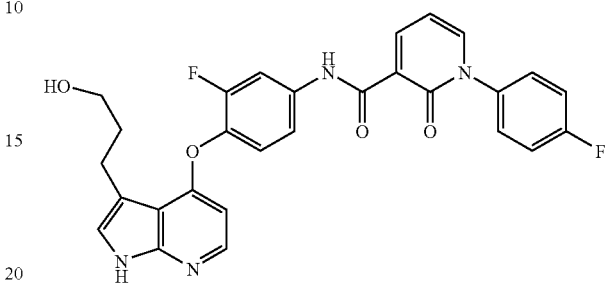

N-(3-Fluoro-4-(3-(3-hydroxypropyl)-1H-pyrrolo[2,3-b]pyridin-4-yloxy)phenyl)-1-(4-fluorophenyl)-2-oxo-1,2-dihydropyridine-3-carboxamide

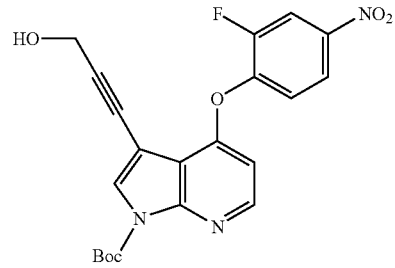

A) tert-Butyl 4-(2-fluoro-4-nitrophenoxy)-3-(3-hydroxyprop-1-ynyl)-1H-pyrrolo[2,3-b]pyridine-1-carboxylate A stream of Ar was bubbled through a mixture of tert-butyl 4-(2-fluoro-4-nitrophenoxy)-3-iodo-1H-pyrrolo[2,3-b]pyridine-1-carboxylate (400 mg, 0.8 mmol, Compound B of Example 283), propargyl alcohol (90 mg, 1.6 mmol), Pd(dppf)$_2$Cl$_2$:CH$_2$Cl$_2$ (66 mg, 0.08 mmol), and CuI (40 mg) in triethylamine (0.8 mL) and THF (6 mL) for 5 min. The reaction mixture was sealed in a tube and heated at 75° C. for 1 h. The mixture was diluted with CH$_2$Cl$_2$ and washed with brine. The organic phase was dried over MgSO$_4$ and concentrated in vacuo. The crude residue was purified by flash column chromatography (silica gel, 30% EtOAc/CH$_2$Cl$_2$) to afford the desired product (220 mg, 64% yield) as a yellow solid. LC/MS ESI$^+$) m/z 428 (M+H)$^+$.

B) 3-(4-(4-Amino-2-fluorophenoxy)-1H-pyrrolo[2,3-b]pyridin-3-yl)propan-1-ol

A mixture of tert-butyl 4-(2-fluoro-4-nitrophenoxy)-3-(3-hydroxyprop-1-ynyl)-1H-pyrrolo[2,3-b]pyridine-1-carboxylate (50 mg, 0.15 mmol) and 10% Pd/C (containing 50% $H_2O$, 120 mg) in THF (10 mL) and MeOH (2 mL) was hydrogenated at 1 atm for 5 h. The mixture was diluted with MeOH and filtered through a pad of Celite®. The crude mixture was purified by preparative HPLC to afford the desired product (6 mg, 13% yield) as a white solid. LC/MS ESI+) m/z 302 (M+H)+.

C) N-(3-Fluoro-4-(3-(3-hydroxypropyl)-1H-pyrrolo[2,3-b]pyridin-4-yloxy)phenyl)-1-(4-fluorophenyl)-2-oxo-1,2-dihydropyridine-3-carboxamide To a stirred mixture of 3-(4-(4-amino-2-fluorophenoxy)-1H-pyrrolo[2,3-b]pyridin-3-yl)propan-1-ol (5 mg, 0.0166 mmol), 1-(4-fluorophenyl)-2-oxo-1,2-dihydropyridine-3-carboxylic acid (5.8 mg, 0.025 mmol, Compound B of Example 242), and HATU (Perseptive Biosystems, 10 mg, 0.025 mmol) in DMF (0.5 mL), was added DIPEA (0.1 mL). The reaction mixture was stirred at rt for 2 h and concentrated in vacuo. The residue was purified by preparative HPLC to give the title compound (6 mg, HCl salt, 66% yield) as a white solid. $^1$H NMR (CD$_3$OD) δ 8.71 (dd, 1H, J=7.2, 2.0 Hz), 8.22 (d, 1H, J=6.8 Hz), 8.10 (dd, 1H, J=12.4, 2.0 Hz), 8.00 (dd, 1H, J=6.4, 2.0 Hz), 7.25–7.60 (m, 7H), 7.70–7.80 (m, 2H), 3.64 (t, 2H, J=6.4 Hz), 3.05 (t, 2H, J=7.2 Hz), 2.00 (m, 2H); LC/MS ESI+) m/z 517 (M+H)+.

We claim:

1. A compound having Formula I or II:

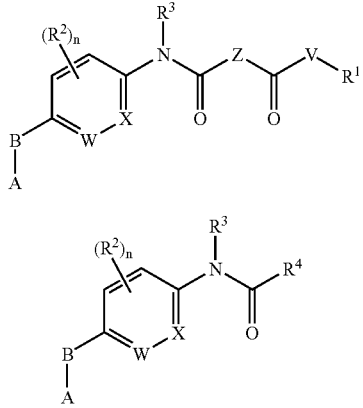

or a pharmaceutically acceptable salt thereof, wherein:
$R^1$ is H, alkyl, substituted alkyl, cycloalkyl, substituted cycloalkyl, arylalkyl, substituted arylalkyl, aryl, substituted aryl, alkenyl, substituted alkenyl, alkynyl, substituted alkynyl, heteroaryl, substituted heteroaryl, heterocyclo, substituted heterocyclo, heteroarylalkyl, substituted heteroarylalkyl, heterocycloalkyl, or substituted heterocycloalkyl;
each $R^2$ is independently, H, halogen, cyano, $NO_2$, $OR^5$, $NR^6R^7$, alkyl, substituted alkyl, cycloalkyl, substituted cycloalkyl, aryl, substituted aryl, heteroaryl, substituted heteroaryl, heterocyclo, substituted heterocyclo, arylalkyl, substituted arylalkyl, heterocycloalkyl, or substituted heterocycloalkyl;
B is O, $NR^8$, S, SO, $SO_2$, $CR^9R^{10}$;
V is $NR^{11}$ or —$(CR^{47}R^{48})_p$—;
W or X are independently C or N;
Y is O, S, or $NR^{12}$;
Z is —$CR^{13}R^{14}$—, —$(CR^{13}R^{14})_mNR^{15}$—;
l is 0 to 4;
m is 0 to 2;
n is 0 to 4;
p is 0 to 4;
$R^3$, $R^5$, $R^6$, $R^7$, $R^8$, $R^{11}$ and $R^{15}$ are each independently H, alkyl, substituted alkyl, cycloalkyl, substituted cycloalkyl, aryl, substituted aryl, heteroaryl, substituted heteroaryl, heterocycloalkyl, or substituted heterocycloalkyl;
$R^4$ is aryl, substituted aryl, heteroaryl, substituted heteroaryl, heterocycloalkyl, or substituted heterocycloalkyl;
$R^9$ and $R^{10}$ are independently H, halogen, hydroxyl, alkyl, substituted alkyl, cycloalkyl, substituted cycloalkyl, aryl, substituted aryl, heteroaryl, substituted heteroaryl, heterocycloalkyl, or substituted heterocycloalkyl;
$R^{12}$ is H, alkyl, substituted alkyl, CN, $NO_2$ or $SO_2NH_2$
$R^{13}$, $R^{14}$, $R^{15}$, $R^{47}$ and $R^{48}$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form a carbocyclic or heterocyclic ring of 3 to 8 atoms;
A is:

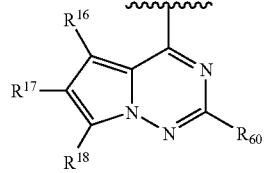

wherein
$R^{16}$ and $R^{17}$, are independently H, halogen, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, —$CO(CH_2)_lR^{41}$, —$CONH(CH_2)_lR^{42}$, —$OCONH(CH_2)_lR^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;
$R^{18}$ and $R^{60}$ are H;
$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, and $R^{42}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

2. The compound according to claim 1 wherein $R^1$ is an optionally substituted $C_1$ to $C_6$ alkyl, $C_2$ to $C_6$ alkenyl, $C_2$ to $C_6$ alkynyl, optionally substituted $C_3$ to $C_7$ cycloalkyl, $C_3$ to $C_7$ heterocycloalkyl, optionally substituted phenyl, optionally substituted biphenyl, or a $C_5$ to $C_{11}$ optionally substituted monocyclic or bicyclic heteroaryl.

3. The compound according to claim 2 wherein $R^1$ is phenyl, fluorophenyl, or cyclopropyl.

4. The compound according to claim 1 wherein $R^2$ is alkoxy, halo, haloalkyl or CN.

5. The compound according to claim 1 wherein $R^4$ is an optionally substituted phenyl, an optionally substituted pyridyl, an optionally substituted furanyl, an optionally substituted thiophene, an optionally substituted pyridinyl, an optionally substituted pyrimidyl, an optionally substituted isoxazole, an optionally substituted thiazole, an optionally substituted benzothiazole, or an optionally substituted quinoxaline.

6. The compound according to claim 5 wherein said phenyl is substituted with methoxy, CN, halo, $C_1$ to $C_4$ alkyl, $NO_2$, $SCH_3$, $SO_2CH_3$, or $COCH_3$.

7. The compound according to claim 1 wherein $R^{16}$ and $R^{17}$ are independently H, $C_1$ to $C_4$ alkyl, —C=$CR^aR^b$ wherein $R^a$ and $R^b$ together with the C to which they are connected form a cyclohexyl; halo; hydroxyalkyl; —$COR^{41}$ wherein $R^{41}$ is H or $C_1$ to C alkyl; —$OR^{26}$ wherein $R^{26}$ is $C_1$ to $C_6$ alkyl; —$C(O)_2R^{29}$ wherein $R^{29}$ is $C_1$ to $C_4$ alkyl; —$OCH_2NHR^{42}$ or —$CONHR^{42}$ wherein $R^{42}$ is $C_1$ to $C_6$ alkyl; phenyl or substituted phenyl; thiophene; pyridine; pyrimidine; isoxazol; pyrazol; or oxadiazole.

8. The compound according to claim 7 wherein $R^{26}$ is $C_1$ to $C_4$ alkyl substituted with amino or substituted with a 4 to 6 membered heterocycloalkyl containing at least one nitrogen atom.

9. The compound according to claim 8 wherein said heterocycloalkyl is morpholine, piperazine, or piperidine.

10. The compound according to claim 7 wherein $R^{16}$ and $R^{17}$ is alkyl or alkenyl substituted with cycloalkyl or heterocycloalkyl.

11. The compound according to claim 9 wherein said heterocycloalkyl is an optionally substituted morpholine, piperidine, pyrrolidine, or azetidine.

12. The compound according to claim 7 wherein $R^{17}$ is pyridyl or substituted pyridyl.

13. The compound according to claim 12 wherein said pyridyl is substituted with a morpholine, piperidine, or piperazine.

14. The compound according to claim 11 wherein the substituent is selected from amino, aminoalkyl, hydroxyl or amido.

15. The compound according to claim 1 wherein Y is O or S.

16. The compound according to claim 1 wherein B is O.

17. The compound according to claim 1 wherein Z is —$CR^{13}R^{14}$ or $NR^{15}$ wherein $R^{13}$, $R^{14}$, and $R^{15}$ are each H or $R^{13}$ and $R^{14}$ together with the carbon to which they are attached form a cyclopropyl.

18. A pharmaceutical composition comprising a therapeutically effective amount of a compound of claim 1 in a pharmaceutically acceptable carrier.

* * * * *